US012753190B2

(12) United States Patent
Achab et al.

(10) Patent No.: US 12,753,190 B2
(45) Date of Patent: Oct. 6, 2026

(54) SPIROTRICYCLE RIPK1 INHIBITORS AND METHODS OF USES THEREOF

(71) Applicant: Merck Sharp & Dohme LLC, Rahway, NJ (US)

(72) Inventors: Abdelghani Abe Achab, Melrose, MA (US); Jenny Lorena Rico Duque, Canton, MA (US); Xavier Fradera, Boston, MA (US); Joey L. Methot, Westwood, MA (US); Phieng Siliphaivanh, Newton, MA (US); Brandon A Vara, Boston, MA (US); Hongjun Zhang, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 335 days.

(21) Appl. No.: 18/702,524

(22) PCT Filed: Oct. 24, 2022

(86) PCT No.: PCT/US2022/047517

§ 371 (c)(1),
(2) Date: Apr. 18, 2024

(87) PCT Pub. No.: WO2023/076133

PCT Pub. Date: May 4, 2023

(65) Prior Publication Data

US 2024/0425524 A1 Dec. 26, 2024

Related U.S. Application Data

(60) Provisional application No. 63/272,265, filed on Oct. 27, 2021.

(51) Int. Cl.

| | |
|---|---|
| ***C07D 519/00*** | (2006.01) |
| ***A61K 31/438*** | (2006.01) |
| ***A61K 31/4709*** | (2006.01) |
| ***A61K 31/519*** | (2006.01) |
| ***C07D 471/20*** | (2006.01) |

(52) U.S. Cl.

CPC .......... *C07D 519/00* (2013.01); *A61K 31/438* (2013.01); *A61K 31/4709* (2013.01); *A61K 31/519* (2013.01); *C07D 471/20* (2013.01)

(58) Field of Classification Search

CPC .. C07D 519/00; C07D 471/20; A61K 31/438; A61K 31/4709; A61K 31/579

See application file for complete search history.

(56) References Cited

U.S. PATENT DOCUMENTS

| | | | | |
|---|---|---|---|---|
| 6,566,357 | B1 | 5/2003 | Laufersweiler et al. | |
| 8,686,020 | B2 | 4/2014 | Hamblett et al. | |
| 12,180,226 | B2 * | 12/2024 | Achab | C07D 498/20 |
| 2019/0337934 | A1 | 11/2019 | Taylor et al. | |

FOREIGN PATENT DOCUMENTS

| | | | |
|---|---|---|---|
| WO | 2018107060 | A1 | 6/2018 |
| WO | 2018213634 | A1 | 11/2018 |
| WO | 2020224656 | A1 | 11/2020 |
| WO | 2021092336 | A1 | 5/2021 |

OTHER PUBLICATIONS

Caccamo, Antonella et al., Necroptosis activation in Alzheimer's disease, Nat Neurosci, vol. 20 | No. 9, 1236-1246, 2017.
Degterev, Alexei et al., Chemical inhibitor of nonapoptotic cell death with therapeutic potential for ischemic brain injury, Nat Chem Biol, vol. 1 | No. 2, 112-119, 2005.
Degterev, Alexei et al., Targeting RIPK1 for the treatment of human diseases, PNAS, vol. 116 | No. 20, 9714-9722, 2019.
Gong, Yitao et al., The role of necroptosis in cancer biology and therapy, Molecular Cancer, 18:100, 1-17, 2019.
Ito, Yasushi et al., RIPK1 mediates axonal degeneration by promoting inflammation and necroptosis in ALS, Science, 353, 603-608, 2016.
Ofengeim, Dimitry et al., Activation of necroptosis in multiple sclerosis, Cell Rep., 10(11), 1836-1849, 2015.
Wang, Jia-Nan et al., RIPK1 inhibitor Cpd-71 attenuates renal dysfunction in cisplatin-treated mice via attenuating necroptosis, inflammation and oxidative stress, Clin Sci, 133(14), 1609-1627, 2019.

* cited by examiner

*Primary Examiner* — Kamal A Saeed
(74) *Attorney, Agent, or Firm* — Daniel Woods; John C. Todaro

(57) ABSTRACT

Described herein are compounds of Formula I; and pharmaceutically acceptable salts thereof, wherein A, X, $R^1$, $R^2$, m, n, and p are as defined herein. The compounds of Formula I, and pharmaceutically acceptable salts thereof, act as RIPK1 inhibitors and can be useful in preventing, treating or acting as a remedial agent for RIPK1-related diseases.

FORMULA I

I

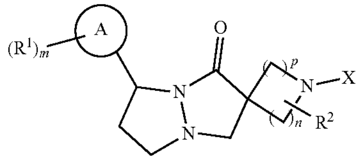

23 Claims, No Drawings

SPIROTRICYCLE RIPK1 INHIBITORS AND METHODS OF USES THEREOF

CROSS-REFERENCE TO RELATED APPLICATIONS

This application is a U.S. National Phase application under 35 U.S.C. § 371 of PCT Application No. PCT/US2022/047517 filed Oct. 24, 2022, which claims the benefit of priority to U.S. Provisional Patent Application No. 63/272,265, filed Oct. 27, 2021.

FIELD OF THE INVENTION

The present invention is directed to RIPK1 inhibitors. Specifically, the RIPK1 inhibitors described herein can be useful in preventing, treating or acting as a remedial agent for RIPK1-related diseases.

BACKGROUND OF THE INVENTION

Receptor-interacting protein-1 kinase (RIPK1) belongs to the family serine/threonine protein kinase involved in innate immune signaling. RIPK1 has emerged as a promising therapeutic target for the treatment of a wide range of human neurodegenerative, autoimmune, and inflammatory diseases. This is supported by extensive studies which have demonstrated that RIPK1 is a key mediator of apoptotic and necrotic cell death as well as inflammatory pathways.

For example, RIPK1 inhibition has been found to be useful as a treatment of acute kidney injury (AKI), a destructive clinical condition induced by multiple insults including ischemic reperfusion, nephrotoxic drugs and sepsis. It has been found that RIPK1-mediated necroptosis plays an important role in AKI and a RIPK1 inhibitor may serve as a promising clinical candidate for AKI treatment. Wang J N, et al., RIPK1 Inhibitor Cpd-71 Attenuates Renal Dysfunction in Cisplatin-Treated Mice via Attenuating Necroptosis, Inflammation and Oxidative Stress. *Clin Sci* (Lond). 2019 Jul. 25:133 (14): 1609-1627.

Additionally, human genetic evidence has linked the dysregulation of RIPK1 to the pathogenesis of amyotrophic lateral sclerosis (ALS), Alzheimer's disease and multiple sclerosis as well as other inflammatory and neurodegenerative diseases. *Alexei* Degterev, Dimitry Ofengeim, and Junying Yuan, Targeting RIPK1 for the treatment of human diseases, *Proc. Natl. Acad. Sci. USA*, May 14, 2019, 116 (20), 9714-9722: I to Y, et al., RIPK1 mediates axonal degeneration by promoting inflammation and necroptosis in ALS, *Science,* 2016, 353:603-8: Caccamo A, et al., Necroptosis activation in Alzheimer's disease, *Nat Neurosci,* 2017, 20:1236-46; Ofengeim D, et al., Activation of necroptosis in multiple sclerosis, *Cell Rep.,* 2015, 10:1836-49.

It also has been demonstrated that necroptosis is a delayed component of ischemic neuronal injury, thus RIPK1 inhibition may also play a promising role as a treatment for stroke. Degterev A, et al., Chemical inhibitor of nonapoptotic cell death with therapeutic potential for ischemic brain injury, *Nat Chem Biol* 2005, 1 (2): 112-119.

Therefore, there is a need for inhibitors of RIPK1 that offer high selectivity which can penetrate the blood-brain barrier, thus offering the possibility to target neuroinflammation and cell death which drive various neurologic conditions including Alzheimer's disease, ALS, and multiple sclerosis as well as acute neurological diseases such as stroke and traumatic brain injuries.

SUMMARY OF THE INVENTION

Described herein are compounds of Formula I:

I

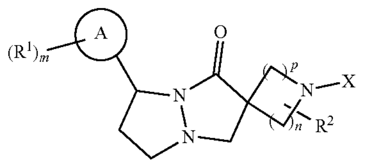

and pharmaceutically acceptable salts thereof, wherein A, X, $R^1$, $R^2$, m, n and p are described below.

The compounds described herein are RIPK1 inhibitors, which can be useful in the prevention, treatment or amelioration of neurodegenerative, autoimmune and inflammatory diseases and other RIPK1-related diseases.

Also described herein are methods of treating neurodegenerative, autoimmune, and inflammatory diseases comprising administering to a patient in need thereof a compound described herein, or a pharmaceutically acceptable salt thereof.

Also described herein are uses of a compound described herein, or a pharmaceutically acceptable salt thereof, to treat neurodegenerative, autoimmune, and inflammatory diseases in a patient in need thereof.

Also described herein are pharmaceutical compositions comprising a compound described herein, or a pharmaceutically acceptable salt thereof and a pharmaceutically acceptable carrier.

Also described herein are pharmaceutical compositions comprising a compound described herein and a pharmaceutically acceptable carrier.

Also described herein are methods of treating neurodegenerative, autoimmune, and inflammatory diseases comprising administering to a patient in need thereof a compound described herein, or a pharmaceutically acceptable salt thereof, and at least one additional therapeutic agent.

Also described herein are uses of a compound described herein, or a pharmaceutically acceptable salt thereof, in combination with at least one additional agent, to treat neurodegenerative, autoimmune, and inflammatory diseases in a patient in need thereof.

Also described herein are pharmaceutical compositions comprising a compound described herein, or a pharmaceutically acceptable salt thereof, at least one additional therapeutic agent and a pharmaceutically acceptable carrier.

Also described herein are pharmaceutical compositions comprising a compound described herein, at least one additional therapeutic agent and a pharmaceutically acceptable carrier.

DETAILED DESCRIPTION OF THE INVENTION

Described herein are compounds compound of Formula I:

I

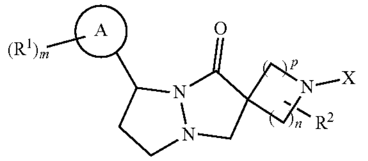

or a pharmaceutically acceptable salt thereof, wherein:

A is aryl, heteroaryl, heterocycloalkyl or $C_3$-$C_6$cycloalkyl;

each occurrence of $R^1$ is independently —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6alkyl)_2$, —$NH(C_1$-$C_6$alkyl) or $C_1$-$C_6$alkoxy;

$R^2$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6alkyl)_2$, —$NH(C_1$-$C_6$alkyl) or $C_1$-$C_6$alkoxy;

X is —CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, $SO_2$heterocycloalkyl, —$COOC_1$-$C_6$alkyl or —$COOC_3$-$C_6$cycloalkyl, wherein the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —$COOC_3$-$C_6$cycloalkyl or —$SO_2$heterocycloalkyl is unsubstituted or substituted with one to four substituents selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —$COOC_1$-$C_6$alkyl, —$COC_1$-$C_6$alkyl, —$SC_1$-$C_6$alkyl, oxo, $C_3$-$C_6$cycloalkyl, aryl, heteroaryl, heterocycloalkyl, —$CONH(C_1$-$C_6$alkyl), —$CONH_2$, —$CON(C_1$-$C_6alkyl)_2$, —$NH(C_1$-$C_6$alkyl), —$NH_2$, and —$N(C_1$-$C_6alkyl)_2$, wherein the heteroaryl, heterocycloalkyl, $C_3$-$C_6$cycloalkyl, aryl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl;

m is 0, 1, 2 or 3;

n is 1, 2 or 3; and pis 1, 2 or 3.

Described herein are compounds wherein A is aryl, heteroaryl, heterocycloalkyl or $C_3$-$C_6$cycloalkyl. In certain embodiments, A is aryl, heteroaryl, or $C_3$-$C_6$cycloalkyl. In certain embodiments, A is aryl. In certain embodiments, wherein A is aryl, the aryl is phenyl.

In certain embodiments A is heteroaryl. Suitable heteroaryls include, but are not limited to, pyridyl (pyridinyl), oxazolyl, imidazolyl, triazolyl, furyl, triazinyl, thienyl, pyrimidyl, pyrazinyl, indolizinyl, cinnolinyl, phthalazinyl, quinazolinyl, naphthyridinyl, quinoxalinyl, purinyl, benzimidazolyl, quinolyl, benothiophenyl, isothiazolyl and isoquinolyl. In certain embodiments, wherein A is heteroaryl, the heteroaryl is pyridinyl, pyrazinyl, benothiophenyl, isothiazolyl or thienyl.

In certain embodiments, wherein A is heteroaryl, the heteroaryl is

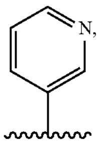
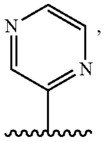
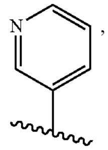
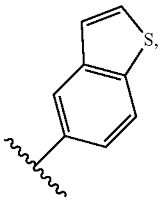
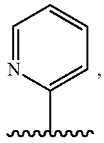
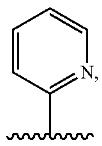
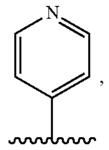
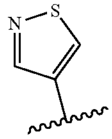
or
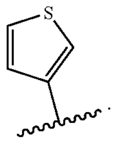

In certain embodiments, A is heterocycloalkyl. Suitable heterocycloalkyls include, but are not limited to, azetidine, tetrahydropyranyl, tetrahydrofuranyl, pyrrolidinyl, piperidinyl, piperazinyl, dioxanyl, imidazolidinyl, 2,3-dihydrofuro (2,3-b)pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl and dihydrocyclopentapyridinyl. In certain embodiments, wherein A is heterocycloalkyl, A is:

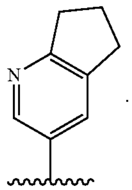 [SMILES: *c1cnc2c(c1)CCC2]
.

In certain embodiments, A is $C_3$-$C_6$cycloalkyl. Suitable cycloalkyls include, but are not limited to, cyclopropyl, cyclobutyl, cyclopentyl and cyclohexyl. In certain embodiments, wherein A is $C_3$-$C_6$cycloalkyl, the $C_3$-$C_6$cycloalkyl is cyclohexyl or cyclopentyl.

In certain embodiments, A is:

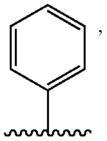
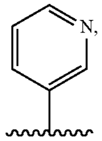
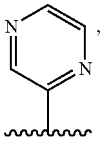
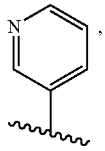
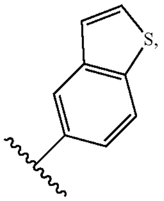
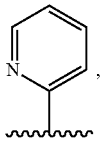
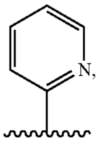
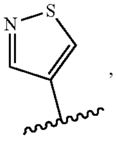
, -continued

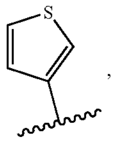
,
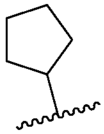
,
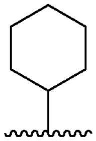
or
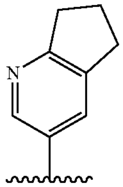
.

In certain embodiments, A is

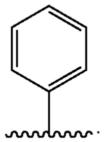

Described herein are compounds, wherein $R^1$ is —OH, $C_1$-$C_6$alkylOH, —CN, $C_1$-$C_6$alkylCN, $C_1$—Ccalkyl, halo$C_1$-$C_6$alkyl, halogen, —$NH_2$, —$N(C_1$-$C_6alkyl)_2$, —NH ($C_1$-$C_6$alkyl) or $C_1$-$C_6$alkoxy. In certain embodiments, $R^1$ is —CN, $C_1$-$C_6$alkyl, halogen, or $C_1$-$C_6$alkoxy.

In certain embodiments, $R^1$ is —OH. In certain embodiments, $R^1$ is $C_1$-$C_6$alkylOH. Suitable alcohols include, but are not limited to, methanol, ethanol, propanol, and butanol.

In certain embodiments, $R^1$ is —CN. In certain embodiments, $R^1$ is $C_1$-$C_6$alkylCN.

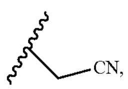
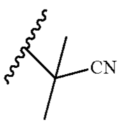
and
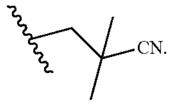

Suitable $C_1$-$C_6$alkylCN groups include, but are not limited to,

In certain embodiments, $R^1$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^1$ is methyl.

In certain embodiments, $R^1$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^1$ is halogen. Suitable halogens include, but are not limited to, fluorine, chlorine, bromine, or iodine. In certain embodiments, $R^1$ is fluorine.

In certain embodiments, $R^1$ is —$NH_2$.

In certain embodiments, $R^1$ is —$N(C_1$-$C_6alkyl)_2$. In certain embodiments, $R^1$ is —$N(CH_3)_2$.

In certain embodiments, $R^1$ is —$NH(C_1$-$C_6$alkyl). In certain embodiments, $R^1$ is —$NH(CH_3)$.

In certain embodiments, $R^1$ is $C_1$-$C_6$alkoxy. Suitable alkoxys include, but are not limited to, methoxy, ethoxy, n-propoxy, isopropoxy and n-butoxy. In certain embodiments, $R^1$ is methoxy.

Described herein are compounds wherein m is 0, 1, 2, or 3. In certain embodiments, m is 0. In certain embodiments, m is 1. In certain embodiments, m is 2. In certain embodiments, m is 3. In certain embodiments, m is 1 or 2.

In certain embodiments of the compounds described herein, A is phenyl, m is 2 and each $R^1$ is fluorine.

In certain embodiments, A, $R^1$ and m are as follows:

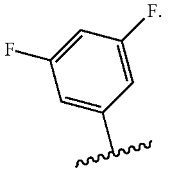

In certain embodiments of the compounds described herein, A is phenyl, m is 0, 1 or 2 and $R^1$ is fluorine, methoxy, methyl or —CN.

In certain embodiments of the compounds described herein, A is pyridinyl, m is 0, 1 or 2 and $R^1$ is fluorine, methyl, or —CN.

Described herein are compounds wherein n is 1, 2 or 3. In certain embodiments, n is 1 or 2. In certain embodiments, n is 1. In certain embodiments, n is 2. In certain embodiments, n is 3.

Described herein are compounds wherein p is 1, 2 or 3. In certain embodiments, p is 1 or 2. In certain embodiments, p is 1. In certain embodiments, p is 2. In certain embodiments, p is 3.

In certain embodiments, n is 3 and p is 2. In other embodiments, n is 2 and p is 3.

In certain embodiments, n and p are both 1, as shown in Formula II.

II

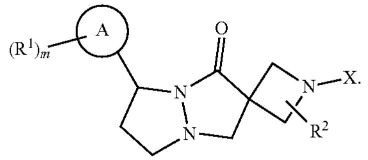

In certain embodiments, n and p are both 2, as shown in Formula III.

III

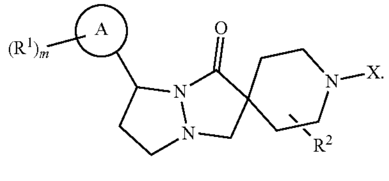

Described herein are compounds wherein, $R^2$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6alkyl)_2$, —NH ($C_1$-$C_6$alkyl) or $C_1$-$C_6$alkoxy.

In certain embodiments, $R^2$ is hydrogen.

In certain embodiments, $R^2$ is —OH. In certain embodiments, $R^2$ is $C_1$-$C_6$alkylOH. Suitable alcohols include, but are not limited to, methanol, ethanol, propanol, and butanol.

In certain embodiments, $R^2$ is —CN. In certain embodiments, $R^2$ is $C_1$-$C_6$alkylCN.

Suitable $C_1$-$C_6$alkylCN groups include, but are not limited to,

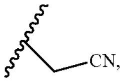

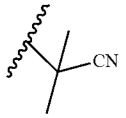

and

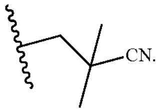

In certain embodiments, $R^2$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^2$ is methyl.

In certain embodiments, $R^2$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^2$ is halogen. Suitable halogens include, but are not limited to, fluorine, chlorine, bromine, or iodine. In certain embodiments, $R^2$ is fluorine.

In certain embodiments, $R^2$ is —$NH_2$.

In certain embodiments, $R^2$ is —N($C_1$-$C_6$alkyl)$_2$. In certain embodiments, $R^2$ is —N($CH_3$)$_2$.

In certain embodiments, $R^2$ is —NH($C_1$-$C_6$alkyl). In certain embodiments, $R^2$ is —NH($CH_3$).

In certain embodiments, $R^2$ is $C_1$-$C_6$alkoxy. Suitable alkoxys include, but are not limited to, methoxy, ethoxy, n-propoxy, isopropoxy and n-butoxy. In certain embodiments, $R^2$ is methoxy.

Described herein are compounds wherein X is —CN, aryl, $C_1$-$C_6$alkylaryl, —COaryl, CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, $CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, COheterocycloalkyl, —CONHheterocycloalkyl, —$SO_2$heterocycloalkyl, —$COOC_1$-$C_6$alkyl or —$COOC_3$-$C_6$cycloalkyl, wherein the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —SO heteroaryl, heterocycloalkyl, $C_1$-$C_6$alkylheterocycloalkyl, —COheterocycloalkyl, CONHheterocycloalkyl, —$COOC_3$-$C_6$cycloalkyl or —$SO_2$heterocycloalkyl, is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —$COOC_1$-$C_6$alkyl, —$COOC_3$-$C_6$alkyl, —$SC_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, —NH($C_1$-$C_6$alkyl), —$NH_2$, and —N($C_1$-$C_6$alkyl), wherein the heteroaryl, heterocycloalkyl, $C_3$-$C_6$cycloalkyl, $C_1$-$C_6$alkynyl, aryl or $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl.

In certain embodiments, X is —CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, CONHheterocycloalkyl, —$SO_2$heterocycloalkyl, —$COOC_1$-$C_6$alkyl or —$COOC_3$-$C_6$cycloalkyl.

In certain embodiments, X is —CN.

In certain embodiments, X is aryl. In certain embodiments, X is phenyl.

In certain embodiments, X is $C_1$-$C_6$alkylaryl. In certain embodiments, X is $C_1$-$C_6$alkylphenyl. In certain embodiments, X is —$CH_2$phenyl.

In certain embodiments, X is —COaryl. In certain embodiments, X is —COphenyl.

In certain embodiments, X is —CONHaryl. In certain embodiments, X is —CONHphenyl.

In certain embodiments, X is —$SO_2$aryl. In certain embodiments, X is —$SO_2$phenyl.

In certain embodiments, X is $C_3$-$C_{10}$cycloalkyl. Suitable cycloalkyls include, but are not limited to, cyclopropyl, cyclobutyl, cyclopentyl and cyclohexyl.

In certain embodiments, X is $C_1$-$C_6$alkyl$C_3$-$C_{10}$cycloalkyl. Suitable $C_1$-$C_6$alkylcycloalkyls include, but are not limited to, $C_1$-$C_6$alkylcyclopropyl, $C_1$-$C_6$alkylcyclobutyl, $C_1$-$C_6$alkylcyclopentyl and $C_1$-$C_6$alkylcyclohexyl.

In certain embodiments, X is —$COC_3$-$C_{10}$cycloalkyl. Suitable —COcycloalkyls include, but are not limited to, —COcyclopropyl, —COcyclobutyl, —COcyclopentyl and —COcyclohexyl.

In certain embodiments, X is —$CONHC_3$-$C_{10}$cycloalkyl. Suitable —CONHcycloalkyls include, but are not limited to, —CONHcyclopropyl, —CONHcyclobutyl, —CONHcyclopentyl and —CONHcyclohexyl.

In certain embodiments, X is —$SO_2C_3$-$C_{10}$cycloalkyl. Suitable —$SO_2$cycloalkyls include, but are not limited to, —$SO_2$cyclopropyl, —$SO_2$cyclobutyl, —$SO_2$cyclopentyl and —$SO_2$cyclohexyl.

In certain embodiments, X is heteroaryl. In certain embodiments, X is a nitrogen-containing heteroaryl. In certain embodiments, the heteroaryl is:

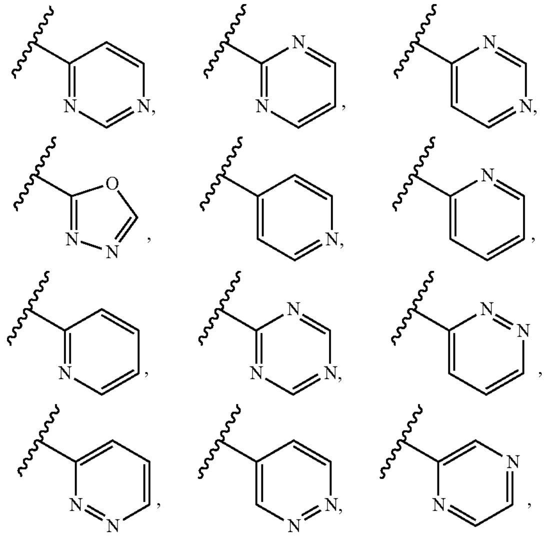

-continued

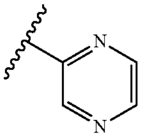,
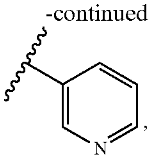,
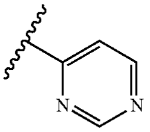 or
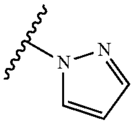.

In certain embodiments, heteroaryl is

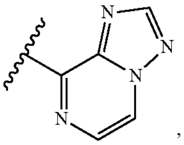,
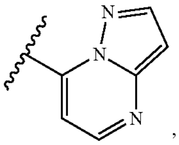,
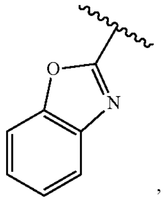,
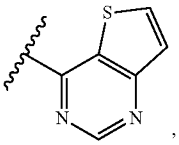,
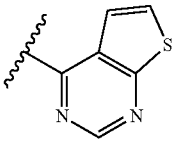,
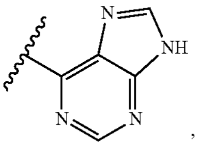,
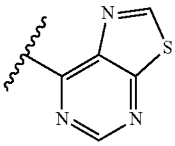,
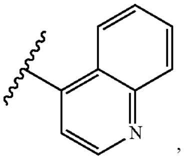,
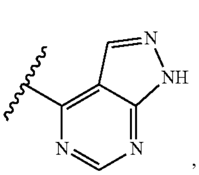,
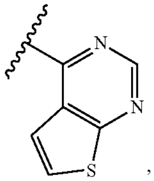,
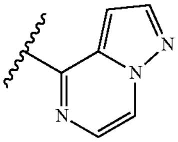,
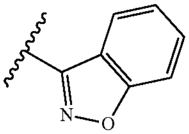,
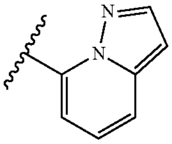 or
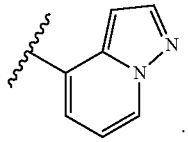.

In certain embodiments. X is $C_1$-$C_6$alkylheteroaryl. In certain embodiments, the $C_1$-$C_6$alkylheteroaryl is

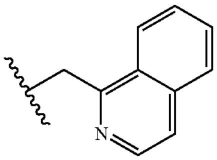.

In certain embodiments. X is —COheteroaryl. In certain embodiments, the —COheteroaryl is

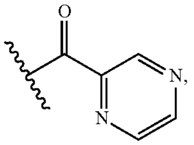
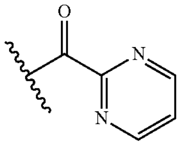,
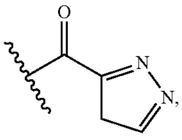
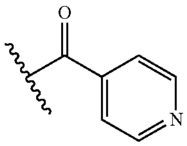 or
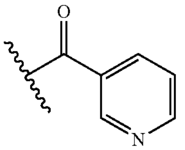.

In certain embodiments, X is —CONHheteroaryl.

In certain embodiments, X is —$SO_2$heteroaryl.

In certain embodiments, X is heterocycloalkyl. In certain embodiments the heterocycloalkyl is

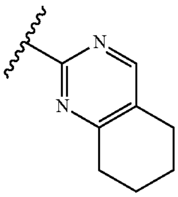 or
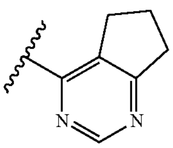.

In certain embodiments, X is $C_1$-$C_6$alkylheterocycloalkyl.

In certain embodiments, X is —COheterocycloalkyl.

In certain embodiments, X is —CONHheterocycloalkyl.

In certain embodiments, X is —$SO_2$heterocycloalkyl.

In certain embodiments, X is —$COOC_1$-$C_6$alkyl. In certain embodiments, X is

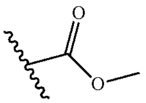.

In certain embodiments, X is —$COOC_3$-$C_6$cycloalkyl. In certain embodiments, —COOcyclobutyl.

In certain embodiments, X is —COaryl, —$SO_2$aryl, heteroaryl, $C_1$-$C_6$alkylheteroaryl, —COheteroaryl, heterocycloalkyl, or —$COOC_1$-$C_6$alkyl.

In certain embodiments, X is unsubstituted. In certain embodiments, X is substituted. In certain embodiments, X is substituted with one to four substituents. In certain embodiments, X is substituted with one substituent. In certain embodiments, X is substituted with two substituents.

In certain embodiments, X is substituted with three substituents. In certain embodiments, X is substituted with four substituents.

In certain embodiments, when X is the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —$COOC_3$-$C_6$cycloalkyl or —$SO_2$heterocycloalkyl, X is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —$COOC_1$-$C_6$alkyl, —$COC_1$-$C_6$alkyl, —$SC_1$-$C_6$alkyl, Oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, —NH($C_1$-$C_6$alkyl), —$NH_2$, and —N($C_1$-$C_6$alkyl)$_2$, wherein the heteroaryl, heterocycloalkyl, $C_3$-$C_6$cycloalkyl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl.

In certain embodiments, X is substituted with —CN.

In certain embodiments, X is substituted with —OH.

In certain embodiments, X is substituted with halogen. Suitable halogens include, but are not limited to, fluorine, chlorine, bromine or iodine. In certain embodiments, X is substituted with fluorine, chlorine, or bromine.

In certain embodiments, X is substituted with $C_1$-$C_6$alkylCN. Suitable $C_1$-$C_6$alkylCN groups include, but are not limited to,

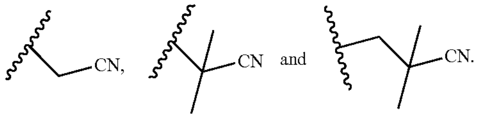

In certain embodiments, X is substituted with $C_1$-$C_6$alkylOH. Suitable alcohols include, but are not limited to, methanol, ethanol, propanol and butanol. In certain embodiments, X is substituted with —$CH_2OH$.

In certain embodiments, X is substituted with $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, X is substituted with methyl, ethyl, n-propyl, or isopropyl.

In certain embodiments, X is substituted with $C_1$-$C_6$alkynyl.

In certain embodiments, X is substituted with $C_1$-$C_6$haloalkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, X is substituted with $C_1$-$C_6$alkoxy. Suitable alkoxys include, but are not limited to, methoxy, ethoxy, n-propoxy, isopropoxy and n-butoxy.

In certain embodiments, X is substituted with $C_1$-$C_6$haloalkoxy.

In certain embodiments, X is substituted with —$COOC_1$-$C_6$alkyl.

In certain embodiments, X is substituted with —$COC_1$-$C_6$alkyl.

In certain embodiments, X is substituted with —$SC_1$-$C_6$alkyl.

In certain embodiments, X is substituted with oxo.

In certain embodiments, X is substituted with $C_3$-$C_6$cycloalkyl. Suitable cycloalkyls include, but are not limited to, cyclopropyl, cyclobutyl, cyclopentyl and cyclohexyl.

In certain embodiments, X is substituted with aryl. Suitable aryls include, but are not limited to, phenyl.

In certain embodiments, X is substituted with heteroaryl. Suitable heteroaryls include, but are not limited to, pyridyl (pyridinyl), oxazolyl, imidazolyl, triazolyl, furyl, triazinyl, thienyl, pyrimidyl, pyrazinyl, indolizinyl, cinnolinyl, phthalazinyl, quinazolinyl, naphthyridinyl, quinoxalinyl, purinyl, benzimidazolyl, quinolyl, benothiophenyl, isothiazolyl and isoquinolyl.

In certain embodiments, X is substituted with heterocycloalkyl. Suitable heterocycloalkyls include, but are not limited to, azetidine, furan, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and dihydrocyclopentapyridinyl.

In certain embodiments, X is substituted with —$CONH_2$.

In certain embodiments, X is substituted with —CONH ($C_1$-$C_6$alkyl). Suitable amides included, but are not limited to, CONH($CH_3$).

In certain embodiments, X is substituted with —CON ($C_1$-$C_6$alkyl)$_2$. Suitable amines included, but are not limited to, —CONH($CH_3$)$_2$.

In certain embodiments, X is substituted with —$NH_2$.

In certain embodiments, X is substituted with —NH($C_1$-$C_6$alkyl). Suitable amines included, but are not limited to, —NH($CH_3$).

In certain embodiments, X is substituted with —N($C_1$-$C_6$alkyl)$_2$. Suitable amines included, but are not limited to, —NH($CH_3$)$_2$.

In certain embodiments, wherein when X is aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, CONHheteroaryl, —$SO_2$heteroaryl, heterocycloalkyl, $C_1$-$C_6$alkylheterocycloalkyl, —COheterocycloalkyl, —CONHheterocycloalkyl or —$SO_2$heterocycloalkyl, the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, or —$SO_2$heterocycloalkyl, is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —$COOC_1$-$C_6$alkyl, —$COC_1$-$C_6$alkyl, —$SC_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, —NH($C_1$-$C_6$alkyl), —$NH_2$, and —N($C_1$-$C_6$alkyl)$_2$, wherein the heteroaryl, heterocycloalkyl, $C_3$-$C_6$cycloalkyl, aryl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl.

In certain embodiments, when X is —COaryl, —$SO_2$aryl, heteroaryl, $C_1$-$C_6$alkylheteroaryl, —COheteroaryl, heterocycloalkyl, or —COO$C_1$-$C_6$alkyl, the —COaryl, heteroaryl, $C_1$-$C_6$alkylheteroaryl, or —COheteroaryl is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, —NH($C_1$-$C_6$alkyl), —$NH_2$, and —N($C_1$-$C_6$alkyl)$_2$, wherein the heteroaryl, heterocycloalkyl, $C_3$-$C_6$cycloalkyl, aryl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl.

In certain embodiments, X is —COaryl, —$SO_2$aryl, heteroaryl, $C_1$-$C_6$alkylheteroaryl, —COheteroaryl, heterocycloalkyl, or —COO$C_1$-$C_6$alkyl, wherein the —COaryl, heteroaryl or $C_1$-$C_6$alkylheteroaryl, —COheteroaryl is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl, or aryl, is unsubstituted or substituted with one to two substituents independently selected from the group consisting of halogen, halo$C_1$-$C_6$alkyl and $C_1$-$C_6$alkyl.

In certain embodiments, X is —COaryl, —$SO_2$aryl, heteroaryl, $C_1$-$C_6$alkylheteroaryl, —COheteroaryl, heterocycloalkyl, or —COO$C_1$-$C_6$alkyl, wherein the —COaryl, heteroaryl, $C_1$-$C_6$alkylheteroaryl, or COheteroaryl is unsubstituted or substituted with one to four substituents, independently selected from the group consisting of —CN, —OH, chlorine, fluorine, bromine, —$CH_2$OH, methyl, ethyl, isopropyl, difluoromethyl, trifluoromethyl, methoxy, isopropoxy, propoxy, difluoromethoxy, —COCH3, —SCH3, oxo, cyclopropyl, phenyl, pyrazole, imidazole, furan, thiazole, pyrrolidine, —CONH($CH_3$), —$CONH_2$, —CON($CH_3$)$_2$, and —N($CH_3$)$_2$, wherein the phenyl, pyrazole, or imidazole is unsubstituted or substituted with one to two substituents, independently selected from the group consisting of chlorine, difluoromethyl, trifluoromethyl, and methyl.

In certain embodiments, wherein X is —COaryl, the —COaryl is unsubstituted or substituted with one, two or three substituents, independently selected from the group consisting of $C_1$-$C_6$alkyl, —CN, $C_1$-$C_6$alkoxy and halogen.

In certain embodiments, wherein X is —COheteroaryl, the —COheteroaryl is unsubstituted or substituted with one, two or three substituents, independently selected from the group consisting of $C_1$-$C_6$alkyl and halogen.

In certain embodiments, wherein X is heteroaryl, the heteroaryl is unsubstituted or substituted with one to four substituents, independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl or aryl, is unsubstituted or substituted with one to two substituents, independently selected from the group consisting of halogen, $C_1$-$C_6$haloalkyl and $C_1$-$C_6$alkyl.

Also described herein are compounds of Formula IV and Formula V:

IV

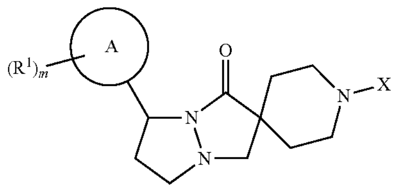

or a pharmaceutically acceptable salt thereof, wherein:

A is aryl:

$R^1$ is halogen:

X is —COaryl, —$SO_2$aryl, heteroaryl, $C_1$-$C_6$alkylheteroaryl, —COheteroaryl, heterocycloalkyl, or COO$C_1$-$C_6$alkyl, wherein the —COaryl, heteroaryl, or —COheteroaryl is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl, or aryl, is unsubstituted or substituted with one to two substituents independently selected from the group consisting of halogen, $C_1$-$C_6$haloalkyl and $C_1$-$C_6$alkyl; and m is 0, 1, 2 or 3.

V

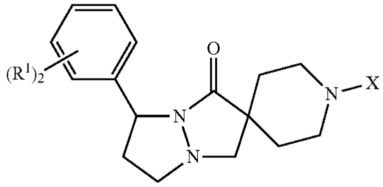

or a pharmaceutically acceptable salt thereof, wherein:

each occurrence of $R^1$ is independently-OH, $C_1$-$C_6$alkylOH, —CN, $C_1$-$C_6$alkylCN, $C_1$-$C_6$alkyl, halo$C_1$-$C_6$alkyl, halogen or $C_1$-$C_6$alkoxy; and X is —COaryl, —$SO_2$aryl, heteroaryl, $C_1$-$C_6$alkylheteroaryl, —COheteroaryl, heterocycloalkyl, or —COO$C_1$-$C_6$alkyl, wherein the —COaryl, heteroaryl, or —COheteroaryl is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl or aryl is unsubstituted or substituted with one to two substituents independently selected from the group consisting of halogen, $C_1$-$C_6$haloalkyl and $C_1$-$C_6$alkyl.

Also, described herein are the following compounds:
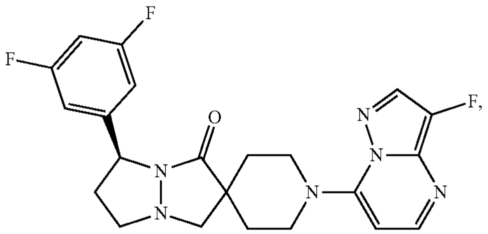
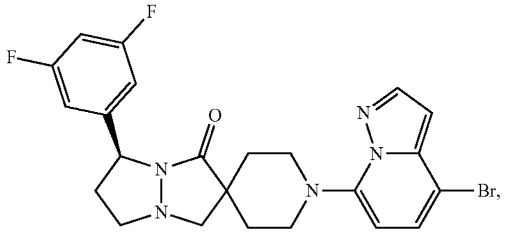
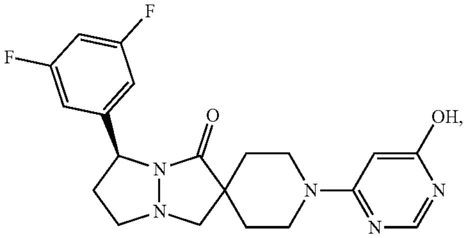
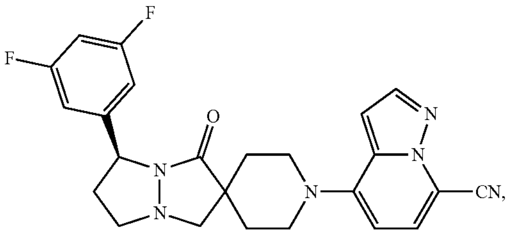
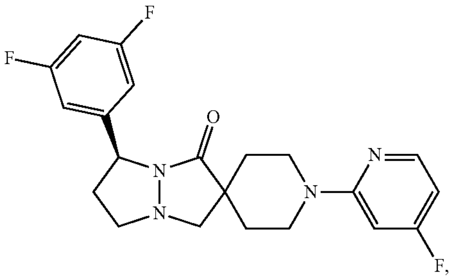
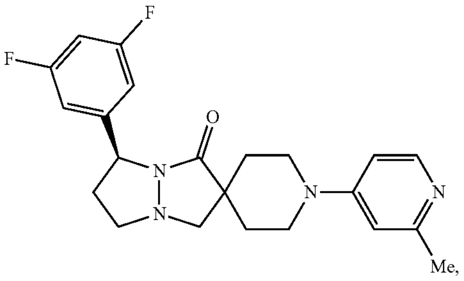
-continued
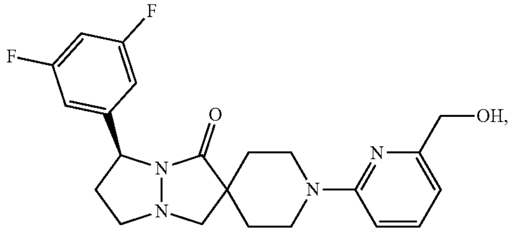
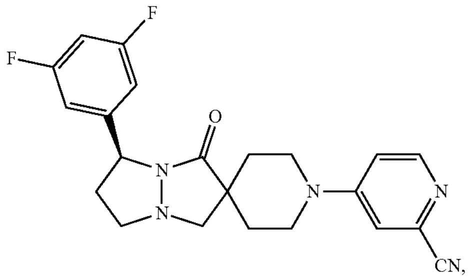
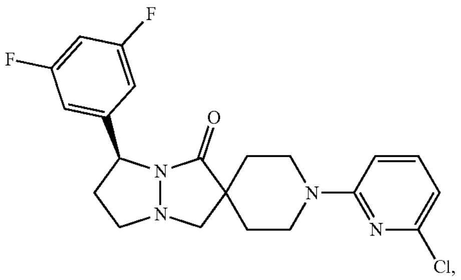
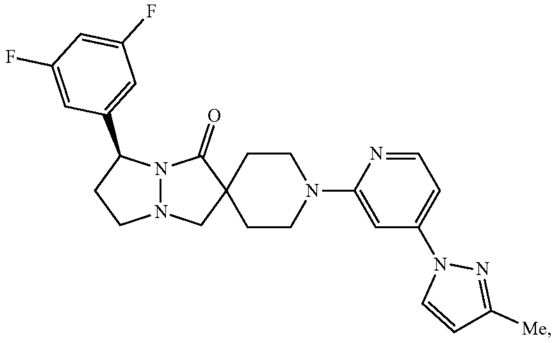
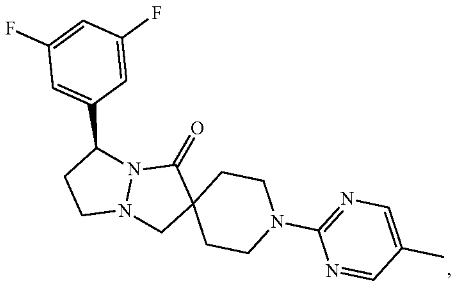
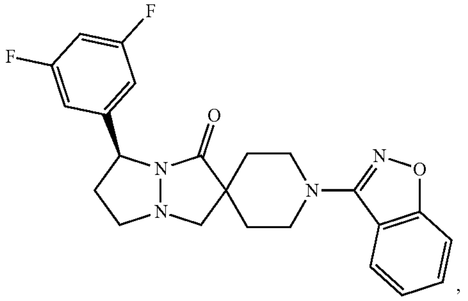

-continued
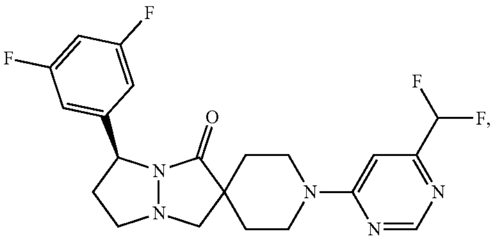
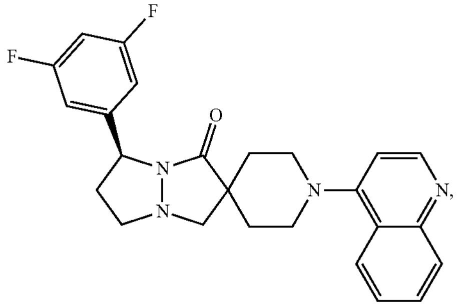
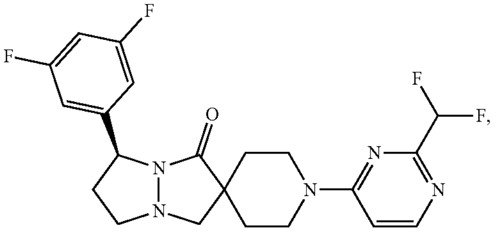
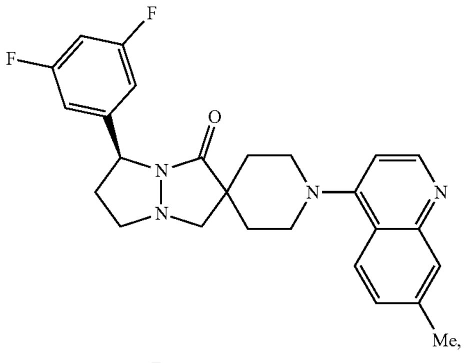
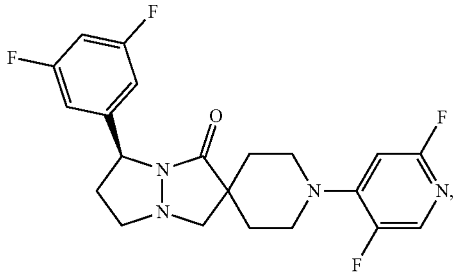
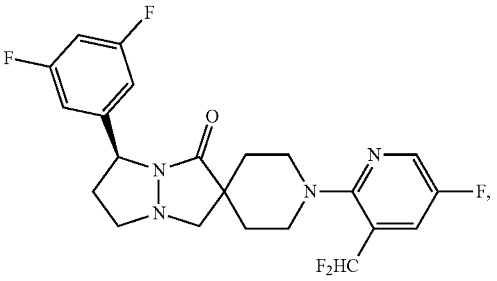
-continued
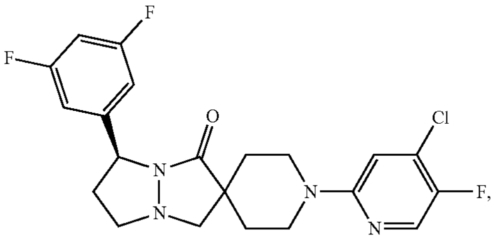
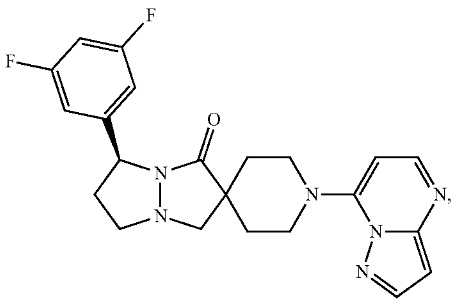
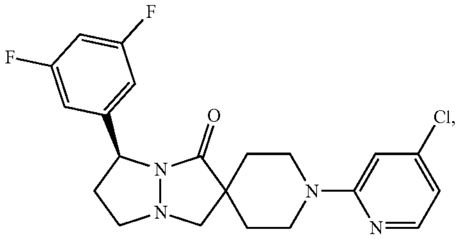
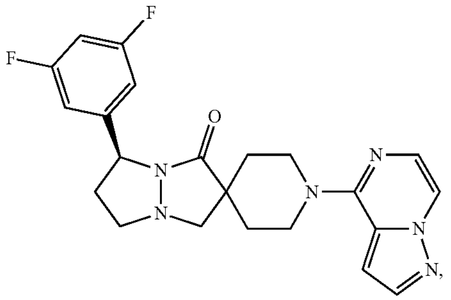
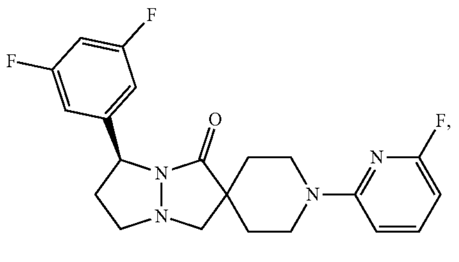
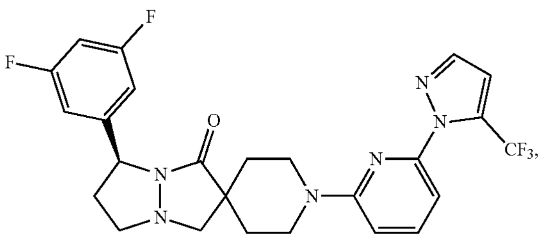

-continued
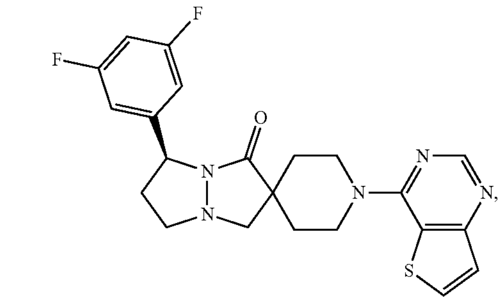
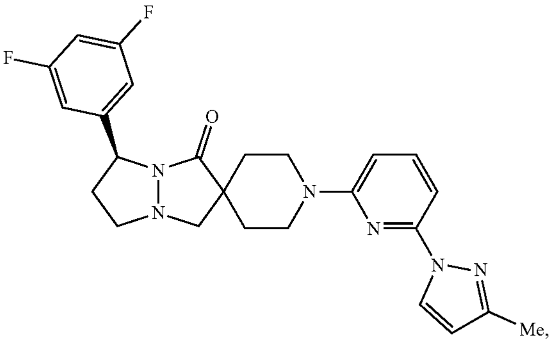
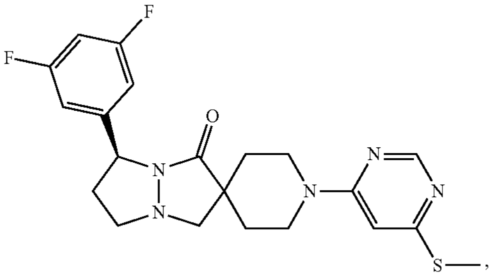
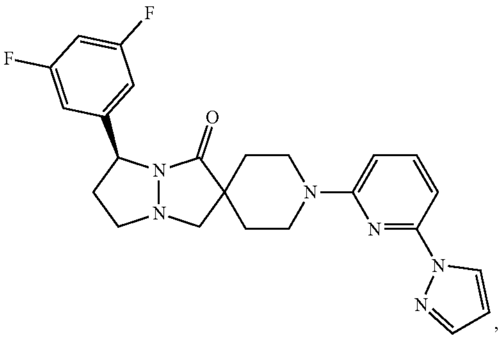
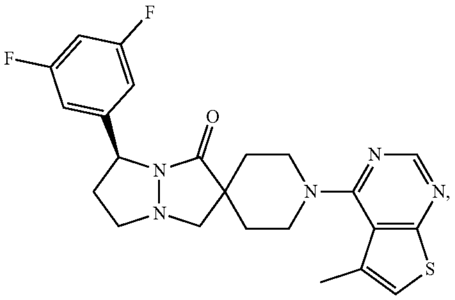
-continued
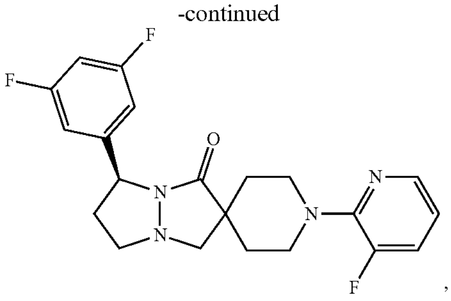
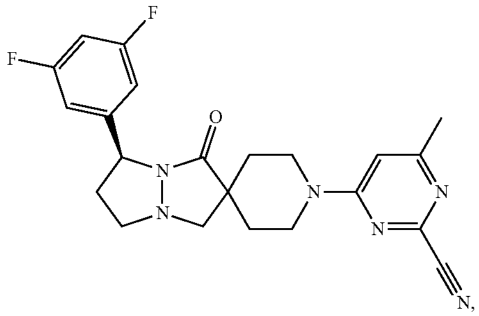
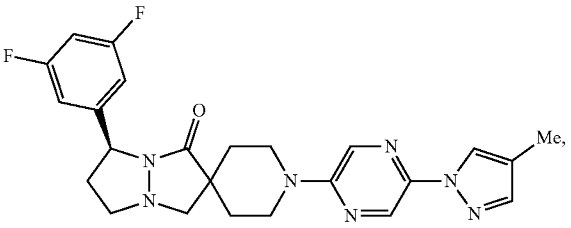
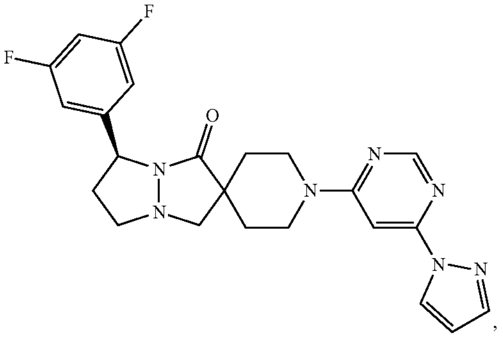
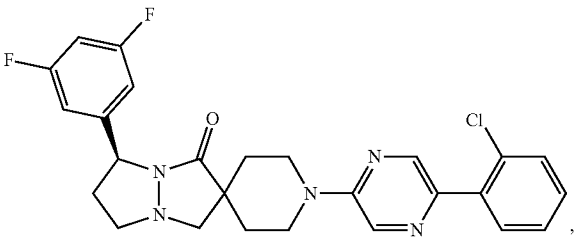
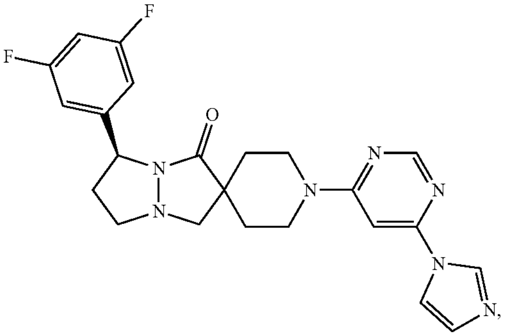

-continued
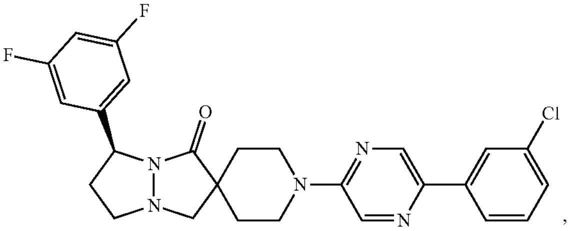
,
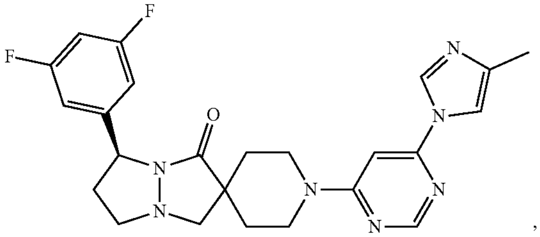
,
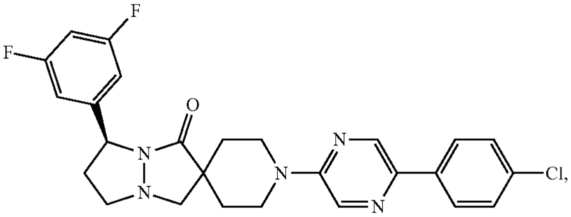
,
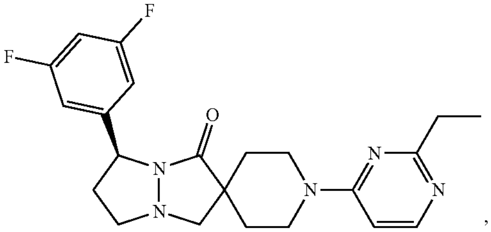
,
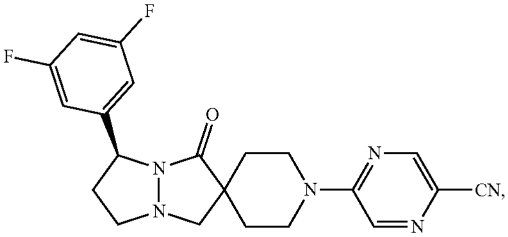
,
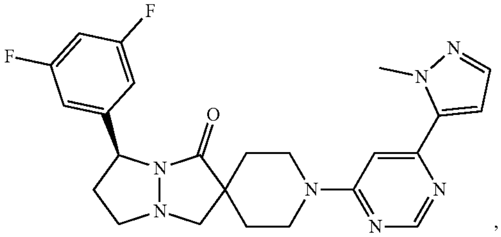
,
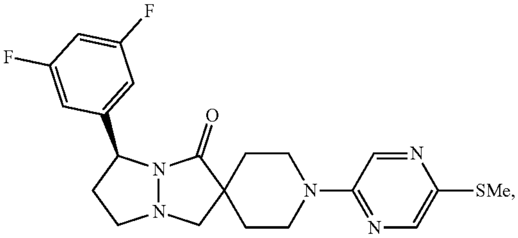
,
-continued
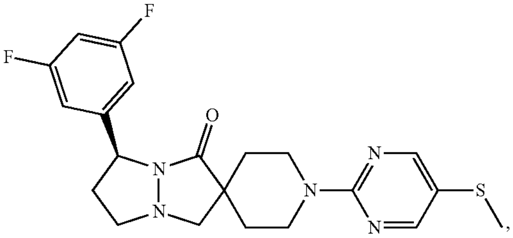
,
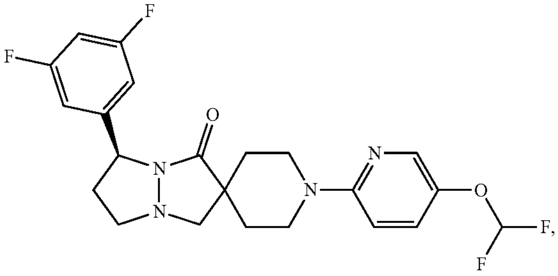
,
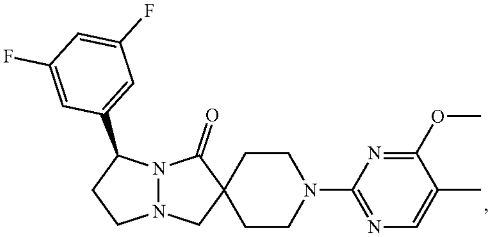
,
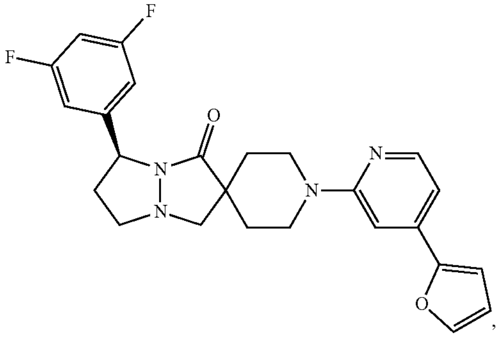
,
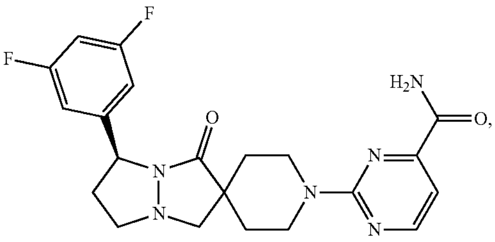
,
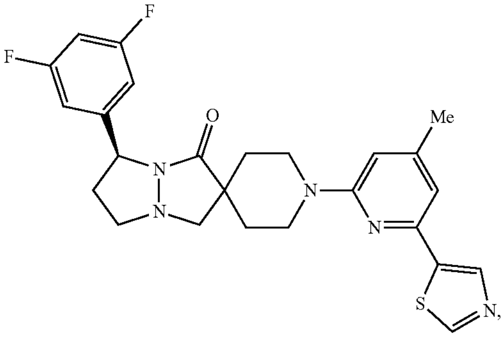
, -continued
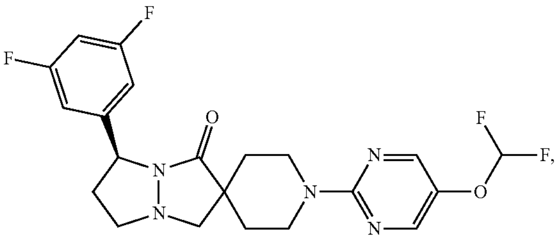
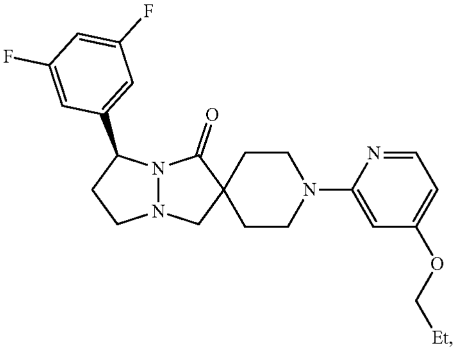
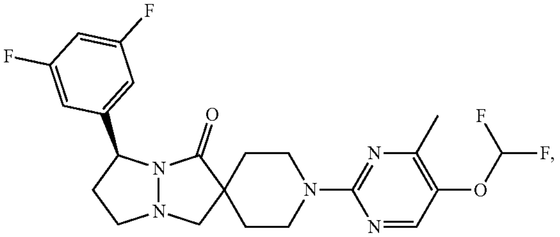
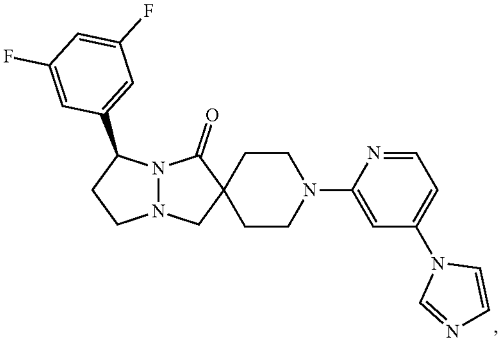
,
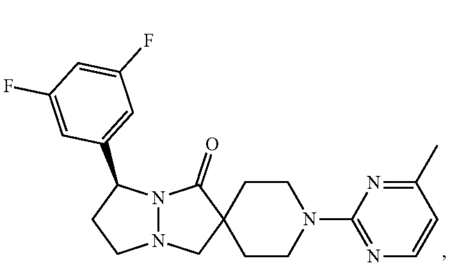
,
-continued
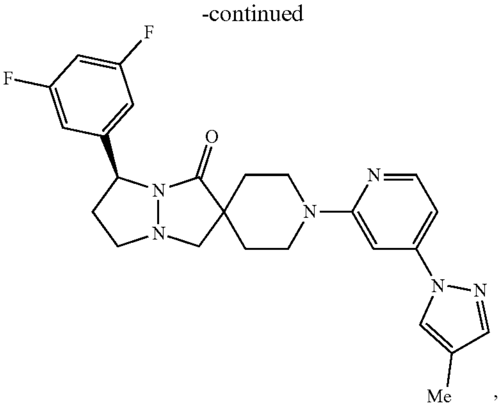
,
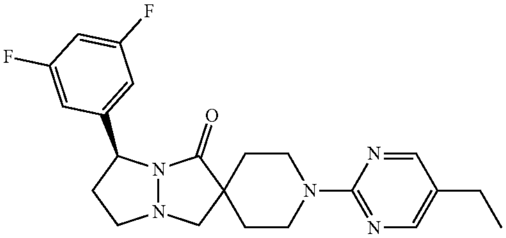
,
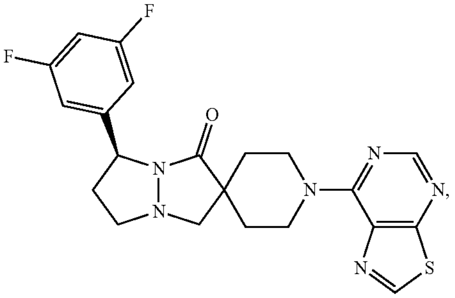
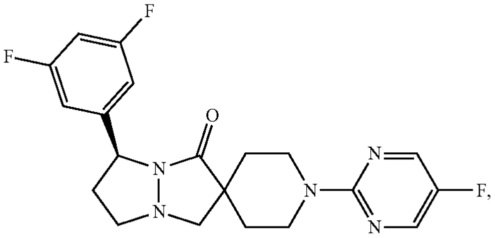
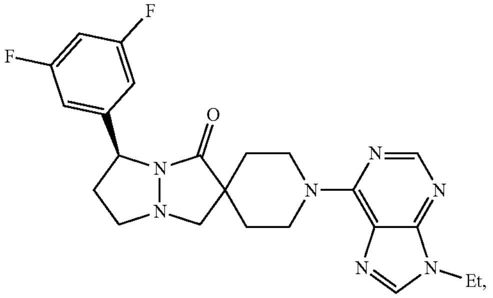
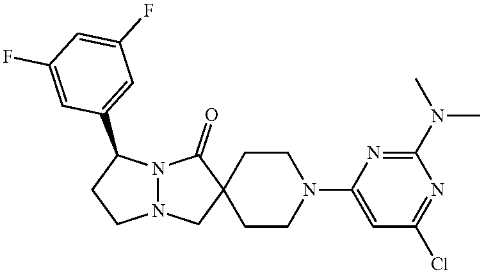
, -continued
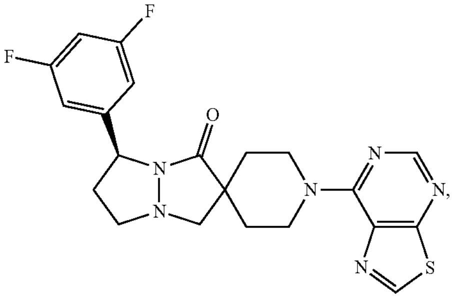
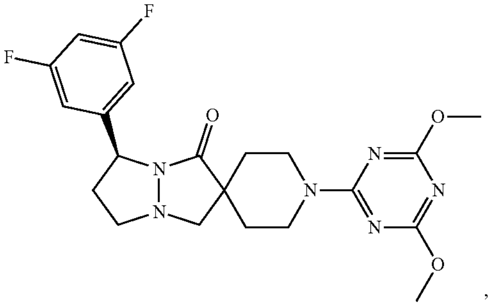
,
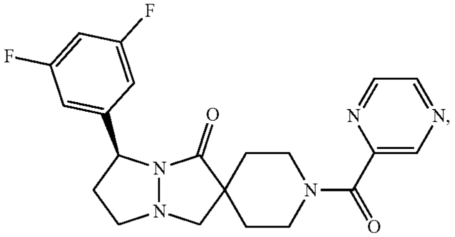
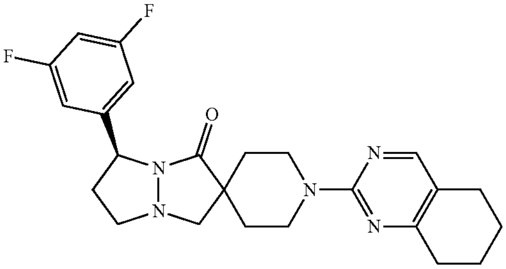
,
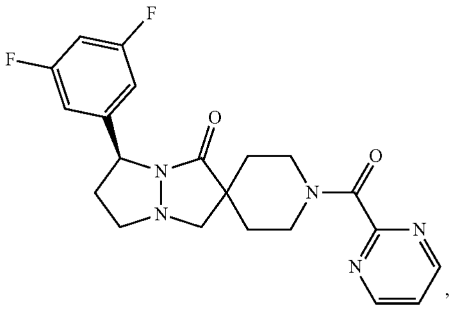
,
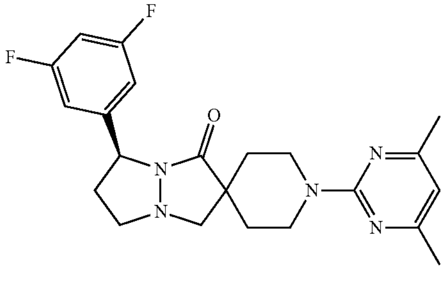
,
-continued
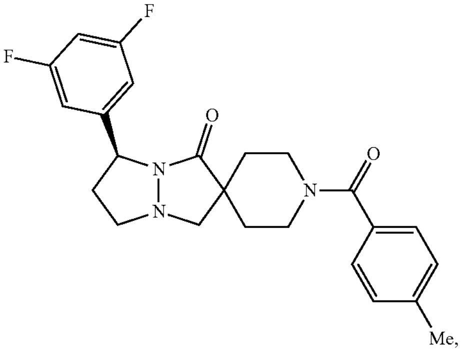
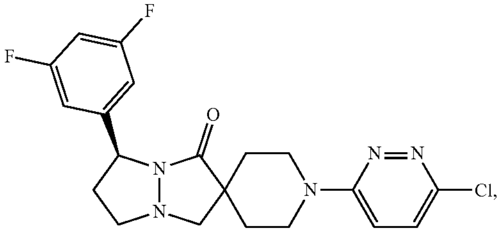
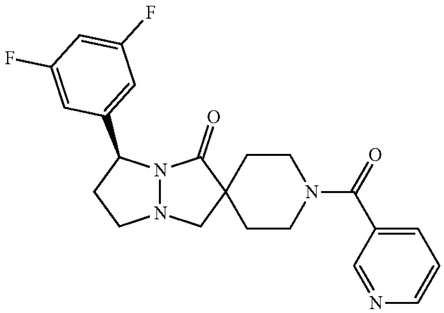
,
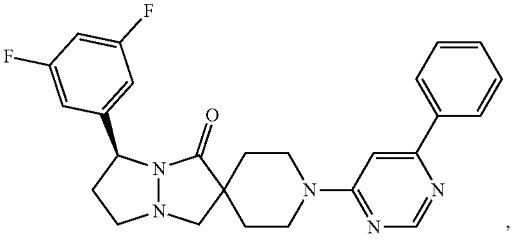
,
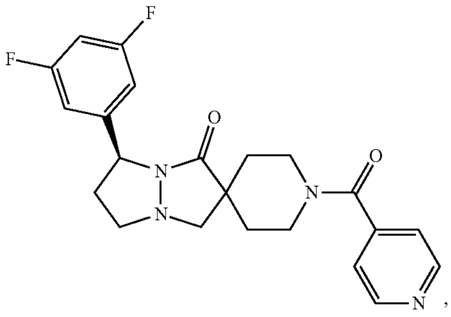
,
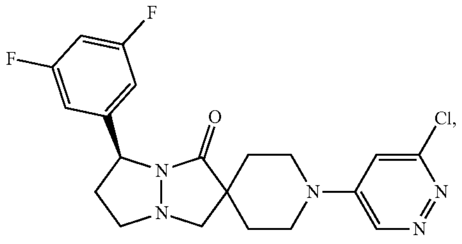

-continued
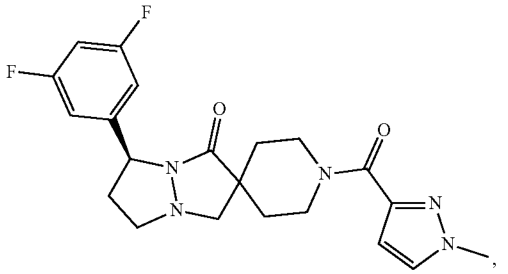
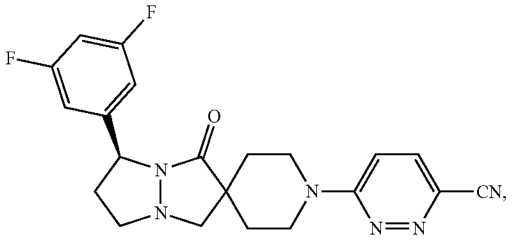
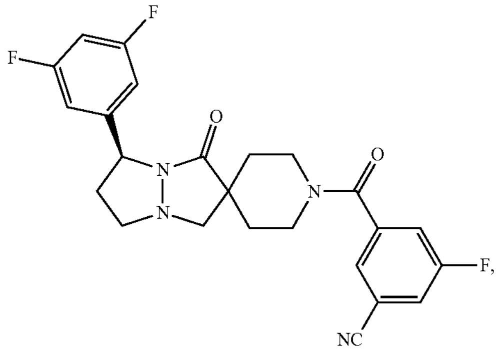
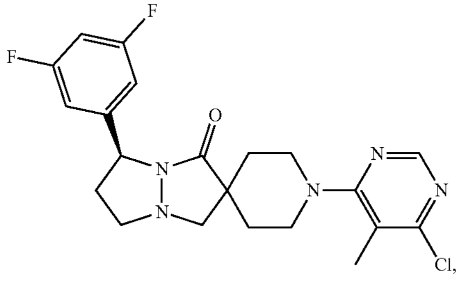
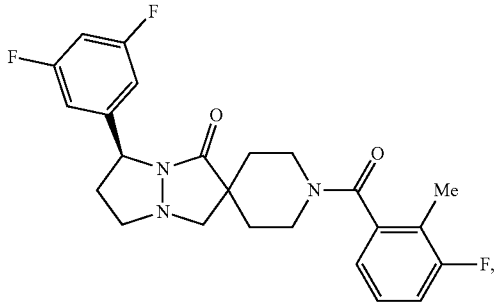
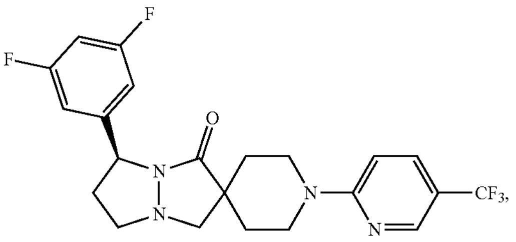
-continued
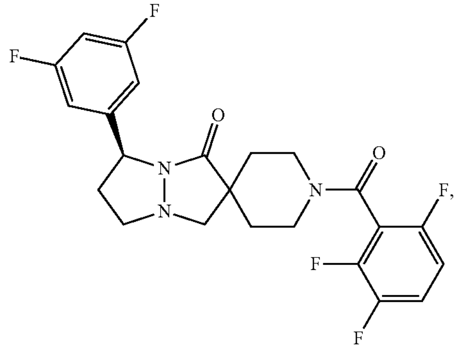
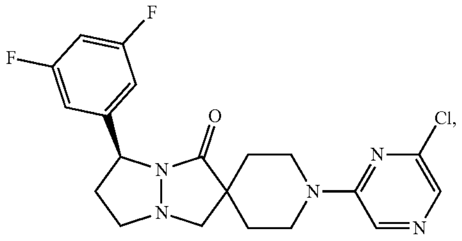
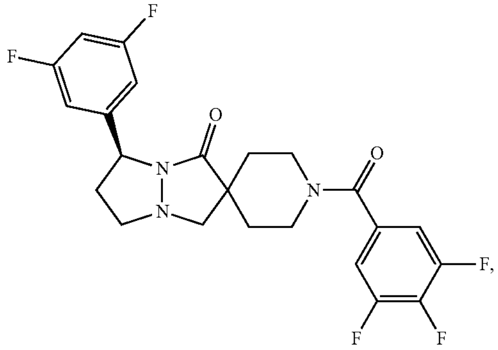
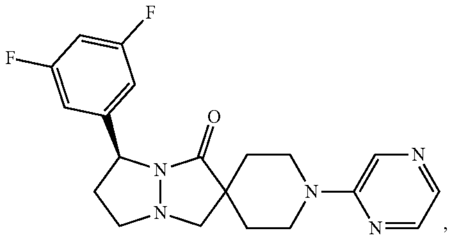
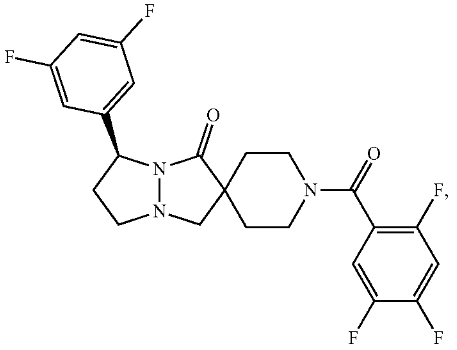

-continued
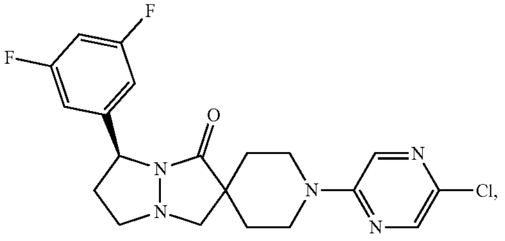
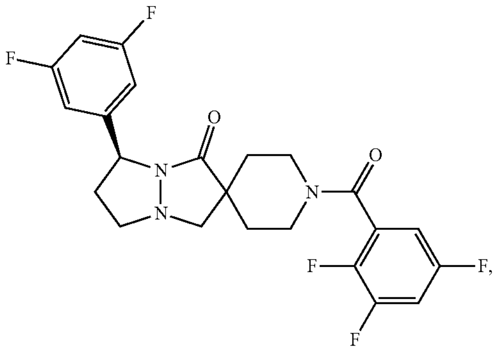
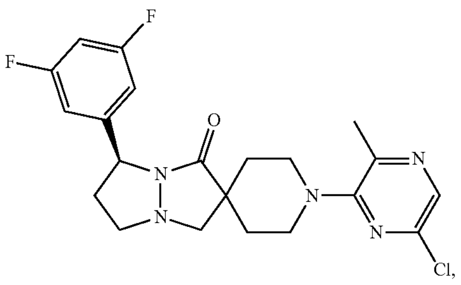
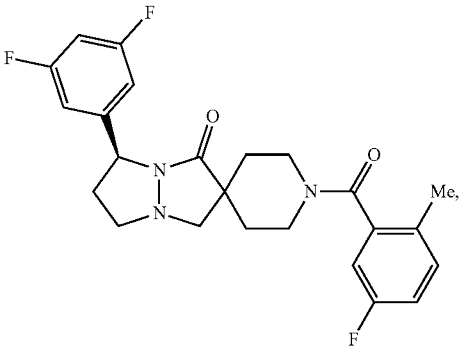
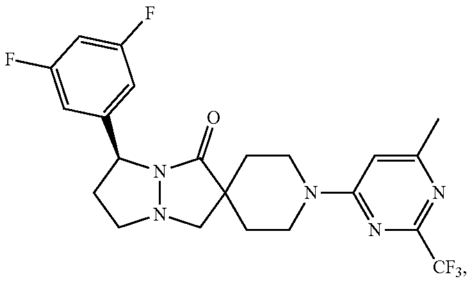
-continued
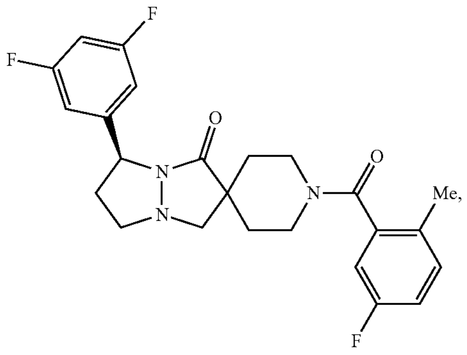
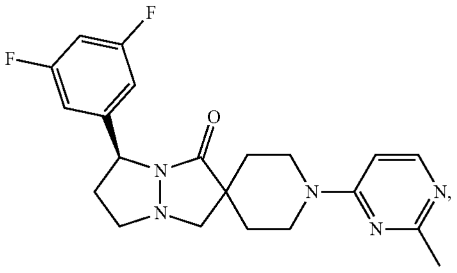
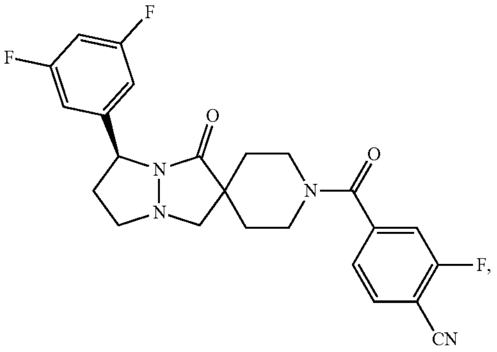
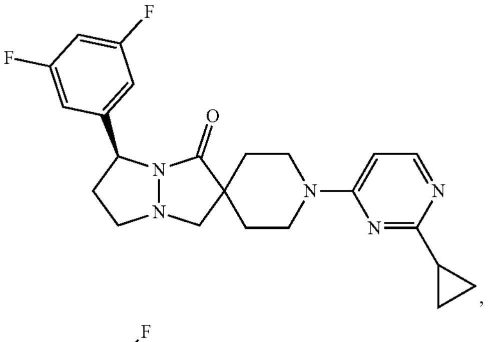
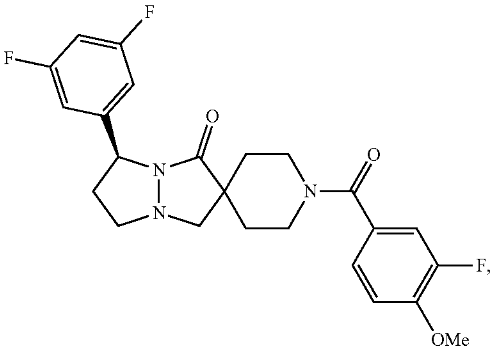

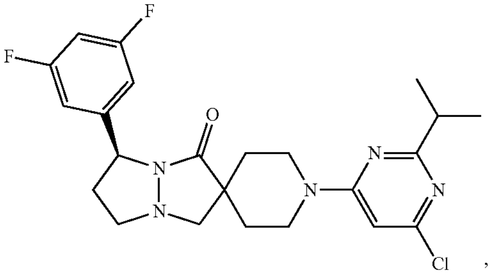
,
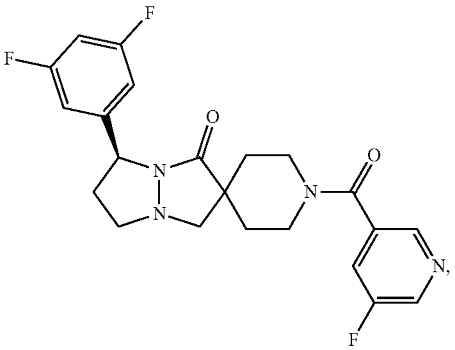
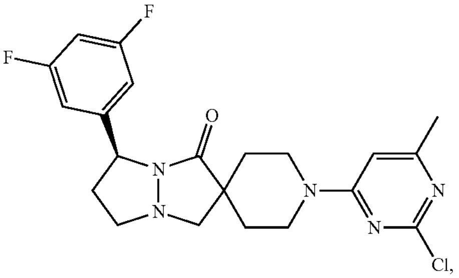
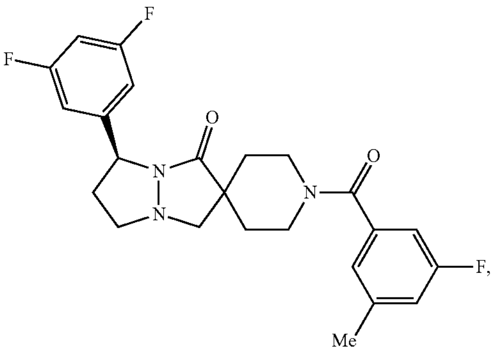
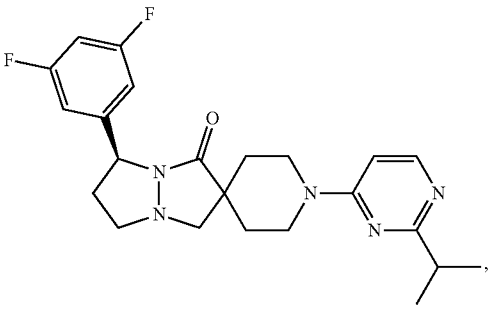
,
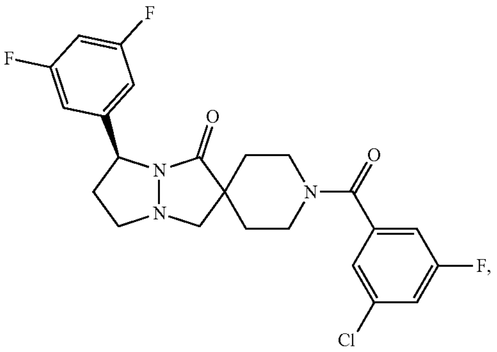
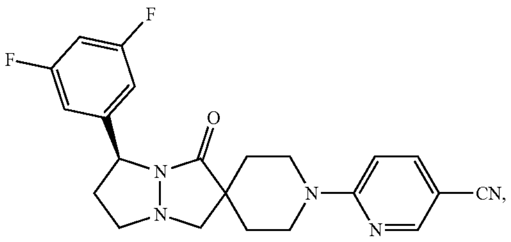
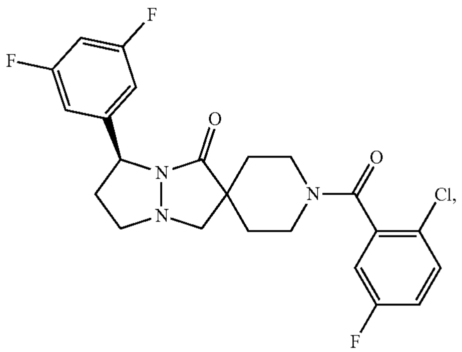
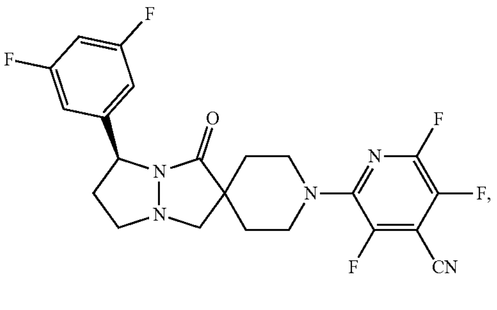
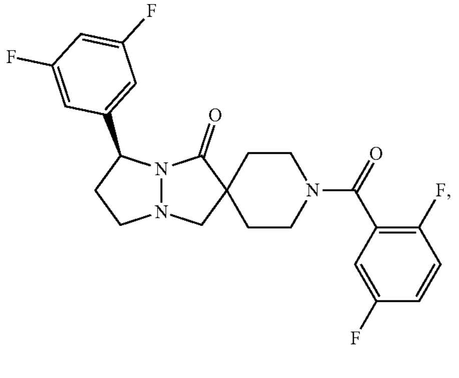

-continued
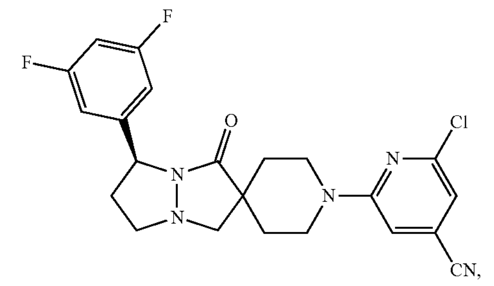
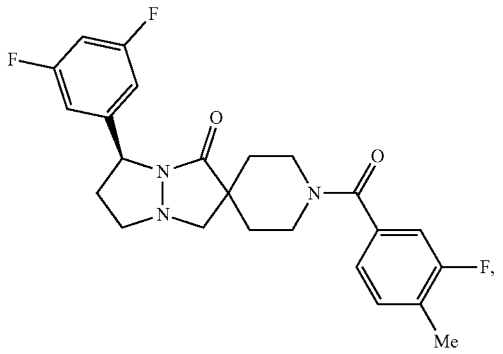
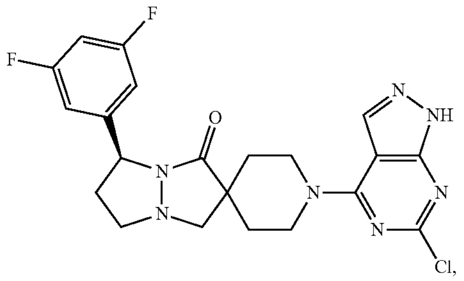
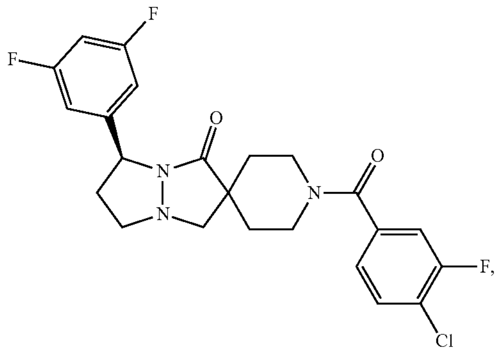
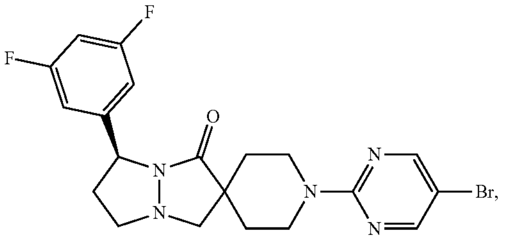
-continued
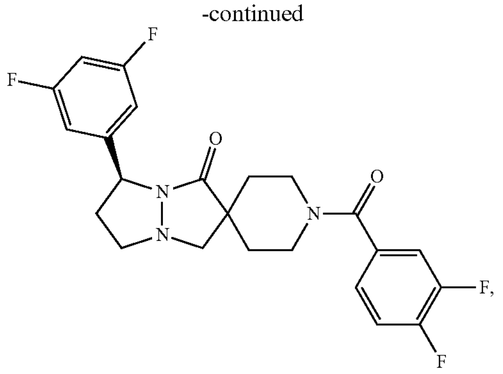
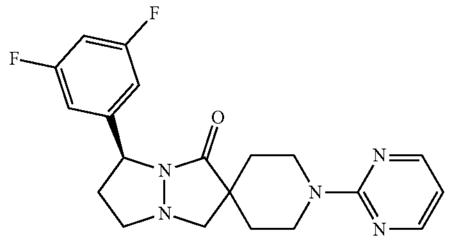
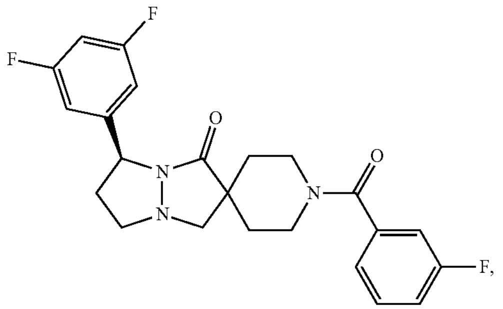
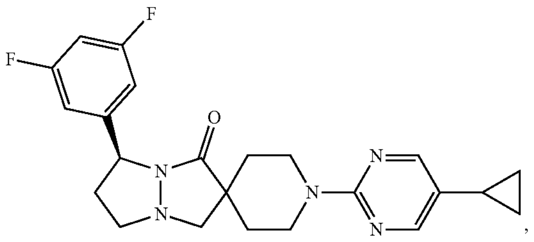
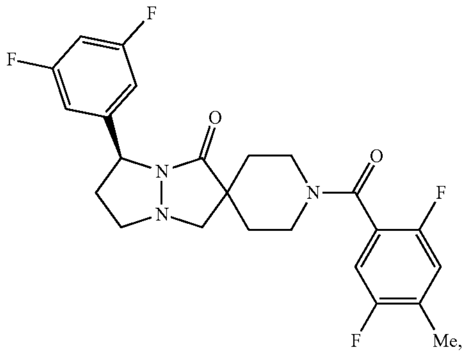
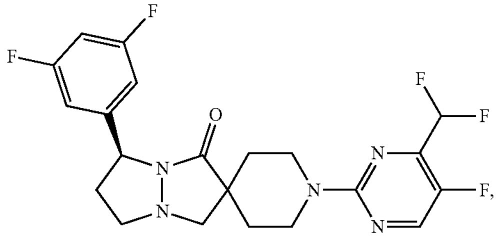

-continued
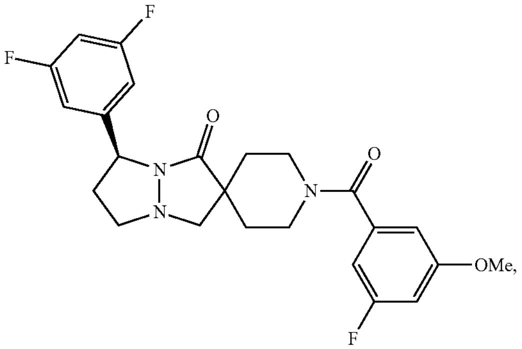
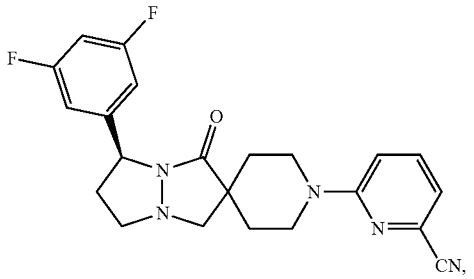
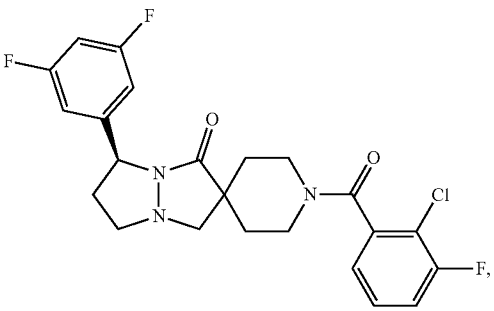
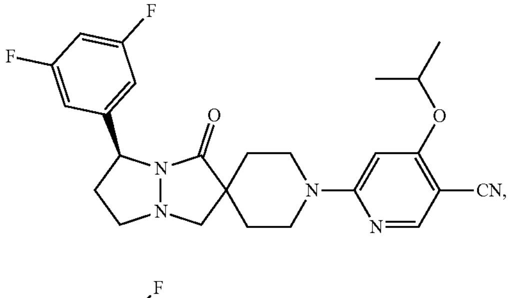
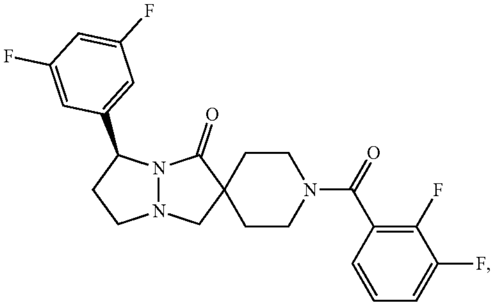
-continued
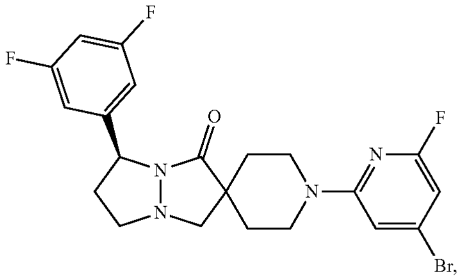
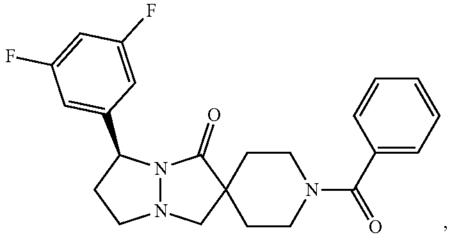
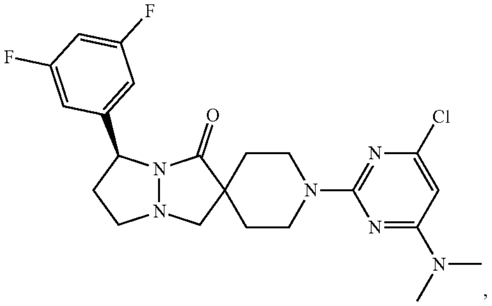
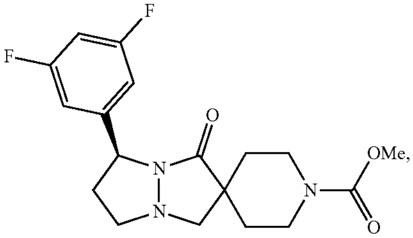
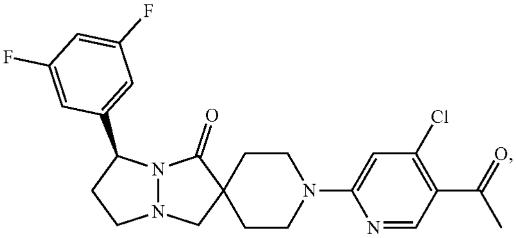
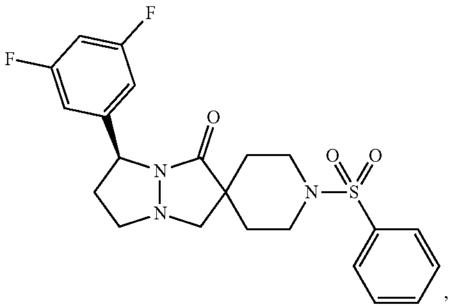

-continued
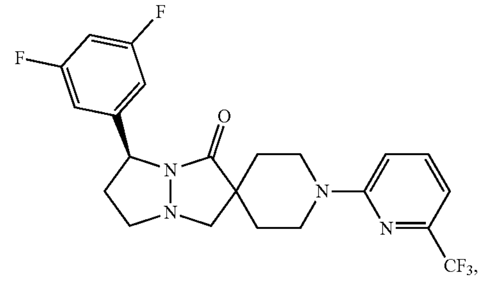
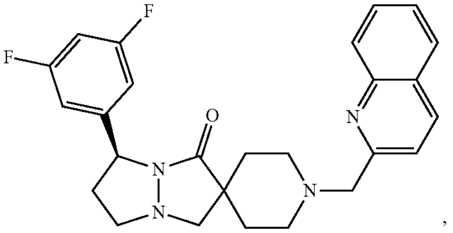
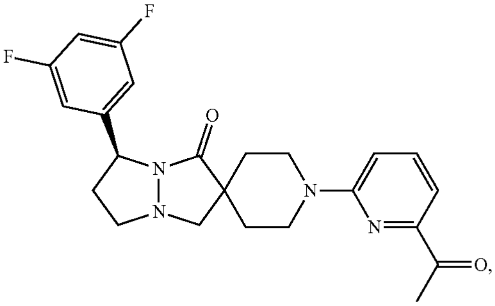
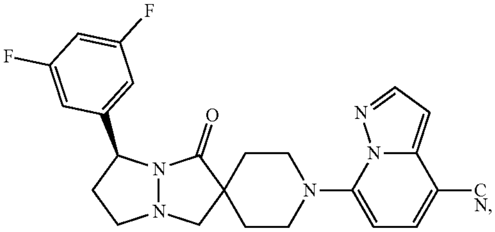
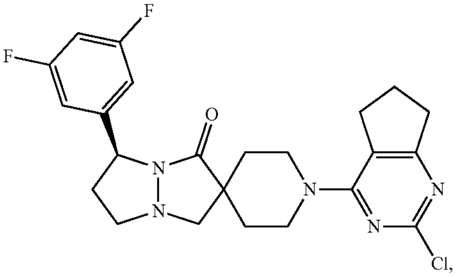
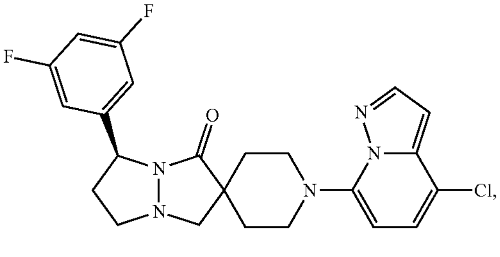
-continued
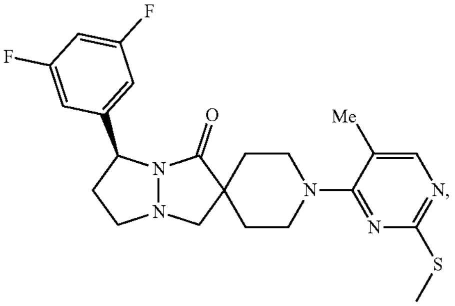
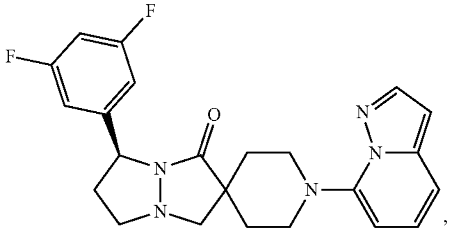
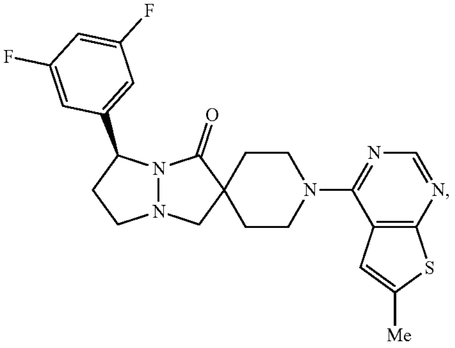
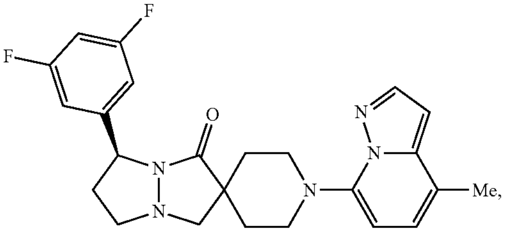
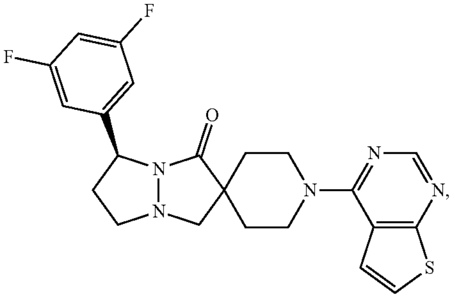
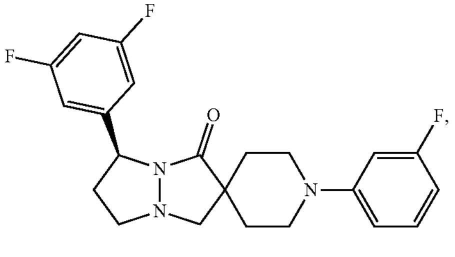

-continued
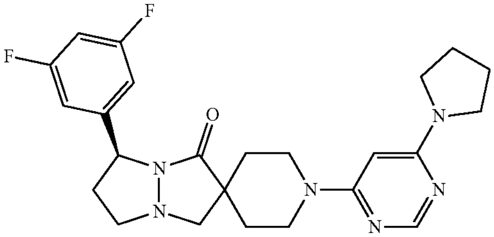
,
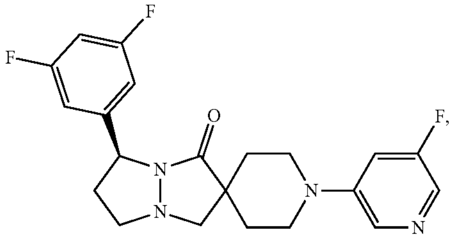
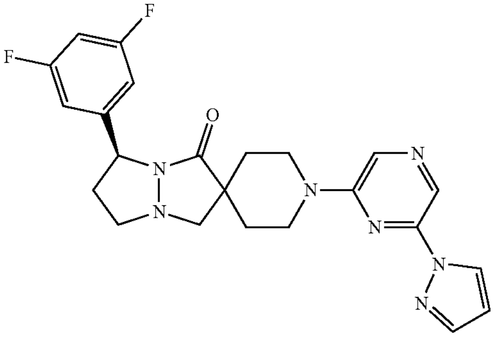
,
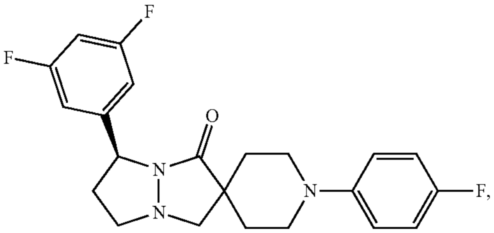
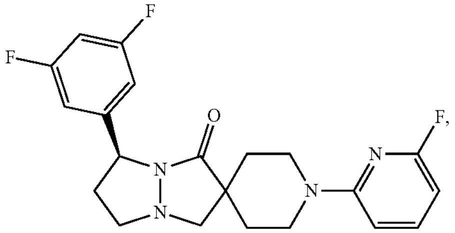
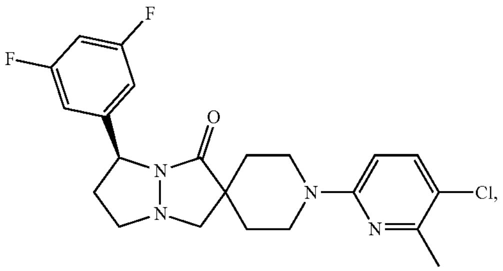
-continued
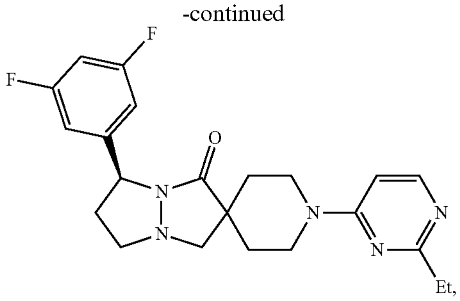
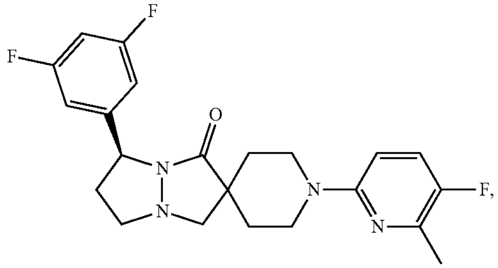
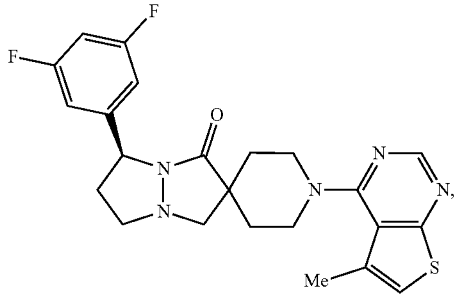
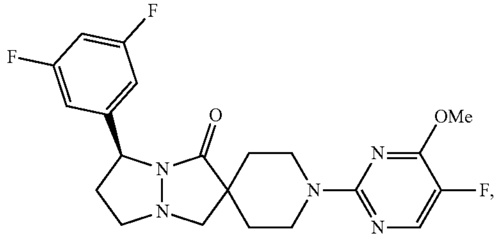
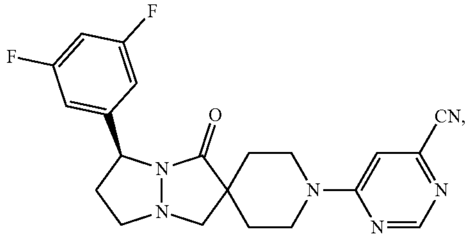
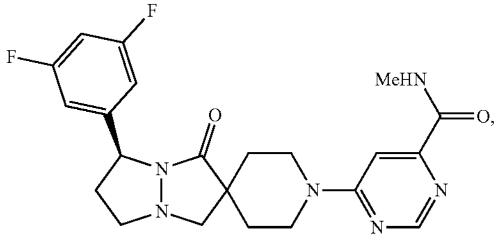

-continued
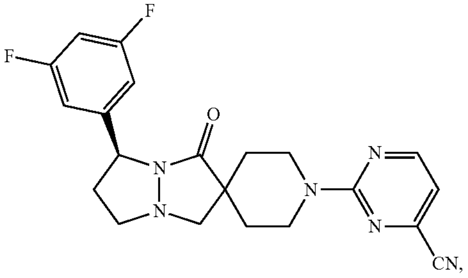
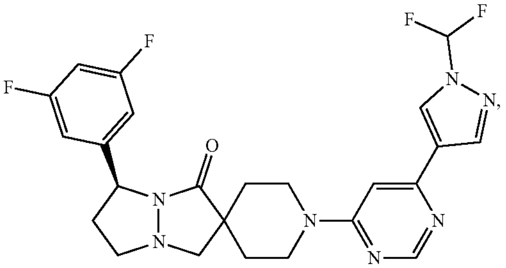
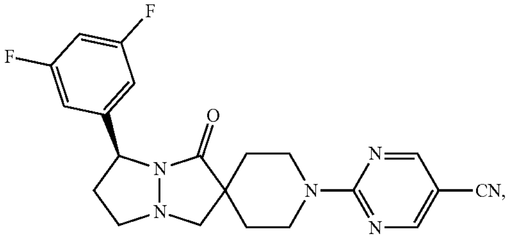
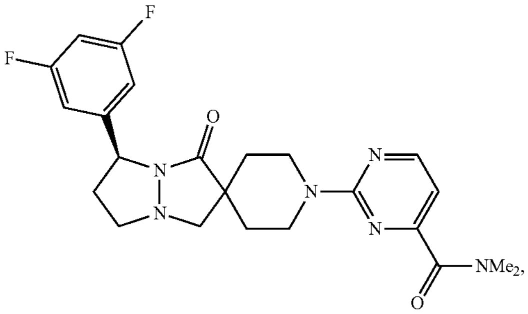
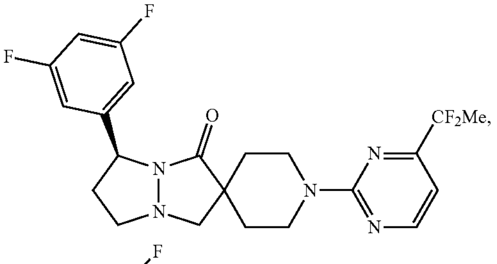
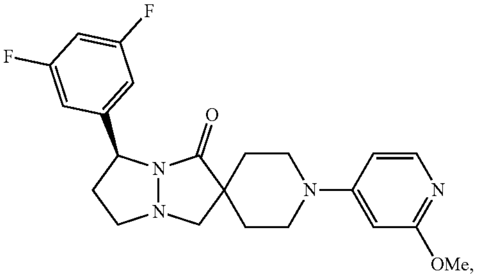
-continued
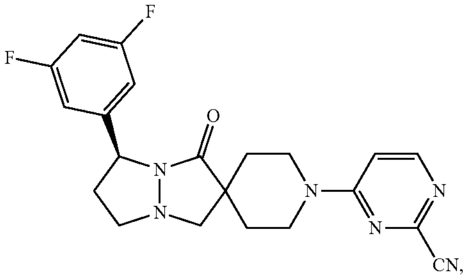
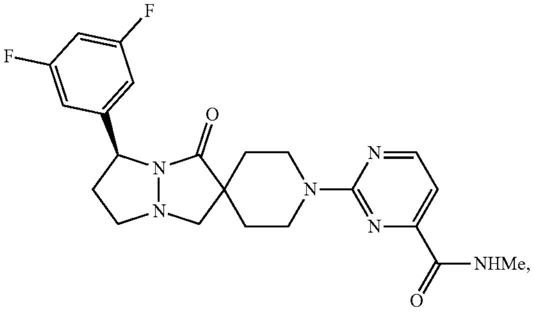
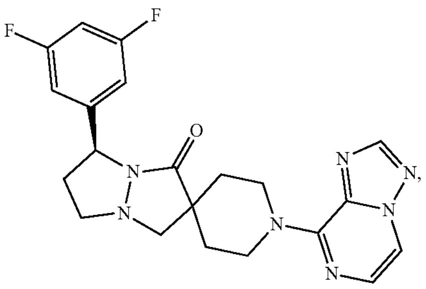
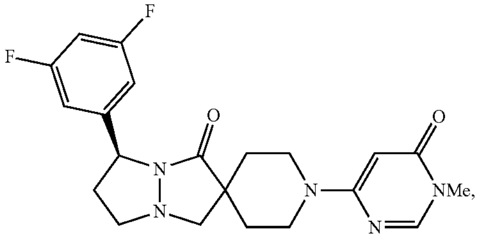
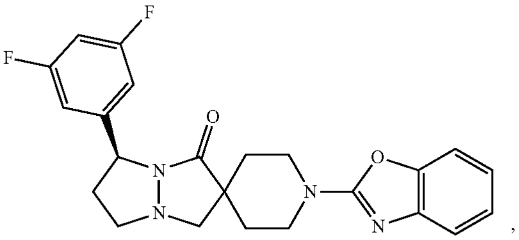
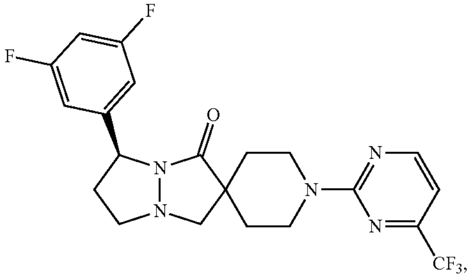

-continued

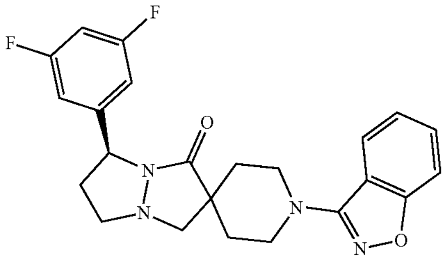

,

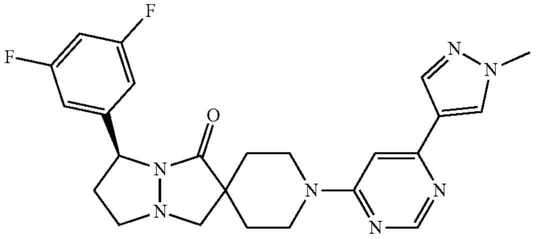

,

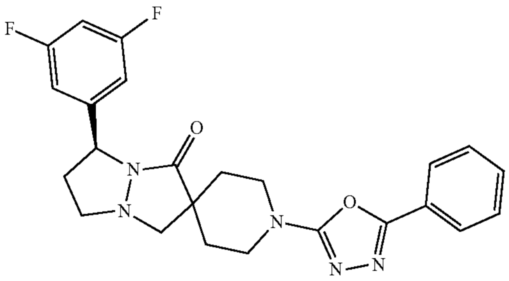

,

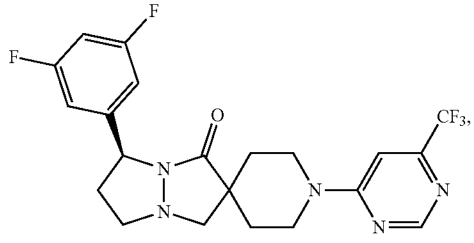

,

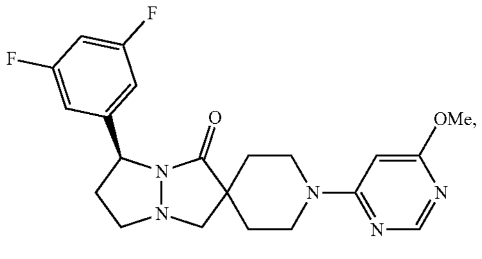

,

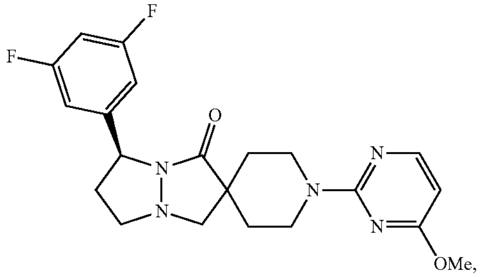

,

-continued

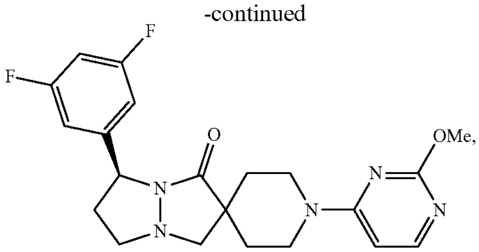

or

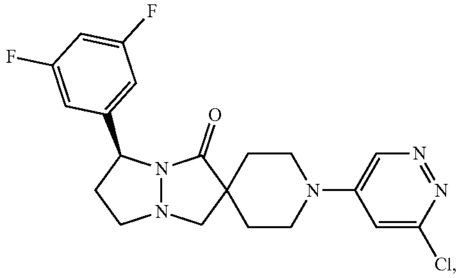

, or a pharmaceutically acceptable salt thereof.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

"Alkoxy" means an alkyl-O— group in which the alkyl group encompasses straight alkyl having a carbon number of 1 to 10 and branched alkyl having a carbon number of 3 to 10. Non-limiting examples of suitable alkoxy groups include methoxy, ethoxy, n-propoxy, isopropoxy and n-butoxy. The bond to the parent moiety is through the ether oxygen.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl. The term "halogen" includes fluorine, chlorine, bromine or iodine.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_3$-$C_6$cycloalkyl" encompasses bridged, saturated or unsaturated cycloalkyl groups having 3 to 6 carbons. Examples of cycloalkyl include cyclopropyl, cyclobutyl, cyclopentyl and cyclohexyl.

The term "$C_3$-$C_{10}$cycloalkyl" encompasses bridged, saturated or unsaturated cycloalkyl groups having 3 to 10 carbons. "Cycloalkyl" also includes non-aromatic rings as well as monocyclic, non-aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like.

"Effective amount" or "therapeutically effective amount" is meant to describe an amount of compound or a composition used in the methods of the present invention effective in inhibiting the above-noted diseases or enzyme activity and thus producing the desired therapeutic, ameliorative, inhibitory or preventative effect.

The term "heteroaryl" means a monocyclic or multicyclic, including bicyclic, aromatic heterocycloalkyl that contains at least one ring heteroatom selected from O, S and N. Examples of heteroaryl groups include pyridyl (pyridinyl), oxazolyl, azabenzothiazole, benzothiazole, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term "heterocycloalkyl" means mono- or bicyclic or bridged partially unsaturated and saturated rings containing at least one heteroatom selected from N, S and O, each of said rings having from 3 to 10 atoms in which the point of attachment may be carbon or nitrogen. Examples include azetidine, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or n-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. Examples described by structure include, is

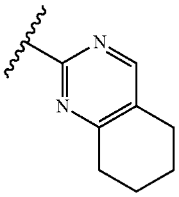

or

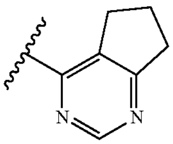

.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethy laminoethanol, 2-dimethylaminoethanol, ethanolamine, ethylenediamine, n-ethylmorpholine, n-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropy lamine, tromethamine, and the like.

The term "patient" refers to a mammalian patient, preferably a human patient, receiving or about to receive medical treatment.

A "patient in need" of a treatment is a patient that has been diagnosed with a disease that could be treated with a treatment described herein.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. A 3H, $^{11}C$, $^{18}F$ labeled compound may be used for PET or SPECT or other imaging studies. Isotopically-enriched compounds can be prepared without undue experimentation by conventional techniques well known to those skilled in the art or by processes analogous to those described in the Schemes and Examples herein using appropriate isotopically-enriched reagents or Intermediates.

It should be noted that chemically unstable compounds are excluded from the embodiments contained herein.

Methods of Treatment

The compounds described herein may be particularly useful for the prevention, treatment or amelioration of RIPK1-mediated diseases or disorders. Such RIPK1-mediated diseases or disorders are likely to be regulated at least in part by programmed necrosis, apoptosis or the production of inflammatory cytokines, particularly inflammatory bowel disease (including Crohn's disease and ulcerative colitis), psoriasis, retinal detachment, retinal degeneration, retinitis pigmentosa, macular degeneration, age-related macular degeneration, pancreatitis, atopic dermatitis, arthritis (including rheumatoid arthritis, spondyloarthritis, gout, juvenile idiopathic arthritis (systemic onset juvenile idiopathic arthritis (SoJIA)), psoriatic arthritis), lupus, systemic lupus erythematosus (SLE). Sjogren's syndrome, systemic scleroderma, anti-phospholipid syndrome (APS), vasculitis, osteoarthritis, liver damage/diseases (non-alcoholic steatohepatitis (NASH), alcoholic steatohepatitis (ASH), autoimmune hepatitis, autoimmune hepatobiliary diseases, primary sclerosing cholangitis (PSC), acetaminophen toxicity, hepatotoxicity), autoimmune hepatitis, non-alcoholic fatty liver disease (NAFL D), kidney damage/injury (nephritis, renal transplant, surgery, administration of nephrotoxic drugs e.g. cisplatin, acute kidney injury (AKI)). Celiac disease, autoimmune idiopathic thrombocytopenia purpura (autoimmune ITP), transplant rejection (rejection of transplant organs, tissues and cells), ischemia reperfusion injury of solid organs, sepsis, systemic inflammatory response syndrome (SIRS), cerebrovascular accident (CV A, stroke), myocardial infarction (MI), atherosclerosis. Huntington's disease. Alzheimer's disease. Parkinson's disease, amyotrophic lateral sclerosis (ALS), progressive supranuclear palsy (PSP), neonatal brain injury, neonatal hypoxic brain injury, ischemic brain injury, traumatic brain injury allergic diseases (including asthma and atopic dermatitis), peripheral nerve injury, burns, multiple sclerosis, type I diabetes, type II diabetes, obesity. Wegener's granulomatosis, pulmonary sarcoidosis. Behcet's disease, interleukin-I converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, peridontitis. NEMO-mutations (mutations of NF-kappa-B essential modulator gene (also known as IKK gamma or IKKG)), particularly. NEMO-deficiency syndrome. HOIL-1 deficiency (also known as RBCKI) hemeoxidized IRP 2 ubiquitin ligase-1 deficiency), linear ubiquitin chain assembly complex (LUBAC) deficiency syndrome, hematological and solid organ malignancies, bacterial infections and viral infections (such as influenza. *staphylococcus*, and *mycobacterium* (tuberculosis)), and Lysosomal storage diseases (particularly. Gaucher disease, and including GM2 gangliosidosis, alpha-mannosidosis, aspartylglucosaminuria, cholesteryl ester storage disease, chronic hexosaminidase A deficiency, cystinosis. Danon disease. Fabry disease. Farber disease, fucosidosis, galactosialidosis. GMI gangliosidosis, mucolipidosis, infantile free sialic acid storage disease, juvenile hexosaminidase A deficiency. Krabbe disease, lysosomal acid lipase deficiency, metachromatic leukodystrophy, mucopolysaccharidoses disorders, multiple sulfatase deficiency. Niemann-Pick disease, neuronal ceroid lipofuscinoses. Pompe disease, pycnodysostosis. Sandhoff disease. Schindler disease, sialic acid storage disease. Tay-Sachs. and Wolman disease). Stevens-Johnson syndrome, toxic epidermal necrolysis, glaucoma, spinal cord injury, fibrosis, complement-mediated cytotoxicity, pancreatic ductal adenocarcinoma, hepatocellular carcinoma, mesothelioma, melanoma, metastasis, breast cancer, non-small cell lung carcinoma (NSCLC), radiation induced necrosis, ischemic kidney damage, ophthalmologic ischemia, intracerebral hemorrhage, subarachnoid hemorrhage, acute liver failure and radiation protection/mitigation, auditory disorders such as noise-induced hearing loss. The compounds described herein are also useful for the treatment of cells ex vivo to preserve vitality and function.

The compounds of the Formulae described herein, or pharmaceutically acceptable salts thereof, may be particularly useful for the treatment of the following RIPK1-mediated diseases or disorders: inflammatory bowel disease (including Crohn's disease and ulcerative colitis), psoriasis, retinal detachment, retinal degeneration, retinitis pigmentosa, macular degeneration, age-related macular degeneration, pancreatitis, atopic dermatitis, arthritis (including rheumatoid arthritis, spondyloarthritis, gout, systemic onset juvenile idiopathic arthritis (SoJIA), psoriatic arthritis), lupus, systemic lupus erythematosus (SLE). Sjogren's syndrome, systemic scleroderma, anti-phospholipid syndrome (APS), vasculitis, osteoarthritis, liver damage/diseases, autoimmune hepatitis, autoimmune hepatobiliary diseases, primary sclerosing cholangitis (PSC), acetaminophen toxicity, hepatotoxicity), non-alcoholic steatohepatitis (NASH), alcoholic steatohepatitis (ASH), autoimmune hepatitis, non-alcoholic fatty liver disease (NAFLD), kidney damage/injury (nephritis, renal transplant, surgery, administration of nephrotoxic drugs e.g. cisplatin, acute kidney injury (AKI)). Celiac disease, autoimmune idiopathic thrombocytopeni purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis. Huntington's disease. Alzheimer's disease. Parkinson's disease, amyotrophic lateral sclerosis (ALS), progressive supranuclear palsy (PSP), neonatal brain injury, neonatal hypoxic brain injury, traumatic brain injury, allergic diseases (including asthma and atopic dermatitis), peripheral nerve injury, burns, multiple sclerosis, type I diabetes, type II diabetes, obesity. Wegener's granulomatosis, pulmonary sarcoidosis. Behcet's disease, interleukin-I converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, melanoma, metastasis, breast cancer, non-small cell lung carcinoma (NSCLC), radiation induced necrosis, ischemic kidney damage, ophthalmologic ischemia, intracerebral hemorrhage, subarachnoid hemorrhage, periodontitis, NEMO-mutations (mutations of NF-kappa-B essential modulator gene (also known as IKK gamma or IKKG)), particularly, NEMO-deficiency syndrome, HOIL-1 deficiency ((also known as RBCKI) heme-oxidized IRP 2 ubiquitin ligase-1 deficiency), linear ubiquitin chain assembly complex (LUBAC) deficiency syndrome, hematological and solid organ malignancies, bacterial infections and viral infections (such as influenza, *staphylococcus*, and *mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GMI gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), spinal cord injury, Stevens-Johnson syndrome, fibrosis, complement-mediated cytotoxicity, toxic epidermal necrolysis, and/or for the treatment of cells ex vivo to preserve vitality and function.

The compounds of the Formulae described herein, and pharmaceutically acceptable salts thereof, may be useful for the treatment of glaucoma.

The compounds of the Formulae described herein, and-pharmaceutically acceptable salts thereof, may be particularly useful for treatment of pancreatic ductal adenocarcinoma, hepatocellular carcinoma, mesothelioma, or melanoma.

The compounds of the Formulae described herein, and-pharmaceutically acceptable salts thereof, may be particularly useful for the treatment of the following RIPK1-mediated diseases or disorders: rheumatoid arthritis, inflammatory bowel disease (including Crohn's disease and ulcerative colitis), and psoriasis.

The treatment of the above-noted diseases/disorders may concern, more specifically, the amelioration of organ injury or damage sustained as a result of the noted diseases/disorders. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcoholic steatohepatitis, alcoholic steatohepatitis, autoimmune hepatitis autoimmune hepatobiliary diseases, or primary sclerosing cholangitis, or overdose of acetaminophen.

The compounds of this invention may be particularly useful for the amelioration of organ injury or damage sustained as a result of radiation therapy, or amelioration of spinal tissue injury or damage following spinal cord injury or amelioration of liver tissue injury or damage associated acute liver failure. The compounds of this invention may be particularly useful for amelioration of auditory disorders, such as noise-induced hearing loss or auditory disorders following the administration of ototoxic drugs or substances e.g. cisplatin.

The compounds of this invention may be particularly useful for amelioration of solid organ tissue (particularly kidney, liver, and heart and/or lung) injury or damage following transplant or the administration of nephrotoxic drugs or substances e.g. cisplatin. It will be understood that amelioration of such tissue damage may be achieved where possible, by pre-treatment with a compound of the Formulae described herein, or a pharmaceutically acceptable salt thereof: for example, by pre-treatment of a patient prior to administration of cisplatin or pre-treatment of an organ or the organ recipient prior to transplant surgery. Amelioration of such tissue damage may be achieved by treatment with a compound of the Formulae described herein, or a pharmaceutically acceptable salt thereof, during transplant surgery.

Amelioration of such tissue damage may also be achieved by short-term treatment of a patient with a compound of the Formulae described herein, or a pharmaceutically acceptable salt thereof, after transplant surgery.

In one embodiment, the compounds of the Formulae described herein, or pharmaceutically acceptable salts thereof, may be useful for the treatment of retinal detachment, macular degeneration, and retinitis pigmentosa.

In another embodiment, the compounds of the Formulae described herein, or pharmaceutically acceptable salts thereof, may be useful for the treatment of multiple sclerosis.

In one embodiment, the compounds of the Formulae described herein, or pharmaceutically acceptable salts thereof, may be useful for the treatment of traumatic brain injury.

In another embodiment, the compounds of the Formulae described herein, or pharmaceutically acceptable salts thereof, may be useful for the treatment of Huntington's Disease or Niemann-Pick disease.

In another embodiment, the compounds of the Formulae described herein, or pharmaceutically acceptable salts thereof, may be useful for the treatment of amyotrophic lateral sclerosis (ALS), progressive supranuclear palsy (PSP), and Alzheimer's disease.

In another embodiment, the compounds of the Formulae described herein, or pharmaceutically acceptable salts thereof, may be useful for the treatment of age-related macular degeneration.

The treatment of retinal detachment, macular degeneration, retinitis pigmentosa, multiple sclerosis, traumatic brain injury, Huntington's Disease, Alzheimer's Disease, amyotrophic lateral sclerosis, and Niemann-Pick disease may concern, more specifically, the amelioration of organ injury or damage sustained as a result of these diseases/disorders. For example, the compounds described herein may be particularly useful for amelioration of brain tissue injury or damage following traumatic brain injury, or for amelioration of brain tissue injury or damage associated of Huntington's Disease, Alzheimer's Disease, amyotrophic lateral sclerosis, and Niemann-Pick disease.

In another embodiment, the compounds of the Formulae described herein, or pharmaceutically acceptable salts thereof, may be useful for the treatment of retinal detachment, macular degeneration, and retinitis pigmentosa, and the amelioration of brain tissue injury or damage as a result of multiple sclerosis, traumatic brain injury, Huntington's Disease, Alzheimer's Disease, amyotrophic lateral sclerosis, and Niemann-Pick disease.

In another embodiment, the compounds of the Formulae described herein, or pharmaceutically acceptable salts thereof, may be useful for the treatment of Crohn's disease, ulcerative colitis, psoriasis, rheumatoid arthritis, spondyloarthritis, systemic onset juvenile idiopathic arthritis (SoJIA), and osteoarthritis.

In yet another embodiment, the compounds of the Formulae described herein, or pharmaceutically acceptable salts thereof, may be useful for the treatment of psoriasis, rheumatoid arthritis, and ulcerative and colitis.

In another embodiment, the compounds of the Formulae described herein, or pharmaceutically acceptable salts thereof, may be useful for the treatment of lupus, inflammatory bowel disease (IBD), Crohn's disease, and ulcerative colitis.

In another embodiment, the compounds of the Formulae described herein, or pharmaceutically acceptable salts thereof, may be useful for the treatment of cerebrovascular accident (CVA, stroke), Huntington's disease, Alzheimer's disease, amyotrophic lateral sclerosis (ALS), traumatic brain injury, multiple sclerosis, Gaucher disease, Niemann-Pick disease, and spinal cord injury.

In another embodiment, the compounds of the Formulae described herein, or pharmaceutically acceptable salts thereof, may be useful for the treatment of amyotrophic lateral sclerosis (ALS).

In another embodiment, the compounds of the Formulae described herein, or pharmaceutically acceptable salts thereof, may be useful for the treatment of multiple sclerosis.

In another embodiment, the compounds of the Formulae described herein, or pharmaceutically acceptable salts thereof, may be useful for the treatment of pancreatic ductal adenocarcinoma (PDAC), metastasis, melanoma, breast cancer, non-small cell lung carcinoma (NSCLC), and radiation induced necrosis.

In another embodiment, the compounds of the Formulae described herein, or pharmaceutically acceptable salts thereof, may be useful for the treatment of pancreatic ductal adenocarcinoma (PDAC), metastasis, melanoma, breast cancer, and non-small cell lung carcinoma (NSCLC).

In another embodiment, the compounds of the Formulae described herein, or pharmaceutically acceptable salts thereof, may be useful for the treatment of pancreatic ductal adenocarcinoma (PDAC).

In another embodiment, the compounds of the Formulae described herein, or pharmaceutically acceptable salts thereof, may be useful for the treatment of intracerebral hemorrhage and subarachnoid hemorrhage.

In another embodiment, the compounds of the Formulae described herein, or pharmaceutically acceptable salts thereof, may be useful for the treatment of type II diabetes and obesity.

In another embodiment, the compounds of the Formulae described herein, or pharmaceutically acceptable salts thereof, may be useful for the treatment of atherosclerosis.

In another embodiment, the compounds of the Formulae described herein, or pharmaceutically acceptable salts thereof, may be useful for the treatment of vasculitis.

In another embodiment, the compounds of the Formulae described herein, or pharmaceutically acceptable salts thereof, may be useful for the treatment of dependent inflammation and cell death that occurs in inherited and sporadic diseases including Alzheimer's disease, amyotrophic lateral sclerosis, multiple sclerosis, Parkinson's disease, chronic traumatic encephalopathy, rheumatoid arthritis, ulcerative colitis, inflammatory bowel disease, psoriasis as well as acute tissue injury caused by stroke, traumatic brain injury, encephalitis.

In another embodiment, the compounds of the Formulae described herein, or pharmaceutically acceptable salts thereof, may be useful for the treatment of ischemic kidney damage, ophthalmologic ischemia, intracerebral hemorrhage, and subarachnoid hemorrhage.

In another embodiment, the compounds of the Formulae described herein, or pharmaceutically acceptable salts thereof, may be useful for the treatment of non-alcoholic steatohepatitis (NASH), alcoholic steatohepatitis (ASH), autoimmune hepatitis, and non-alcoholic fatty liver disease (NAFLD).

The compounds of the invention, particularly the compounds of the Formulae described herein, or a pharmaceutically acceptable salts thereof, may be particularly useful for the treatment of the RIPK1-mediated, cancer-related diseases or disorders. Gong et al., The role of necroptosis in cancer biology and therapy, *Molecular Cancer* (2019) 18:100. In one aspect the human has a solid tumor. In one aspect the tumor is selected from head and neck cancer, gastric cancer, melanoma, renal cell carcinoma (RCC), esophageal cancer, non-small cell lung carcinoma (NSCLC), prostate cancer, colorectal cancer, ovarian cancer, pancreatic cancer, and pancreatic ductal adenocarcinoma. In one aspect the human has one or more of the following: colorectal cancer (CRC), esophageal cancer, cervical, bladder, breast cancer, head and neck cancer, ovarian cancer, melanoma, renal cell carcinoma (RCC), EC squamous cell carcinoma, non-small cell lung carcinoma, mesothelioma, prostate cancer, and pancreatic ductal adenocarcinoma. In another aspect, the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, astrocytomas, Bannayan-Zonana syndrome, Cowden disease, Lhermitte-Duclos disease, breast cancer, triple negative breast cancer, inflammatory breast cancer, Wilm's tumor, Ewing's sarcoma, Rhabdomyosarcoma, ependymoma, medulloblastoma, colon cancer, head and neck cancer (including squamous cell carcinoma of head and neck), kidney cancer, lung cancer (including lung squamous cell carcinoma, lung adenocarcinoma, lung small cell carcinoma, and non-small cell lung carcinoma), liver cancer (including hepatocellular carcinoma), melanoma, ovarian cancer, pancreatic cancer (including squamous pancreatic cancer), prostate cancer, sarcoma, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma. Hodgkin's lymphoma. Non-Hodgkin's lymphoma, lymphoblastic T cell lymphoma. Burkitt's lymphoma, follicular lymphoma, neuroblastoma, bladder cancer, urothelial cancer, lung cancer, vulval cancer, cervical cancer, endometrial cancer, cancer of the uterus, renal cancer (including kidney clear cell cancer, kidney papillary cancer, renal cell carcinoma), mesothelioma, esophageal cancer, salivary gland cancer, hepatocellular cancer, gastric cancer, nasopharangeal cancer, buccal cancer, cancer of the mouth. GIST (gastrointestinal stromal tumor) and testicular cancer.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT): as well as myelofibrosis (MFS) with or without agnogenic myeloid metaplasia.

Specific examples of clinical conditions based on hematologic tumors include leukemias such as chronic myelocytic leukemia, acute myelocytic leukemia, chronic lymphocytic leukemia and acute lymphocytic leukemia: plasma cell malignancies such as multiple myeloma. MGUS and Waldenstrom's macroglobulinemia: lymphomas such as non-Hodgkin's lymphoma. Hodgkin's lymphoma; and the like. Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate grade (or aggressive) or high-grade (very aggressive). Indolent B cell lymphomas include follicular lymphoma (FL): small lymphocytic lymphoma (SLL); marginal zone lymphoma (MZL) including nodal MZL, extranodal MZL, splenic MZL and splenic MZL with villous lymphocytes: lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL). Burkitt-like lymphoma, small non-cleaved cell lymphoma (SNCCL) and lymphoblastic lymphoma. Other B-NHLs include immunoblastic lymphoma (or immunocytoma), primary effusion lymphoma. HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL). Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL). Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow: peripheral blood: thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Thus, in one aspect, the invention relates to a method for treating any of the diseases or disorders described herein comprising administering to a patient in need thereof an effective amount of a compound of Formula I, II, III, IV, or V. In another embodiment, the method comprises administering to a patient in need thereof a pharmaceutical composition comprising an effective amount of a pharmaceutical composition comprising an effective amount compound of any of Formulae I, II, III, IV, or V and a pharmaceutically acceptable carrier.

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

Thus, the invention relates to a pharmaceutical composition comprising an effective amount of a compound of Formula I, II, III, IV, or V, as defined herein, or a pharmaceutically acceptable salt thereof, and a pharmaceutically acceptable carrier. The pharmaceutical composition may further comprise an effective amount of another active agent for the treatment of the same or a different disease or disorder. In one embodiment, the additional therapeutic agent is effective against RIPK1-mediated diseases or disorders.

Also described herein are pharmaceutical compositions comprising an effective amount of a compound of any one of the compounds described herein, or a pharmaceutically acceptable salt thereof and a pharmaceutically acceptable carrier.

Also described herein are pharmaceutical composition comprising an effective amount of a compound described herein and a pharmaceutically acceptable carrier.

In clinical use of the compounds described herein, usually, the compound is formulated into various preparations together with pharmaceutically acceptable additives according to the dosage form and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use.

Especially for injections, if desired, the preparations may be dissolved or suspended in physiological saline or glucose liquid, and a buffer or a preservative may be optionally added thereto.

The pharmaceutical compositions may contain a compound of the invention (i.e., a compound of any one of Formula I, II, III, IV, or V) in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

EXAMPLES

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

Abbreviations used herein have the following meaning:

| | |
|---|---|
| ° C. | Degrees Celsius |
| µL | Microliter |
| µW | Microwave irradiation |
| aq. | Aqueous |
| BINAP | (2,2'-bis(diphenylphosphino)-1,1'-binaphthyl) |
| Bn | Benzyl |
| Boc | Tert-butoxycarbonyl |
| $Boc_2O$ | Di-tert-butyl dicarbonate |
| $Cs_2CO_3$ | Cesium carbonate |
| DCM | Dichloromethane |
| DIPEA | N,N-Diisopropylethylamine |
| DMA | N,N-Dimethylaniline |
| DMF | Dimethylformamide |
| DMSO | Dimethyl Sulfoxide |
| DMSO-$d_6$ | Deuterated Dimethyl Sulfoxide |
| (dppf)$PdCl_2$ = $PdCl_2$(dppf) | [1,1'-Bis(diphenylphosphino)ferrocene]dichloropalladium(II) |
| ESI | Electrospray Ionization |
| EtOAc | Ethyl acetate |
| EtOH | Ethyl alcohol |
| g | Grams |
| h | Hour/Hours |
| $H_2O$ | Water |
| HATU | 1-[Bis(dimethylamino)methylene]-1H-1,2,3-triazolo[4,5-b]pyridinium 3-oxide hexafluorophosphate |
| HCl | Hydrochloric acid |
| HPLC | High Performance Liquid Chromatography |
| i-PrOH | Isopropyl alcohol |
| $K_2CO_3$ | Potassium carbonate |
| $K_3PO_4$ | Potassium Phosphate |
| $LiEt_3BH$ | Lithium triethylborohydride |
| LDA | Lithium diisopropylamide |
| M | Molar |
| MeCl | Chloromethane |
| MeCN | Acetonitrile |
| MeOH | Methanol |
| mg | milligrams |
| MHz | Megahertz |
| min | Minutes |
| mL | Milliliters |
| mmol | Millimoles |
| MS | Mass Spectroscopy |
| MTBE | Methyl tert-Butyl Ether |
| $NaHCO_3$ | Sodium Bicarbonate |
| NaOH | Sodium hydroxide |
| $Na_2SO_4$ | Sodium Sulfate |
| $NH_4Cl$ | Ammonium chloride |
| nM | Nanomolar |
| NMP | N-Methylpyrrolidone |
| NMR | Nuclear Magnetic Resonance |
| SFC | Supercritical Fluid ($CO_2$) Chromatography |
| sat. | Saturated |
| TEA | Triethylamine |
| TFA | Trifluoroacetic acid |
| THF | Tetrahydrofuran |

General Experimental Information:

Unless otherwise noted, all reactions were magnetically stirred and performed under an inert atmosphere such as nitrogen or argon.

Unless otherwise noted, "concentrated" means evaporating the solvent from a solution or mixture using a rotary evaporator or vacuum pump.

Unless otherwise noted, flash chromatography was carried out on an ISCO®, Analogix®, or Biotage® automated chromatography system using a commercially available cartridge as the column. Columns were usually filled with silica gel as the stationary phase. Reversed phase preparative HPLC was run under one of two methods (A and B), and conditions for both can be found at the end of the experimental section. Aqueous solutions were concentrated on a Genevac® evaporator or were lyophilized.

Unless otherwise noted, proton nuclear magnetic resonance ($^1H$ NMR) spectra and proton-decoupled carbon nuclear magnetic resonance ($^{13}C$ {$^1H$} NMR) spectra were recorded on 400, 500, or 600 MHz Bruker or Varian NMR spectrometers at ambient temperature. All chemical shifts (8) were reported in parts per million (ppm). Proton resonances were referenced to residual protium in the NMR solvent, which can include, but is not limited to, CDCl3, DMSO-$d_6$, and MeOD-$d_4$. Carbon resonances are referenced to the carbon resonances of the NMR solvent. Data are represented as follows: chemical shift, multiplicity (br=broad, br s=broad singlet, s=singlet, d=doublet, dd=doublet of doublets, ddd=doublet of doublet of doublets, t=triplet, q=quartet, m=multiplet), coupling constants (J) in Hertz (Hz), integration. Preparation of intermediate J.1, (R)-7'-(3,5-difluorophenyl)dihydro-1'H,3'H,5'H-spiro[piperidine-4,2'-pyrazolo[1,2-a]pyrazol]-1'-one and and J.2, (S)-7'-(3,5-difluorophenyl)dihydro-1'H,3'H,5'H-spiro[piperidine-4,2'-pyrazolo[1,2-a]pyrazol]-1'-one.

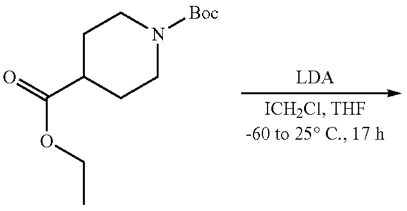

A.1

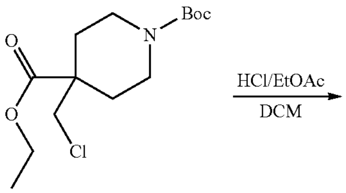

A.2

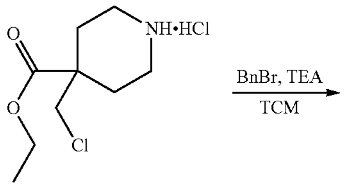

B.1

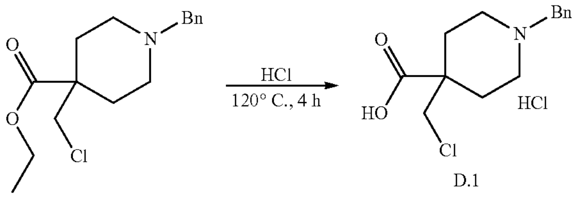

D.1

C.1

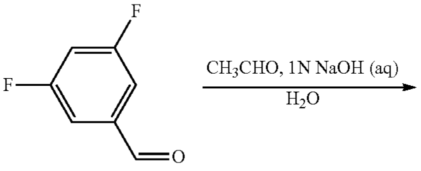

E.1

-continued
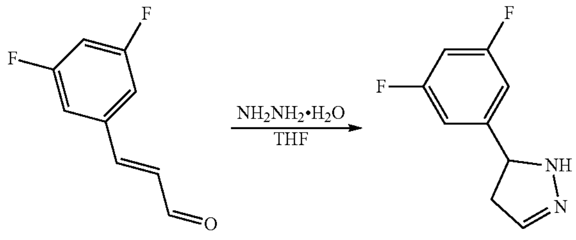
E.2
F.1
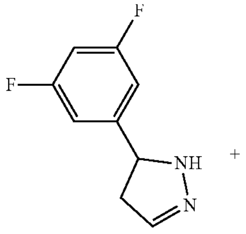
F.1
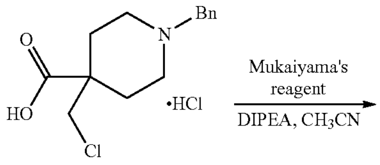
D.1
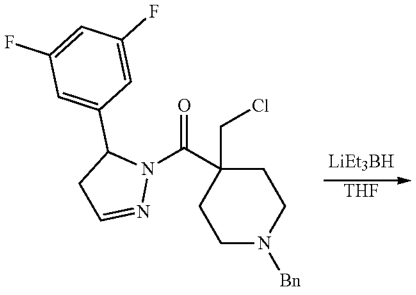
G.1
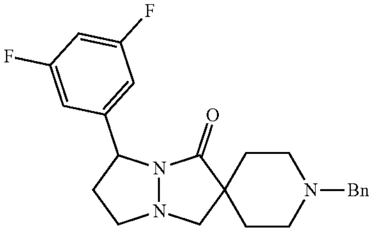
H.1
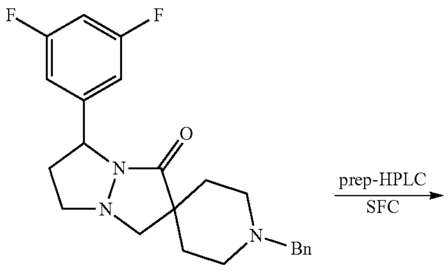
H.1
-continued
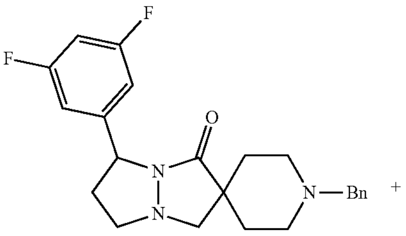
I.1
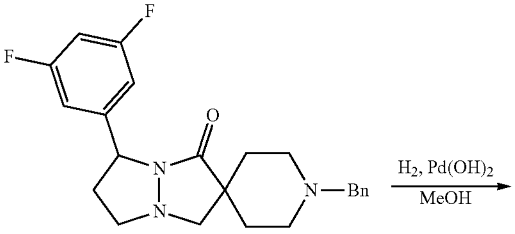
I.2
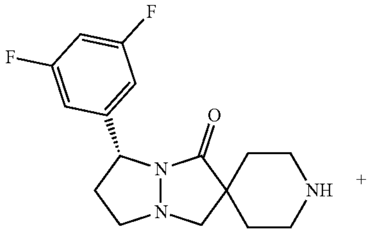
J.1
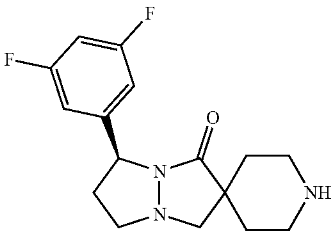
J.2
Preparation of Intermediate A.2,1-(tert-butyl) 4-ethyl 4-(chloromethyl) piperidine-1,4-dicarboxylate
Scheme A
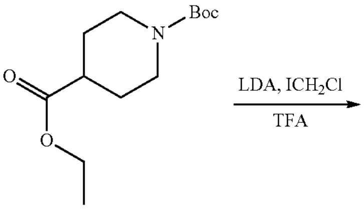
A.1

-continued

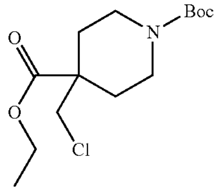

A.2

A solution of 1-(tert-butyl) 4-ethyl piperidine-1,4-dicarboxylate (300 g, 1.17 mmol) in THF (1.2 L) was added to a solution of LDA (2 M, 700 mL) at −60° C. under an atmosphere of nitrogen. The resulting mixture was stirred at −60° C. for 1 h. A solution of chloroiodomethane (247 g, 1.40 mol) in THF (600 mL) at −60° C. was added dropwise to the mixture. The reaction mixture was then stirred at 25° C. for 16 h under an inert atmosphere of nitrogen. The reaction was quenched by the slow addition of a saturated aqueous solution of $NH_4Cl$ (15 L) at 0° C. The mixture was then extracted with EtOAc (3 L×3). The combined organic layers were washed with brine (3 L x 4), dried over $Na_2SO_4$, filtered, and concentrated under reduced pressure. The residue was purified by column chromatography (Petroleum ether/EtOAc 0-1%) to give 1-(tert-butyl) 4-ethyl 4-(chloromethyl) piperidine-1,4-dicarboxylate. $^1H$ NMR (400 MHZ, CDC13), δ 4.22 (q, J=7.1 Hz, 2H), 3.86 (br d, J=13.8 Hz, 2H), 3.58 (s, 2H), 2.99 (br t, J=11.4 Hz, 2H), 2.20-2.10 (m, 2H), 1.44 (s, 9H), 1.29-1.26 (m, 3H).

Preparation of Intermediate B.1, ethyl 4-(chloromethyl) piperidine-4-carboxylate hydrochloride Scheme B

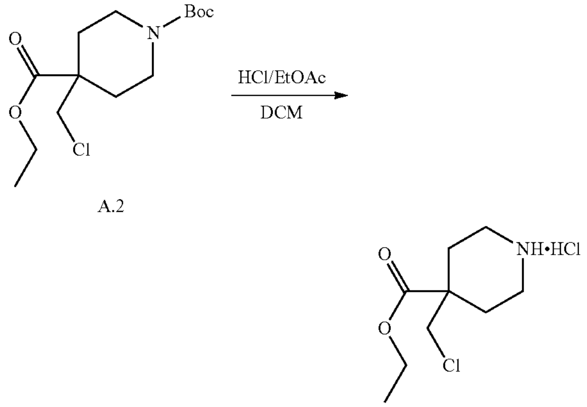

A.2

B.1

A solution of HCl in EtOAc (3.0 L, 4 M) was added to a solution of 1-(tert-butyl) 4-ethyl 4-(chloromethyl) piperidine-1,4-dicarboxylate (300 g, 0.981 mol) in DCM (1.2 L) at 0° C. The reaction mixture was stirred at 25° C. for 1 h, and then concentrated under reduced pressure. The reaction residue was diluted with MTBE (3.0 L) and stirred at 25° C. for 1 hour. The reaction mixture was filtered, and the collected solids were dried under vacuum to give ethyl 4-(chloromethyl) piperidine-4-carboxylate hydrochloride. $^1$HNMR (400 MHZ, DMSO), δ 4.18 (q, J=7.1 Hz, 2H), 3.83

(s, 2H), 3.36 (s, 4H), 3.22 (br d, J=12.9 Hz, 2H), 2.89 (br s, 2H), 2.16 (td, J=3.7, 14.4 Hz, 2H), 1.80 (ddd, J=4.0, 10.5, 14.4 Hz, 2H), 1.21 (t, J=7.1 Hz, 3H).

Preparation of Intermediate C.1, ethyl 1-benzyl-4-(chloromethyl) piperidine-4-carboxylate Scheme C

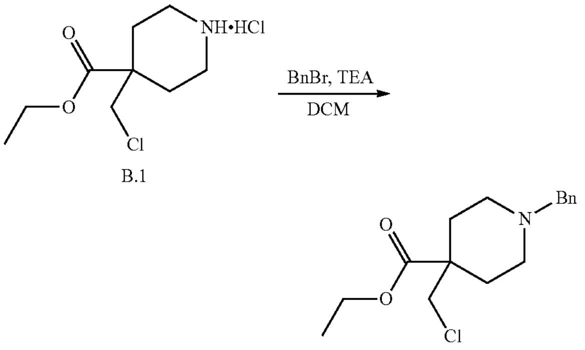

B.1

C.1

TEA (685 g, 6.77 mmol) was added dropwise to a solution of 1-(tert-butyl) 4-ethyl 4-(chloromethyl) piperidine-1,4-dicarboxylate (410 g, 1.69 mol) in DCM (2.5 L) at 0° C., followed by the addition of benzyl bromide (347 g, 2.03 mol) dropwise. The reaction mixture was stirred at 25° C. for 16 h under an atmosphere of nitrogen. The reaction was filtered, and the filter cake was rinsed with DCM (200 mL×6). The filtrate was then washed with water (1.5 L) and brine (1.5 L) and subsequently dried over $Na_2SO_4$, filtered, and concentrated under reduced pressure. The residue was purified by column chromatography (Petroleum ether/EtOAc 0-1%) to give ethyl 1-benzyl-4-(chloromethyl) piperidine-4-carboxylate. $^1$HNMR (400 MHZ, DMSO), δ 4.18 (q, J=7.1 Hz, 2H), 3.83 (s, 2H), 3.36 (s, 4H), 3.22 (br d, J=12.9 Hz, 2H), 2.89 (br s, 2H), 2.16 (td, J=3.7, 14.4 Hz, 2H), 1.80 (ddd, J=4.0, 10.5, 14.4 Hz, 2H), 1.21 (t, J=7.1 Hz, 3H).

Preparation of Intermediate D.1,1-benzyl-4-(chloromethyl) piperidine-4-carboxylic acid hydrochloride Scheme D

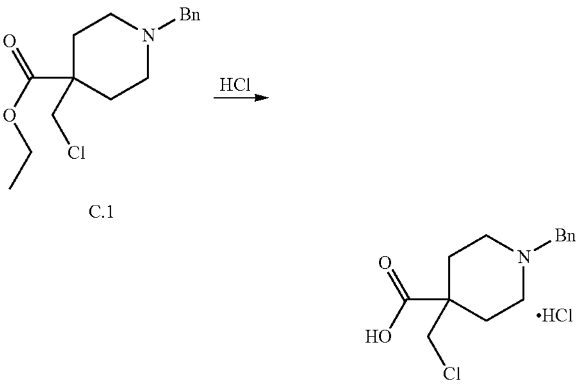

C.1

D.1

12 M aqueous HCl (2.0 L), followed by the addition of ethyl 1-benzyl-4-(chloromethyl) piperidine-4-carboxylate (200 g, 0.68 mol) was added to a 3 L, three-neck round bottom flask. The reaction mixture was stirred at 120° C. for 4 h. The reaction mixture was cooled to 20° C., filtered, and the filter cake was collected to give 1-benzyl-4-(chloromethyl) piperidine-4-carboxylic acid hydrochloride. $^1$HNMR (400 MHZ, DMSO), δ 10.75 (br d, J=3.7 Hz, 1H), 7.60 (br d, J=3.9 Hz, 2H), 7.48-7.42 (m, 3H), 4.30 (br s, 2H), 4.07 (s, 1H), 3.68 (s, 1H), 3.61-3.50 (m, 1H), 3.34-3.22 (m, 2H), 3.21-3.08 (m, 1H), 2.94-2.83 (m, 1H), 2.20 (br d, J=14.3 Hz, 2H), 2.03-1.96 (m, 1H), 1.93-1.84 (m, 1H).

Preparation of Intermediate E.2, (E)-3-(3,5-difluorophenyl) acrylaldehyde

Scheme E

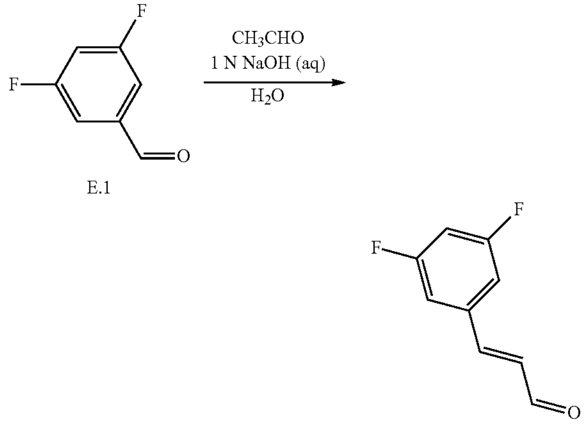

E.1

E.2

Water (1.2 L) was added to a 3 L, three-neck round bottom flask, followed by addition of 1-benzyl-4-(chloromethyl) piperidine-4-carboxylic acid hydrochloride (200 g, 1.41 mol). Acetaldehyde (232 g, 2.11 mol, 40% purity) was added to the reaction mixture, at 0° C., followed by dropwise addition of a 1 M solution of NaOH in water (1.4 L). The reaction mixture was stirred at 25° C. for 16 h. The reaction mixture was filtered, and the filter cake was washed with water (400 mL×3) to give (E)-3-(3,5-difluorophenyl) acrylaldehyde. MS (ESI) m/z calc'd for $C_9H_7F_2O[M+H]^+$169, found 169.

Preparation of Intermediate F.1, (E)-3-(3,5-difluorophenyl) acrylaldehyde

Scheme F

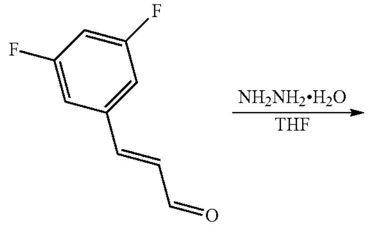

E.2

-continued

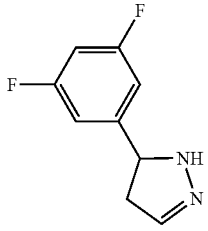

F.1

THF (1.0 L), followed by hydrazine ($NH_2NH_2$) $H_2O$ (657 g, 13.1 mol), was added to a 3 L, three-neck round bottom flask, at 25° C. A solution of (E)-3-(3,5-difluorophenyl) acrylaldehyde (170 g, 1.01 mol) in THF (1.0 L) was added dropwise over a period of 2 h. The reaction mixture was stirred at 25° C. for 1 h. The reaction mixture was concentrated under reduced pressure, and the residue was purified by column chromatography (petroleum ether/EtOAc 0-100%) to give 5-(3,5-Difluorophenyl)-4,5-dihydro-1H-pyrazole. $^1$HNMR (400 MHZ, CDCl3), δ 6.93-6.85 (m, 2H), 6.83-6.80 (m, 1H), 6.72 (tt, J=2.3, 8.8 Hz, 1H), 4.71 (t, J=10.1 Hz, 1H), 3.16 (ddd, J=1.6, 10.8, 17.1 Hz, 1H), 2.65 (ddd, J=1.6, 9.4, 17.1 Hz, 1H).

Preparation of Intermediate G.1, (1-benzyl-4-(chloromethyl) piperidin-4-yl) (5-(3,5-difluorophenyl)-4, 5-dihydro-1H-pyrazol-1-yl) methanone

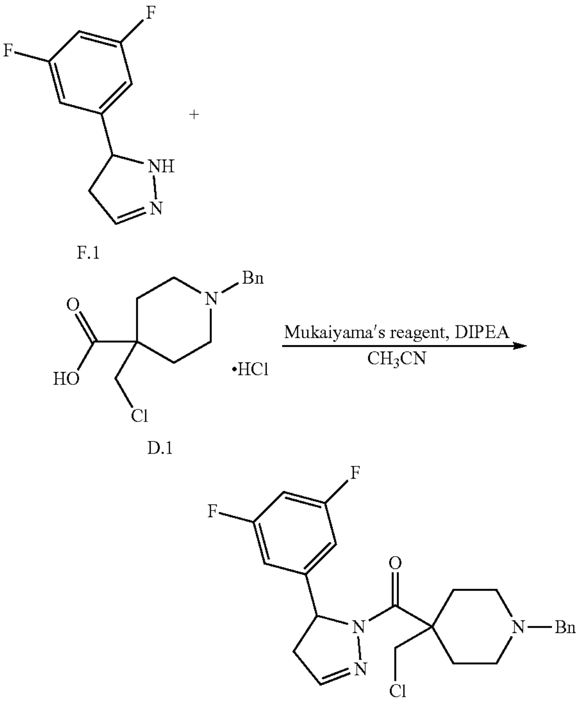

F.1

D.1

G.1

Acetonitrile (600 mL) and (E)-3-(3,5-difluorophenyl) acrylaldehyde was added to a 2 L, three-neck round bottom flask. 1-benzyl-4-(chloromethyl) piperidine-4-carboxylic acid hydrochloride (167 g, 0.55 mol, 1.0 equiv) at 0° C., was added to the reaction mixture followed by the addition of Mukaiyama's reagent (210 g, 0.82 mol). DIPEA (213 g, 1.65 mol) was then added slowly to the reaction mixture at 0° C. The reaction mixture was stirred at 25° C. for 2 h. The reaction mixture was concentrated under reduced pressure. The residue was then dissolved in EtOAc (1.2 L) and then washed with water (400 mL×2) and brine (400 mL×2). The combined organic layers were dried over $Na_2SO_4$, filtered, and the filtrate was concentrated under reduced pressure. The resulting residue was purified by column chromatography (petroleum ether/EtOAc 0-100%) to give (1-benzyl-4-(chloromethyl) piperidin-4-yl) (5-(3,5-difluorophenyl)-4,5-dihydro-1H-pyrazol-1-yl) methanone. $^1$HNMR (400 MHZ, CDCl3), δ 7.62-7.56 (m, 2H), 7.43-7.38 (m, 3H), 7.06 (s, 1H), 6.76-6.67 (m, 3H), 5.37 (dd, J=5.2, 11.9 Hz, 1H), 4.17-4.01 (m, 5H), 3.54 (s, 2H), 3.49-3.27 (m, 3H), 2.91-2.64 (m, 5H), 2.45-2.29 (m, 2H).

Preparation of Intermediate H.1,1-benzyl-7'-(3,5-difluorophenyl)dihydro-1'H,3'H,5'H-spiro[piperidine-4,2'-pyrazolo[1,2-a]pyrazol]-1'-one Scheme H

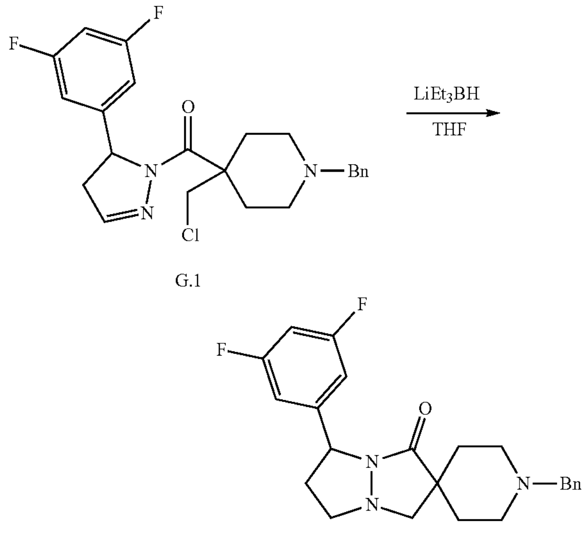

G.1

H.1

A solution of (1-benzyl-4-(chloromethyl) piperidin-4-yl) (5-(3,5-difluorophenyl)-4,5-dihydro-1H-pyrazol-1-yl) methanone (100 g, 231 mmol) in THF (600 mL) was added to a solution of LiEtsBH (1 M, 694 mL) in THF (600 mL) under atmosphere of nitrogen at −60° C.

The reaction mixture was stirred at 25° C. for 2 hours under an atmosphere of nitrogen. The reaction was quenched with NaHCO; saturated aqueous solution, 4.5 L at 0° C., and the aqueous layer was extracted with EtOAc (3.0 L). The organic layer was washed with brine (1 L×2) and dried over $Na_2SO_4$, filtered, and concentrated under reduced pressure. The crude residue was purified by reversed-phase HPLC to give 1-benzyl-7'-(3,5-difluorophenyl)dihydro-1'H,3'H,5'H-spiro[piperidine-4,2'-pyrazolo[1,2-a]pyrazol]-1'-one. $^1$HNMR (400 MHZ, CDCl3), δ 7.30-7.16 (m, 5H), 6.80-6.71 (m, 2H), 6.63 (tt, J=2.3, 8.8 Hz, 1H), 4.94 (t, J=7.8 Hz, 1H), 3.61 (br d, J=9.5 Hz, 1H), 3.52-3.41 (m, 2H), 3.28 (br d, J=6.5 Hz, 1H), 2.88-2.66 (m, 4H), 2.50-2.38 (m, 1H), 2.23-2.06 (m, 3H), 2.04-1.93 (m, 3H), 1.78 (br d, J=13.1 Hz, 1H), 1.46 (br d, J=13.1 Hz, 1H).

SFC separation of I.1 and I.2 (R)-1-benzyl-7'-(3,5-difluorophenyl)dihydro-1'H,3'H,5'H-spiro[piperidine-4,2'-pyrazolo[1,2-a]pyrazol]-1'-one and(S)-1-benzyl-7'-(3,5-difluorophenyl)dihydro-1'H,3'H,5'H-spiro[piperidine-4,2'-pyrazolo[1,2-a]pyrazol]-1'-one Scheme I

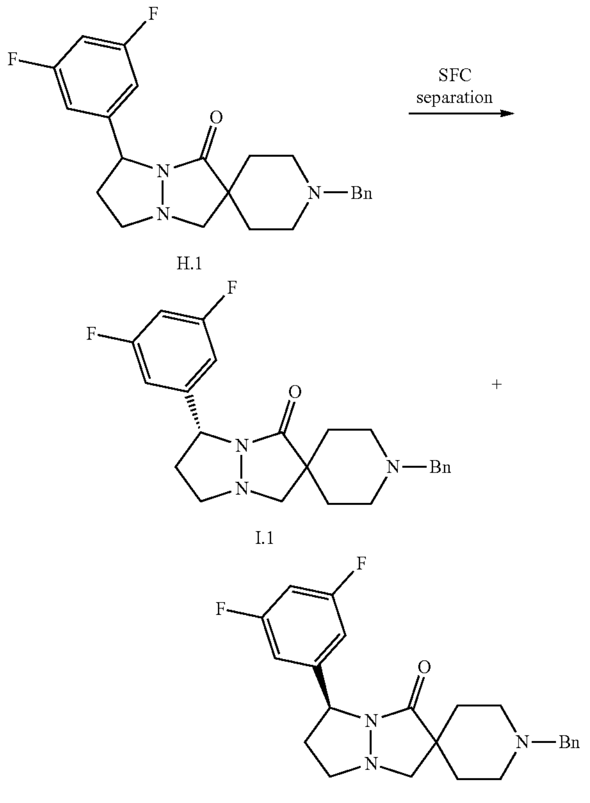

H.1

I.1

I.2

1-benzyl-7'-(3,5-difluorophenyl)dihydro-1'H,3'H,5'H-spiro[piperidine-4,2'-pyrazolo[1,2-a]pyrazol]-1'-one was purified by CHIRAL-Prep SFC [column: DAICEL CHIRALPAK AD ( ) mobile phase: (0.1% $NH_3H_2O$/EtOH) 40%: 6.5 min; first eluting peak (I.1) and second eluting peak (I.2)]. This gave (R)-1-benzyl-7'-(3,5-difluorophenyl) dihydro-1'H,3'H,5'H-spiro[piperidine-4,2'-pyrazolo[1,2-a] pyrazol]-1'-one (I.1) and(S)-1-benzyl-7'-(3,5-difluorophenyl)dihydro-1'H,3'H,5'H-spiro[piperidine-4,2'-pyrazolo[1,2-a]pyrazol]-1'-one (I.2) I.1: $^1$HNMR (400 MHZ, CDCl3), δ 7.37-7.23 (m, 5H), 6.86-6.76 (m, 2H), 6.69 (tt, J=2.3, 8.9 Hz, 1H), 4.99 (t, J=7.8 Hz, 1H), 3.66 (br d, J=9.0 Hz, 1H), 3.59-3.45 (m, 2H), 3.33 (br s, 1H), 2.95-2.73 (m, 4H), 2.49 (br d, J=7.5 Hz, 1H), 2.31-2.00 (m, 6H), 1.85 (br d, J=12.4 Hz, 1H), 1.53 (br d, J=11.4 Hz, 1H). 1.2: $^1$HNMR (400 MHZ, CDCl3), δ 7.37-7.23 (m, 5H), 6.87-6.77 (m, 2H), 6.69 (tt, J=2.3, 8.9 Hz, 1H), 4.99 (t, J=7.8 Hz, 1H), 3.66 (br d, J=9.3 Hz, 1H), 3.58-3.48 (m, 2H), 3.33 (br s, 1H), 2.94-2.71 (m, 4H), 2.56-2.43 (m, 1H), 2.30-1.99 (m, 6H), 1.85 (br d, J=12.4 Hz, 1H), 1.53 (br d, J=10.5 Hz, 1H).

Preparation of Intermediate J.1 and J.2, (R)-7'-(3,5-difluorophenyl)dihydro-1'H,3'H,5'H-spiro[piperidine-4,2'-pyrazolo[1,2-a]pyrazol]-1'-one and(S)-7'-(3,5-difluorophenyl)dihydro-1'H,3'H,5'H-spiro[piperidine-4,2'-pyrazolo[1,2-a]pyrazol]-1'-one Scheme J

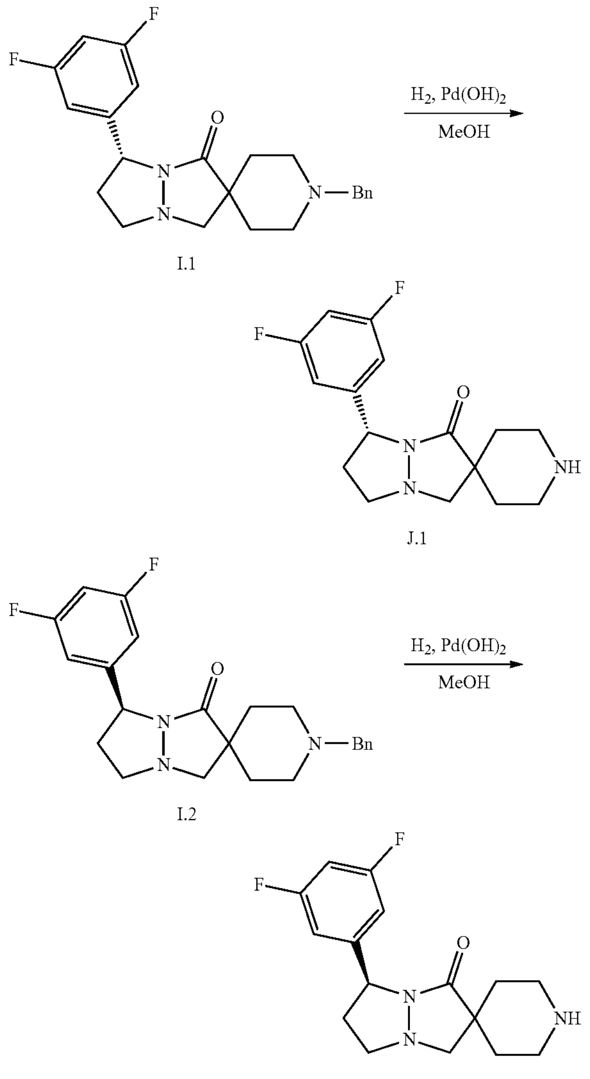

I.1

J.1

I.2

J.2

$Pd(OH)_2$ (6 g, 10%) was added to a solution of (R)-1-benzyl-7'-(3,5-difluorophenyl)dihydro-1'H,3'H,5'H-spiro[piperidine-4,2'-pyrazolo[1,2-a]pyrazol]-1'-one (24.0 g, 60.3 mmol, 1.00 eq) in MeOH (240 mL). The resulting suspension was degassed and purged with hydrogen gas three times. The reaction mixture was stirred at 25° C. for 5 h under 30 psi of hydrogen gas. The suspension was filtered through a pad of Celite® and the pad was washed with THF (600 mL×2). The combined filtrates were concentrated to dryness under reduced pressure. The resulting residue was triturated with MTBE (30 mL) at 20° C. for 1 h to give (R)-7'-(3,5-difluorophenyl)dihydro-1'H,3'H,5'H-spiro[piperidine-4,2'-pyrazolo[1,2-a]pyrazol]-1'-one (J.1).

$^1$HNMR (400 MHZ, CDCl3), δ 6.86-6.78 (m, 2H), 6.69 (tt, J=2.3, 8.9 Hz, 1H), 5.00 (t, J=7.8 Hz, 1H), 3.74 (br d, J=9.4 Hz, 1H), 3.35 (br s, 1H), 3.21-3.08 (m, 2H), 2.88-2.74 (m, 3H), 2.67-2.58 (m, 1H), 2.50 (br d, J=7.5 Hz, 1H), 2.30-2.19 (m, 1H), 2.02 (ddd, J=4.2, 11.1, 13.5 Hz, 1H), 1.93-1.77 (m, 2H), 1.50 (br d, J=13.6 Hz, 1H). Similar conditions were used to prepare J.2.

Preparation of Intermediate K.1,4-chloro-6-(1-(difluoromethyl)-1H-pyrazol-4-yl)pyrimidine

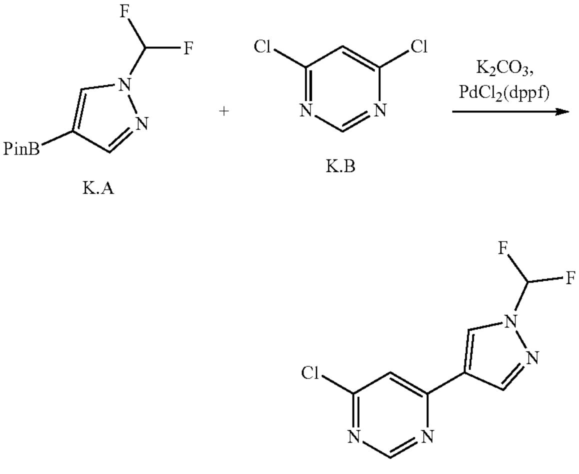

K.A

K.B

K.1

$PdCl_2$ (dppf) (24.6 mg, 0.034 mmol) was added to a mixture of 1-(difluoromethyl)-4-(4,4,5,5-tetramethyl-1,3,2-dioxaborolan-2-yl)-1H-pyrazole (82 mg, 0.336 mmol), 4,6-dichloropyrimidine (50 mg, 0.336 mmol), and $K_2CO_3$ (139 mg, 1.01 mmol) in dioxane (0.5 mL), at 20° C. and the mixture was stirred at 100° C. for 12 h under $N_2$ atmosphere. The mixture was washed with water (20 mL), extracted with EtOAc (10 mL×2), dried over $Na_2SO_4$, filtered, concentrated and the residue was purified by preparative TLC (Petroleum ether:EtOAc 1:1) to give 4-chloro-6-(1-(difluoromethyl)-1H-pyrazol-4-yl)pyrimidine. MS (ESI) m/z $C_8H_6ClF_2N_4$ $[M+H]^+$ calc'd 231, found 231.

Preparation of Example 1.1, (S)-7'-(3,5-difluorophenyl)-1-(3-fluoropyrazolo[1,5-a]pyrimidin-7-yl)dihydro-1'H,3'H,5'H-spiro[piperidine-4,2'-pyrazolo[1,2-a]pyrazol]-1'-one Scheme 1

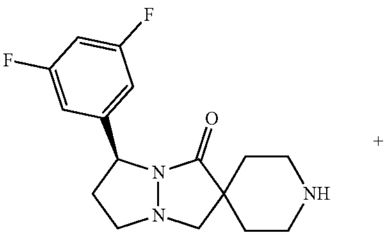

J.2

-continued

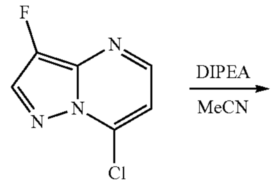

1.A

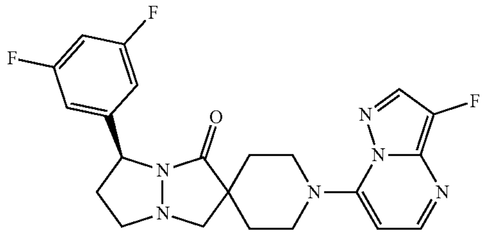

1.1

DIPEA (30.7 µl, 0.176 mmol) was added, in one portion, to a mixture of(S)-7'-(3,5-difluorophenyl)dihydro-1'H,3'H,5'H-spiro[piperidine-4,2'-pyrazolo[1,2-a]pyrazol]-1'-one (27 mg, 0.088 mmol) and 7-chloro-3-fluoropyrazolo[1,5-a] pyrimidine (16.6 mg, 0.097 mmol) in acetonitrile (0.6 mL). The mixture was capped and heated to 80° C. for 2 h. The mixture was then concentrated, diluted in DMA, filtered, and purified via reversed phase HPLC [Method B], to give(S)-7'-(3,5-difluorophenyl)-1-(3-fluoropyrazolo[1,5-a] pyrimidin-7-yl)dihydro-1'H,3'H,5'H-spiro [piperidine-4,2'-pyrazolo[1,2-a]pyrazol]-1'-one. MS (ESI) m/z $C_{22}H_{22}F_3N_6O$ $[M+H]^+$ calc'd 459, found 459. $^1H$ NMR (499 MHz, Chloroform-d) δ 8.31-8.16 (m, 1H), 7.98 (dd, J=42.4, 3.5 Hz, 1H), 6.95 (dd, J=26.2, 6.2 Hz, 2H), 6.77 (t, J=8.6 Hz, 1H), 5.19-5.01 (m, 1H), 4.24-3.97 (m, 2H), 3.87 (d, J=35.4 Hz, 1H), 3.65 (dt, J=69.6, 8.8 Hz, 3H), 3.06 (d, J=28.3 Hz, 1H), 2.99-2.70 (m, 2H), 2.60-2.38 (m, 2H), 2.38-2.28 (m, 1H), 2.24 (s, 1H), 1.90 (s, 2H).

The following examples in Table 1 were prepared according to Scheme 1 above, using intermediate J.2, and the appropriate heteroaryl halide, either commercially available or intermediate K.1. For Example 1.21 through Example 1.73, and Example 1.96, a slightly modified procedure was used wherein DIPEA was replaced by TEA and the reaction was run at 100° C. in DMF for 16 h. The compounds were generally purified by reversed phase HPLC.

TABLE 1

Examples Prepared According to Scheme 1.

| Ex. No. | Structure | Name | Observed m/z $[M+H]^+$ | RIPK1 $EC_{50}$ (nM) |
|---|---|---|---|---|
| 1.2 | 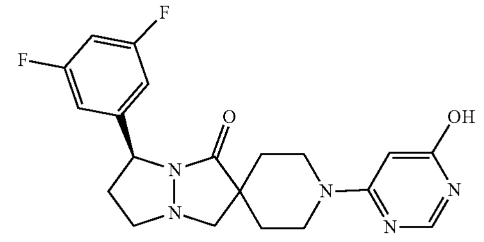 [SMILES: O=C1N2[C@H](c3cc(F)cc(F)c3)CCN2CC12CCN(c1cc(O)ncn1)CC2] | (7'S)-7'-(3,5-difluorophenyl)-1-(6-hydroxypyrimidin-4-yl)dihydro-1'H,3'H,5'H-spiro [piperidine-4,2'-pyrazolo[1,2-a] pyrazol]-1'-one | 402 | 151 |
| 1.3 | 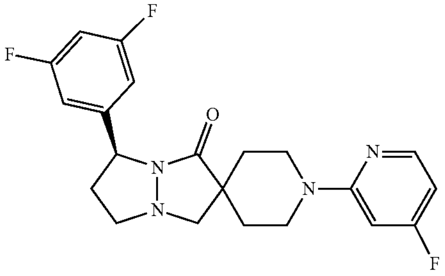 [SMILES: O=C1N2[C@H](c3cc(F)cc(F)c3)CCN2CC12CCN(c1cc(F)ccn1)CC2] | (7'S)-7'-(3,5-difluorophenyl)-1-(4-fluoropyridin-2-yl) dihydro-1'H,3'H,5'H-spiro[piperidine-4,2'-pyrazolo[1,2-a] pyrazol]-1'-one | 403 | 19 |
| 1.4 | 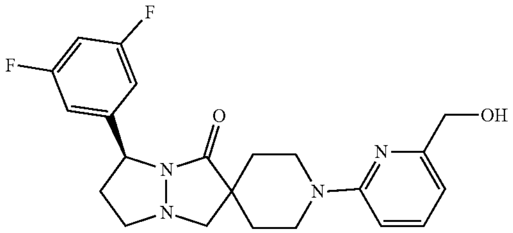 [SMILES: O=C1N2[C@H](c3cc(F)cc(F)c3)CCN2CC12CCN(c1cccc(CO)n1)CC2] | (7'S)-7'-(3,5-difluorophenyl)-1-[6-(hydroxymethyl) pyridin-2-yl]dihydro-1'H,3'H,5'H-spiro [piperidine-4,2'-pyrazolo[1,2-a] pyrazol]-1'-one | 415 | 629 |

TABLE 1-continued

Examples Prepared According to Scheme 1.

| Ex. No. | Structure | Name | Observed m/z [M + H]+ | RIPK1 $EC_{50}$ (nM) |
|---|---|---|---|---|
| 1.5 | 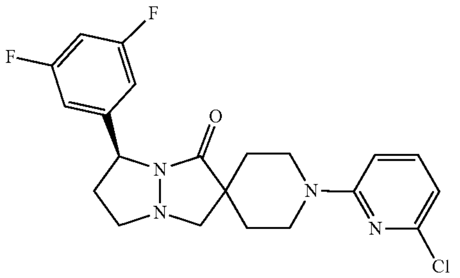 [SMILES: O=C1N2[C@H](c3cc(F)cc(F)c3)CCN2CC12CCN(c1cccc(Cl)n1)CC2] | (7'S)-1-(6-chloropyridin-2-yl)-7'-(3,5-difluorophenyl) dihydro-1'H,3'H,5'H-spiro[piperidine-4,2'-pyrazolo[1,2-a] pyrazol]-1'-one | 419 | 24 |
| 1.6 | 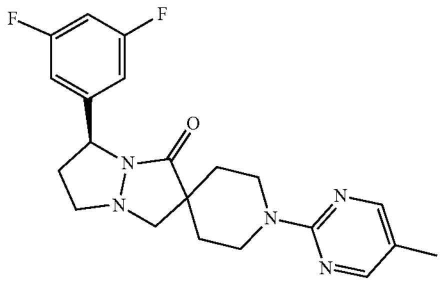 [SMILES: Cc1cnc(N2CCC3(CC2)CN2CC[C@@H](c4cc(F)cc(F)c4)N2C3=O)nc1] | (7'S)-7'-(3,5-difluorophenyl)-1-(5-methylpyrimidin-2-yl) dihydro-1'H,3'H,5'H-spiro[piperidine-4,2'-pyrazolo[1,2-a] pyrazol]-1'-one | 400 | 393 |
| 1.7 | 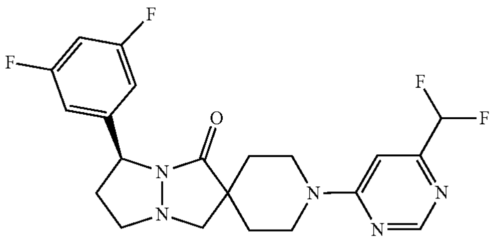 [SMILES: O=C1N2[C@H](c3cc(F)cc(F)c3)CCN2CC12CCN(c1cc(C(F)F)ncn1)CC2] | (7'S)-1-[6-(difluoromethyl) pyrimidin-4-yl]-7'-(3,5-difluorophenyl) dihydro-1'H,3'H,5'H-spiro [piperidine-4,2'-pyrazolo[1,2-a] pyrazol]-1'-one | 436 | 39 |
| 1.8 | 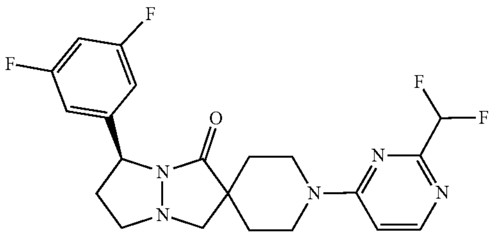 [SMILES: O=C1N2[C@H](c3cc(F)cc(F)c3)CCN2CC12CCN(c1ccnc(C(F)F)n1)CC2] | (7'S)-1-[2-(difluoromethyl) pyrimidin-4-yl]-7'-(3,5-difluorophenyl) dihydro-1'H,3'H,5'H-spiro[piperidine-4,2'-pyrazolo[1,2-a] pyrazol]-1'-one | 436 | 16 |
| 1.9 | 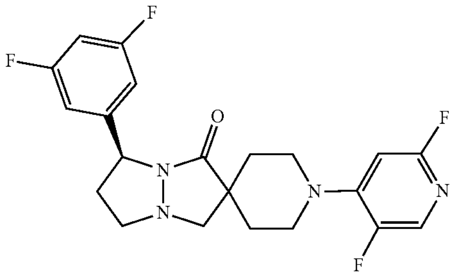 [SMILES: O=C1N2[C@H](c3cc(F)cc(F)c3)CCN2CC12CCN(c1cc(F)ncc1F)CC2] | (7'S)-7'-(3,5-difluorophenyl)-1-(2,5-difluoropyridin-4-yl)dihydro-1'H,3'H,5'H-spiro [piperidine-4,2'-pyrazolo[1,2-a] pyrazol]-1'-one | 421 | 37 |

TABLE 1-continued

Examples Prepared According to Scheme 1.

| Ex. No. | Structure | Name | Observed m/z [M + H]$^+$ | RIPK1 $EC_{50}$ (nM) |
|---|---|---|---|---|
| 1.10 | 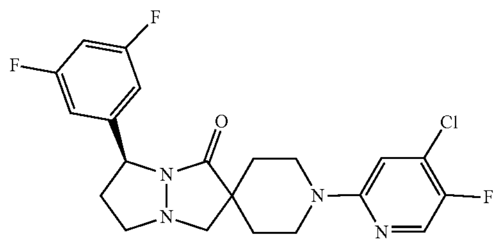 [SMILES: O=C1N2[C@H](c3cc(F)cc(F)c3)CCN2CC12CCN(c1cc(Cl)c(F)cn1)CC2] | (7'S)-1-(4-chloro-5-fluoropyridin-2-yl)-7'-(3,5-difluorophenyl) dihydro-1'H,3'H,5'H-spiro[piperidine-4,2'-pyrazolo[1,2-a] pyrazol]-1'-one | 421 | 10 |
| 1.11 | 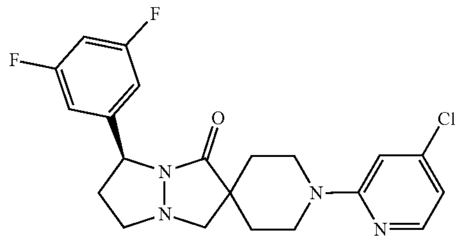 [SMILES: O=C1N2[C@H](c3cc(F)cc(F)c3)CCN2CC12CCN(c1cc(Cl)ccn1)CC2] | (7'S)-1-(4-chloropyridin-2-yl)-7'-(3,5-difluorophenyl) dihydro-1'H,3'H,5'H-spiro[piperidine-4,2'-pyrazolo[1,2-a] pyrazol]-1'-one | 419 | 28 |
| 1.12 | 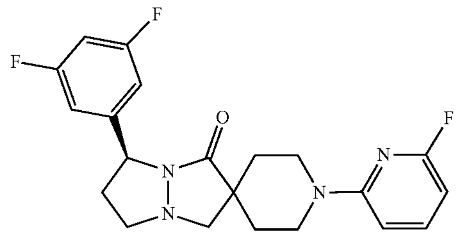 [SMILES: O=C1N2[C@H](c3cc(F)cc(F)c3)CCN2CC12CCN(c1cccc(F)n1)CC2] | (7'S)-7'-(3,5-difluorophenyl)-1-(6-fluoropyridin-2-yl) dihydro-1'H,3'H,5'H-spiro[piperidine-4,2'-pyrazolo[1,2-a] pyrazol]-1'-one | 403 | 29 |
| 1.13 | 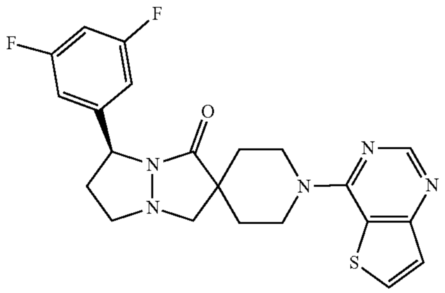 [SMILES: O=C1N2[C@H](c3cc(F)cc(F)c3)CCN2CC12CCN(c1ncnc3ccsc13)CC2] | (S)-7'-(3,5-difluorophenyl)-1-(thieno[3,2-d] pyrimidin-4-yl) dihydro-1'H,3'H,5'H-spiro[piperidine-4,2'-pyrazolo[1,2-a] pyrazol]-1'-one | 442 | 16 |
| 1.14 | 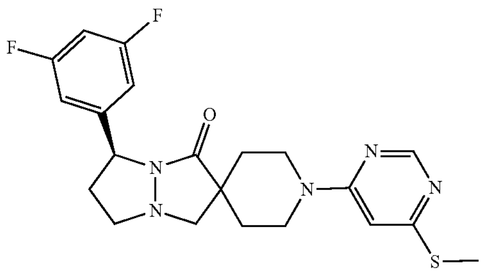 [SMILES: CSc1cc(N2CCC3(CC2)CN2CC[C@@H](c4cc(F)cc(F)c4)N2C3=O)ncn1] | (S)-7'-(3,5-difluorophenyl)-1-(6-(methylthio) pyrimidin-4-yl) dihydro-1'H,3'H,5'H-spiro[piperidine-4,2'-pyrazolo[1,2-a] pyrazol]-1'-one | 432 | 17 |

TABLE 1-continued

| Ex. No. | Structure | Name | Observed m/z [M + H]+ | RIPK1 $EC_{50}$ (nM) |
|---|---|---|---|---|
| Examples Prepared According to Scheme 1. | | | | |
| 1.15 | 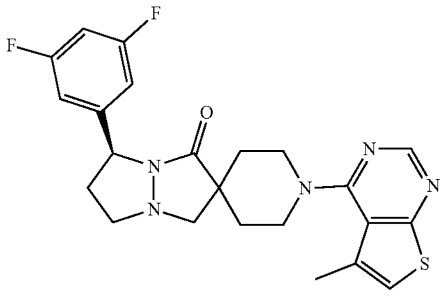 [SMILES: Cc1csc2ncnc(N3CCC4(CC3)CN3CC[C@@H](c5cc(F)cc(F)c5)N3C4=O)c12] | (S)-7'-(3,5-difluorophenyl)-1-(5-methylthieno[2,3-d]pyrimidin-4-yl)dihydro-1'H,3'H,5'H-spiro[piperidine-4,2'-pyrazolo[1,2-a]pyrazol]-1'-one | 455 | 17 |
| 1.16 | 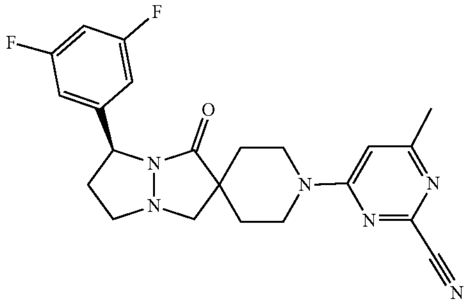 [SMILES: Cc1cc(N2CCC3(CC2)CN2CC[C@@H](c4cc(F)cc(F)c4)N2C3=O)nc(C#N)n1] | (S)-4-(7'-(3,5-difluorophenyl)-1'-oxodihydro-1'H,3'H,5'H-spiro[piperidine-4,2'-pyrazolo[1,2-a]pyrazol]-1-yl)-6-methylpyrimidine-2-carbonitrile | 425 | 67 |
| 1.17 | 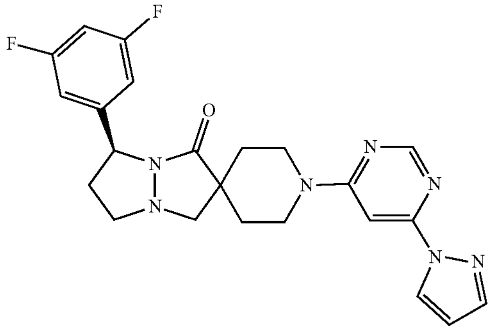 [SMILES: O=C1N2[C@H](c3cc(F)cc(F)c3)CCN2CC12CCN(c1cc(-n3cccn3)ncn1)CC2] | (S)-1-(6-(1H-pyrazol-1-yl)pyrimidin-4-yl)-7'-(3,5-difluorophenyl)dihydro-1'H,3'H,5'H-spiro[piperidine-4,2'-pyrazolo[1,2-a]pyrazol]-1'-one | 452 | 20 |
| 1.18 | 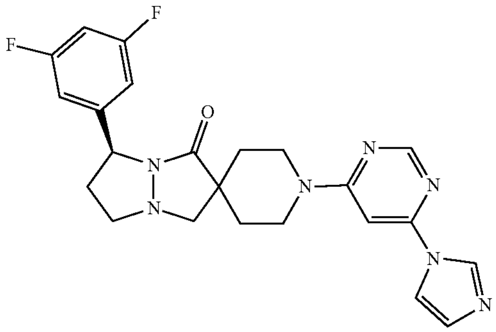 [SMILES: O=C1N2[C@H](c3cc(F)cc(F)c3)CCN2CC12CCN(c1cc(-n3ccnc3)ncn1)CC2] | (S)-1-(6-(1H-imidazol-1-yl)pyrimidin-4-yl)-7'-(3,5-difluorophenyl)dihydro-1'H,3'H,5'H-spiro[piperidine-4,2'-pyrazolo[1,2-a]pyrazol]-1'-one | 452 | 27 |

TABLE 1-continued

Examples Prepared According to Scheme 1.

| Ex. No. | Structure | Name | Observed m/z [M + H]+ | RIPK1 $EC_{50}$ (nM) |
|---|---|---|---|---|
| 1.19 | 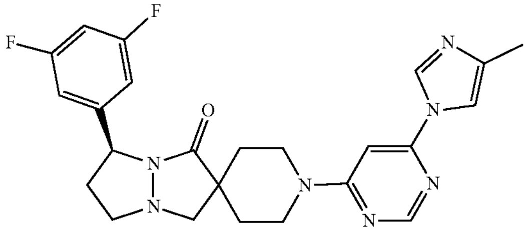 [SMILES: Cc1cn(-c2cc(N3CCC4(CC3)CN3CC[C@@H](c5cc(F)cc(F)c5)N3C4=O)ncn2)cn1] | (S)-7'-(3,5-difluorophenyl)-1-(6-(4-methyl-1H-imidazol-1-yl) pyrimidin-4-yl) dihydro-1'H,3'H,5'H-spiro [piperidine-4,2'-pyrazolo[1,2-a] pyrazol]-1'-one | 466 | 37 |
| 1.20 | 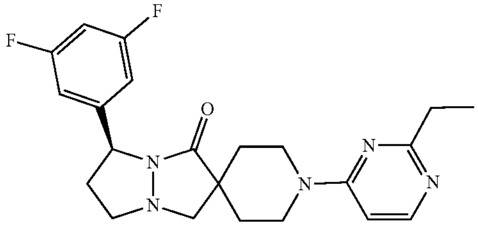 [SMILES: CCc1nccc(N2CCC3(CC2)CN2CC[C@@H](c4cc(F)cc(F)c4)N2C3=O)n1] | (S)-7'-(3,5-difluorophenyl)-1-(2-ethylpyrimidin-4-yl) dihydro-1'H,3'H,5'H-spiro[piperidine-4,2'-pyrazolo[1,2-a] pyrazol]-1'-one | 414 | 159 |
| 1.21 | 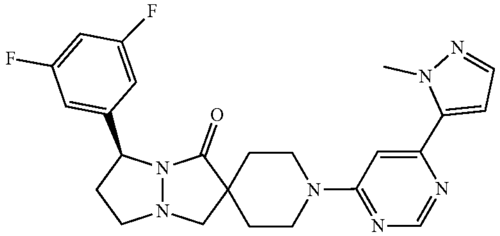 [SMILES: Cn1nccc1-c1cc(N2CCC3(CC2)CN2CC[C@@H](c4cc(F)cc(F)c4)N2C3=O)ncn1] | (S)-7'-(3,5-difluorophenyl)-1-(6-(1-methyl-1H-pyrazol-5-yl) pyrimidin-4-yl) dihydro-1'H,3'H,5'H-spiro[piperidine-4,2'-pyrazolo[1,2-a] pyrazol]-1'-one | 466 | 15 |
| 1.22 | 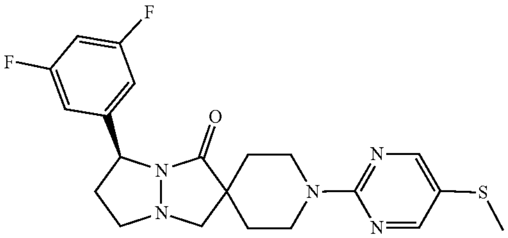 [SMILES: CSc1cnc(N2CCC3(CC2)CN2CC[C@@H](c4cc(F)cc(F)c4)N2C3=O)nc1] | (S)-7'-(3,5-difluorophenyl)-1-(5-(methylthio) pyrimidin-2-yl) dihydro-1'H,3'H,5'H-spiro [piperidine-4,2'-pyrazolo[1,2-a] pyrazol]-1'-one | 432 | 89 |
| 1.23 | 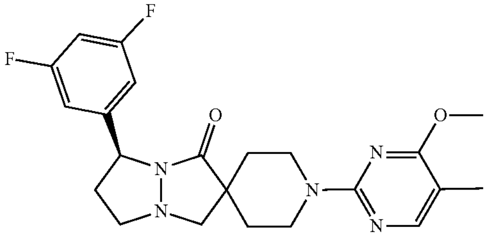 [SMILES: COc1nc(N2CCC3(CC2)CN2CC[C@@H](c4cc(F)cc(F)c4)N2C3=O)ncc1C] | (S)-7'-(3,5-difluorophenyl)-1-(4-methoxy-5-methylpyrimidin-2-yl)dihydro-1'H,3'H,5'H-spiro [piperidine-4,2'-pyrazolo[1,2-a] pyrazol]-1'-one | 430 | 68 |
| 1.24 | 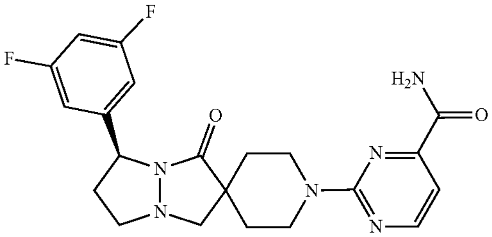 [SMILES: NC(=O)c1ccnc(N2CCC3(CC2)CN2CC[C@@H](c4cc(F)cc(F)c4)N2C3=O)n1] | (S)-2-(7'-(3,5-difluorophenyl)-1'-oxodihydro-1'H,3'H,5'H-spiro [piperidine-4,2'-pyrazolo[1,2-a] pyrazol]-1-yl)pyrimidine-4-carboxamide | 429 | 136 |

TABLE 1-continued

| Ex. No. | Structure | Name | Observed m/z [M + H]+ | RIPK1 $EC_{50}$ (nM) |
|---|---|---|---|---|
| | Examples Prepared According to Scheme 1. | | | |
| 1.25 | 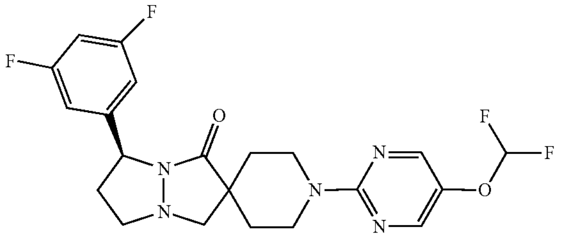 [SMILES: O=C1N2[C@H](c3cc(F)cc(F)c3)CCN2CC12CCN(c1ncc(OC(F)F)cn1)CC2] | (S)-1-(5-(difluoromethoxy)pyrimidin-2-yl)-7'-(3,5-difluorophenyl)dihydro-1'H,3'H,5'H-spiro[piperidine-4,2'-pyrazolo[1,2-a]pyrazol]-1'-one | 452 | 38 |
| 1.26 | 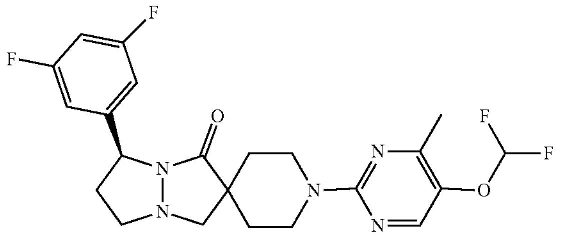 [SMILES: Cc1nc(N2CCC3(CC2)CN2CC[C@@H](c4cc(F)cc(F)c4)N2C3=O)ncc1OC(F)F] | (S)-1-(5-(difluoromethoxy)-4-methylpyrimidin-2-yl)-7'-(3,5-difluorophenyl)dihydro-1'H,3'H,5'H-spiro[piperidine-4,2'-pyrazolo[1,2-a]pyrazol]-1'-one | 466 | 15 |
| 1.27 | 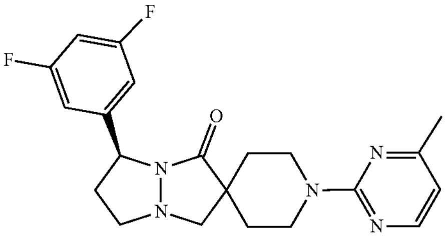 [SMILES: Cc1ccnc(N2CCC3(CC2)CN2CC[C@@H](c4cc(F)cc(F)c4)N2C3=O)n1] | (S)-7'-(3,5-difluorophenyl)-1-(4-methylpyrimidin-2-yl)dihydro-1'H,3'H,5'H-spiro[piperidine-4,2'-pyrazolo[1,2-a]pyrazol]-1'-one | 400 | 637 |
| 1.28 | 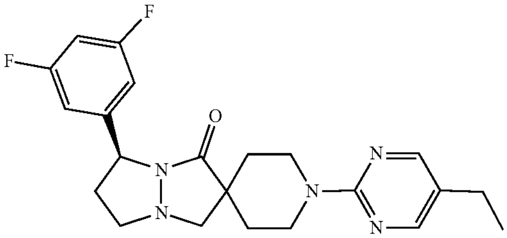 [SMILES: CCc1cnc(N2CCC3(CC2)CN2CC[C@@H](c4cc(F)cc(F)c4)N2C3=O)nc1] | (S)-7'-(3,5-difluorophenyl)-1-(5-ethylpyrimidin-2-yl)dihydro-1'H,3'H,5'H-spiro[piperidine-4,2'-pyrazolo[1,2-a]pyrazol]-1'-one | 414 | 409 |
| 1.29 | 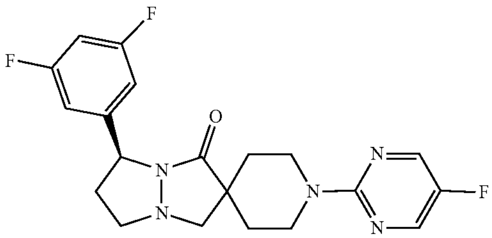 [SMILES: O=C1N2[C@H](c3cc(F)cc(F)c3)CCN2CC12CCN(c1ncc(F)cn1)CC2] | (S)-7'-(3,5-difluorophenyl)-1-(5-fluoropyrimidin-2-yl)dihydro-1'H,3'H,5'H-spiro[piperidine-4,2'-pyrazolo[1,2-a]pyrazol]-1'-one | 404 | 84 |

TABLE 1-continued

Examples Prepared According to Scheme 1.

| Ex. No. | Structure | Name | Observed m/z [M + H]+ | RIPK1 $EC_{50}$ (nM) |
|---|---|---|---|---|
| 1.30 | 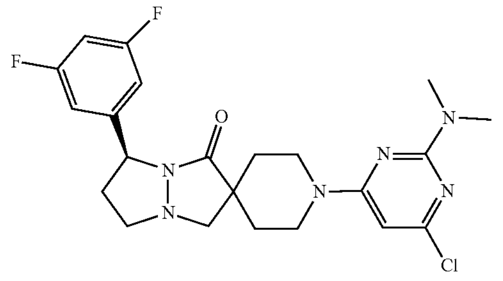 [SMILES: CN(C)c1nc(Cl)cc(N2CCC3(CC2)CN2CC[C@@H](c4cc(F)cc(F)c4)N2C3=O)n1] | (S)-1-(6-chloro-2-(dimethylamino) pyrimidin-4-yl)-7'-(3,5-difluorophenyl) dihydro-1'H,3'H,5'H-spiro [piperidine-4,2'-pyrazolo[1,2-a] pyrazol]-1'-one | 463 | 110 |
| 1.31 | 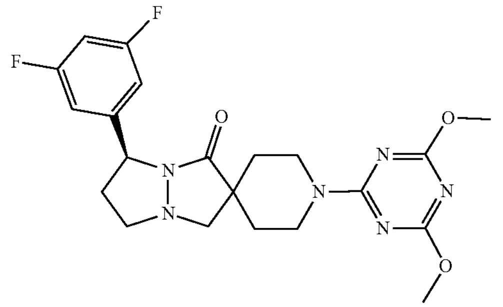 [SMILES: COc1nc(OC)nc(N2CCC3(CC2)CN2CC[C@@H](c4cc(F)cc(F)c4)N2C3=O)n1] | (S)-7'-(3,5-difluorophenyl)-1-(4,6-dimethoxy-1,3,5-triazin-2-yl)dihydro-1'H,3'H,5'H-spiro [piperidine-4,2'-pyrazolo[1,2-a] pyrazol]-1'-one | 447 | 285 |
| 1.32 | 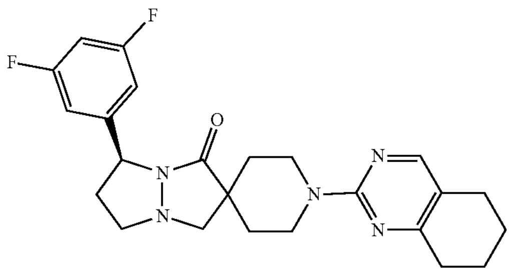 [SMILES: O=C1N2[C@H](c3cc(F)cc(F)c3)CCN2CC12CCN(c1ncc3c(n1)CCCC3)CC2] | (S)-7'-(3,5-difluorophenyl)-1-(5,6,7,8-tetrahydroquinazolin-2-yl)dihydro-1'H,3'H,5'H-spiro[piperidine-4,2'-pyrazolo[1,2-a] pyrazol]-1'-one | 440 | 288 |
| 1.33 | 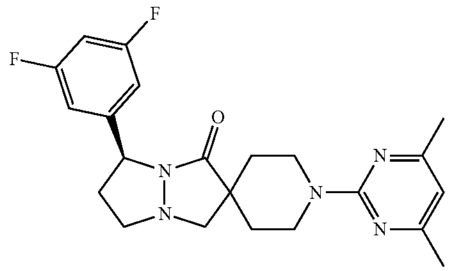 [SMILES: Cc1cc(C)nc(N2CCC3(CC2)CN2CC[C@@H](c4cc(F)cc(F)c4)N2C3=O)n1] | (S)-7'-(3,5-difluorophenyl)-1-(4,6-dimethylpyrimidin-2-yl)dihydro-1'H,3'H,5'H-spiro[piperidine-4,2'-pyrazolo[1,2-a] pyrazol]-1'-one | 400 | 596 |
| 1.34 | 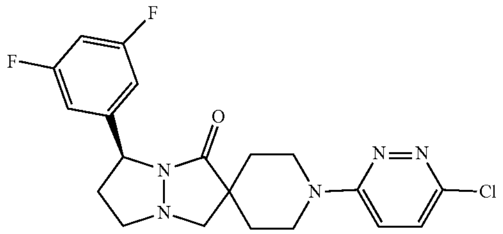 [SMILES: O=C1N2[C@H](c3cc(F)cc(F)c3)CCN2CC12CCN(c1ccc(Cl)nn1)CC2] | (S)-1-(6-chloropyridazin-3-yl)-7'-(3,5-difluorophenyl) dihydro-1'H,3'H,5'H-spiro[piperidine-4,2'-pyrazolo[1,2-a] pyrazol]-1'-one | 420 | 457 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.35 | 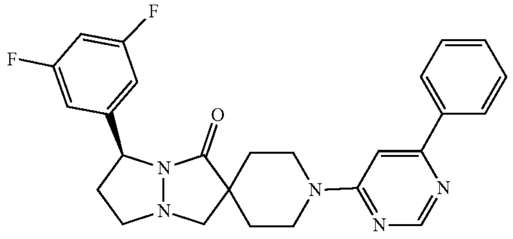 [SMILES: O=C1N2[C@H](c3cc(F)cc(F)c3)CCN2CC12CCN(c1cc(-c3ccccc3)ncn1)CC2] | (S)-7'-(3,5-difluorophenyl)-1-(6-phenylpyrimidin-4-yl)dihydro-1'H,3'H,5'H-spiro[piperidine-4,2'-pyrazolo[1,2-a]pyrazol]-1'-one | 462 | 15 |
| 1.36 | 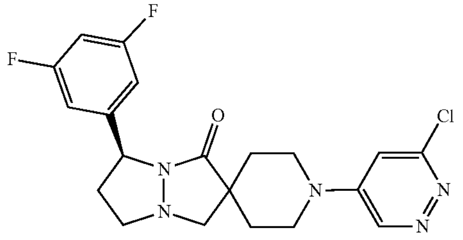 [SMILES: O=C1N2[C@H](c3cc(F)cc(F)c3)CCN2CC12CCN(c1cnnc(Cl)c1)CC2] | (S)-1-(6-chloropyridazin-4-yl)-7'-(3,5-difluorophenyl)dihydro-1'H,3'H,5'H-spiro[piperidine-4,2'-pyrazolo[1,2-a]pyrazol]-1'-one | 420 | 571 |
| 1.37 | 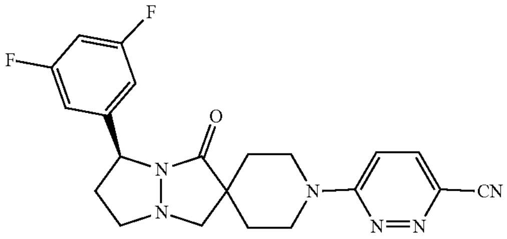 [SMILES: N#Cc1ccc(N2CCC3(CC2)CN2CC[C@@H](c4cc(F)cc(F)c4)N2C3=O)nn1] | (S)-6-(7'-(3,5-difluorophenyl)-1'-oxodihydro-1'H,3'H,5'H-spiro[piperidine-4,2'-pyrazolo[1,2-a]pyrazol]-1-yl)pyridazine-3-carbonitrile | 411 | 473 |
| 1.38 | 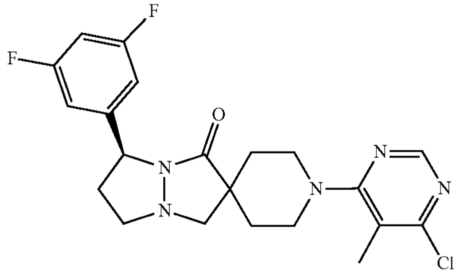 [SMILES: Cc1c(Cl)ncnc1N1CCC2(CC1)CN1CC[C@@H](c3cc(F)cc(F)c3)N1C2=O] | (S)-1-(6-chloro-5-methylpyrimidin-4-yl)-7'-(3,5-difluorophenyl)dihydro-1'H,3'H,5'H-spiro[piperidine-4,2'-pyrazolo[1,2-a]pyrazol]-1'-one | 434 | 20 |
| 1.39 | 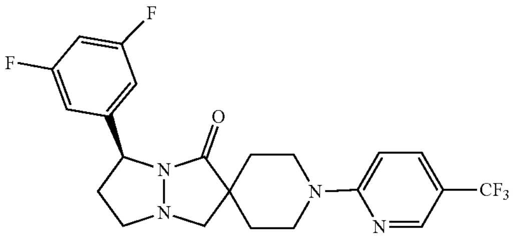 [SMILES: O=C1N2[C@H](c3cc(F)cc(F)c3)CCN2CC12CCN(c1ccc(C(F)(F)F)cn1)CC2] | (S)-7'-(3,5-difluorophenyl)-1-(5-(trifluoromethyl)pyridin-2-yl)dihydro-1'H,3'H,5'H-spiro[piperidine-4,2'-pyrazolo[1,2-a]pyrazol]-1'-one | 453 | 77 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.40 | 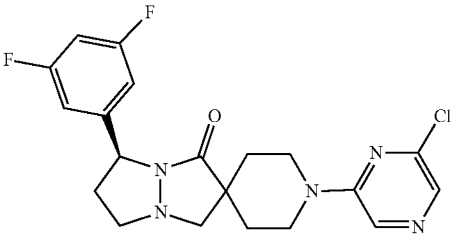 [SMILES: O=C1N2[C@H](c3cc(F)cc(F)c3)CCN2CC12CCN(c1cncc(Cl)n1)CC2] | (S)-1-(6-chloropyrazin--2-yl)7'-(3,5-difluorophenyl) dihydro-1'H,3'H,5'H-spiro[piperidine-4,2'-pyrazolo[1,2-a] pyrazol]-1'-one | 420 | 407 |
| 1.41 | 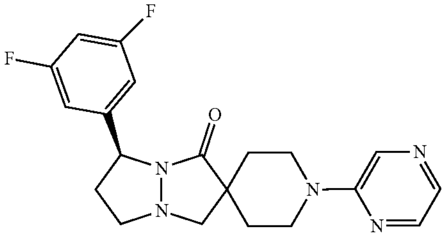 [SMILES: O=C1N2[C@H](c3cc(F)cc(F)c3)CCN2CC12CCN(c1cnccn1)CC2] | (S)-7'-(3,5-difluorophenyl)-1-(pyrazin-2-yl) dihydro-1'H,3'H,5'H-spiro[piperidine-4,2'-pyrazolo[1,2-a] pyrazol]-1'-one | 386 | 308 |
| 1.42 | 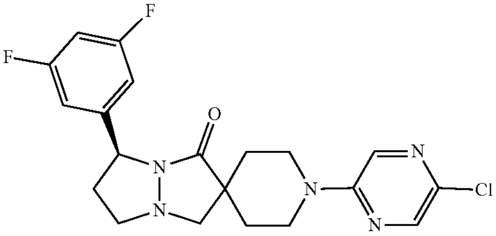 [SMILES: O=C1N2[C@H](c3cc(F)cc(F)c3)CCN2CC12CCN(c1cnc(Cl)cn1)CC2] | (S)-1-(5-chloropyrazin-2-yl)-7'-(3,5-difluorophenyl) dihydro-1'H,3'H,5'H-spiro[piperidine-4,2'-pyrazolo[1,2-a] pyrazol]-1'-one | 420 | 86 |
| 1.43 | 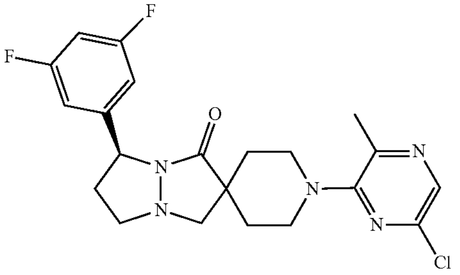 [SMILES: Cc1ncc(Cl)nc1N1CCC2(CC1)CN1CC[C@@H](c3cc(F)cc(F)c3)N1C2=O] | (S)-1-(6-chloro-3-methylpyrazin-2-yl)-7'-(3,5-difluorophenyl) dihydro-1'H,3'H,5'H-spiro[piperidine-4,2'-pyrazolo [1,2-a]pyrazol]-1'-one | 434 | 876 |
| 1.44 | 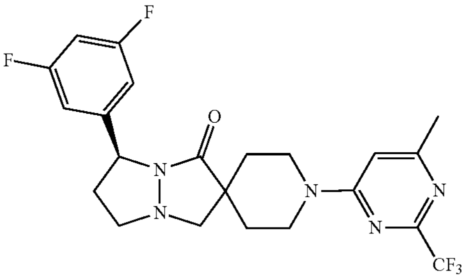 [SMILES: Cc1cc(N2CCC3(CC2)CN2CC[C@@H](c4cc(F)cc(F)c4)N2C3=O)nc(C(F)(F)F)n1] | (S)-7'-(3,5-difluorophenyl)-1-(6-methyl-2-(trifluoromethyl) pyrimidin-4-yl) dihydro-1'H,3'H,5'H-spiro[piperidine-4,2'-pyrazolo[1,2-a] pyrazol]-1'-one | 468 | 274 |

TABLE 1-continued

| Ex. No. | Structure | Name | Observed m/z [M + H]+ | RIPK1 $EC_{50}$ (nM) |
|---|---|---|---|---|
| | Examples Prepared According to Scheme 1. | | | |
| 1.45 | 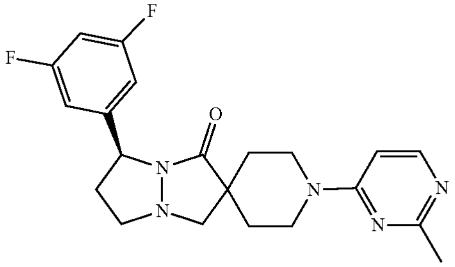 [SMILES: Cc1nccc(N2CCC3(CC2)CN2CC[C@@H](c4cc(F)cc(F)c4)N2C3=O)n1] | (S)-7'-(3,5-difluorophenyl)-1-(2-methylpyrimidin-4-yl)dihydro-1'H,3'H,5'H-spiro[piperidine-4,2'-pyrazolo[1,2-a]pyrazol]-1'-one | 400 | 176 |
| 1.46 | 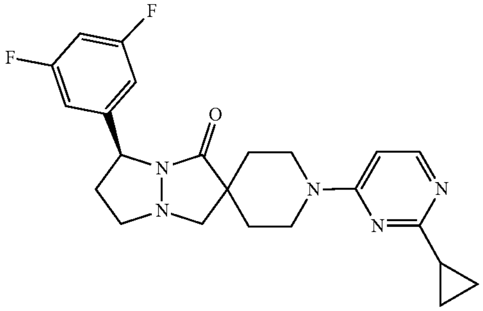 [SMILES: O=C1N2[C@H](c3cc(F)cc(F)c3)CCN2CC12CCN(c1ccnc(C3CC3)n1)CC2] | (S)-1-(2-cyclopropyl-pyrimidin-4-yl)-7'-(3,5-difluorophenyl)dihydro-1'H,3'H,5'H-spiro[piperidine-4,2'-pyrazolo[1,2-a]pyrazol]-1'-one | 426 | 59 |
| 1.47 | 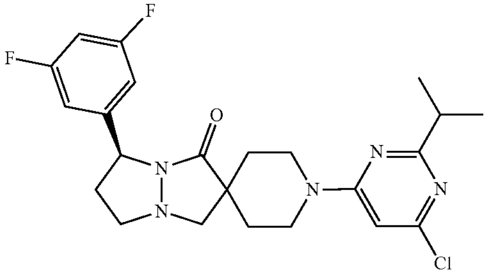 [SMILES: CC(C)c1nc(Cl)cc(N2CCC3(CC2)CN2CC[C@@H](c4cc(F)cc(F)c4)N2C3=O)n1] | (S)-1-(6-chloro-2-isopropylpyrimidin-4-yl)-7'-(3,5-difluorophenyl)dihydro-1'H,3'H,5'H-spiro[piperidine-4,2'-pyrazolo[1,2-a]pyrazol]-1'-one | 462 | 153 |
| 1.48 | 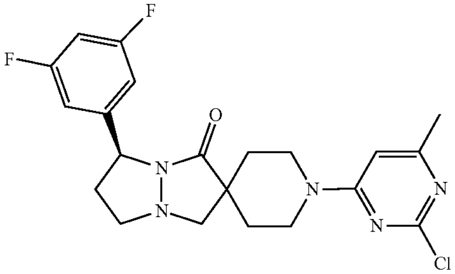 [SMILES: Cc1cc(N2CCC3(CC2)CN2CC[C@@H](c4cc(F)cc(F)c4)N2C3=O)nc(Cl)n1] | (S)-1-(2-chloro-6-methylpyrimidin-4-yl)-7'-(3,5-difluorophenyl)dihydro-1'H,3'H,5'H-spiro[piperidine-4,2'-pyrazolo[1,2-a]pyrazol]-1'-one | 434 | 144 |
| 1.49 | 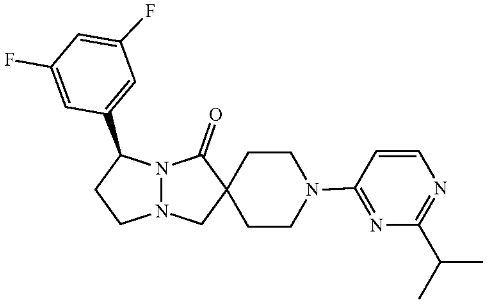 [SMILES: CC(C)c1nccc(N2CCC3(CC2)CN2CC[C@@H](c4cc(F)cc(F)c4)N2C3=O)n1] | (S)-7'-(3,5-difluorophenyl)-1-(2-isopropylpyrimidin-4-yl)dihydro-1'H,3'H,5'H-spiro[piperidine-4,2'-pyrazolo[1,2-a]pyrazol]-1'-one | 428 | 295 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.50 | 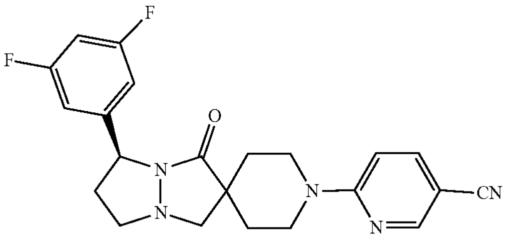 [SMILES: N#Cc1ccc(N2CCC3(CC2)CN2CC[C@@H](c4cc(F)cc(F)c4)N2C3=O)nc1] | (S)-6-(7'-(3,5-difluorophenyl)-1'-oxodihydro-1'H,3'H,5'H-spiro [piperidine-4,2'-pyrazolo[1,2-a] pyrazol]-1-yl)nicotinonitrile | 410 | 64 |
| 1.51 | 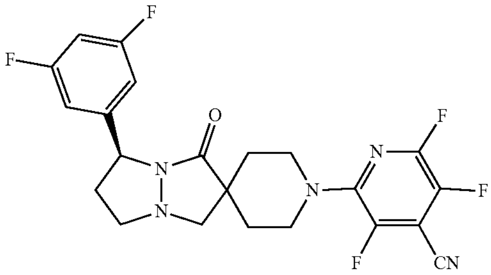 [SMILES: N#Cc1c(F)c(F)nc(N2CCC3(CC2)CN2CC[C@@H](c4cc(F)cc(F)c4)N2C3=O)c1F] | (S)-2-(7'-(3,5-difluorophenyl)-1'-oxodihydro-1'H,3'H,5'H-spiro [piperidine-4,2'-pyrazolo[1,2-a] pyrazol]-1-yl)-3,5,6-trifluoroiso-nicotinonitrile | 464 | 189 |
| 1.52 | 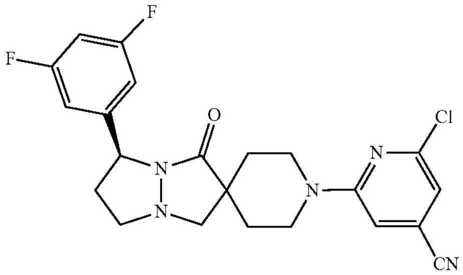 [SMILES: N#Cc1cc(Cl)nc(N2CCC3(CC2)CN2CC[C@@H](c4cc(F)cc(F)c4)N2C3=O)c1] | (S)-2-chloro-6-(7'-(3,5-difluorophenyl)-1'-oxodihydro-1'H,3'H,5'H-spiro [piperidine-4,2'-pyrazolo[1,2-a] pyrazol]-1-yl)isonicotinonitrile | 444 | 54 |
| 1.53 | 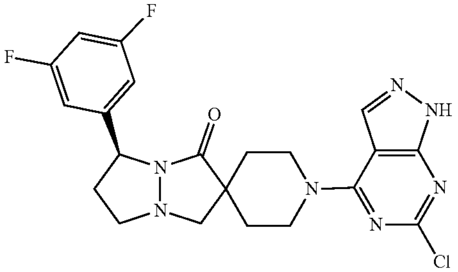 [SMILES: O=C1N2[C@H](c3cc(F)cc(F)c3)CCN2CC12CCN(c1nc(Cl)nc3[nH]ncc13)CC2] | (S)-1-(6-chloro-1H-pyrazolo[3,4-d] pyrimidin-4-yl)-7'-(3,5-difluorophenyl) dihydro-1'H,3'H,5'H-spiro[piperidine-4,2'-pyrazolo[1,2-a] pyrazol]-1'-one | 460 | 857 |
| 1.54 | 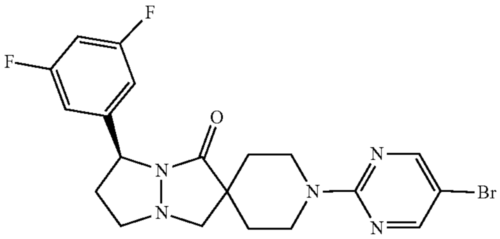 [SMILES: O=C1N2[C@H](c3cc(F)cc(F)c3)CCN2CC12CCN(c1ncc(Br)cn1)CC2] | (S)-1-(5-bromopyrimidin-2-yl)-7'-(3,5-difluorophenyl) dihydro-1'H,3'H,5'H-spiro[piperidine-4,2'-pyrazolo [1,2-a]pyrazol]-1'-one | 464 | 17 |

TABLE 1-continued

| Examples Prepared According to Scheme 1. | | | | |
|---|---|---|---|---|
| Ex. No. | Structure | Name | Observed m/z $[M+H]^+$ | RIPK1 $EC_{50}$ (nM) |
| 1.55 | 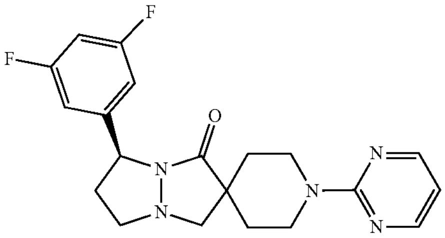 [SMILES: O=C1N2[C@H](c3cc(F)cc(F)c3)CCN2CC12CCN(c1ncccn1)CC2] | (S)-7'-(3,5-difluorophenyl)-1-(pyrimidin-2-yl)dihydro-1'H,3'H,5'H-spiro[piperidine-4,2'-pyrazolo[1,2-a]pyrazol]-1'-one | 386 | 804 |
| 1.56 | 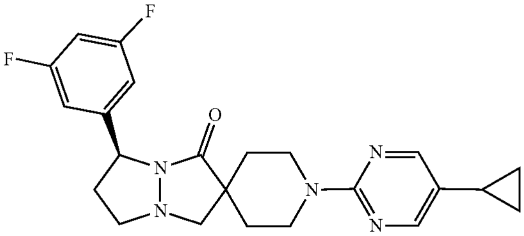 [SMILES: O=C1N2[C@H](c3cc(F)cc(F)c3)CCN2CC12CCN(c1ncc(C3CC3)cn1)CC2] | (S)-1-(5-cyclopropyl-pyrimidin-2-yl)-7'-(3,5-difluorophenyl)dihydro-1'H,3'H,5'H-spiro[piperidine-4,2'-pyrazolo[1,2-a]pyrazol]-1'-one | 426 | 321 |
| 1.57 | 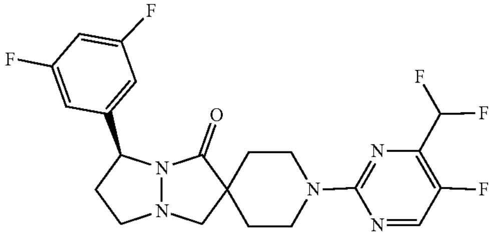 [SMILES: O=C1N2[C@H](c3cc(F)cc(F)c3)CCN2CC12CCN(c1ncc(F)c(C(F)F)n1)CC2] | (S)-1-(4-(difluoromethyl)-5-fluoropyrimidin-2-yl)-7'-(3,5-difluorophenyl)dihydro-1'H,3'H,5'H-spiro[piperidine-4,2'-pyrazolo[1,2-a]pyrazol]-1'-one | 454 | 26 |
| 1.58 | 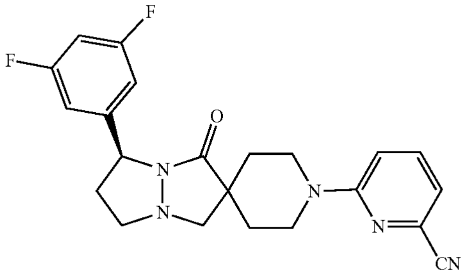 [SMILES: N#Cc1cccc(N2CCC3(CC2)CN2CC[C@@H](c4cc(F)cc(F)c4)N2C3=O)n1] | (S)-6-(7'-(3,5-difluorophenyl)-1'-oxodihydro-1'H,3'H,5'H-spiro[piperidine-4,2'-pyrazolo[1,2-a]pyrazol]-1-yl)picolinonitrile | 410 | 34 |
| 1.59 | 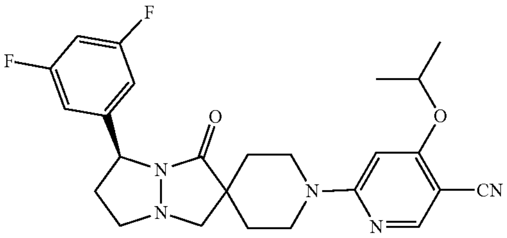 [SMILES: CC(C)Oc1cc(N2CCC3(CC2)CN2CC[C@@H](c4cc(F)cc(F)c4)N2C3=O)ncc1C#N] | (S)-6-(7'-(3,5-difluorophenyl)-1'-oxodihydro-1'H,3'H,5'H-spiro[piperidine-4,2'-pyrazolo[1,2-a]pyrazol]-1-yl)-4-isopropoxy-nicotinonitrile | 468 | 18 |

TABLE 1-continued

| Ex. No. | Structure | Name | Observed m/z [M + H]+ | RIPK1 $EC_{50}$ (nM) |
|---|---|---|---|---|
| | Examples Prepared According to Scheme 1. | | | |
| 1.60 | 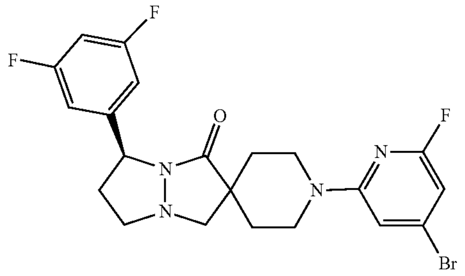 [SMILES: O=C1N2[C@H](c3cc(F)cc(F)c3)CCN2CC12CCN(c1cc(Br)cc(F)n1)CC2] | (S)-1-(4-bromo-6-fluoropyridin-2-yl)-7'-(3,5-difluorophenyl) dihydro-1'H,3'H,5'H-spiro[piperidine-4,2'-pyrazolo[1,2-a] pyrazol]-1'-one | 481 | 17 |
| 1.61 | 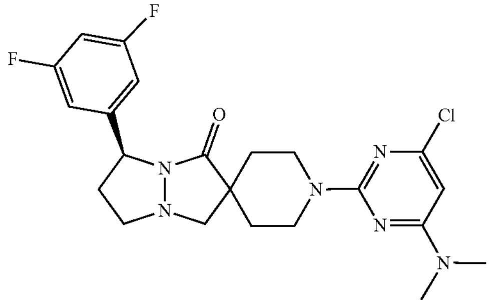 [SMILES: CN(C)c1cc(Cl)nc(N2CCC3(CC2)CN2CC[C@@H](c4cc(F)cc(F)c4)N2C3=O)n1] | (S)-1-(4-chloro-6-(dimethylamino) pyrimidin-2-yl)-7'-(3,5-difluorophenyl) dihydro-1'H,3'H,5'H-spiro[piperidine-4,2'-pyrazolo [1,2-a]pyrazol]-1'-one | 463 | 904 |
| 1.62 | 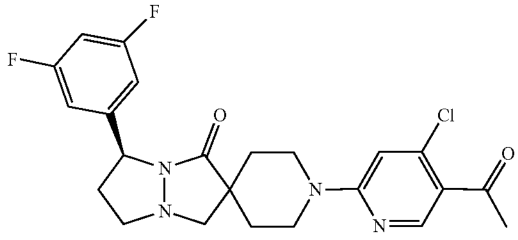 [SMILES: CC(=O)c1cnc(N2CCC3(CC2)CN2CC[C@@H](c4cc(F)cc(F)c4)N2C3=O)cc1Cl] | (S)-1-(5-acetyl-4-chloropyridin-2-yl)-7'-(3,5-difluorophenyl) dihydro-1'H,3'H,5'H-spiro[piperidine-4,2'-pyrazolo[1,2-a] pyrazol]-1'-one | 461 | 20 |
| 1.63 | 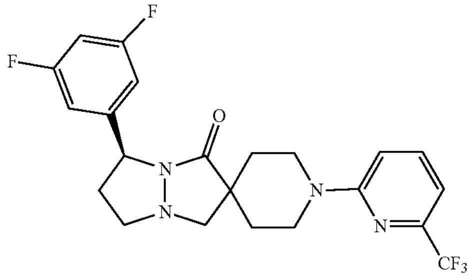 [SMILES: O=C1N2[C@H](c3cc(F)cc(F)c3)CCN2CC12CCN(c1cccc(C(F)(F)F)n1)CC2] | (S)-7'-(3,5-difluorophenyl)-1-(6-(trifluoromethyl) pyridin-2-yl) dihydro-1'H,3'H,5'H-spiro[piperidine-4,2'-pyrazolo[1,2-a] pyrazol]-1'-one | 453 | 83 |
| 1.64 | 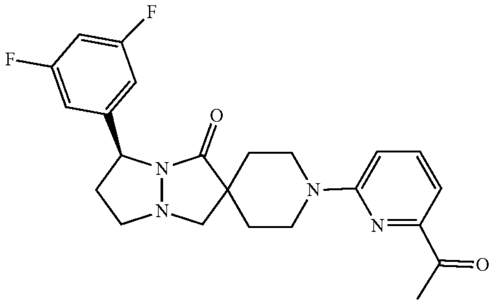 [SMILES: CC(=O)c1cccc(N2CCC3(CC2)CN2CC[C@@H](c4cc(F)cc(F)c4)N2C3=O)n1] | (S)-1-(6-acetylpyridin-2-yl)-7'-(3,5-difluorophenyl) dihydro-1'H,3'H,5'H-spiro[piperidine-4,2'-pyrazolo[1,2-a] pyrazol]-1'-one | 427 | 25 |

TABLE 1-continued

Examples Prepared According to Scheme 1.

| Ex. No. | Structure | Name | Observed m/z [M + H]+ | RIPK1 $EC_{50}$ (nM) |
|---|---|---|---|---|
| 1.65 | 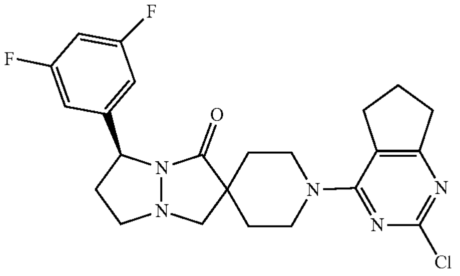 [SMILES: O=C1N2[C@H](c3cc(F)cc(F)c3)CCN2CC12CCN(c1nc(Cl)nc3c1CCC3)CC2] | (S)-1-(2-chloro-6,7-dihydro-5H-cyclopenta[d] pyrimidin-4-yl)-7'-(3,5-difluorophenyl) dihydro-1'H,3'H,5'H-spiro[piperidine-4,2'-pyrazolo[1,2-a] pyrazol]-1'-one | 460 | 144 |
| 1.66 | 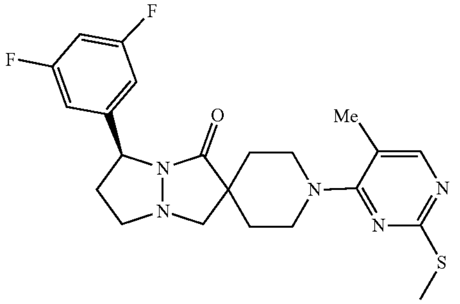 [SMILES: CSc1ncc(C)c(N2CCC3(CC2)CN2CC[C@@H](c4cc(F)cc(F)c4)N2C3=O)n1] | (S)-7'-(3,5-difluorophenyl)-1-(5-methyl-2-(methylthio) pyrimidin-4-yl) dihydro-1'H,3'H,5'H-spiro[piperidine-4,2'-pyrazolo[1,2-a] pyrazol]-1'-one | 446 | 673 |
| 1.67 | 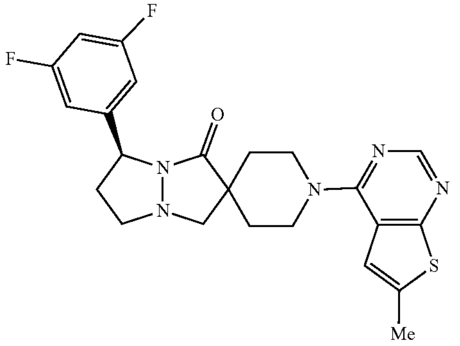 [SMILES: Cc1cc2c(N3CCC4(CC3)CN3CC[C@@H](c5cc(F)cc(F)c5)N3C4=O)ncnc2s1] | (S)-7'-(3,5-difluorophenyl)-1-(6-methylthieno[2,3-d]pyrimidin-4-yl) dihydro-1'H,3'H,5'H-spiro[piperidine-4,2'-pyrazolo[1,2-a] pyrazol]-1'-one | 456 | 38 |
| 1.68 | 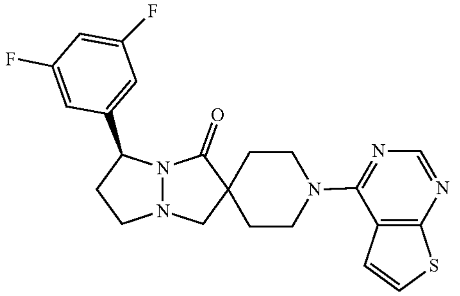 [SMILES: O=C1N2[C@H](c3cc(F)cc(F)c3)CCN2CC12CCN(c1ncnc3sccc13)CC2] | (S)-7'-(3,5-difluorophenyl)-1-(thieno[2,3-d] pyrimidin-4-yl) dihydro-1'H,3'H,5'H-spiro [piperidine-4,2'-pyrazolo[1,2-a] pyrazol]-1'-one | 442 | 24 |
| 1.69 | 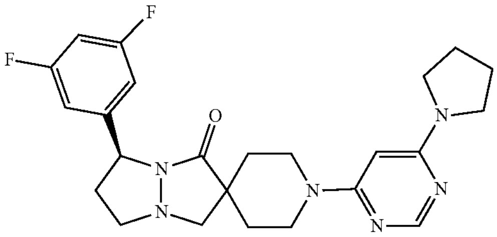 [SMILES: O=C1N2[C@H](c3cc(F)cc(F)c3)CCN2CC12CCN(c1cc(N3CCCC3)ncn1)CC2] | (S)-7'-(3,5-difluorophenyl)-1-(6-(pyrrolidin-1-yl)pyrimidin-4-yl) dihydro-1'H,3'H,5'H-spiro[piperidine-4,2'-pyrazolo[1,2-a] pyrazol]-1'-one | 455 | 296 |

TABLE 1-continued

Examples Prepared According to Scheme 1.

| Ex. No. | Structure | Name | Observed m/z [M + H]+ | RIPK1 $EC_{50}$ (nM) |
|---|---|---|---|---|
| 1.70 | 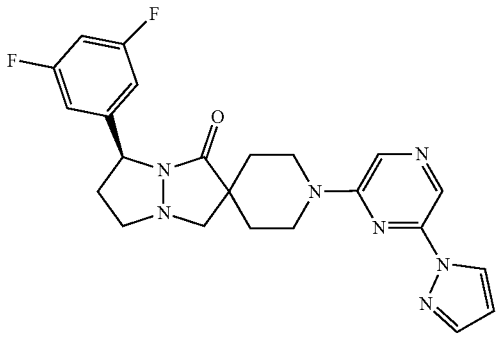 [SMILES: O=C1N2[C@H](c3cc(F)cc(F)c3)CCN2CC12CCN(c1cncc(-n3cccn3)n1)CC2] | (S)-1-(6-(1H-pyrazol-1-yl) pyrazin-2-yl)-7'-(3,5-difluorophenyl)-dihydro1'H,3'H,5'H-spiro[piperidine-4,2'-pyrazolo[1,2-a] pyrazol]-1'-one | 452 | 82 |
| 1.71 | 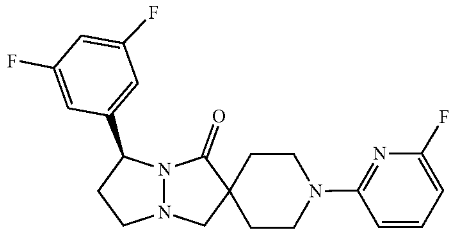 [SMILES: O=C1N2[C@H](c3cc(F)cc(F)c3)CCN2CC12CCN(c1cccc(F)n1)CC2] | (S)-7'-(3,5-difluorophenyl)-1-(6-fluoropyridin-2-yl)dihydro-1'H,3'H,5'H-spiro [piperidine-4,2'-pyrazolo[1,2-a] pyrazol]-1'-one | 403 | 28 |
| 1.72 | 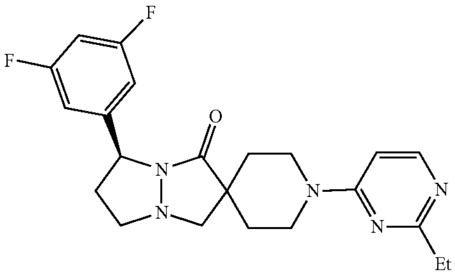 [SMILES: CCc1nccc(N2CCC3(CC2)CN2CC[C@@H](c4cc(F)cc(F)c4)N2C3=O)n1] | (S)-7'-(3,5-difluorophenyl)-1-(2-ethylpyrimidin-4-yl)dihydro-1'H,3'H,5'H-spiro [piperidine-4,2'-pyrazolo[1,2-a] pyrazol]-1'-one | 414 | 208 |
| 1.73 | 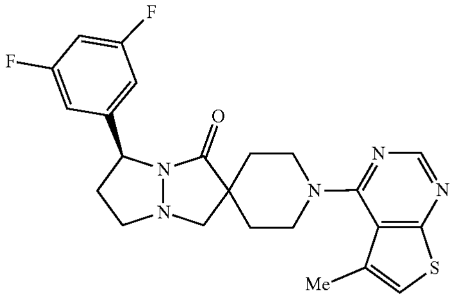 [SMILES: Cc1csc2ncnc(N3CCC4(CC3)CN3CC[C@@H](c5cc(F)cc(F)c5)N3C4=O)c12] | (S)-7'-(3,5-difluorophenyl)-1-(5-methylthieno [2,3-d]pyrimidin-4-yl)dihydro-1'H,3'H,5'H-spiro [piperidine-4,2'-pyrazolo[1,2-a] pyrazol]-1'-one | 456 | 4 |
| 1.74 | 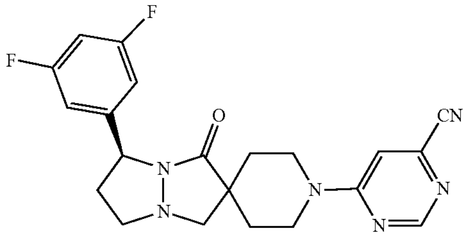 [SMILES: N#Cc1cc(N2CCC3(CC2)CN2CC[C@@H](c4cc(F)cc(F)c4)N2C3=O)ncn1] | (S)-6-(7'-(3,5-difluorophenyl)-1'-oxodihydro-1'H,3'H,5'H-spiro [piperidine-4,2'-pyrazolo[1,2-a] pyrazol]-1-yl) pyrimidine-4-carbonitrile | 411 | 30 |

TABLE 1-continued

| Ex. No. | Structure | Name | Observed m/z [M + H]+ | RIPK1 $EC_{50}$ (nM) |
|---|---|---|---|---|
| Examples Prepared According to Scheme 1. | | | | |
| 1.75 | 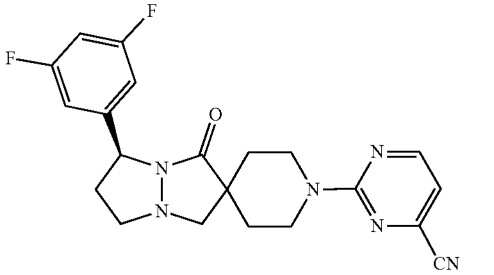 [SMILES: N#Cc1ccnc(N2CCC3(CC2)CN2CC[C@@H](c4cc(F)cc(F)c4)N2C3=O)n1] | (S)-2-(7'-(3,5-difluorophenyl)-1'-oxodihydro-1'H,3'H,5'H-spiro[piperidine-4,2'-pyrazolo[1,2-a]pyrazol]-1-yl)pyrimidine-4-carbonitrile | 411 | 49 |
| 1.76 | 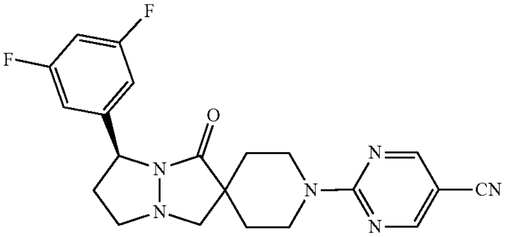 [SMILES: N#Cc1cnc(N2CCC3(CC2)CN2CC[C@@H](c4cc(F)cc(F)c4)N2C3=O)nc1] | (S)-2-(7'-(3,5-difluorophenyl)-1'-oxodihydro-1'H,3'H,5'H-spiro[piperidine-4,2'-pyrazolo[1,2-a]pyrazol]-1-yl)pyrimidine-5-carbonitrile | 411 | 35 |
| 1.77 | 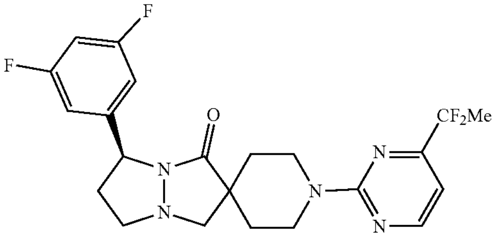 | (S)-1-(4-(1,1-difluoroethyl)pyrimidin-2-yl)-7'-(3,5-difluorophenyl)dihydro-1'H,3'H,5'H-spiro[piperidine-4,2'-pyrazolo[1,2-a]pyrazol]-1'-one | 450 | 200 |
| 1.78 | 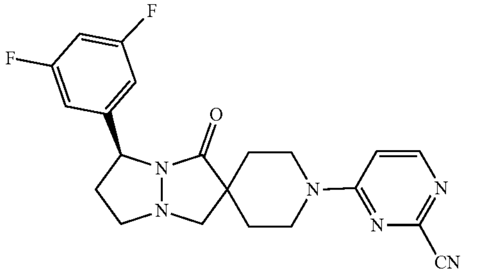 [SMILES: N#Cc1nccc(N2CCC3(CC2)CN2CC[C@@H](c4cc(F)cc(F)c4)N2C3=O)n1] | (S)-4-(7'-(3,5-difluorophenyl)-1'-oxodihydro-1'H,3'H,5'H-spiro[piperidine-4,2'-pyrazolo[1,2-a]pyrazol]-1-yl)pyrimidine-2-carbonitrile | 411 | 73 |
| 1.79 | 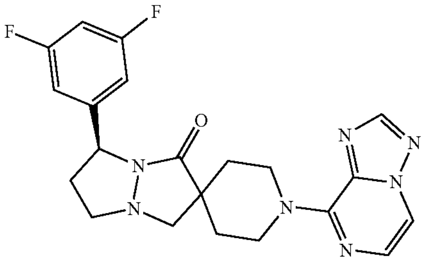 [SMILES: O=C1N2[C@H](c3cc(F)cc(F)c3)CCN2CC12CCN(c1nccn3ncnc13)CC2] | (S)-1-([1,2,4]triazolo[1,5-a]pyrazin-8-yl)-7'-(3,5-difluorophenyl)dihydro-1'H,3'H,5'H-spiro[piperidine-4,2'-pyrazolo[1,2-a]pyrazol]-1'-one | 426 | 30 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.80 | 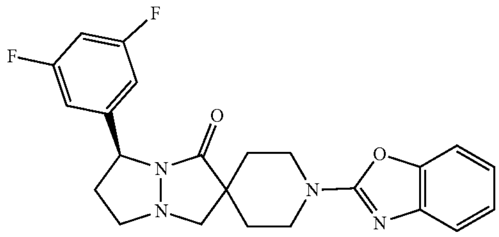 [SMILES: O=C1N2[C@H](c3cc(F)cc(F)c3)CCN2CC12CCN(c1nc3ccccc3o1)CC2] | (S)-1-(benzo[d]oxazol-2-yl)-7'-(3,5-difluorophenyl)dihydro-1'H,3'H,5'H-spiro[piperidine-4,2'-pyrazolo[1,2-a]pyrazol]-1'-one | 425 | 50 |
| 1.81 | 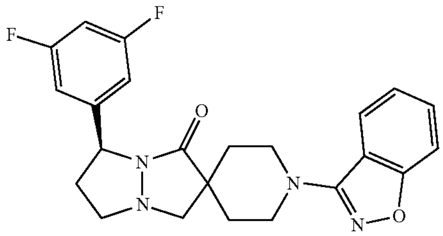 [SMILES: O=C1N2[C@H](c3cc(F)cc(F)c3)CCN2CC12CCN(c1noc3ccccc13)CC2] | (S)-1-(benzo[d]isoxazol-3-yl)-7'-(3,5-difluorophenyl)dihydro-1'H,3'H,5'H-spiro[piperidine-4,2'-pyrazolo[1,2-a]pyrazol]-1'-one | 425 | 366 |
| 1.82 | 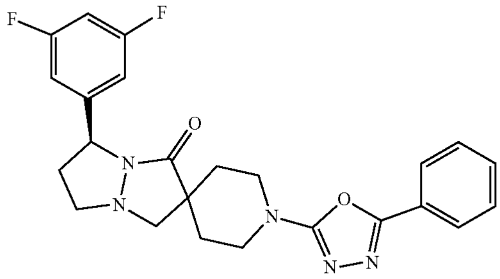 [SMILES: O=C1N2[C@H](c3cc(F)cc(F)c3)CCN2CC12CCN(c1nnc(-c3ccccc3)o1)CC2] | (S)-7'-(3,5-difluorophenyl)-1-(5-phenyl-1,3,4-oxadiazol-2-yl)dihydro-1'H,3'H,5'H-spiro[piperidine-4,2'-pyrazolo[1,2-a]pyrazol]-1'-one | 452 | 333 |
| 1.83 | 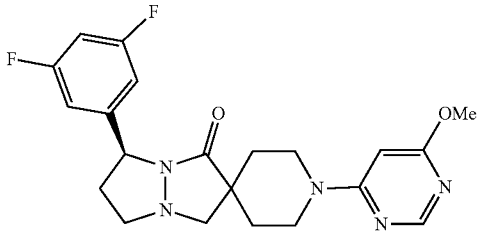 [SMILES: COc1cc(N2CCC3(CC2)CN2CC[C@@H](c4cc(F)cc(F)c4)N2C3=O)ncn1] | (S)-7'-(3,5-difluorophenyl)-1-(6-methoxypyrimidin-4-yl)dihydro-1'H,3'H,5'H-spiro[piperidine-4,2'-pyrazolo[1,2-a]pyrazol]-1'-one | 416 | 28 |
| 1.84 | 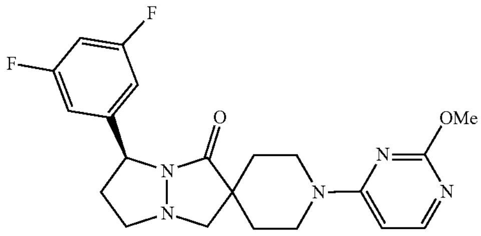 [SMILES: COc1nccc(N2CCC3(CC2)CN2CC[C@@H](c4cc(F)cc(F)c4)N2C3=O)n1] | (S)-7'-(3,5-difluorophenyl)-1-(2-methoxypyrimidin-4-yl)dihydro-1'H,3'H,5'H-spiro[piperidine-4,2'-pyrazolo[1,2-a]pyrazol]-1'-one | 416 | 30 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.85 | 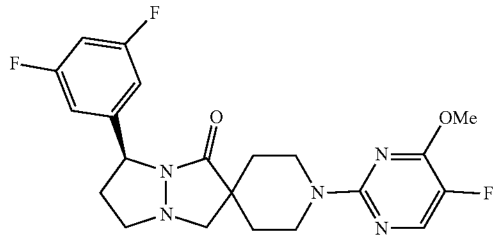 [SMILES: COc1nc(N2CCC3(CC2)CN2CC[C@@H](c4cc(F)cc(F)c4)N2C3=O)ncc1F] | (S)-7'-(3,5-difluorophenyl)-1-(5-fluoro-4-methoxypyrimidin-2-yl)dihydro-1'H,3'H,5'H-spiro[piperidine-4,2'-pyrazolo[1,2-a]pyrazol]-1'-one | 434 | 22 |
| 1.86 | 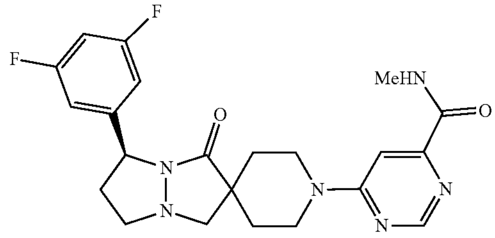 [SMILES: CNC(=O)c1cc(N2CCC3(CC2)CN2CC[C@@H](c4cc(F)cc(F)c4)N2C3=O)ncn1] | (S)-6-(7'-(3,5-difluorophenyl)-1'-oxodihydro-1'H,3'H,5'H-spiro[piperidine-4,2'-pyrazolo[1,2-a]pyrazol]-1-yl)-N-methylpyrimidine-4-carboxamide | 443 | 555 |
| 1.87 | 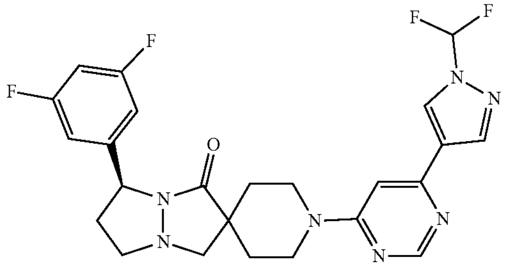 [SMILES: O=C1N2[C@H](c3cc(F)cc(F)c3)CCN2CC12CCN(c1cc(-c3cnn(C(F)F)c3)ncn1)CC2] | (S)-1-(6-(1-(difluoromethyl)-1H-pyrazol-4-yl)pyrimidin-4-yl)-7'-(3,5-difluorophenyl)dihydro-1'H,3'H,5'H-spiro[piperidine-4,2'-pyrazolo[1,2-a]pyrazol]-1'-one | 502 | 6 |
| 1.88 | 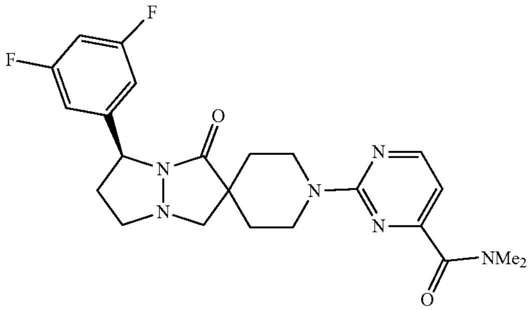 [SMILES: CN(C)C(=O)c1ccnc(N2CCC3(CC2)CN2CC[C@@H](c4cc(F)cc(F)c4)N2C3=O)n1] | (S)-2-(7'-(3,5-difluorophenyl)-1'-oxodihydro-1'H,3'H,5'H-spiro[piperidine-4,2'-pyrazolo[1,2-a]pyrazol]-1-yl)-N,N-dimethylpyrimidine-4-carboxamide | 457 | 111 |
| 1.89 | 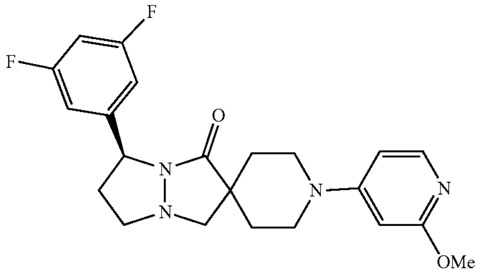 [SMILES: COc1cc(N2CCC3(CC2)CN2CC[C@@H](c4cc(F)cc(F)c4)N2C3=O)ccn1] | (S)-7'-(3,5-difluorophenyl)-1-(2-methoxypyridin-4-yl)dihydro-1'H,3'H,5'H-spiro[piperidine-4,2'-pyrazolo[1,2-a]pyrazol]-1'-one | 415 | 24 |

TABLE 1-continued

| Examples Prepared According to Scheme 1. | | | | |
|---|---|---|---|---|
| Ex. No. | Structure | Name | Observed m/z [M + H]+ | RIPK1 $EC_{50}$ (nM) |
| 1.90 | 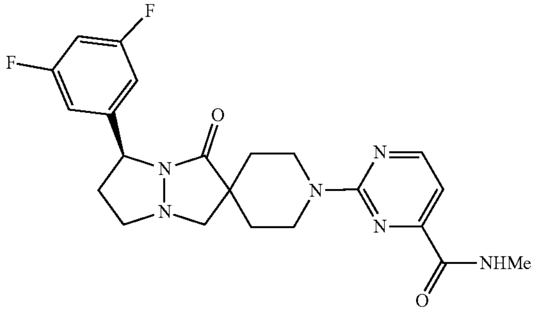 [SMILES: CNC(=O)c1ccnc(N2CCC3(CC2)CN2CC[C@@H](c4cc(F)cc(F)c4)N2C3=O)n1] | (S)-2-(7'-(3,5-difluorophenyl)-1'-oxodihydro-1'H,3'H,5'H-spiro[piperidine-4,2'-pyrazolo[1,2-a]pyrazol]-1-yl)-N-methylpyrimidine-4-carboxamide | 443 | 106 |
| 1.91 | 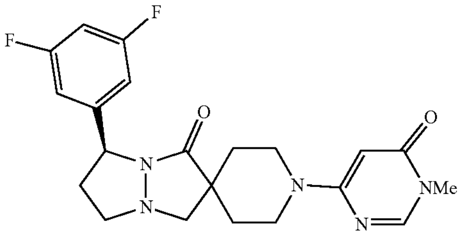 [SMILES: Cn1cnc(N2CCC3(CC2)CN2CC[C@@H](c4cc(F)cc(F)c4)N2C3=O)cc1=O] | (S)-7'-(3,5-difluorophenyl)-1-(1-methyl-6-oxo-1,6-dihydropyrimidin-4-yl)dihydro-1'H,3'H,5'H-spiro[piperidine-4,2'-pyrazolo[1,2-a]pyrazol]-1'-one | 416 | 750 |
| 1.92 | 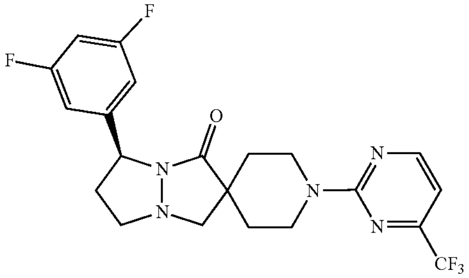 [SMILES: O=C1N2[C@H](c3cc(F)cc(F)c3)CCN2CC12CCN(c1nccc(C(F)(F)F)n1)CC2] | (S)-7'-(3,5-difluorophenyl)-1-(4-(trifluoromethyl)pyrimidin-2-yl)dihydro-1'H,3'H,5'H-spiro[piperidine-4,2'-pyrazolo[1,2-a]pyrazol]-1'-one | 454 | 91 |
| 1.93 | 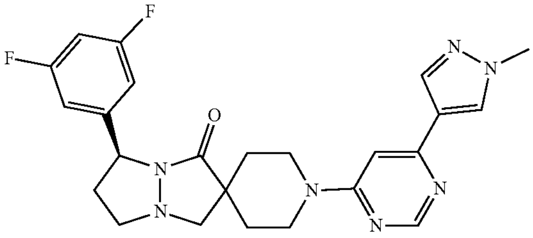 [SMILES: Cn1cc(-c2cc(N3CCC4(CC3)CN3CC[C@@H](c5cc(F)cc(F)c5)N3C4=O)ncn2)cn1] | (S)-7'-(3,5-difluorophenyl)-1-(6-(1-methyl-1H-pyrazol-4-yl)pyrimidin-4-yl)dihydro-1'H,3'H,5'H-spiro[piperidine-4,2'-pyrazolo[1,2-a]pyrazol]-1'-one | 466 | 17 |
| 1.94 | 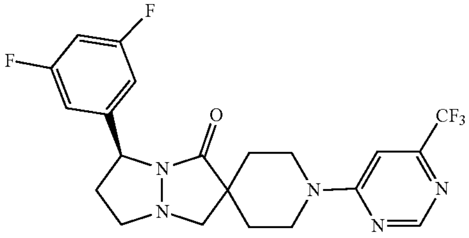 [SMILES: O=C1N2[C@H](c3cc(F)cc(F)c3)CCN2CC12CCN(c1cc(C(F)(F)F)ncn1)CC2] | (S)-7'-(3,5-difluorophenyl)-1-(6-(trifluoromethyl)pyrimidin-4-yl)dihydro-1'H,3'H,5'H-spiro[piperidine-4,2'-pyrazolo[1,2-a]pyrazol]-1'-one | 454 | 85 |

TABLE 1-continued

| Examples Prepared According to Scheme 1. | | | | |
|---|---|---|---|---|
| Ex. No. | Structure | Name | Observed m/z [M + H]$^+$ | RIPK1 $EC_{50}$ (nM) |
| 1.95 | 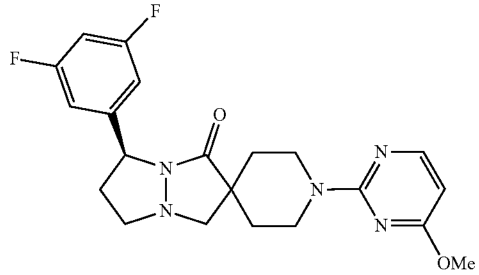 [SMILES: COc1ccnc(N2CCC3(CC2)CN2CC[C@@H](c4cc(F)cc(F)c4)N2C3=O)n1] | (S)-7'-(3,5-difluorophenyl)-1-(4-methoxypyrimidin-2-yl)dihydro-1'H,3'H,5'H-spiro[piperidine-4,2'-pyrazolo[1,2-a]pyrazol]-1'-one | 416 | 86 |
| 1.96 | 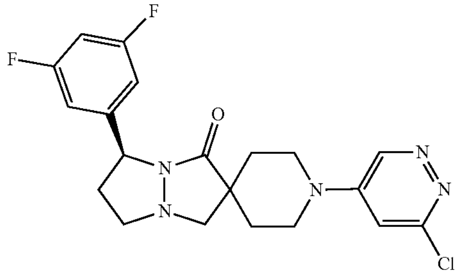 [SMILES: O=C1N2[C@H](c3cc(F)cc(F)c3)CCN2CC12CCN(c1cnnc(Cl)c1)CC2] | (S)-1-(6-chloropyridazin-4-yl)-7'-(3,5-difluorophenyl)dihydro-1'H,3'H,5'H-spiro[piperidine-4,2'-pyrazolo[1,2-a]pyrazol]-1'-one | 420 | 571 |

Preparation of Example 2.1, (S)-1-(4-bromopyrazolo[1,5-a]pyridin-7-yl)-7'-(3,5-difluorophenyl)dihydro-1'H,3'H,5'H-spiro[piperidine-4,2'-pyrazolo[1,2-a]pyrazol]-1'-one, TFA salt Scheme 2

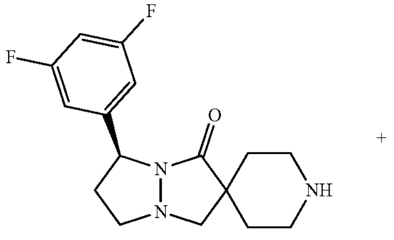

J.2

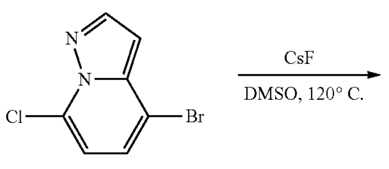

2.A

-continued

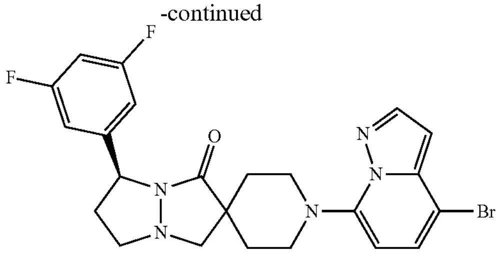

2.1

A scintillation vial containing(S)-7'-(3,5-difluorophenyl)dihydro-1'H,3'H,5'H-spiro[piperidine-4,2'-pyrazolo[1,2-a]pyrazol]-1'-one (100 mg, 0.325 mmol), 4-bromo-7-chloro-pyrazolo[1,5-a]pyridine (113 mg, 0.488 mmol), and CsF (148 mg, 0.976 mmol) was taken up in DMSO (3.3 mL), and the resulting mixture was stirred for 16 h at 120° C. After cooling, the reaction mixture was directly filtered and purified via reversed phase HPLC [Method A]. This provided (S)-1-(4-bromopyrazolo[1,5-a]pyridin-7-yl)-7'-(3,5-difluorophenyl)dihydro-1'H,3'H,5'H-spiro[piperidine-4,2'-pyrazolo[1,2-a]pyrazol]-1'-one, TFA salt. MS (ESI) m z $C_{23}H_{23}BrF2N_5O$ [M+1]$^+$ calc'd 502, found 502, 504. $^1$HNMR (600 MHZ, DMSO-$d_6$) δ 8.10 (d, J=2.2 Hz, 1H), 7.48 (d, J=7.9 Hz, 1H), 7.19-7.11 (m, 1H), 7.01 (d, J=6.4 Hz, 2H), 6.63 (d, J=2.2 Hz, 1H), 6.30 (d, J=8.0 Hz, 1H), 5.05 (app t, J=7.7 Hz, 1H), 3.92-3.84 (m, 1H), 3.84-3.75 (m, 2H), 3.33 (br s, 1H), 3.20-3.11 (m, 1H), 3.03-2.92 (m, 2H), 2.92-2.82 (m, 1H), 2.63 (br s, 1H), 2.15-2.03 (m, 2H), 2.92-1.92 (m, 2H), 1.73 (d, J=13.5 Hz, 1H). RIPK1 $EC_{50}$ 7.5 nM.

The following examples in Table 2 were prepared according to Scheme 2 using intermediate J.2, and the appropriate commercially available heteroaryl halide. The compounds were generally purified by reversed phase HPLC.

TABLE 2

Examples Prepared According to Scheme 2.

| Ex. No. | Structure | Name | Observed m/z [M + H]$^+$ | RIPK1 $EC_{50}$ (nM) |
|---|---|---|---|---|
| 2.2 | 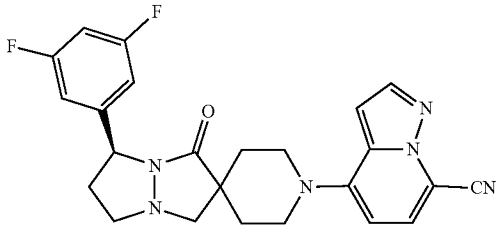 [SMILES: N#Cc1ccc(N2CCC3(CC2)CN2CC[C@@H](c4cc(F)cc(F)c4)N2C3=O)c2ccnn12] | (S)-4-(7'-(3,5-difluorophenyl)-1'-oxodihydro-1'H,3'H,5'H-spiro [piperidine-4,2'-pyrazolo[1,2-a] pyrazol]-1-yl)pyrazolo [1,5-a]pyridine-7-carbonitrile | 449 | 9 |
| 2.3 | 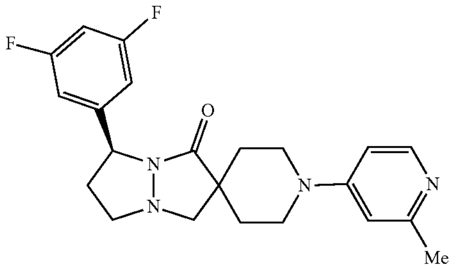 [SMILES: Cc1cc(N2CCC3(CC2)CN2CC[C@@H](c4cc(F)cc(F)c4)N2C3=O)ccn1] | (S)-7'-(3,5-difluorophenyl)-1-(2-methylpyridin-4-yl)dihydro-1'H,3'H,5'H-spiro[piperidine-4,2'-pyrazolo [1,2-a] pyrazol]-1'-one | 399 | 501 |
| 2.4 | 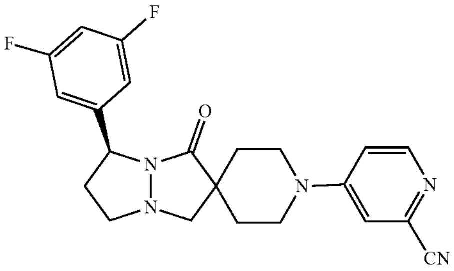 [SMILES: N#Cc1cc(N2CCC3(CC2)CN2CC[C@@H](c4cc(F)cc(F)c4)N2C3=O)ccn1] | (S)-4-(7'-(3,5-difluorophenyl)-1'-oxodihydro-1'H,3'H,5'H-spiro [piperidine-4,2'-pyrazolo [1,2-a] pyrazol]-1-yl) picolinonitrile | 410 | 49 |
| 2.5 | 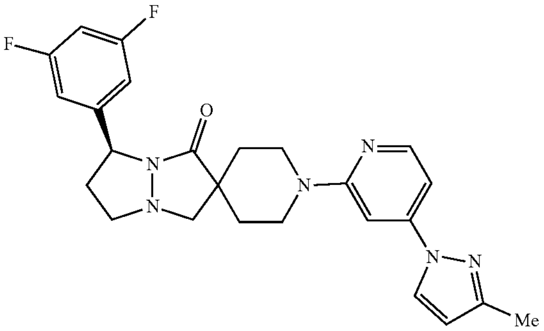 [SMILES: Cc1ccn(-c2ccnc(N3CCC4(CC3)CN3CC[C@@H](c5cc(F)cc(F)c5)N3C4=O)c2)n1] | (S)-7'-(3,5-difluorophenyl)-1-(4-(3-methyl-1H-pyrazol-1-yl) pyridin-2-yl) dihydro-1'H,3'H,5'H-spiro [piperidine-4,2'-pyrazolo[1,2-a] pyrazol]-1'-one | 465 | 118 |
| 2.6 | 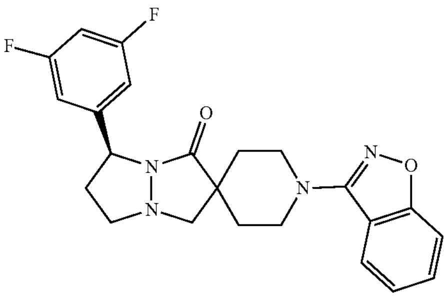 [SMILES: O=C1N2[C@H](c3cc(F)cc(F)c3)CCN2CC12CCN(c1noc3ccccc13)CC2] | (S)-1-(benzo[d] isoxazol-3-yl)-7'-(3,5-difluorophenyl) dihydro-1'H,3'H,5'H-spiro [piperidine-4,2'-pyrazolo[1,2-a] pyrazol]-1'-one | 425 | 145 |

TABLE 2-continued

Examples Prepared According to Scheme 2.

| Ex. No. | Structure | Name | Observed m/z [M + H]+ | RIPK1 $EC_{50}$ (nM) |
|---|---|---|---|---|
| 2.7 | 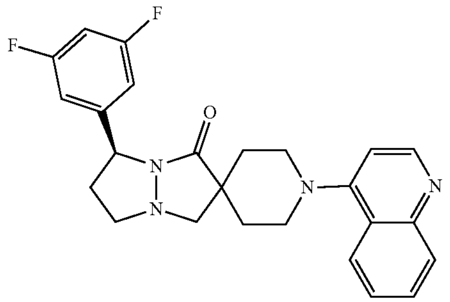 [SMILES: O=C1N2[C@H](c3cc(F)cc(F)c3)CCN2CC12CCN(c1ccnc3ccccc13)CC2] | (S)-7'-(3,5-difluorophenyl)-1-(quinolin-4-yl)dihydro-1'H,3'H,5'H-spiro[piperidine-4,2'-pyrazolo[1,2-a]pyrazol]-1'-one | 435 | 24 |
| 2.8 | 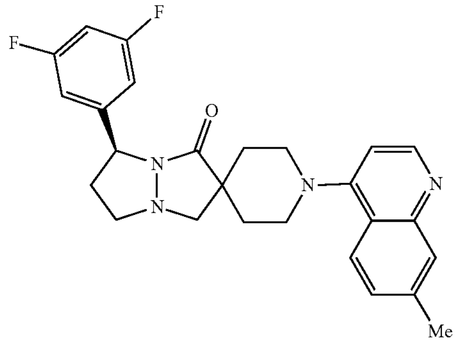 [SMILES: Cc1ccc2c(N3CCC4(CC3)CN3CC[C@@H](c5cc(F)cc(F)c5)N3C4=O)ccnc2c1] | (S)-7'-(3,5-difluorophenyl)-1-(7-methylquinolin-4-yl)dihydro-1'H,3'H,5'H-spiro[piperidine-4,2'-pyrazolo[1,2-a]pyrazol]-1'-one | 449 | 24 |
| 2.9 | 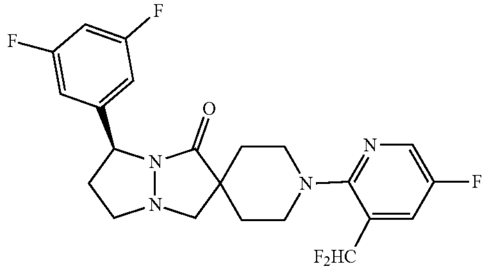 [SMILES: O=C1N2[C@H](c3cc(F)cc(F)c3)CCN2CC12CCN(c1ncc(F)cc1C(F)F)CC2] | (S)-1-(3-(difluoro-methyl)-5-fluoropyridin-2-yl)-7'-(3,5-difluorophenyl)dihydro-1'H,3'H,5'H-spiro[piperidine-4,2'-pyrazolo[1,2-a]pyrazol]-1'-one | 453 | 792 |
| 2.10 | 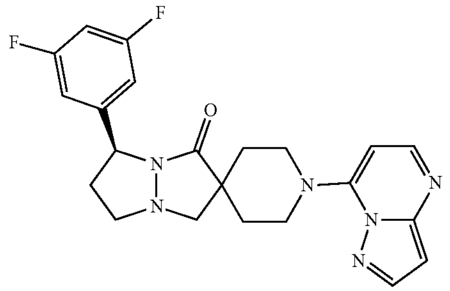 [SMILES: O=C1N2[C@H](c3cc(F)cc(F)c3)CCN2CC12CCN(c1ccnc3ccnn13)CC2] | (S)-7'-(3,5-difluorophenyl)-1-(pyrazolo[1,5-a]pyrimidin-7-yl)dihydro-1'H,3'H,5'H-spiro[piperidine-4,2'-pyrazolo[1,2-a]pyrazol]-1'-one | 425 | 33 |

TABLE 2-continued

| Examples Prepared According to Scheme 2. | | | | |
|---|---|---|---|---|
| Ex. No. | Structure | Name | Observed m/z [M + H]+ | RIPK1 $EC_{50}$ (nM) |
| 2.11 | 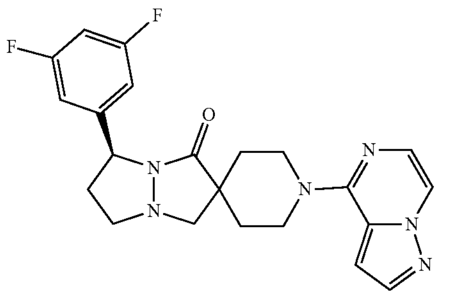 [SMILES: O=C1N2[C@H](c3cc(F)cc(F)c3)CCN2CC12CCN(c1nccn3nccc13)CC2] | (S)-7'-(3,5-difluorophenyl)-1-(pyrazolo[1,5-a]pyrazin-4-yl)dihydro-1'H,3'H,5'H-spiro[piperidine-4,2'-pyrazolo[1,2-a]pyrazol]-1'-one | 425 | 34 |
| 2.12 | 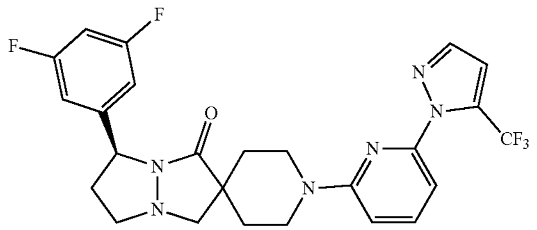 [SMILES: O=C1N2[C@H](c3cc(F)cc(F)c3)CCN2CC12CCN(c1cccc(-n3nccc3C(F)(F)F)n1)CC2] | (S)-7'-(3,5-difluorophenyl)-1-(6-(5-(trifluoro-methyl)-1H-pyrazol-1-yl)pyridin-2-yl)dihydro-1'H,3'H,5'H-spiro[piperidine-4,2'-pyrazolo[1,2-a]pyrazol]-1'-one | 519 | 6 |
| 2.13 | 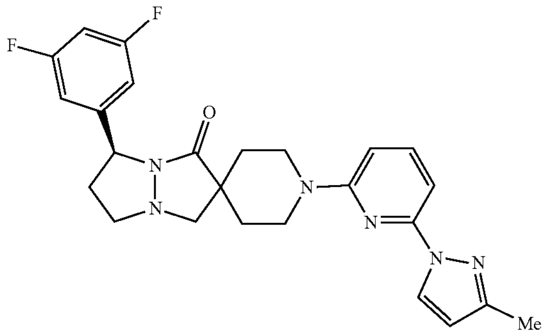 [SMILES: Cc1ccn(-c2cccc(N3CCC4(CC3)CN3CC[C@@H](c5cc(F)cc(F)c5)N3C4=O)n2)n1] | (S)-7'-(3,5-difluorophenyl)-1-(6-(3-methyl-1H-pyrazol-1-yl)pyridin-2-yl)dihydro-1'H,3'H,5'H-spiro[piperidine-4,2'-pyrazolo[1,2-a]pyrazol]-1'-one | 465 | 17 |
| 2.14 | 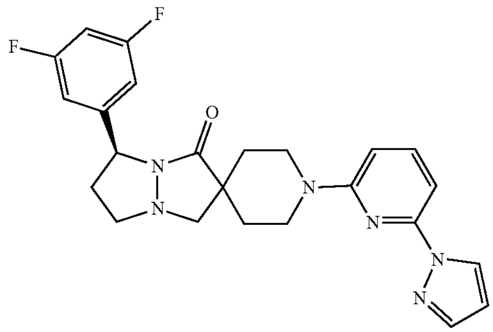 [SMILES: O=C1N2[C@H](c3cc(F)cc(F)c3)CCN2CC12CCN(c1cccc(-n3cccn3)n1)CC2] | (S)-1-(6-(1H-pyrazol-1-yl)pyridin-2-yl)-7'-(3,5-difluorophenyl)dihydro-1'H,3'H,5'H-spiro[piperidine-4,2'-pyrazolo[1,2-a]pyrazol]-1'-one | 451 | 11 |

TABLE 2-continued

Examples Prepared According to Scheme 2.

| Ex. No. | Structure | Name | Observed m/z [M + H]+ | RIPK1 $EC_{50}$ (nM) |
|---|---|---|---|---|
| 2.14 | 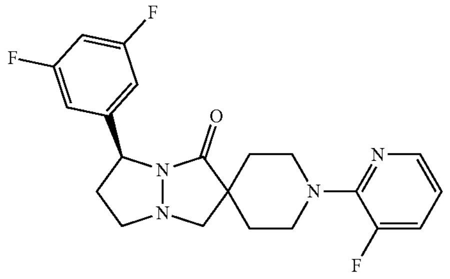 [SMILES: O=C1N2[C@H](c3cc(F)cc(F)c3)CCN2CC12CCN(c1ncccc1F)CC2] | (S)-7'-(3,5-difluorophenyl)-1-(3-fluoropyridin-2-yl)dihydro-1'H,3'H,5'H-spiro [piperidine-4,2'-pyrazolo[1,2-a] pyrazol]-1'-one | 403 | 190 |
| 2.15 | 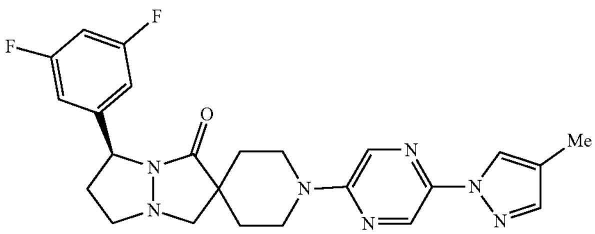 [SMILES: Cc1cnn(-c2cnc(N3CCC4(CC3)CN3CC[C@@H](c5cc(F)cc(F)c5)N3C4=O)cn2)c1] | (S)-7'-(3,5-difluorophenyl)-1-(5-(4-methyl-1H-pyrazol-1-yl) pyrazin-2-yl) dihydro-1'H,3'H,5'H-spiro [piperidine-4,2'-pyrazolo[1,2-a] pyrazol]-1'-one | 466 | 80 |
| 2.16 | 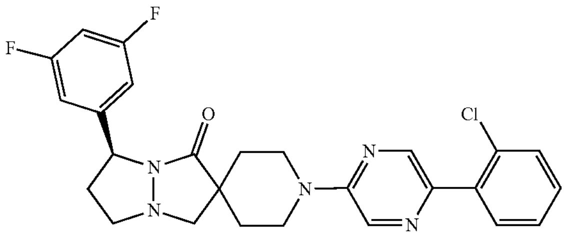 [SMILES: O=C1N2[C@H](c3cc(F)cc(F)c3)CCN2CC12CCN(c1cnc(-c3ccccc3Cl)cn1)CC2] | (S)-1-(5-(2-chlorophenyl) pyrazin-2-yl)-7'-(3,5-difluorophenyl) dihydro-1'H,3'H,5'H-spiro [piperidine-4,2'-pyrazolo[1,2-a] pyrazol]-1'-one | 496 | 25 |
| 2.17 | 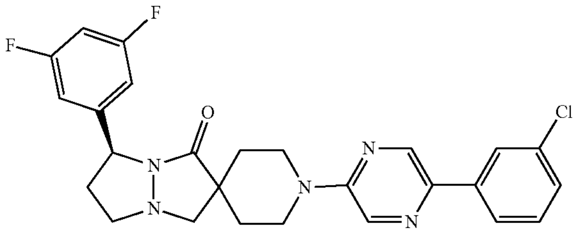 [SMILES: O=C1N2[C@H](c3cc(F)cc(F)c3)CCN2CC12CCN(c1cnc(-c3cccc(Cl)c3)cn1)CC2] | (S)-1-(5-(3-chlorophenyl) pyrazin-2-yl)-7'-(3,5-difluorophenyl) dihydro-1'H,3'H,5'H-spiro [piperidine-4,2'-pyrazolo[1,2-a] pyrazol]-1'-one | 496 | 96 |
| 2.18 | 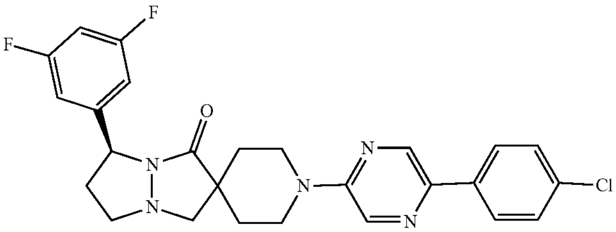 [SMILES: O=C1N2[C@H](c3cc(F)cc(F)c3)CCN2CC12CCN(c1cnc(-c3ccc(Cl)cc3)cn1)CC2] | (S)-1-(5-(4-chlorophenyl) pyrazin-2-yl)-7'-(3,5-difluorophenyl) dihydro-1'H,3'H,5'H-spiro [piperidine-4,2'-pyrazolo[1,2-a] pyrazol]-1'-one | 496 | 152 |

TABLE 2-continued

| Ex. No. | Structure | Name | Observed m/z [M + H]+ | RIPK1 $EC_{50}$ (nM) |
|---|---|---|---|---|
| Examples Prepared According to Scheme 2. | | | | |
| 2.19 | 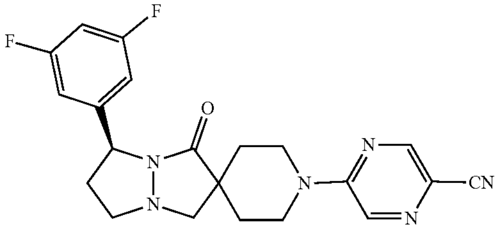 [SMILES: N#Cc1cnc(N2CCC3(CC2)CN2CC[C@@H](c4cc(F)cc(F)c4)N2C3=O)cn1] | (S)-5-(7'-(3,5-difluorophenyl)-1'-oxodihydro-1'H,3'H,5'H-spiro[piperidine-4,2'-pyrazolo[1,2-a]pyrazol]-1-yl)pyrazine-2-carbonitrile | 411 | 27 |
| 2.20 | 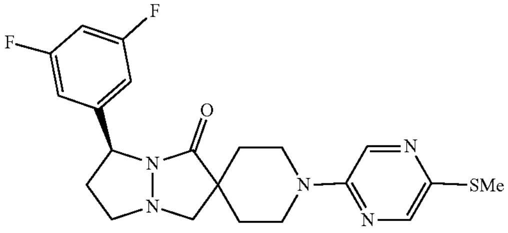 [SMILES: CSc1cnc(N2CCC3(CC2)CN2CC[C@@H](c4cc(F)cc(F)c4)N2C3=O)cn1] | (S)-7'-(3,5-difluorophenyl)-1-(5-(methylthio)pyrazin-2-yl)dihydro-1'H,3'H,5'H-spiro[piperidine-4,2'-pyrazolo[1,2-a]pyrazol]-1'-one | 432 | 30 |
| 2.21 | 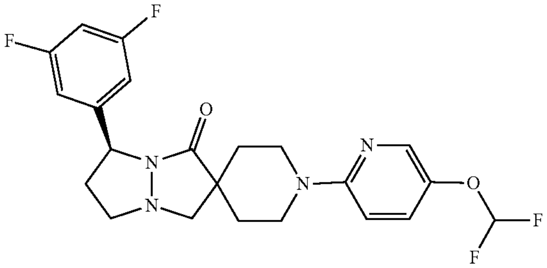 [SMILES: O=C1N2[C@H](c3cc(F)cc(F)c3)CCN2CC12CCN(c1ccc(OC(F)F)cn1)CC2] | (S)-1-(5-(difluoromethoxy)pyridin-2-yl)-7'-(3,5-difluorophenyl)dihydro-1'H,3'H,5'H-spiro[piperidine-4,2'-pyrazolo[1,2-a]pyrazol]-1'-one | 451 | 28 |
| 2.22 | 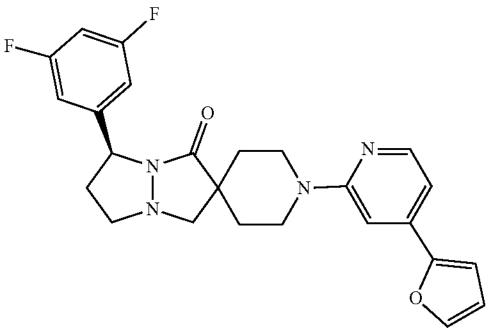 [SMILES: O=C1N2[C@H](c3cc(F)cc(F)c3)CCN2CC12CCN(c1cc(-c3ccco3)ccn1)CC2] | (S)-7'-(3,5-difluorophenyl)-1-(4-(furan-2-yl)pyridin-2-yl)dihydro-1'H,3'H,5'H-spiro[piperidine-4,2'-pyrazolo[1,2-a]pyrazol]-1'-one | 451 | 132 |

TABLE 2-continued

| Ex. No. | Structure | Name | Observed m/z [M + H]+ | RIPK1 $EC_{50}$ (nM) |
|---|---|---|---|---|
| Examples Prepared According to Scheme 2. | | | | |
| 2.23 | 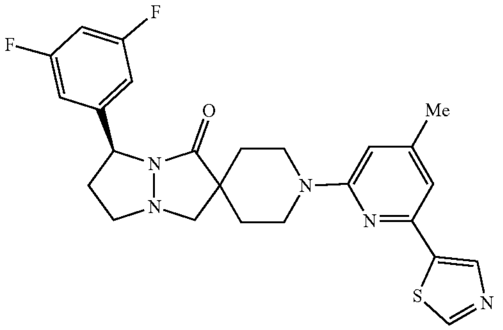 [SMILES: Cc1cc(-c2cncs2)nc(N2CCC3(CC2)CN2CC[C@@H](c4cc(F)cc(F)c4)N2C3=O)c1] | (S)-7'-(3,5-difluorophenyl)-1-(4-methyl-6-(thiazol-5-yl)pyridin-2-yl)dihydro-1'H,3'H,5'H-spiro[piperidine-4,2'-pyrazolo[1,2-a]pyrazol]-1'-one | 482 | 48 |
| 2.24 | 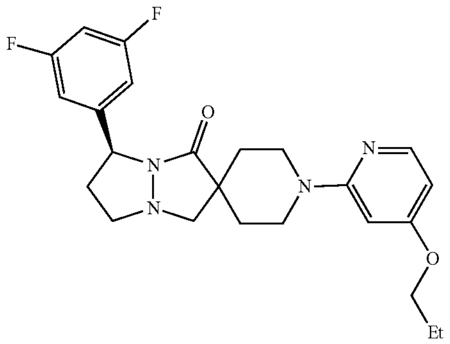 [SMILES: CCCOc1ccnc(N2CCC3(CC2)CN2CC[C@@H](c4cc(F)cc(F)c4)N2C3=O)c1] | (S)-7'-(3,5-difluorophenyl)-1-(4-propoxypyridin-2-yl)dihydro-1'H,3'H,5'H-spiro[piperidine-4,2'-pyrazolo[1,2-a]pyrazol]-1'-one | 443 | 907 |
| 2.25 | 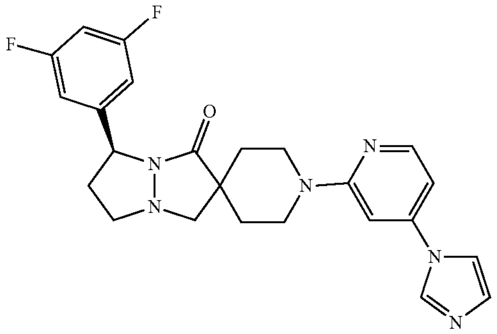 [SMILES: O=C1N2[C@H](c3cc(F)cc(F)c3)CCN2CC12CCN(c1cc(-n3ccnc3)ccn1)CC2] | (S)-1-(4-(1H-imidazol-1-yl)pyridin-2-yl)-7'-(3,5-difluorophenyl)dihydro-1'H,3'H,5'H-spiro[piperidine-4,2'-pyrazolo[1,2-a]pyrazol]-1'-one | 451 | 50 |
| 2.26 | 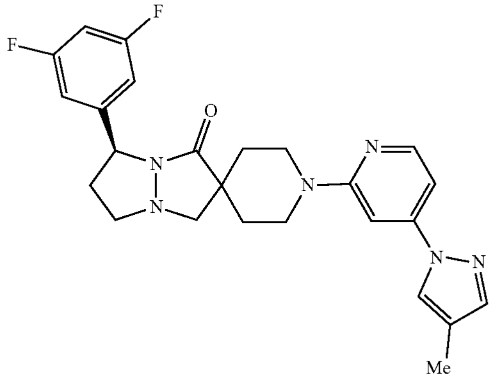 [SMILES: Cc1cnn(-c2ccnc(N3CCC4(CC3)CN3CC[C@@H](c5cc(F)cc(F)c5)N3C4=O)c2)c1] | (S)-7'-(3,5-difluorophenyl)-1-(4-(4-methyl-1H-pyrazol-1-yl)pyridin-2-yl)dihydro-1'H,3'H,5'H-spiro[piperidine-4,2'-pyrazolo[1,2-a]pyrazol]-1'-one | 465 | 98 |

Preparation of Example 3.1, (S)-7'-(3,5-difluorophenyl)-1-(thiazolo[5,4-d]pyrimidin-7-yl)dihydro-1'H, 3'H,5'H-spiro[piperidine-4,2'-pyrazolo[1,2-a]pyrazol]-1'-one, TFA salt

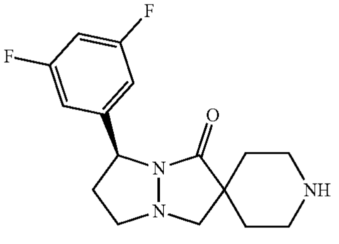

J.2

+

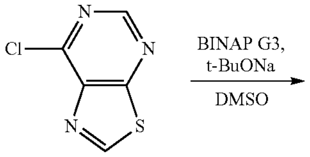

3.A

-continued

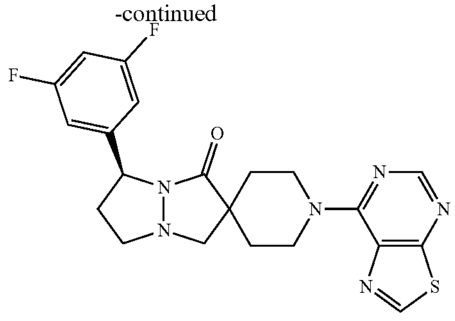

3.1

A vial was charged with(S)-7'-(3,5-difluorophenyl)dihydro-1'H,3'H,5'H-spiro[piperidine-4,2'-pyrazolo[1,2-a] pyrazol]-1'-one (15.4 mg, 50.0 μmol), 7-chlorothiazolo[5,4-d]pyrimidine (8.6 mg, 50.0 μmol) and BINAP G3 (2.48 mg, 2.50 μmol) and DMSO (500 μL), followed by the addition of 2-methylpropan-2-olate (14.4 mg, 150 μmol). The mixture was stirred at 100° C. for 16 h. The reaction mixture was then concentrated, and the residue was dissolved in MeCN and $H_2O$ and purified via reversed phase HPLC [Method A] to give(S)-7'-(3,5-difluorophenyl)-1-(thiazolo[5,4-d]pyrimidin-7-yl)dihydro-1'H,3'H,5'H-spiro[piperidine-4,2'-pyrazolo[1,2-a]pyrazol]-1'-one, TFA salt. MS (ESI) m/z $C_{21}H_{21}F_2N_6OS$ $[M+1]^+$ calc'd 443, found 443. RIPK1 ECso: 24 nM.

The following examples in Table 3 were prepared according to Scheme 3 above, using intermediate J.2, and the appropriate commercially available heteroaryl halide. The compounds were generally purified by reversed phase HPLC.

TABLE 3

Examples Prepared According to Scheme 3

| Ex. No. | Structure | Name | Observed m/z $[M + H]^+$ | RIPK1 $EC_{50}$ (nM) |
|---|---|---|---|---|
| 3.2 | 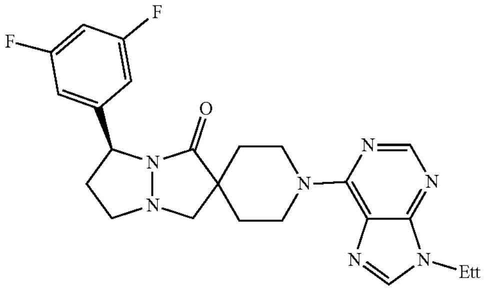 | (S)-7'-(3,5-difluorophenyl)-1-(9-ethyl-9H-purin-6-yl) dihydro-1'H,3'H,5'H-spiro [piperidine-4,2'-pyrazolo[1,2-a] pyrazol]-1'-one | 454 | 765 |
| 3.3 | 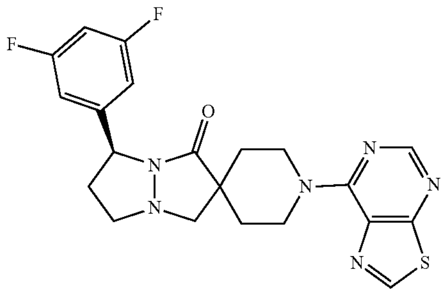 [SMILES: O=C1N2[C@H](c3cc(F)cc(F)c3)CCN2CC12CCN(c1ncnc3scnc13)CC2] | (S)-7'-(3,5-difluorophenyl)-1-(thiazolo[5,4-d]pyrimidin-7-yl) dihydro-1'H,3'H,5'H-spiro [piperidine-4,2'-pyrazolo[1,2-a] pyrazol]-1'-one | 443 | 14 |

Preparation of Example 4.1, (S)-7'-(3,5-difluorophenyl)-1-(pyrazine-2-carbonyl)dihydro-1'H,3'H,5'H-spiro[piperidine-4,2'-pyrazolo[1,2-a]pyrazol]-1'-one Scheme 4

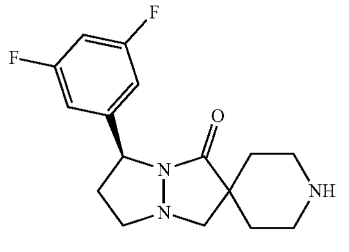

J.2

+

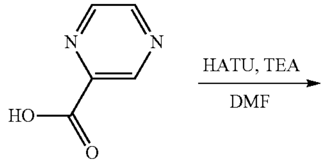

4A

-continued

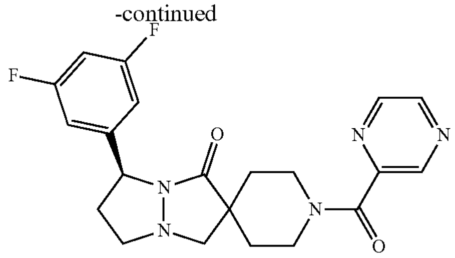

4.1

(S)-7'-(3,5-difluorophenyl)dihydro-1'H,3'H,5'H-spiro[piperidine-4,2'-pyrazolo[1,2-a]pyrazol]-1'-one (10 mg, 0.033 mmol) and pyrazine-2-carboxylic acid (4.9 mg, 0.04 mmol) was dissolved in DMF (325 μl) at 25° C., in a vial. TEA (13.6 μl, 0.098 mmol) was added followed by HATU (14.9 mg, 0.04 mmol) in one portion. The mixture stirred at 25° C. for 90 min. The mixture was concentrated and taken up in DMA, then purified via reversed phase HPLC [Method B] to give(S)-7'-(3,5-difluorophenyl)-1-(pyrazine-2-carbonyl)dihydro-1'H,3'H,5'H-spiro[piperidine-4,2'-pyrazolo[1,2-a]pyrazol]-1'-one. MS (ESI) m/z $C_{21}H_{21}F_2N_5O_2$ $[M+H]^+$ calc'd 414, found 414. $^1$HNMR (499 MHz, DMSO-$d_6$) δ 8.85 (s, 1H), 8.75 (d, J=2.5 Hz, 1H), 8.71-8.56 (m, 1H), 7.14 (q, J=9.5 Hz, 1H), 6.98 (dd, J=6.6, 15.6 Hz, 2H), 5.02 (s, 1H), 4.24 (dd, J=51.3, 13.2 Hz, 1H), 3.72 (d, J=13.5 Hz, 1H), 3.64 (d, J=14.2 Hz, 1H), 3.29-3.12 (m, 2H), 2.98-2.75 (m, 2H), 2.06 (dq, J=10.6, 5.1 Hz, 1H), 1.99-1.82 (m, 2H), 1.77 (dd, J=9.2, 4.4 Hz, 2H), 1.67 (d, J=14.0 Hz, 1H), 1.55 (d, J=13.5 Hz, 1H). RIPK1 ECso: 50 nM.

The following examples in Table 4 were prepared according to Scheme 4 above, using intermediate J.2, and the appropriate carboxylic acid commercially available. The compounds were generally purified by reversed phase HPLC

TABLE 4

Examples Prepared According to Scheme 4

| Ex. No. | Structure | Name | Observed m/z $[M + H]^+$ | RIPK1 $EC_{50}$ (nM) |
|---|---|---|---|---|
| 4.2 | 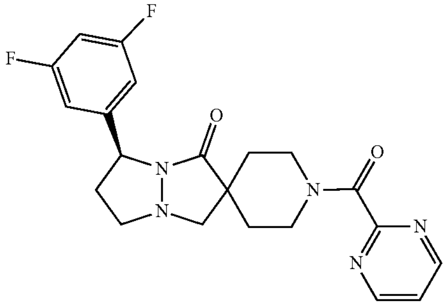 [SMILES: O=C(c1ncccn1)N1CCC2(CC1)CN1CC[C@@H](c3cc(F)cc(F)c3)N1C2=O] | (S)-7'-(3,5-difluorophenyl)-1-(pyrimidine-2-carbonyl)dihydro-1'H,3'H,5'H-spiro[piperidine-4,2'-pyrazolo[1,2-a]pyrazol]-1'-one | 414 | 434 |

TABLE 4-continued

| Ex. No. | Structure | Name | Observed m/z $[M + H]^+$ | RIPK1 $EC_{50}$ (nM) |
| --- | --- | --- | --- | --- |
| Examples Prepared According to Scheme 4 | | | | |
| 4.3 | 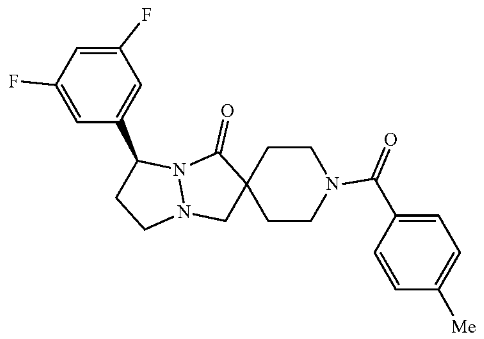 [SMILES: Cc1ccc(C(=O)N2CCC3(CC2)CN2CC[C@@H](c4cc(F)cc(F)c4)N2C3=O)cc1] | (S)-7'-(3,5-difluorophenyl)-1-(4-methylbenzoyl) dihydro-1'H,3'H,5'H-spiro[piperidine-4,2'-pyrazolo[1,2-a]pyrazol]-1'-one | 426 | 38 |
| 4.4 | 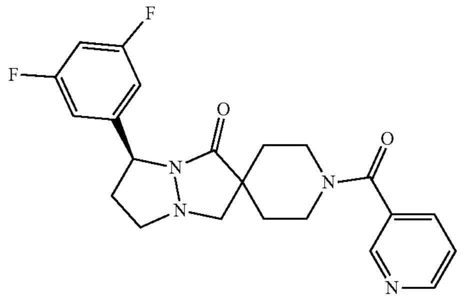 [SMILES: O=C(c1cccnc1)N1CCC2(CC1)CN1CC[C@@H](c3cc(F)cc(F)c3)N1C2=O] | (S)-7'-(3,5-difluorophenyl)-1-nicotinoyldihydro-1'H,3'H,5'H-spiro[piperidine-4,2'-pyrazolo[1,2-a]pyrazol]-1'-one | 413 | 209 |
| 4.5 | 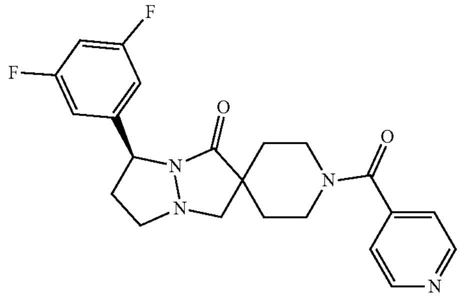 [SMILES: O=C(c1ccncc1)N1CCC2(CC1)CN1CC[C@@H](c3cc(F)cc(F)c3)N1C2=O] | (S)-7'-(3,5-difluorophenyl)-1-isonicotinoyldihydro-1'H,3'H,5'H-spiro[piperidine-4,2'-pyrazolo[1,2-a]pyrazol]-1'-one | 413 | 414 |
| 4.6 | 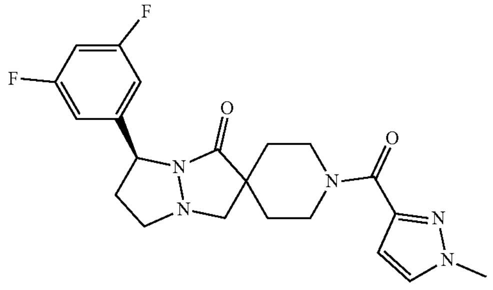 [SMILES: Cn1ccc(C(=O)N2CCC3(CC2)CN2CC[C@@H](c4cc(F)cc(F)c4)N2C3=O)n1] | (S)-7'-(3,5-difluorophenyl)-1-(1-methyl-1H-pyrazole-3-carbonyl)dihydro-1'H,3'H,5'H-spiro[piperidine-4,2'-pyrazolo[1,2-a]pyrazol]-1'-one | 416 | 594 |

TABLE 4-continued

| Ex. No. | Structure | Name | Observed m/z [M + H]+ | RIPK1 $EC_{50}$ (nM) |
|---|---|---|---|---|
| Examples Prepared According to Scheme 4 | | | | |
| 4.7 | 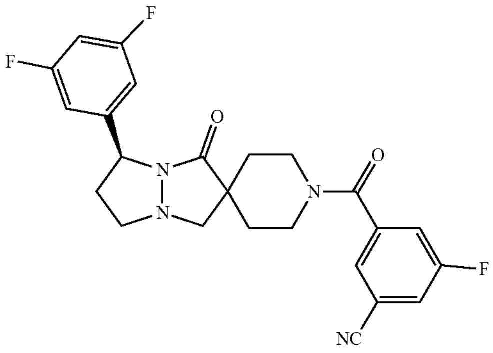 [SMILES: N#Cc1cc(F)cc(C(=O)N2CCC3(CC2)CN2CC[C@@H](c4cc(F)cc(F)c4)N2C3=O)c1] | (S)-3-(7'-(3,5-difluorophenyl)-1'-oxodihydro-1'H,3'H,5'H-spiro[piperidine-4,2'-pyrazolo[1,2-a]pyrazole]-1-carbonyl)-5-fluorobenzonitrile | 455 | 211 |
| 4.8 | 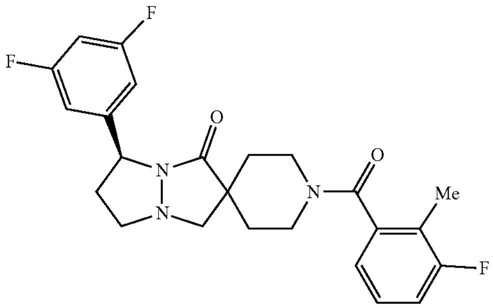 | (S)-7'-(3,5-difluorophenyl)-1-(3-fluoro-2-methylbenzoyl)dihydro-1'H,3'H,5'H-spiro[piperidine-4,2'-pyrazolo[1,2-a]pyrazol]-l'-one | 444 | 158 |
| 4.9 | 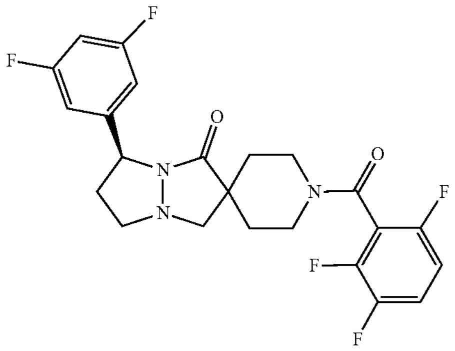 [SMILES: O=C(c1c(F)ccc(F)c1F)N1CCC2(CC1)CN1CC[C@@H](c3cc(F)cc(F)c3)N1C2=O] | (S)-7'-(3,5-difluorophenyl)-1-(2,3,6-trifluorobenzoyl) dihydro-1'H,3'H,5'H-spiro[piperidine-4,2'-pyrazolo[1,2-a]pyrazol]-l'-one | 466 | 31 |
| 4.10 | 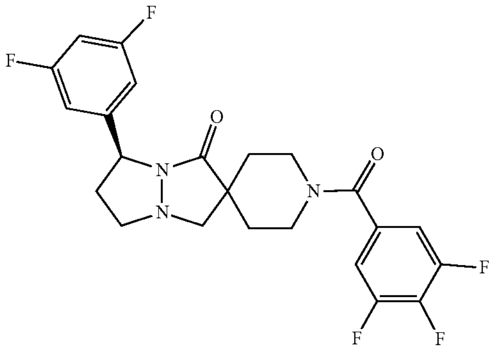 [SMILES: O=C(c1cc(F)c(F)c(F)c1)N1CCC2(CC1)CN1CC[C@@H](c3cc(F)cc(F)c3)N1C2=O] | (S)-7'-(3,5-difluorophenyl)-1-(3,4,5-trifluorobenzoyl) dihydro-1'H,3'H,5'H-spiro[piperidine-4,2'-pyrazolo[1,2-a]pyrazol]-l'-one | 466 | 67 |

TABLE 4-continued

Examples Prepared According to Scheme 4

| Ex. No. | Structure | Name | Observed m/z $[M + H]^+$ | RIPK1 $EC_{50}$ (nM) |
|---|---|---|---|---|
| 4.11 | 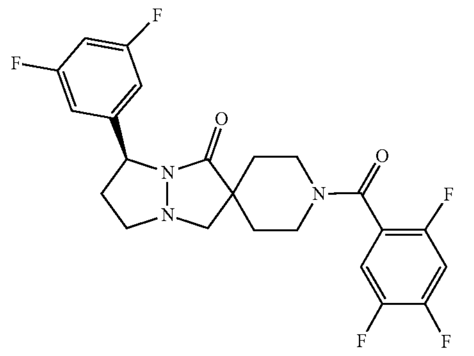 [SMILES: O=C(c1cc(F)c(F)cc1F)N1CCC2(CC1)CN1CC[C@@H](c3cc(F)cc(F)c3)N1C2=O] | (S)-7'-(3,5-difluorophenyl)-1-(2,4,5-trifluorobenzoyl) dihydro-1'H,3'H,5'H-spiro[piperidine-4,2'-pyrazolo[1,2-a]pyrazol]-1'-one | 466 | 19 |
| 4.12 | 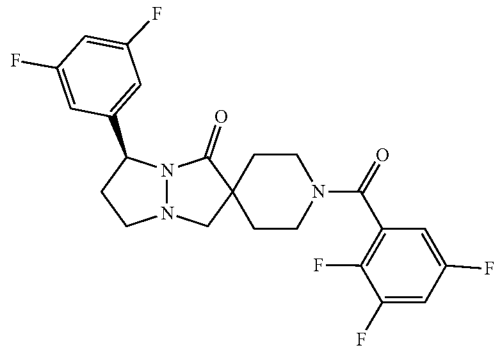 [SMILES: O=C(c1cc(F)cc(F)c1F)N1CCC2(CC1)CN1CC[C@@H](c3cc(F)cc(F)c3)N1C2=O] | (S)-7'-(3,5-difluorophenyl)-1-(2,3,5-trifluorobenzoyl) dihydro-1'H,3'H,5'H-spiro[piperidine-4,2'-pyrazolo[1,2-a]pyrazol]-1'-one | 466 | 26 |
| 4.13 | 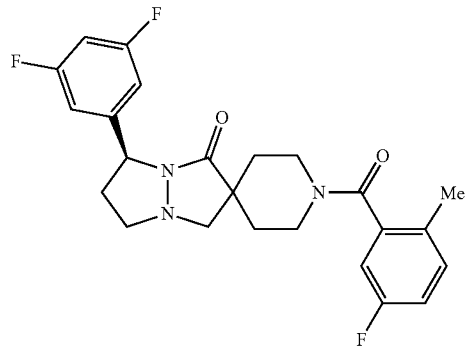 [SMILES: Cc1ccc(F)cc1C(=O)N1CCC2(CC1)CN1CC[C@@H](c3cc(F)cc(F)c3)N1C2=O] | (S)-7'-(3,5-difluorophenyl)-1-(5-fluoro-2-methylbenzoyl) dihydro-1'H,3'H,5'H-spiro[piperidine-4,2'-pyrazolo[1,2-a]pyrazol]-1'-one | 444 | 335 |
| 4.14 | 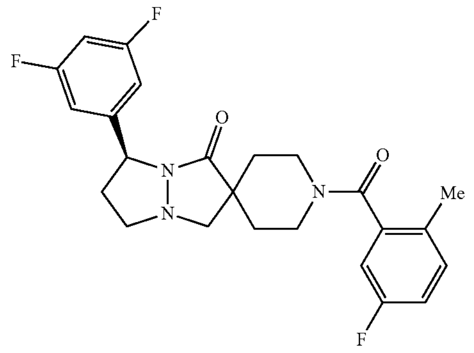 [SMILES: Cc1ccc(F)cc1C(=O)N1CCC2(CC1)CN1CC[C@@H](c3cc(F)cc(F)c3)N1C2=O] | (S)-7'-(3,5-difluorophenyl)-1-(5-fluoro-2-methoxybenzoyl) dihydro-1'H,3'H,5'H-spiro[piperidine-4,2'-pyrazolo[1,2-a]pyrazol]-1'-one | 460 | 386 |

TABLE 4-continued

| Examples Prepared According to Scheme 4 | | | | |
|---|---|---|---|---|
| Ex. No. | Structure | Name | Observed m/z $[M + H]^+$ | RIPK1 $EC_{50}$ (nM) |
| 4.15 | 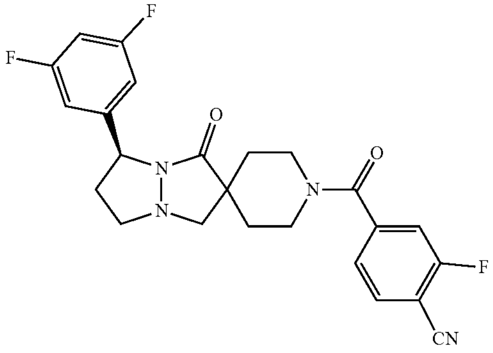 | (S)-4-(7'-(3,5-difluorophenyl)-1'-oxodihydro-1'H,3'H,5'H-spiro[piperidine-4,2'-pyrazolo[1,2-a]pyrazole]-1-carbonyl)-2-fluorobenzonitrile | 455 | 858 |
| 4.16 | 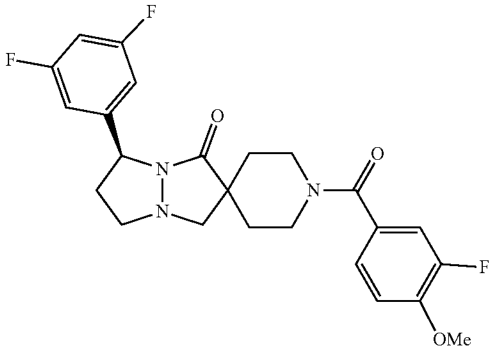 [SMILES: N#Cc1ccc(C(=O)N2CCC3(CC2)CN2CC[C@@H](c4cc(F)cc(F)c4)N2C3=O)cc1F] | (S)-7'-(3,5-difluorophenyl)-1-(3-fluoro-4-methoxybenzoyl) dihydro-1'H,3'H,5'H-spiro[piperidine-4,2'-pyrazolo[1,2-a]pyrazol]-1'-one | 460 | 83 |
| 4.17 | 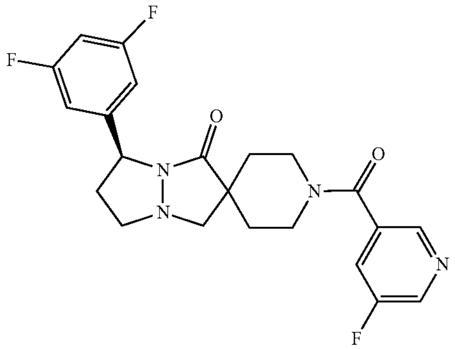 [SMILES: O=C(c1cncc(F)c1)N1CCC2(CC1)CN1CC[C@@H](c3cc(F)cc(F)c3)N1C2=O] | (S)-7'-(3,5-difluorophenyl)-1-(5-fluoronicotinoyl) dihydro-1'H,3'H,5'H-spiro[piperidine-4,2'-pyrazolo[1,2-a]pyrazol]-1'-one | 431 | 446 |
| 4.18 | 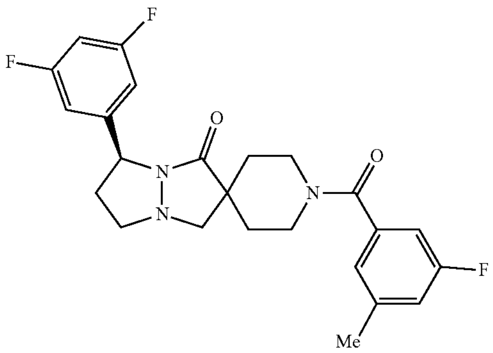 [SMILES: Cc1cc(F)cc(C(=O)N2CCC3(CC2)CN2CC[C@@H](c4cc(F)cc(F)c4)N2C3=O)c1] | (S)-7'-(3,5-difluorophenyl)-1-(3-fluoro-5-methylbenzoyl) dihydro-1'H,3'H,5'H-spiro[piperidine-4,2'-pyrazolo[1,2-a]pyrazol]-1'-one | 444 | 18 |

TABLE 4-continued

| Ex. No. | Structure | Name | Observed m/z $[M + H]^+$ | RIPK1 $EC_{50}$ (nM) |
| --- | --- | --- | --- | --- |
| Examples Prepared According to Scheme 4 | | | | |
| 4.19 | 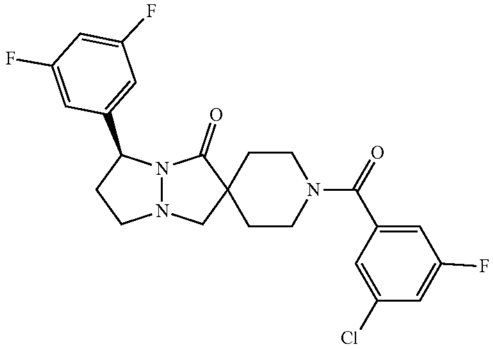 [SMILES: O=C(c1cc(F)cc(Cl)c1)N1CCC2(CC1)CN1CC[C@@H](c3cc(F)cc(F)c3)N1C2=O] | (S)-1-(3-chloro-5-fluorobenzoyl)-7'-(3,5-difluorophenyl) dihydro-1'H,3'H,5'H-spiro[piperidine-4,2'-pyrazolo[1,2-a]pyrazol]-1'-one | 464 | 18 |
| 4.20 | 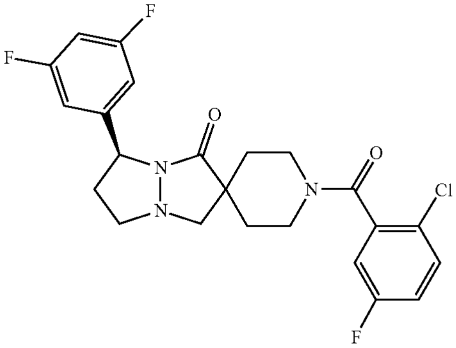 [SMILES: O=C(c1cc(F)ccc1Cl)N1CCC2(CC1)CN1CC[C@@H](c3cc(F)cc(F)c3)N1C2=O] | (S)-1-(2-chloro-5-fluorobenzoyl)-7'-(3,5-difluorophenyl) dihydro-1'H,3'H,5'H-spiro[piperidine-4,2'-pyrazolo[1,2-a]pyrazol]-1'-one | 464 | 50 |
| 4.21 | 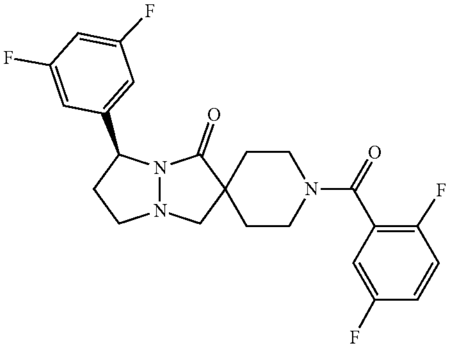 [SMILES: O=C(c1cc(F)ccc1F)N1CCC2(CC1)CN1CC[C@@H](c3cc(F)cc(F)c3)N1C2=O] | (S)-1-(2,5-difluorobenzoyl)-7'-(3,5-difluorophenyl) dihydro-1'H,3'H,5'H-spiro[piperidine-4,2'-pyrazolo[1,2-a]pyrazol]-1'-one | 448 | 15 |
| 4.22 | 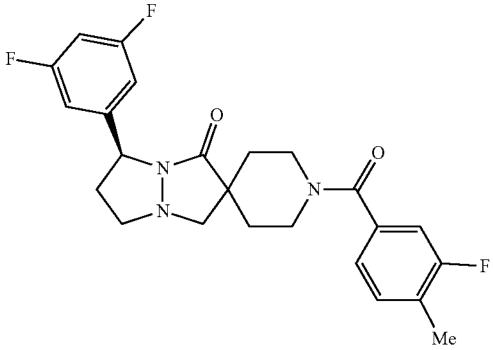 | (S)-7'-(3,5-difluorophenyl)-1-(3-fluoro-4-methylbenzoyl) dihydro-1'H,3'H,5'H-spiro[piperidine-4,2'-pyrazolo[1,2-a]pyrazol]-1'-one | 444 | 46 |

TABLE 4-continued

Examples Prepared According to Scheme 4

| Ex. No. | Structure | Name | Observed m/z [M + H]+ | RIPK1 $EC_{50}$ (nM) |
|---|---|---|---|---|
| 4.23 | 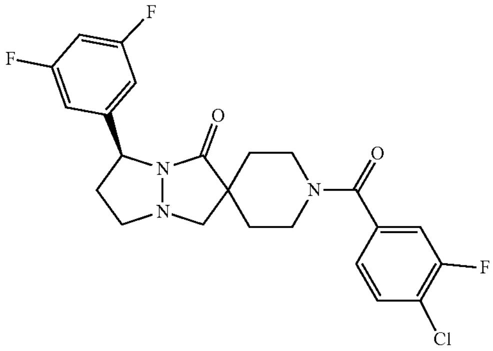 | (S)-1-(4-chloro-3-fluorobenzoyl)-7'-(3,5-difluorophenyl) dihydro-1'H,3'H,5'H-spiro[piperidine-4,2'-pyrazolo[1,2-a]pyrazol]-1'-one | 464 | 23 |
| 4.24 | 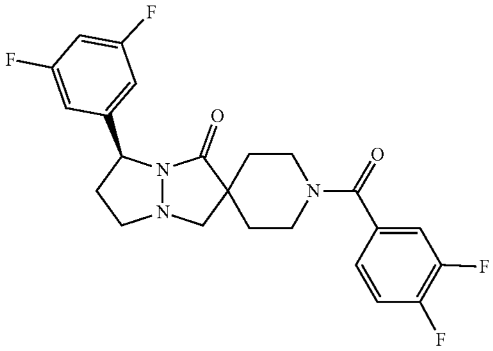 [SMILES: O=C(c1ccc(F)c(F)c1)N1CCC2(CC1)CN1CC[C@@H](c3cc(F)cc(F)c3)N1C2=O] | (S)-1-(3,4-difluorobenzoyl)-7'-(3,5-difluorophenyl) dihydro-1'H,3'H,5'H-spiro[piperidine-4,2'-pyrazolo[1,2-a]pyrazol]-1'-one | 448 | 32 |
| 4.25 | 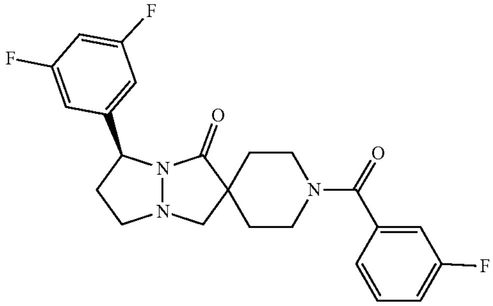 [SMILES: O=C(c1cccc(F)c1)N1CCC2(CC1)CN1CC[C@@H](c3cc(F)cc(F)c3)N1C2=O] | (S)-7'-(3,5-difluorophenyl)-1-(3-fluorobenzoyl) dihydro-1'H,3'H,5'H-spiro[piperidine-4,2'-pyrazolo[1,2-a]pyrazol]-1'-one | 430 | 35 |
| 4.26 | 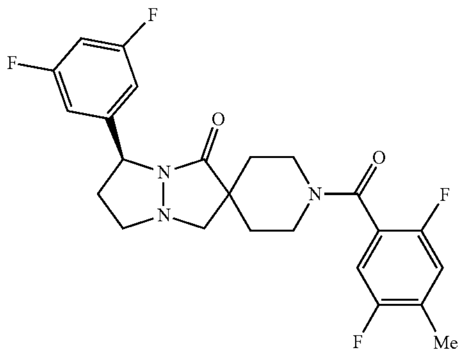 [SMILES: Cc1cc(F)c(C(=O)N2CCC3(CC2)CN2CC[C@@H](c4cc(F)cc(F)c4)N2C3=O)cc1F] | (S)-1-(2,5-difluoro-4-methylbenzoyl)-7'-(3,5-difluorophenyl) dihydro-1'H,3'H,5'H-spiro[piperidine-4,2'-pyrazolo[1,2-a]pyrazol]-1'-one | 462 | 23 |

TABLE 4-continued

Examples Prepared According to Scheme 4

| Ex. No. | Structure | Name | Observed m/z $[M + H]^+$ | RIPK1 $EC_{50}$ (nM) |
|---|---|---|---|---|
| 4.27 | 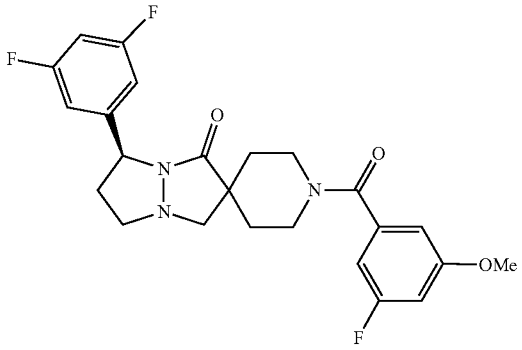 [SMILES: COc1cc(F)cc(C(=O)N2CCC3(CC2)CN2CC[C@@H](c4cc(F)cc(F)c4)N2C3=O)c1] | (S)-7'-(3,5-difluorophenyl)-1-(3-fluoro-5-methoxybenzoyl) dihydro-1'H,3'H,5'H-spiro[piperidine-4,2'-pyrazolo[1,2-a]pyrazol]-1'-one | 460 | 26 |
| 4.28 | 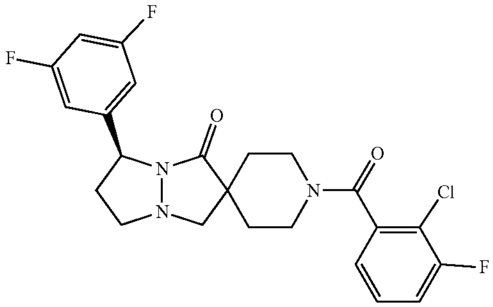 [SMILES: O=C(c1cccc(F)c1Cl)N1CCC2(CC1)CN1CC[C@@H](c3cc(F)cc(F)c3)N1C2=O] | (S)-1-(2-chloro-3-fluorobenzoyl)-7'-(3,5-difluorophenyl)dihydro-1'H,3'H,5'H-spiro[piperidine-4,2'-pyrazolo[1,2-a]pyrazol]-1'-one | 464 | 36 |
| 4.29 | 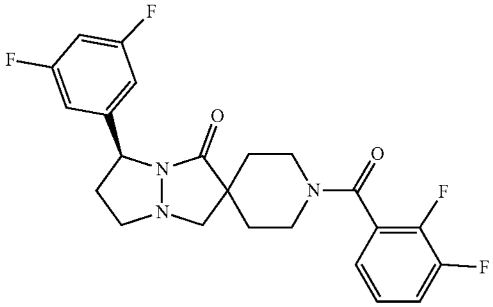 | (S)-1-(2,3-difluorobenzoyl)-7'-(3,5-difluorophenyl) dihydro-1'H,3'H,5'H-spiro[piperidine-4,2'-pyrazolo[1,2-a]pyrazol]-1'-one | 448 | 23 |

Preparation of Example 5.1, (S)-1-Benzoyl-7'-(3,5-difluorophenyl)dihydro-1'H,3'H,5'H-spiro[piperidine-4,2'-pyrazolo[1,2-a]pyrazol]-1'-one Scheme 5

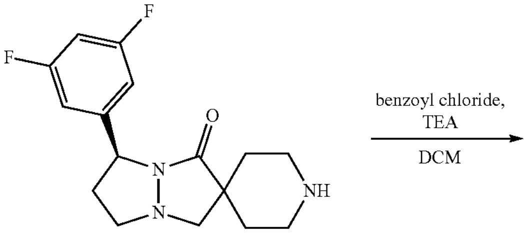

J.2

-continued

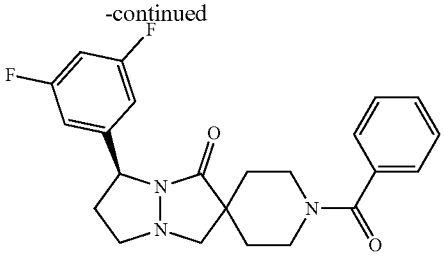

5.1

In a vial, (S)-7'-(3,5-difluorophenyl)dihydro-1'H,3'H,5'H-spiro[piperidine-4,2'-pyrazolo[1,2-α]pyrazol]-1'-one (10 mg, 0.033 mmol) was dissolved in DCM (325 μl) at 25° C. TEA (11.3 μl, 0.081 mmol) was added, followed by benzoyl chloride (4.5 μl, 0.039 mmol) in one portion. The mixture was stirred at 25° C. for 90 min, then concentrated. The residue was taken up in DMA and purified via reversed phase HPLC [Method A] to give(S)-1-benzoyl-7'-(3,5-difluorophenyl)dihydro-1'H,3'H,5'H-spiro[piperidine-4,2'-pyrazolo[1,2-α]pyrazol]-1'-one. MS (ESI) m/z $C_{23}H_{24}F_2N_3O_2$ $[M+H]^+$ calc'd 412, found 412. $^1$HNMR (499 MHz, DMSO-$d_6$) δ 7.45 (dd, J=1.6,5.0, Hz, 2H), 7.39 (dd, J=6.5, 3.1 Hz, 2H), 7.13 (s, 1H), 6.98 (s, 2H), 5.02 (t, J=7.7 Hz, 1H), 4.35-4.05 (m, 1H), 3.70 (s, 2H), 3.28 (s, 1H), 3.12 (s, 1H), 3.03-2.78 (m, 2H), 2.16-1.97 (m, 1H), 1.65 1.95-1.45 (m, 4H). RIPK1 ECso: 13 nM.

The following examples in Table 5 were prepared according to Scheme 5, using intermediate J.2, and the appropriate commercially available acyl chloride. The compounds were generally purified by reversed phase HPLC.

TABLE 5

Examples Prepared According to Scheme 5

| Ex. No. | Structure | Name | Observed m/z $[M + H]^+$ | RIPK1 $EC_{50}$ (nM) |
|---|---|---|---|---|
| 5.2 | 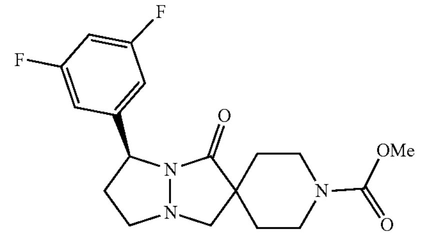 [SMILES: COC(=O)N1CCC2(CC1)CN1CC[C@@H](c3cc(F)cc(F)c3)N1C2=O] | methyl (S)-7'-(3,5-difluorophenyl)-1'-oxodihydro-1'H,3'H,5'H-spiro [piperidine-4,2'-pyrazolo[1,2-a]pyrazole]-1-carboxylate | 366 | 139 |
| 5.3 | 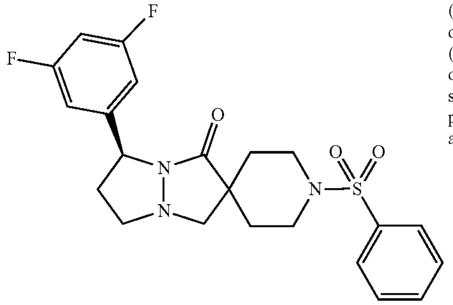 | (S)-7'-(3,5-difluorophenyl)-1-(phenylsulfonyl) dihydro-1'H,3'H,5'H-spiro[piperidine-4,2'-pyrazolo[1,2-a]pyrazol]-1'-one | 448 | 830 |

Preparation of Example 6.1, (S)-7'-(3,5-difluorophenyl)-1-(quinolin-2-ylmethyl)dihydro-1'H,3'H,5'H-spiro[piperidine-4,2'-pyrazolo[1,2-α]pyrazol]-1'-one, TFA salt Scheme 6

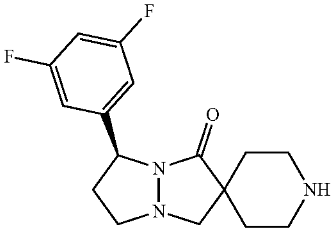

J.2

+

-continued

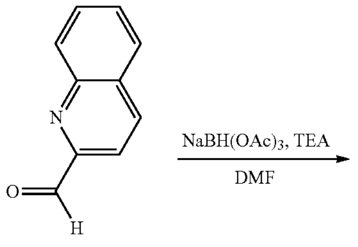

6.A

-continued

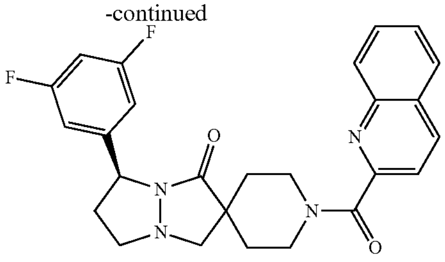

6.1

To a vial, (S)-7'-(3,5-difluorophenyl)dihydro-1'H,3'H,5'H-spiro[piperidine-4,2'-pyrazolo[1,2-α]pyrazol]-1'-one (110 mg, 3.6 mmol) in DCM (2.3 mL) was added, followed by TEA (113 mg, 11.3 mmol) and sodium triacetoxyborohydride (119 mg, 5.6 mmol) at 25° C. The mixture was stirred at 25° C. for 90 min. The mixture was then concentrated, taken up in DMA, and purified via reversed phase HPLC [Method A] to give(S)-7'-(3,5-difluorophenyl)-1-(pyrazine-2-carbonyl)dihydro-1'H,3'H,5'H-spiro[piperidine- 4,2'-pyrazolo[1,2-α]pyrazol]-1'-one, TFA salt. MS (ESI) m/z $C_{26}H_{27}F_2N_4O$ [M+H]$^+$ calc'd 449, found 449. $^1$HNMR (600 MHZ, DMSO-$d_6$) δ 8.50 (d, J=12.0 Hz, 1H), 8.11-8.04 (m, 2H), 7.85 (t, J=12.0 Hz, 1H), 7.71-7.68 (m, 1H), 7.61 (d, J=12.0 Hz, 1H), 7.32-7.28 (m, 1H), 6.99 (d, J=12.0 Hz, 2H), 5.01 (t, J=6.0 Hz, 1H), 4.68 (s, 2H), 3.49-3.35 (m, 2H), 3.28-3.16 (m, 2H), 2.90-2.86 (m, 2H), 2.22-2.19 (m, 2H), 2.10-2.03 (m, 4H), 1.88-1.84 (m, 2H). RIPK1 ECso: 706 nM.

Preparation of Example 7.1, (S)-7-(7'-(3,5-difluorophenyl)-1'-oxodihydro-1'H,3'H,5'H-spiro[piperidine-4,2'-pyrazolo[1,2-α]pyrazol]-1-yl)pyrazolo[1,5-a]pyridine-4-carbonitrile, TFA salt Scheme 7

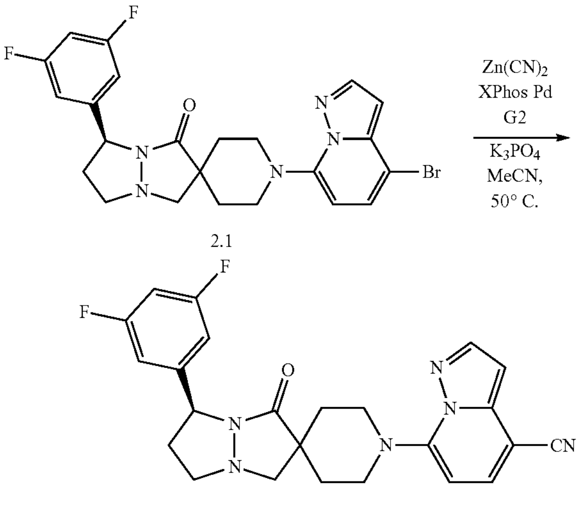

2.1

7.1

A 2 mL Biotage® microwave vial equipped with a stir bar was charged with(S)-1-(4-bromopyrazolo[1,5-α]pyridin-7-yl)-7'-(3,5-difluorophenyl)dihydro-1'H,3'H,5'H-spiro[piperidine-4,2'-pyrazolo[1,2-α]pyrazol]-1'-one (20 mg, 0.040 mmol), 2nd generation Xphos Pd precatalyst (3.1 mg, 0.004 mmol), $Zn(CN)_2$ (7.0 mg, 0.060 mmol) and $K_3PO4$ (12.7 mg, 0.060 mmol). The vial was evacuated and backfilled with nitrogen (3×). A sample of MeCN (0.4 mL) was purged with argon for 15 min with sonication, then added to the reaction vial. The resulting suspension was then stirred at 50° C. for 3 days. After cooling, the reaction was quenched with 1 M NaOH (3 mL) and DCM (3 mL). The layers were separated, and the aqueous layer was extracted with DCM (3 mL, ×3). The combined organic layers were dried (MgSO4), filtered and concentrated under reduced pressure. The crude residue was taken up in DMSO (2 mL), filtered and purified via reversed phase HPLC [Method A] to give(S)-7-(7'-(3,5-difluorophenyl)-1'-oxodihydro-1'H,3'H,5'H-spiro[piperidine-4,2'-pyrazolo[1,2-α]pyrazol]-1-yl) pyrazolo[1,5-α]pyridine-4-carbonitrile, TFA salt. MS (ESI) m/z $C_{24}H_{23}F_2N_6O$ [M+1]$^+$ calc'd 449, found 449. $^1$HNMR (600 MHz, DMSO-$d_6$) δ 8.20 (d, J=2.3 Hz, 1H), 7.86 (d, J=8.0 Hz, 1H), 7.19-7.11 (m, 1H), 7.00 (d, J=6.2 Hz, 2H), 6.74 (d, J=2.3 Hz, 1H), 6.44 (d, J=8.0 Hz, 1H), 5.05 (app t, J=7.7 Hz, 1H), 4.20-4.12 (m, 1H), 4.06 (d, J=12.6 Hz, 1H), 3.82 (br s, 1H), 3.42 (app t, J=10.4 Hz, 1H), 3.33 (br s, 1H), 3.23 (app t, J=10.3 Hz, 1H), 2.99 (br s, 1H), 2.95-2.85 (m, 1H), 2.63 (br s, 1H), 2.14-2.04 (m, 2H), 2.03-1.93 (m, 2H), 1.74 (d, J=13.8 Hz, 1H). RIPK1 $EC_{50}$:6 nM.

Preparation of Example 8.1, (S)-1-(4-chloropyrazolo[1,5-alpyridin-7-yl)-7'-(3,5-difluorophenyl)dihydro-1'H,3'H,5'H-spiro[piperidine-4,2'-pyrazolo[1,2-α]pyrazol]-1'-one, TFA salt and 8.2 and(S)-7'-(3,5-difluorophenyl)-1-(pyrazolo[1,5-α]pyridin-7-yl) dihydro-1'H,3'H,5'H-spiro[piperidine-4,2'-pyrazolo[1,2-α]pyrazol]-1'-one, TFA salt

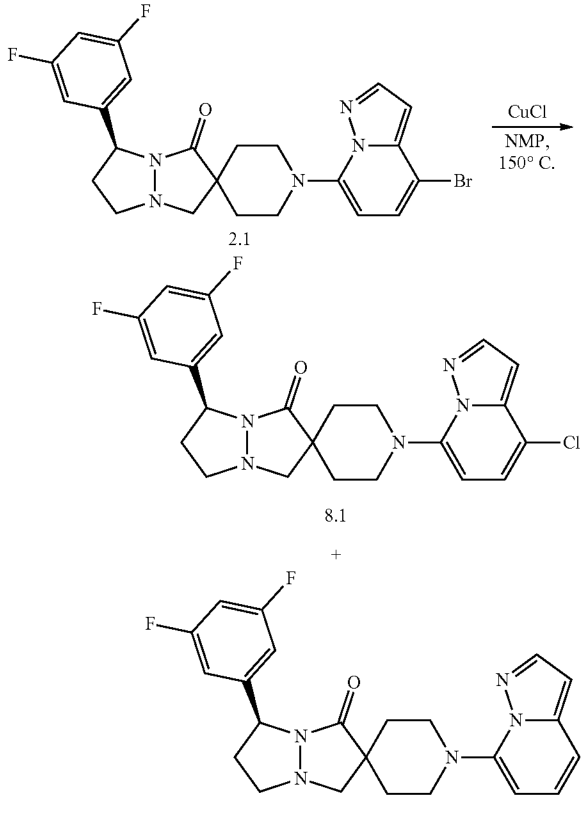

2.1

8.1

+

8.2

A 2 mL Biotage® microwave vial equipped with a stir bar was charged with(S)-1-(4-bromopyrazolo[1,5-α]pyridin-7-yl)-7'-(3,5-difluorophenyl)dihydro-1'H,3'H,5'H-spiro[piperidine-4,2'-pyrazolo[1,2-α]pyrazol]-1'-one (15 mg, 0.030 mmol), CuCl (8.9 mg, 0.090 mmol), and NMP (0.5 mL). The resulting reaction mixture was then stirred at 150° C. under microwave irradiation for 2 h. The reaction was quenched with water (3 mL) and DCM (3 mL). The layers were separated, and the aqueous layer was extracted with DCM (3 mL, ×2). The combined organic layers were dried (MgSO4), filtered through CeliteR), and concentrated under reduced pressure. The crude residue was taken up in DMSO (2 mL), filtered and purified via reversed phase HPLC [Method A]. This provided(S)-1-(4-chloropyrazolo[1,5-α]pyridin-7-yl)-7'-(3,5-difluorophenyl)dihydro-1'H,3'H,5'H-spiro[piperidine-4,2'-pyrazolo[1,2-α]pyrazol]-1'-one, TFA salt (8.1) and (S)-7'-(3,5-difluorophenyl)-1-(pyrazolo[1,5-α]pyridin-7-yl) dihydro-1'H,3'H,5'H-spiro[piperidine-4,2'-pyrazolo[1,2-α] pyrazol]-1'-one, TFA salt (8.2). (S)-1-(4-chloropyrazolo[1,5-a]pyridin-7-yl)-7'-(3,5-difluorophenyl)dihydro-1'H,3'H, 5'H-spiro[piperidine-4,2'-pyrazolo[1,2-a]pyrazol]-1'-one, TFA salt (8.1). MS (ESI) m/z $C_{23}H_{23}ClF_2N_5O$ $[M+1]^+$ calc'd 458, found 458. $^1$HNMR (600 MHZ, DMSO-$d_6$) δ 8.11 (d, J=2.2 Hz, 1H), 7.35 (d, J=8.0 Hz, 1H), 7.18-7.10 (m, 1H), 7.01 (d, J=5.4 Hz, 2H), 6.68 (d, J=2.2 Hz, 1H), 6.33 (d, J=8.0 Hz, 1H), 5.05 (app t, J=7.6 Hz, 1H), 3.91-3.84 (m, 1H), 3.83-3.74 (m, 2H), 3.34 (br s, 1H), 3.20-3.11 (m, 1H), 3.06-2.93 (m, 2H), 2.89 (dt, J=12.8, 6.6 Hz, 1H), 2.64 (br s, 1H), 2.18-2.05 (m, 2H), 2.03-1.93 (m, 2H), 1.73 (d, J=12.7 Hz, 1H). RIPK1 $EC_{50}$ 7 nM. (S)-7'-(3,5-difluorophenyl)-1-(pyrazolo[1,5-a]pyridin-7-yl)dihydro-1'H,3'H,5'H-spiro[piperidine-4,2'-pyrazolo[1,2-α]pyrazol]-1'-one, TFA salt (8.2) MS (ESI) m/z $C_{23}H_{24}F_2N_5O$ $[M+1]^+$ calc'd 424, found 424. $^1$HNMR (600 MHZ, DMSO-$d_6$) δ 8.00 (d, J=1.7 Hz, 1H), 7.33 (d, J=8.7 Hz, 1H), 7.22-7.12 (m, 2H), 7.02 (d, J=6.6 Hz, 2H), 6.59 (d, J=1.6 Hz, 1H), 6.32 (d, J=7.3 Hz, 1H), 5.06 (app t, J=7.6 Hz, 2H), 3.93-3.75 (m, 3H), 3.37 (br s, 1H), 3.16-3.07 (m, 1H), 3.04 (br s, 1H), 2.98-2.86 (m, 2H), 2.69 (br s, 1H), 2.19-2.05 (m, 2H), 2.03-1.95 (m, 2H), 1.74 (d, J=13.8 Hz, 1H). RIPK1 ECso 34 nM.

Preparation of Example 9.1, (S)-7'-(3,5-difluorophenyl)-1-(4-methylpyrazolo[1,5-α]pyridin-7-yl)dihydro-1'H,3'H,5'H-spiro[piperidine-4,2'-pyrazolo[1,2-α]pyrazol]-1'-one, TFA salt Scheme 9

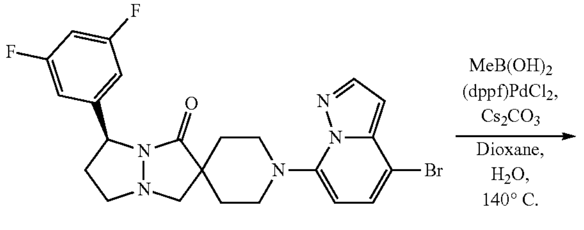

2.1

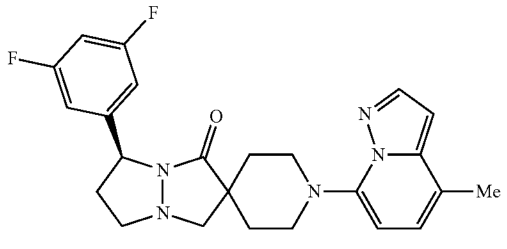

9.1

A 2 mL Biotage® microwave vial equipped with a stir bar was charged with(S)-1-(4-bromopyrazolo[1,5-α]pyridin-7-yl)-7'-(3,5-difluorophenyl)dihydro-1'H,3'H,5'H-spiro[piperidine-4,2'-pyrazolo[1,2-α]pyrazol]-1'-one (20 mg, 0.040 mmol), methylboronic acid (3.6 mg, 0.060 mmol), (dppf) $PdCl_2$ (2.9 mg, 0.004 mmol), and $Cs_2CO_3$ (19.5 mg, 0.060 mmol). The vial was evacuated and backfilled with nitrogen (3×). A sample of dioxane (0.4 mL) and water (0.1 mL) was purged with argon for 15 min with sonication, then added to the reaction vial. The resulting reaction mixture was then stirred at 140° C. under microwave irradiation for 3 h. After cooling, the reaction was partitioned with DCM (3 mL) and water (3 mL), then extracted with DCM (5 mL, x 3). The combined organic layers were dried (MgSO4), filtered through Celite®, and concentrated under reduced pressure. The crude residue was taken up in DMSO (2 mL), filtered and purified via reversed phase HPLC [Method A] to give(S)-7'-(3,5-difluorophenyl)-1-(4-methylpyrazolo[1,5-α]pyridin-7-yl)dihydro-1'H,3'H,5'H-spiro[piperidine-4,2'-pyrazolo[1,2-a]pyrazol]-1'-one, TFA salt. MS (ESI) m/z $C_{24}H_{26}F_3N_5O$ $[M+1]^+$ calc'd 438, found 438. $^1$HNMR (600 MHz, DMSO-$d_6$) δ 7.99 (d, J=2.2 Hz, 1H), 7.14 (t, J=9.3 Hz, 1H), 7.00 (d, J=6.4 Hz, 2H), 6.96 (d, J=6.6 Hz, 1H), 6.59 (d, J=2.2 Hz, 1H), 6.25 (d, J=7.4 Hz, 1H), 5.04 (app t, J=7.6 Hz, 1H), 3.85-3.69 (m, 3H), 3.31 (br s, 1H), 3.10-3.02 (m, 1H), 2.95 (br s, 1H), 2.93-2.83 (m, 2H), 2.59 (br s, 1H), 2.38 (s, 3H), 2.17-2.03 (m, 2H), 2.00-1.93 (m, 2H), 1.71 (d, J=13.1 Hz, 1H). RIPK1 ECso 17 nM.

Preparation of Example 10.1, (S)-7'-(3,5-difluorophenyl)-1-(3-fluorophenyl)dihydro-1'H,3'H,5'H-spiro[piperidine-4,2'-pyrazolo[1,2-α]pyrazol]-1'-one, TFA salt Scheme 10

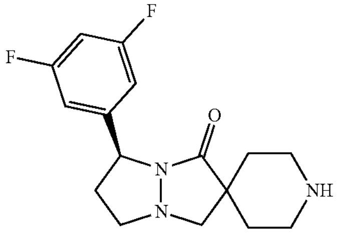

+

J.2

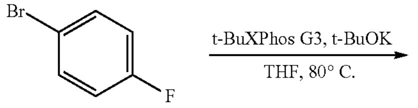

10.A

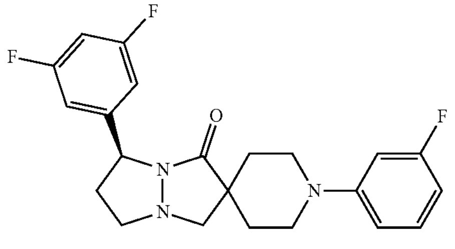

10.1

In the glove box, t-BuXPhos G3 (7.75 mg, 9.76 μmol) was added to a mixture of(S)-7'-(3,5-difluorophenyl)dihydro-1'H,3'H,5'-spiro[piperidine-4,2'-pyrazolo[1,2-α]pyrazol]-1'-one (30 mg, 0.098 mmol), 1-bromo-3-fluorobenzene (25.6 mg, 0.146 mmol) and sodium 2-methylpropan-2-olate (18.76 mg, 0.195 mmol) in THF (1 mL). The reaction was then stirred at 80° C. for 12 h. The mixture was concentrated and purified by via reversed phase HPLC [Method A] to give(S)-7'-(3,5-difluorophenyl)-1-(3-fluorophenyl)dihydro-1'H,3'H,5'H-spiro[piperidine-4,2'-pyrazolo[1,2-α]pyrazol]-1'-one. MS (ESI) m/z $C_{22}H_{23}F_3N_3O$ $[M+1]^+$ calc'd 402, found 402. $^1$H NMR (400 MHZ, CHLOROFORM-d) δ 7.16 (q, J=8.0 Hz, 1H), 6.76-6.85 (m, 2H), 6.63-6.72 (m, 2H), 6.58 (td, J=2.4, 12.4 Hz, 1H), 6.50 (dt, J=1.6, 8.0 Hz, 1H), 4.99 (t, J=8.0 Hz, 1H), 3.54-3.76 (m, 3H), 3.35 (br s, 1H), 3.04 (ddd, J=3.2, 10.0, 12.8 Hz, 1H), 2.70-2.94 (m, 3H), 2.50 (br d, J=7.2 Hz, 1H), 2.16-2.31 (m, 2H), 2.10 (ddd, J=4.0, 10.0, 13.6 Hz, 1H), 1.89-2.01 (m, 1H), 1.64 (br d, J=14.0 Hz, 1H). RIPK1 $EC_{50}$ 47 nM.

The following examples in Table 10 were prepared according to Scheme 10, using intermediate J.2, and the appropriate commercially available aryl or heteroaryl bromide. The compounds were generally purified by reversed phase HPLC.

TABLE 10

Examples Prepared According to Scheme 10

| Ex. No. | Structure | Name | Exact Mass $[M + H]^+$ | RIPK1 $EC_{50}$ (nM) |
| --- | --- | --- | --- | --- |
| 10.2 | 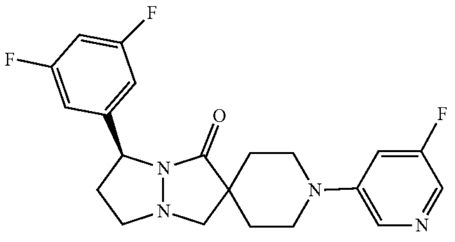 [SMILES: O=C1N2[C@H](c3cc(F)cc(F)c3)CCN2CC12CCN(c1cncc(F)c1)CC2] | (S)-7'-(3,5-difluorophenyl)-1-(5-fluoropyridin-3-yl)dihydro-1'H,3'H,5'H-spiro[piperidine-4,2'-pyrazolo[1,2-a]pyrazol]-1'-one | 403 | 338 |
| 10.3 | 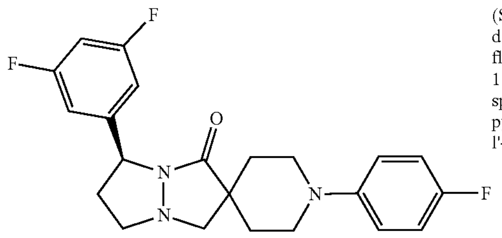 | (S)-7'-(3,5-difluorophenyl)-1-(4-fluorophenyl)dihydro-1'H,3'H,5'H-spiro[piperidine-4,2'-pyrazolo[1,2-a]pyrazol]-1'-one | 402 | 122 |

Preparation of Example 11.1, (S)-1-(5-chloro-6-methylpyridin-2-yl)-7'-(3,5-difluorophenyl)dihydro-1'H,3'H,5'H-spiro[piperidine-4,2'-pyrazolo[1,2-α]pyrazol]-1'-one Scheme 11

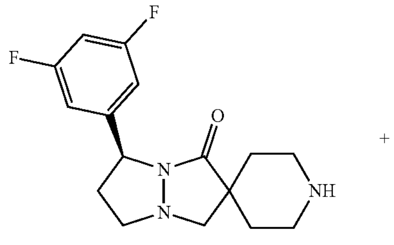

J.2

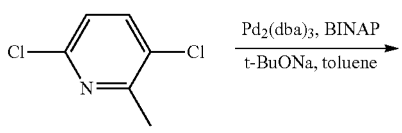

11.A

-continued

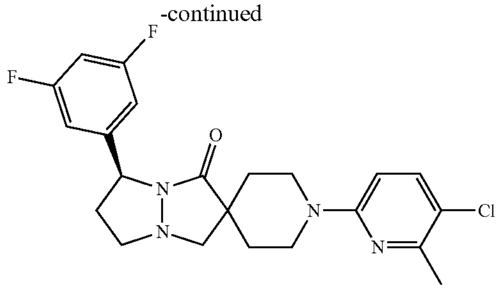

11.1

A vial was charged with(S)-7'-(3,5-difluorophenyl)dihydro-1'H,3'H,5'H-spiro[piperidine-4,2'-pyrazolo[1,2-α]pyrazol]-1'-one (12.3 mg, 40 μmol), 7-bromopyrazolo[1,5-α]pyrimidine (9.51 mg, 48.0 μmol), tris (dibenzylideneacetone) dipalladium (0) (1.83 mg, 2.00 μmol), (R)-(+)-2,2'-bis(diphenylphosphino)-1,1'-binaphthyl (1.3 mg, 2.0 μmol), followed by addition of sodium tert-butoxide (7.69 mg, 80 μmol) in toluene (400 μl). The mixture was stirred at 90° C. for 16 h. MS (ESI) m/z $C_{22}H_{24}ClF_2N_4O$ $[M+1]^+$ calc'd 433, found 433. RIPK1 $EC_{50}$ 23 nM.

The following example in Table 11 was prepared according to Scheme 11, using intermediate J.2, and the appropriate commercially available heteroaryl chloride. The compound was purified by reversed phase HPLC.

TABLE 11

Examples Prepared According to Scheme 11

| Ex. No. | Structure | Name | Exact Mass $[M + H]^+$ | RIPK1 $EC_{50}$ (nM) |
|---|---|---|---|---|
| 11.2 | 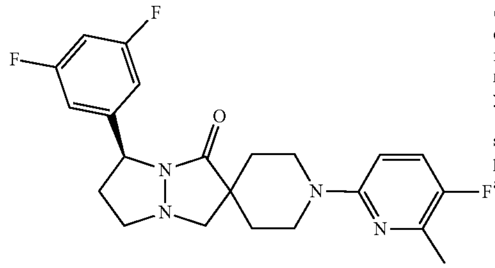 [SMILES: Cc1nc(N2CCC3(CC2)CN2CC[C@@H](c4cc(F)cc(F)c4)N2C3=O)ccc1F] | (S)-7'-(3,5-difluorophenyl)-1-(5-fluoro-6-methylpyridin-2-yl)dihydro-1'H,3'H,5'H-spiro[piperidine-4,2'-pyrazolo[1,2-a]pyrazol]-1'-one | 417 | 43 |

Reversed Phase prep-HPLC Methods:
Method A-Acid Modifier $C_{18}$ reversed-phase Prep-HPLC (gradient elution, MeCN/$H_2O$/0.1% TFA). Electrospray (ESI)

Mass-triggered fraction collection was employed using positive ion polarity scanning to monitor for the target mass.
Method B-Basic Modifier $C_{18}$ reversed-phase Prep-HPLC (gradient elution, MeCN/$H_2O$/basic modifier-either 0.1% $NH_4OH$ or 0.05% $NH_4HCO3$). Electrospray (ESI) Mass-triggered fraction collection was employed using positive ion polarity scanning to monitor for the target mass.

RIPK1-ADP-Glo Enzymatic Assay

The enzymatic activity of RIPK1 was measured using an assay derived from ADP-Glo kit (™Promega), which provides a luminescent-based ADP detection system. Specifically, the ADP generated by RIPK1 kinase was proportionally detected as luminescent signals in a homogenous fashion. In this context, the assessment of the inhibitory effect of small molecules ($EC_{50}$) was measured by the effectiveness of the compounds to inhibit the ATP to ADP conversion by RIPK1.

In this assay, the potency ($EC_{50}$) of each compound was determined from a ten-point (1:3 serial dilution; top compound concentration of 100000 nM) titration curve using the following outlined procedure. To each well of a white ProxiPlus 384 well-plate, 30 nL of compound (1% DMSO in final assay volume of 3 μL) was dispensed, followed by the addition of 2 μL of 1× assay buffer (25 mM Hepes 7.3, 20 mM MgCl2, 50 mM NaCl, 1 mM DTT, 0.005% Tween20, and 0.02% BSA) containing 37.5 nM of GST-RIPK1 (recombinant GST-RIPK1 kinase domain (residues 1-327) enzyme produced from baculovirus-transfected Sf21 cells: MW=62 kDa). Plates were placed in an ambient temperature humidified chamber for a 30 minutes pre-incubation with compound. Subsequently, each reaction was initiated by the addition of 1 μL 1× assay buffer containing 900 μM ATP and 3 μM dephosphorylated-MBP substrate. The final reaction in each well of 3 μL consists of 25 nM of GST-RIPK1, 300 M ATP, and 3 μM dephosphorylated-MBP. Kinase reactions were allowed to proceed for 150 minutes prior to adding ADP-Glo reagents per Promega's outlined kit protocol. Dose-response curves were generated by plotting percent effect (% product conversion: Y-axis) vs. $Log_{10}$ compound concentrations (X-axis). $EC_{50}$ values were calculated using a non-linear regression, four-parameters sigmoidal dose-response model and are provided for example compounds of the invention (labeled "RIPK1 $EC_{50}$ (nM)" throughout the above examples).

What is claimed is:

1. A compound of Formula I:

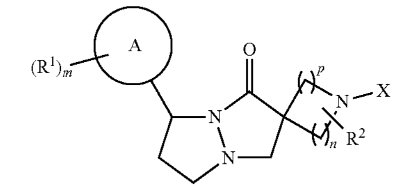

I or a pharmaceutically acceptable salt thereof, wherein:

A is aryl, heteroaryl, heterocycloalkyl or $C_3$-$C_6$cycloalkyl;

each occurrence of $R^1$ is independently —OH, $C_1$-$C_6$alkylOH, —CN, $C_1$-$C_6$alkylCN, $C_1$-$C_6$alkyl, halo$C_1$-$C_6$alkyl, halogen, —$NH_2$, —N($C_1$-$C_6$alkyl)$_2$, —NH($C_1$-$C_6$alkyl) or $C_1$-$C_6$alkoxy;

$R^2$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —N($C_1$-$C_6$alkyl)$_2$, —NH($C_1$-$C_6$alkyl) or $C_1$-$C_6$alkoxy;

X is-CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, $SO_2$heterocycloalkyl, —COO$C_1$-$C_6$alkyl or —COO$C_3$-$C_6$cycloalkyl, wherein the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —COO$C_3$-$C_6$cycloalkyl or —$SO_2$heterocycloalkyl is unsubstituted or substituted with one to four substituents selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl$)_2$, —NH($C_1$-$C_6$alkyl), —$NH_2$, and —N($C_1$-$C_6$alkyl$)_2$, wherein the heteroaryl, heterocycloalkyl, $C_3$-$C_6$cycloalkyl, aryl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl;

m is 0, 1, 2 or 3;

n is 1, 2 or 3; and p is 1, 2 or 3.

2. The compound of claim 1, or a pharmaceutically acceptable salt thereof, wherein A is aryl.

3. The compound of claim 2, or a pharmaceutically acceptable salt thereof, wherein A is phenyl.

4. The compound of claim 1, or a pharmaceutically acceptable salt thereof, wherein $R^1$ is halogen.

5. The compound of claim 4, or a pharmaceutically acceptable salt thereof, wherein $R^1$ is fluorine and m is 2.

6. The compound of claim 1, or a pharmaceutically acceptable salt thereof, wherein n and p are both 2.

7. The compound of claim 1, or a pharmaceutically acceptable salt thereof, wherein $R^2$ is hydrogen.

8. The compound of claim 1, or a pharmaceutically acceptable salt thereof, wherein X is —COaryl, and the —COaryl is unsubstituted or substituted with one, two or three substituents independently selected from the group consisting of: $C_1$-$C_6$alkyl, —CN, $C_1$-$C_6$alkoxy and halogen.

9. The compound of claim 1, or a pharmaceutically acceptable salt thereof, wherein X is —COheteroaryl, and the —COheteroaryl is unsubstituted or substituted with one, two or three substituents independently selected from the group consisting of $C_1$-$C_6$alkyl and halogen.

10. The compound of claim 1, or a pharmaceutically acceptable salt thereof, wherein X is heteroaryl, and the heteroaryl is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl$)_2$, and —N($C_1$-$C_6$alkyl$)_2$, wherein the heteroaryl or aryl is unsubstituted or substituted with one to two substituents independently selected from the group consisting of halogen, $C_1$-$C_6$haloalkyl and $C_1$-$C_6$alkyl.

11. The compound of claim 10, or a pharmaceutically acceptable salt thereof, wherein X is heteroaryl, wherein the heteroaryl is

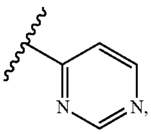 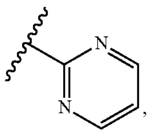 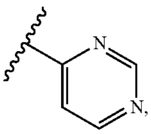

-continued

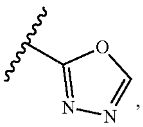, 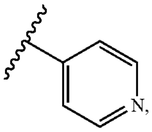 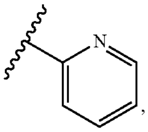,

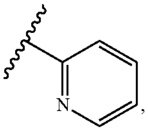, 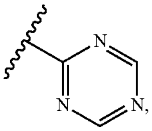 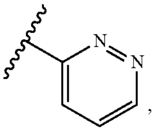,

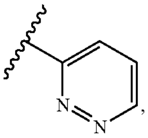, 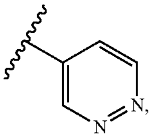 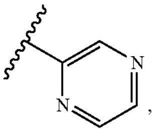,

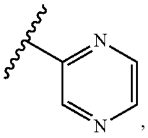, 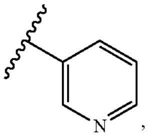, 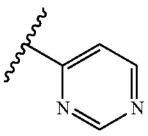 or

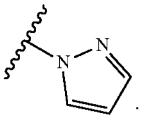.

12. The compound of claim 10, or a pharmaceutically acceptable salt thereof, wherein X is heteroaryl, wherein the heteroaryl is

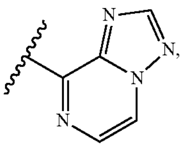 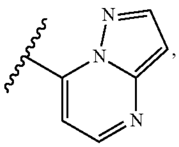, 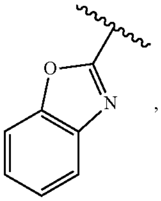,

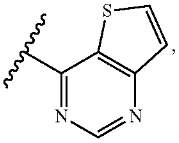, 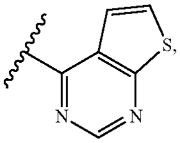 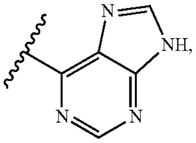

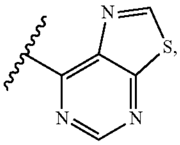 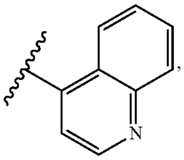,

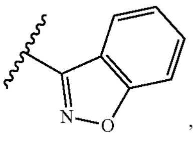, 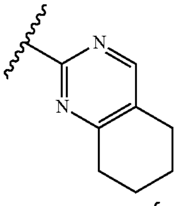,

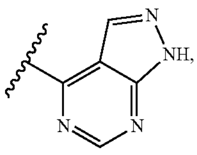 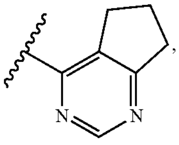, 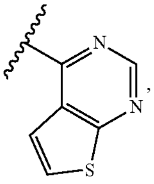

-continued

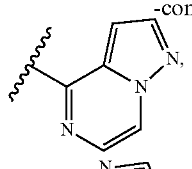

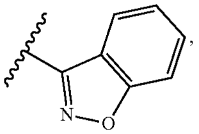

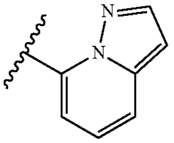

or

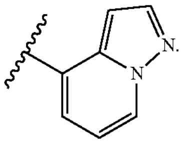

13. The compound of claim 1, or a pharmaceutically acceptable salt thereof, wherein X is —$SO_2$aryl.

14. The compound of claim 9, or a pharmaceutically acceptable salt thereof, wherein X is —COheteroaryl, wherein the —COheteroaryl is

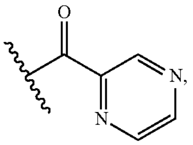

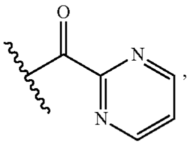

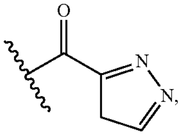

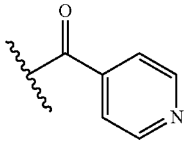

or

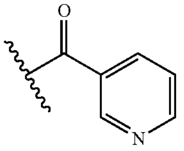

15. The compound of claim 1, or a pharmaceutically acceptable salt thereof, wherein X is

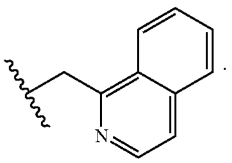 [SMILES: *Cc1nccc2ccccc12]

16. The compound of claim 1, or a pharmaceutically acceptable salt thereof, wherein when X is aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl or —$SO_2$heterocycloalkyl, X is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —$COC_1$-$C_6$alkyl, —$SC_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl or aryl is unsubstituted or substituted with one to two substituents independently selected from the group consisting of halogen, $C_1$-$C_6$haloalkyl and $C_1$-$C_6$alkyl.

17. A compound of Formula IV:

IV

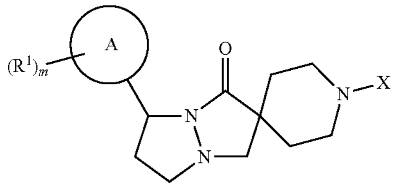

or a pharmaceutically acceptable salt thereof, wherein:

A is aryl;

$R^1$ is halogen;

X is —COaryl, —$SO_2$aryl, heteroaryl, $C_1$-$C_6$alkylheteroaryl, —COheteroaryl, heterocycloalkyl, or —$COOC_1$-$C_6$alkyl, wherein the —COaryl, heteroaryl, or —COheteroaryl is unsubstituted or substituted with one to four substituents independently selected from the group consisting of —CN, —OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —$COC_1$-$C_6$alkyl, —$SC_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl or aryl is unsubstituted or substituted with one to two substituents independently selected from the group consisting of halogen, $C_1$-$C_6$haloalkyl and $C_1$-$C_6$alkyl; and m is 0, 1, 2 or 3.

18. A compound of Formula V:

V

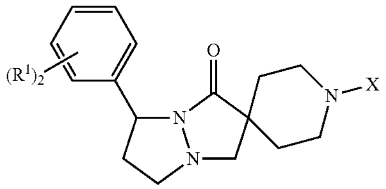

or a pharmaceutically acceptable salt thereof, wherein:

each occurrence of $R^1$ is independently —OH, $C_1$-$C_6$alkylOH, —CN, $C_1$-$C_6$alkylCN, $C_1$-$C_6$alkyl, halo$C_1$-$C_6$alkyl, halogen or $C_1$-$C_6$alkoxy;

X is —COaryl, —$SO_2$aryl, heteroaryl, $C_1$-$C_6$alkylheteroaryl, —COheteroaryl, heterocycloalkyl, or —$COOC_1$-$C_6$alkyl, wherein the —COaryl, heteroaryl, or —COheteroaryl is unsubstituted or substituted with one to four substituents independently selected from the group consisting of CN, OH, halogen, $C_1$-$C_6$alkylOH, $C_1$-$C_6$alkyl, $C_1$-$C_6$haloalkyl, $C_1$-$C_6$alkoxy, $C_1$-$C_6$haloalkoxy, —$COC_1$-$C_6$alkyl, —$SC_1$-$C_6$alkyl, oxo, $C_3$-$C_6$cycloalkyl, aryl, heteroaryl, heterocycloalkyl, —CONH($C_1$-$C_6$alkyl), —$CONH_2$, —CON($C_1$-$C_6$alkyl)$_2$, and —N($C_1$-$C_6$alkyl)$_2$, wherein the heteroaryl, or aryl, is unsubstituted or substituted with one to two substituents independently selected from the group consisting of halogen, $C_1$-$C_6$haloalkyl and $C_1$-$C_6$alkyl; and m is 0, 1, 2 or 3.

19. The compound of claim 1 having the following structure:
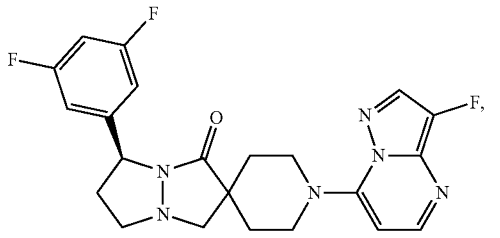
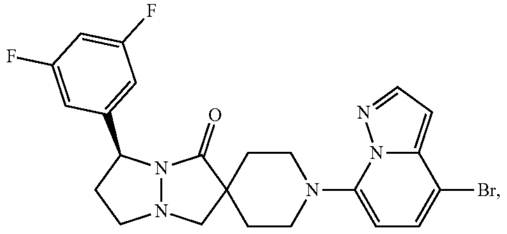
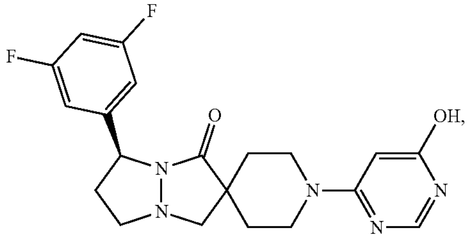
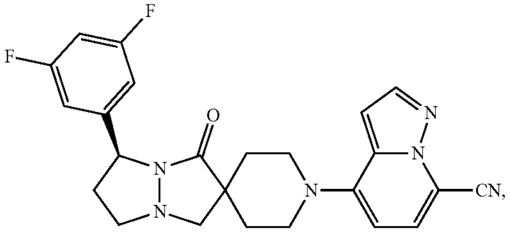
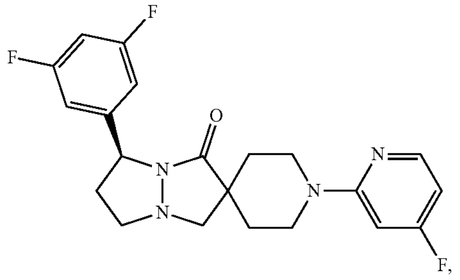
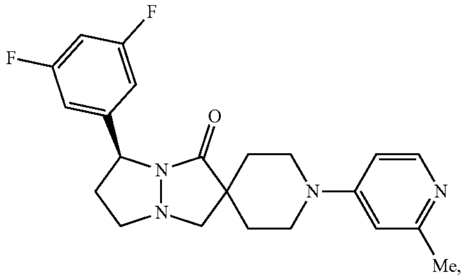
-continued
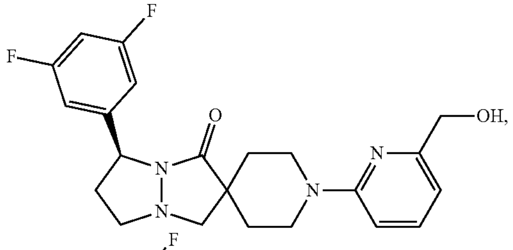
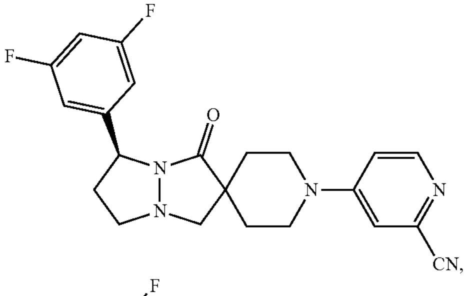
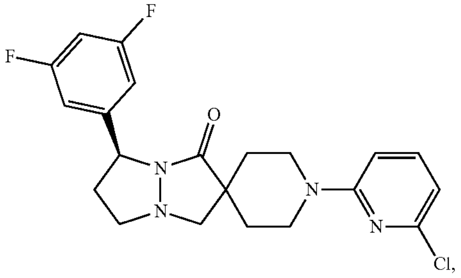
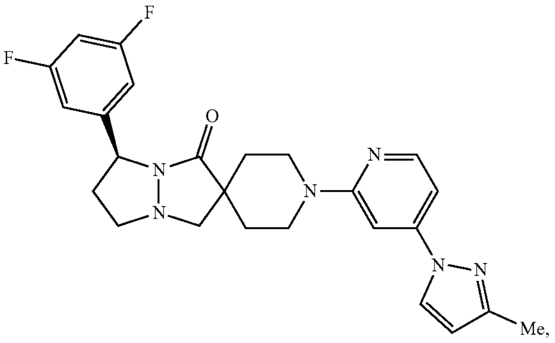
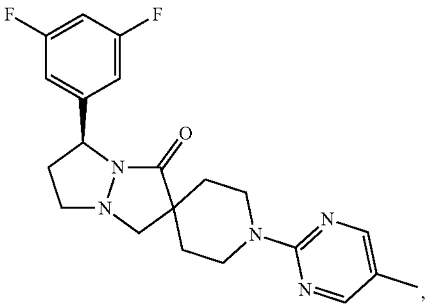
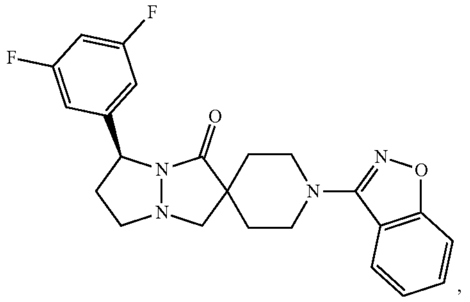

-continued
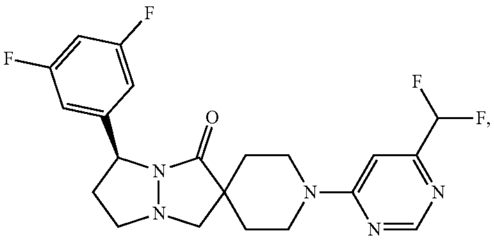
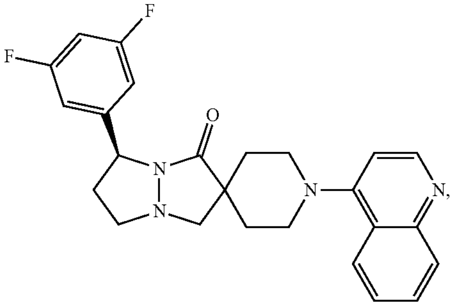
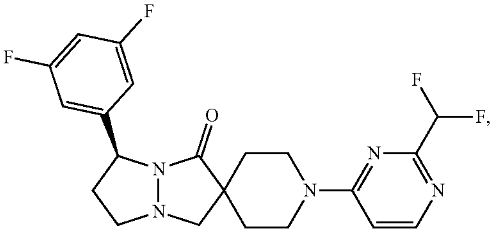
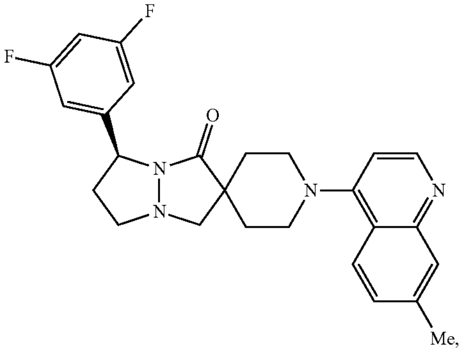
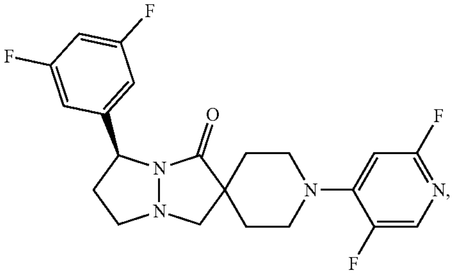
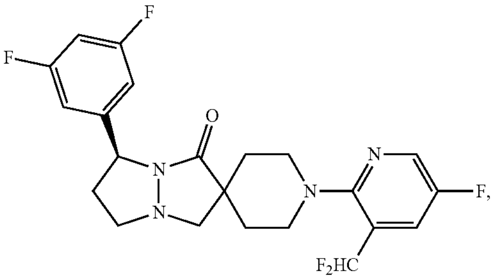
-continued
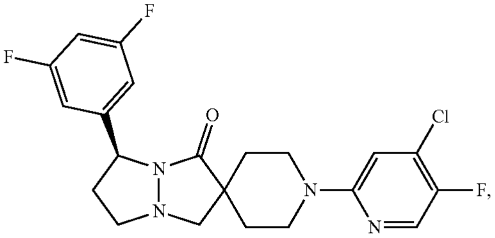
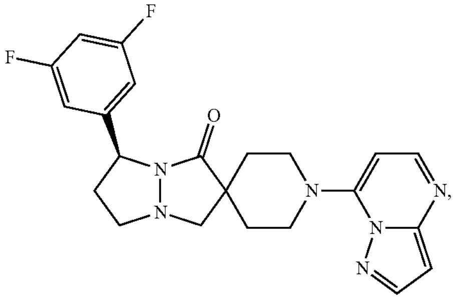
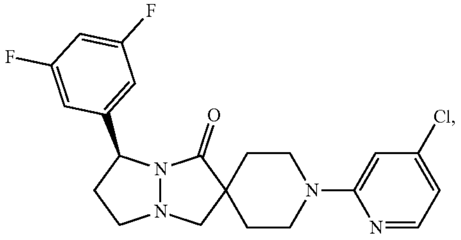
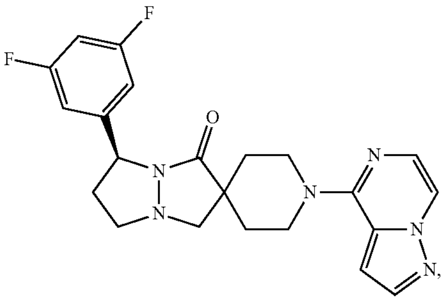
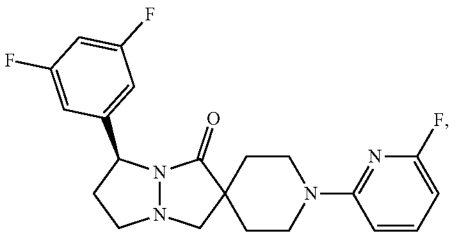
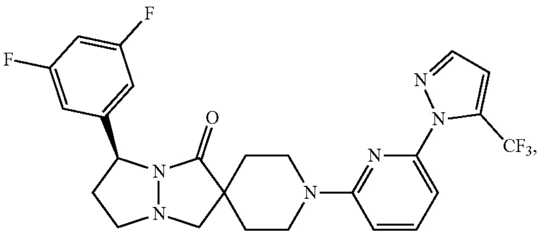

-continued
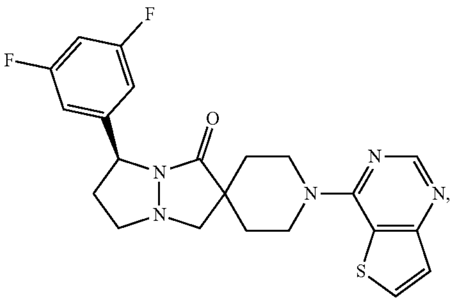
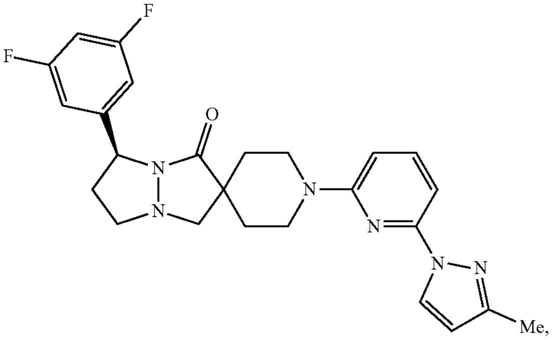
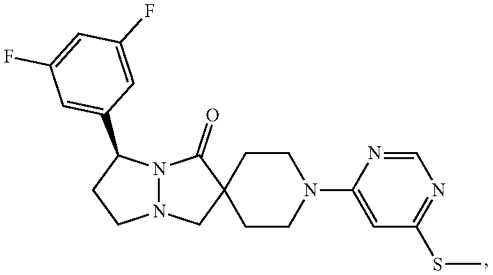
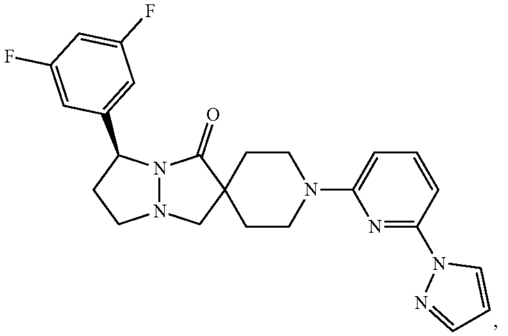
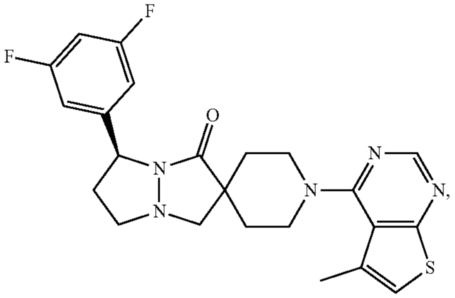
-continued
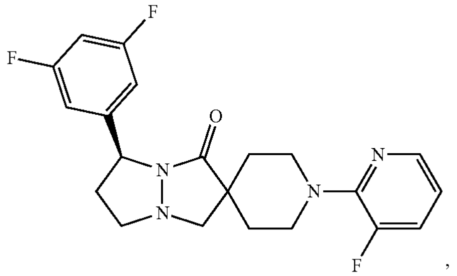
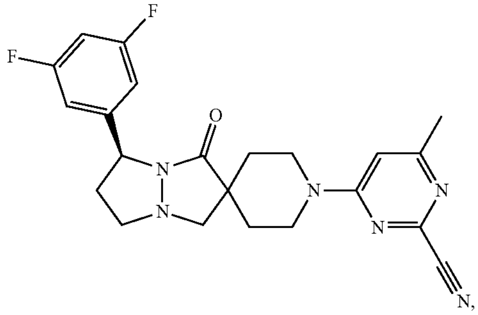
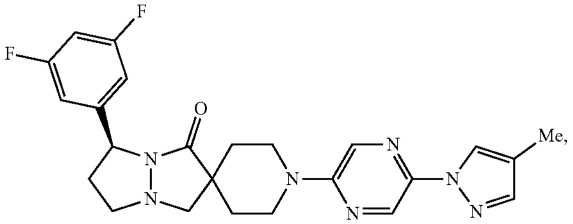
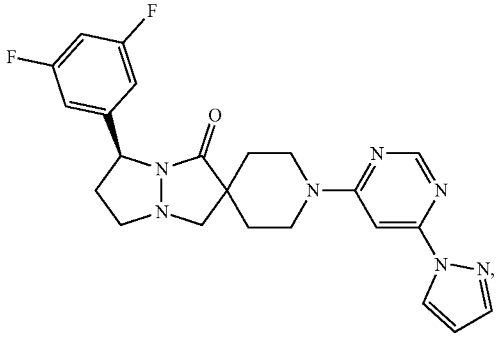
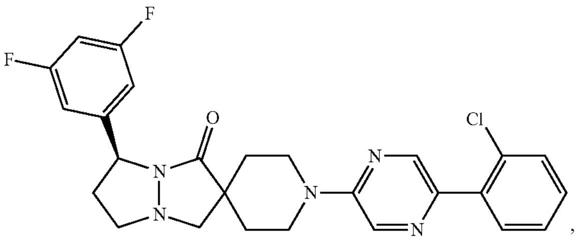
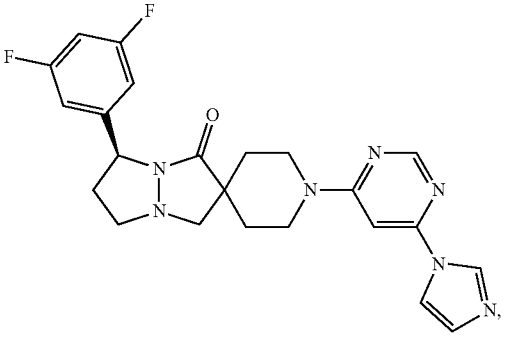

-continued
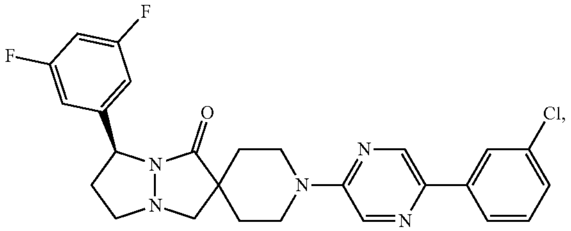
,
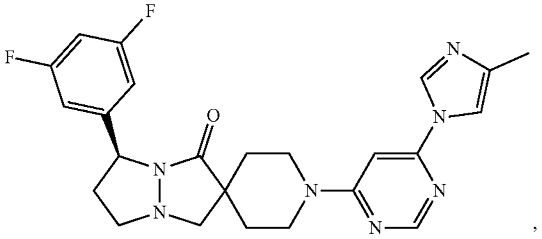
,
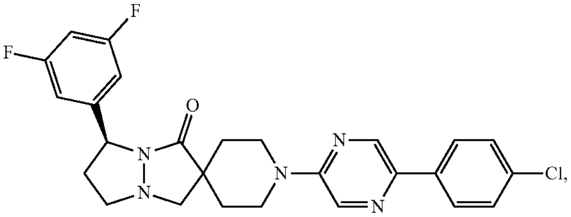
,
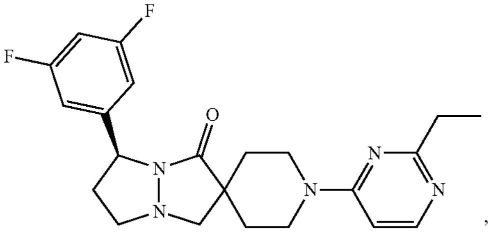
,
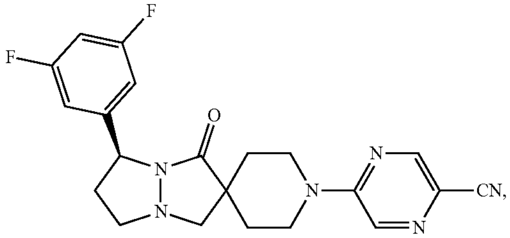
,
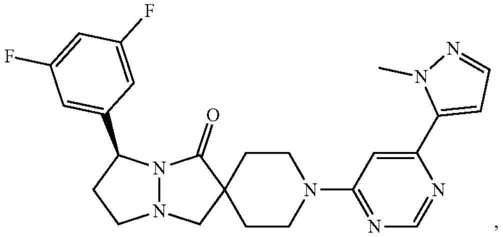
,
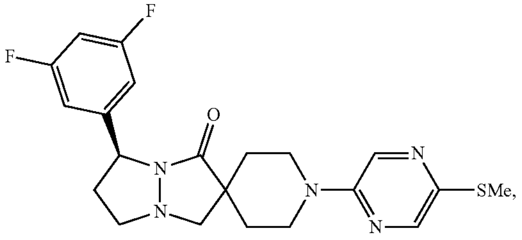
,
-continued
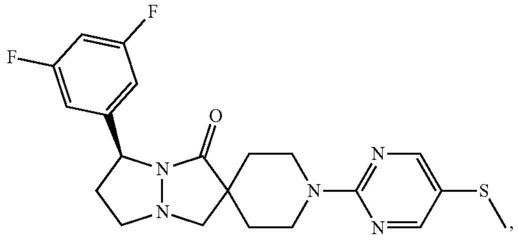
,
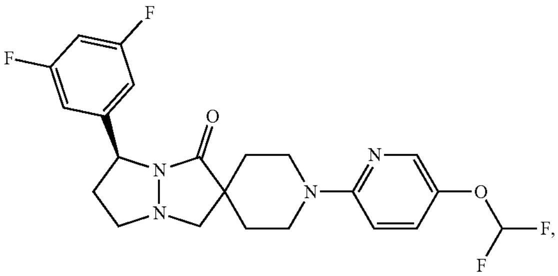
,
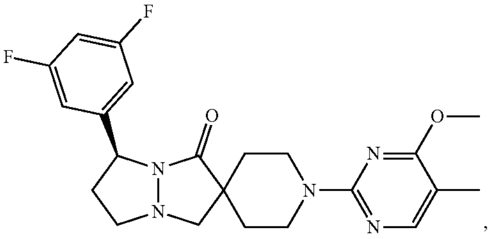
,
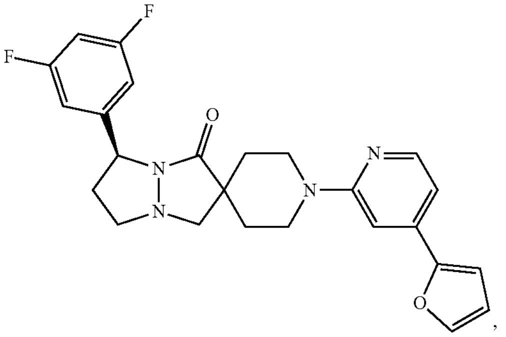
,
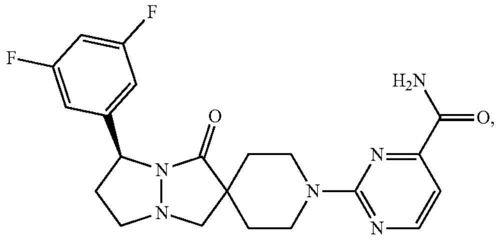
,
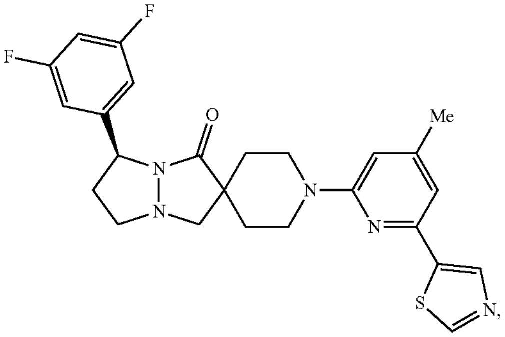
, -continued
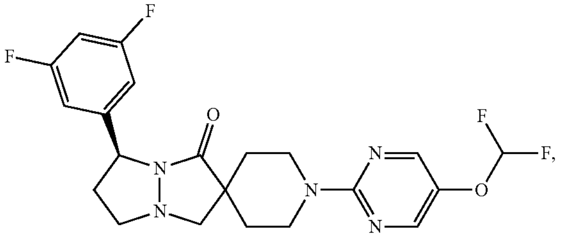
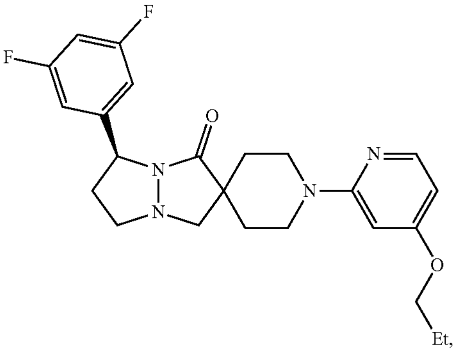
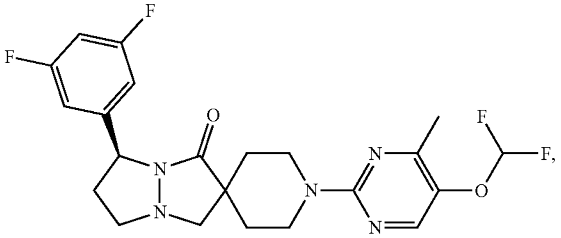
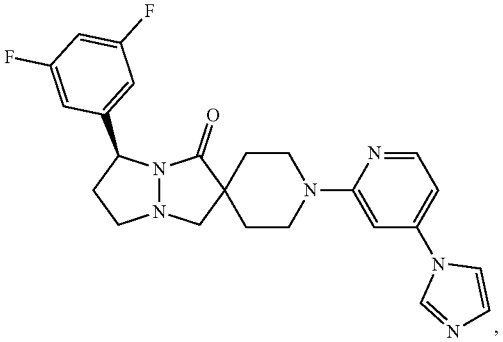
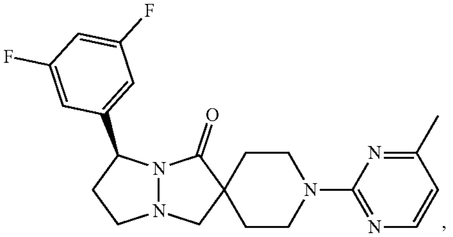
-continued
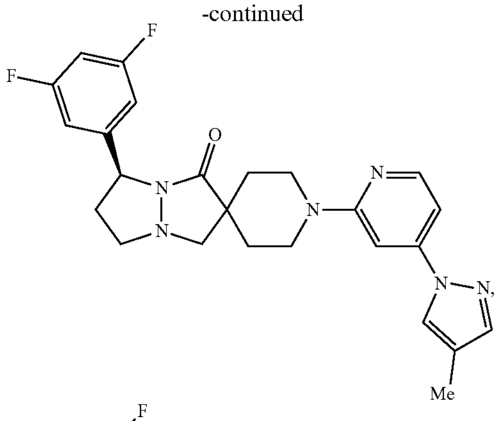
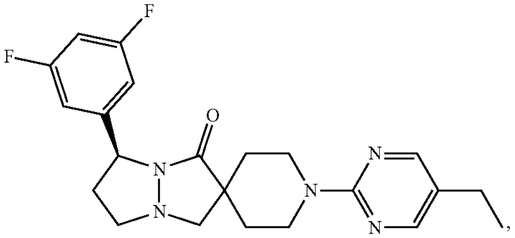
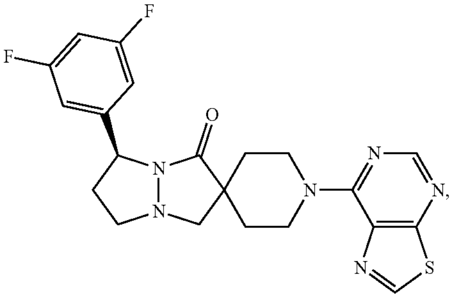
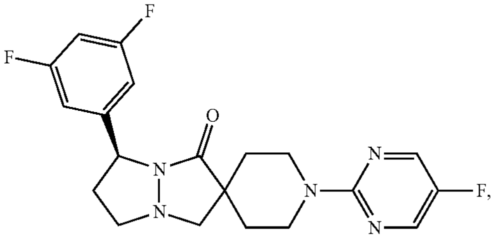
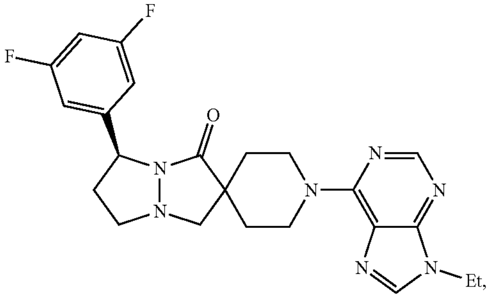
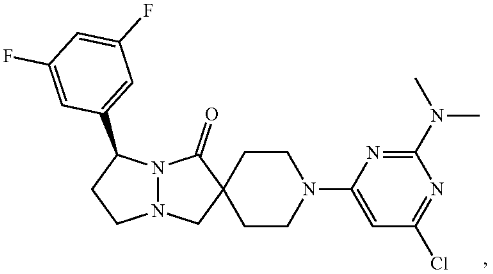

-continued
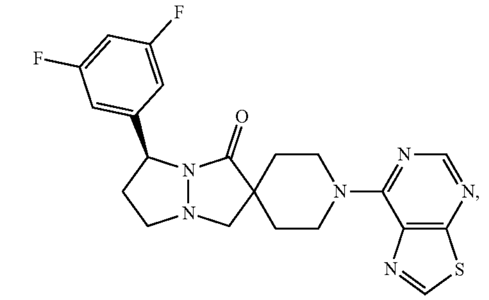
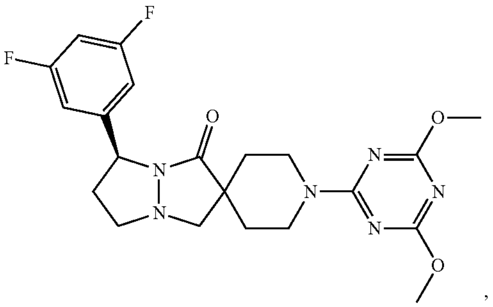
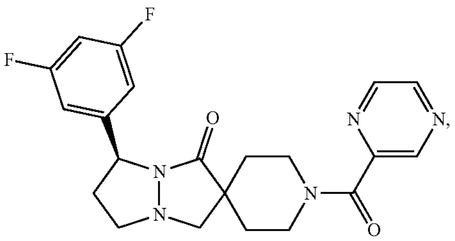
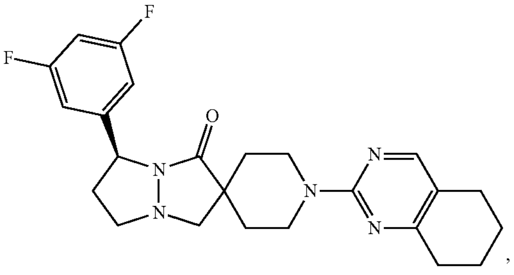
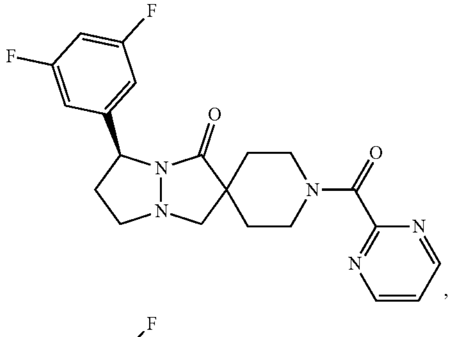
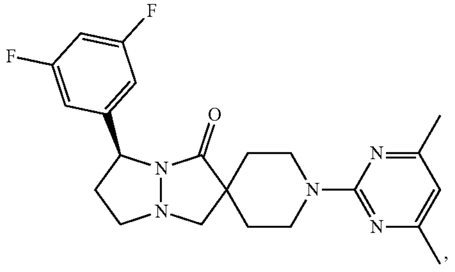
-continued
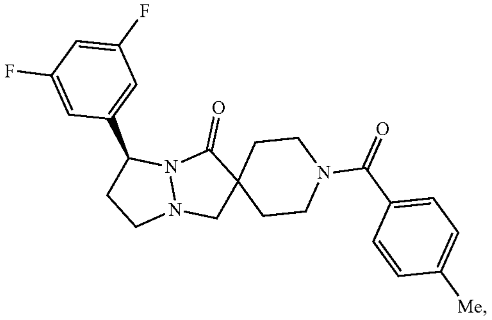
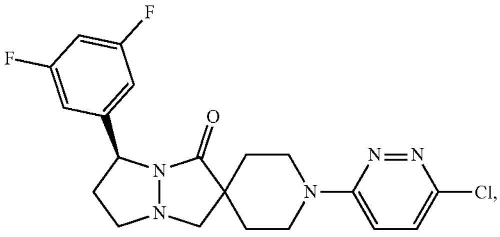
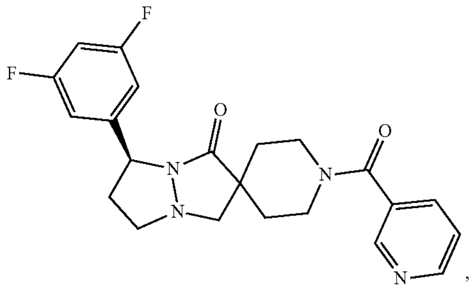
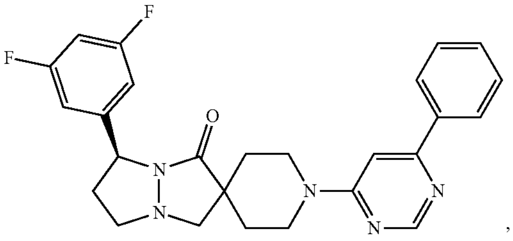
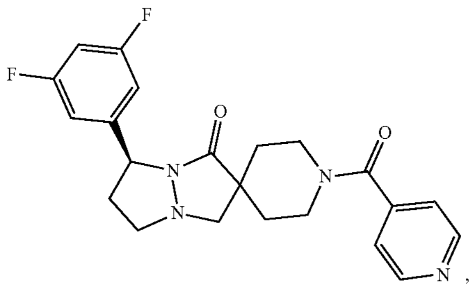
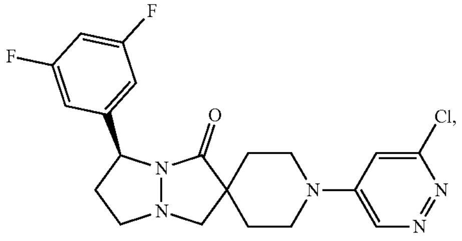

-continued
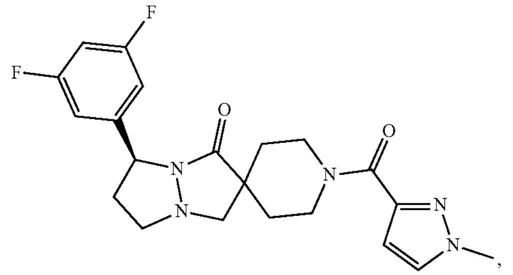
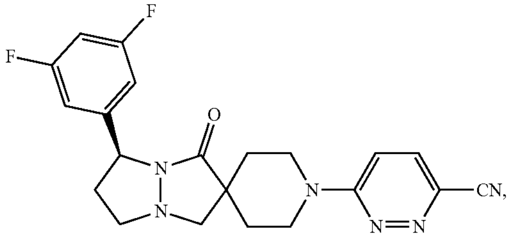
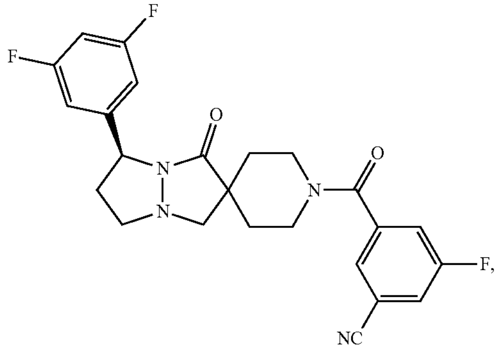
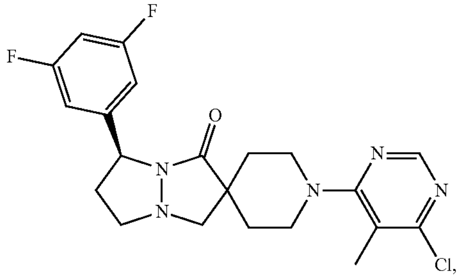
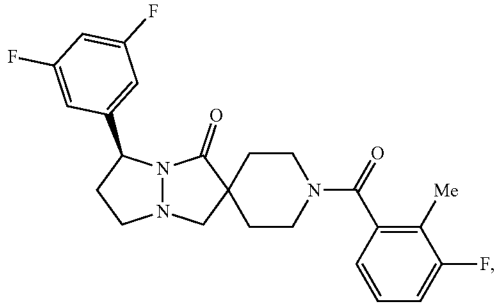
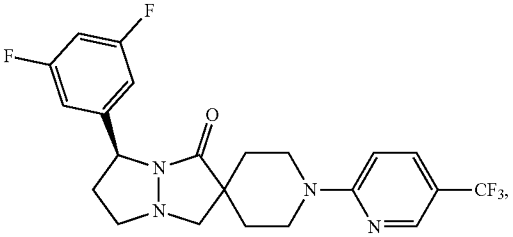
-continued
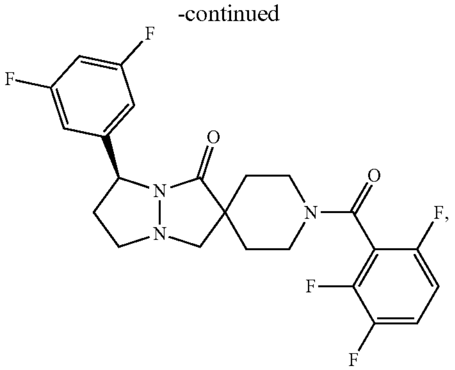
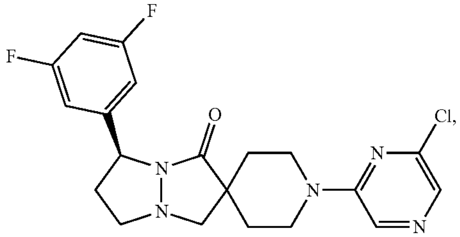
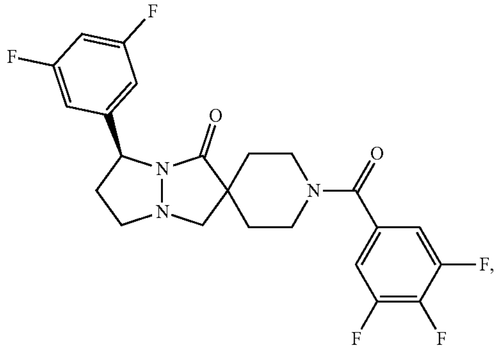
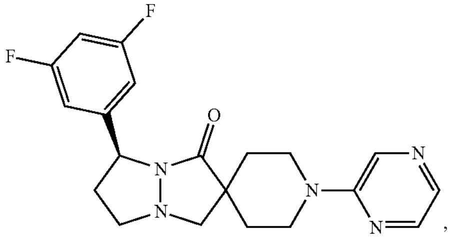
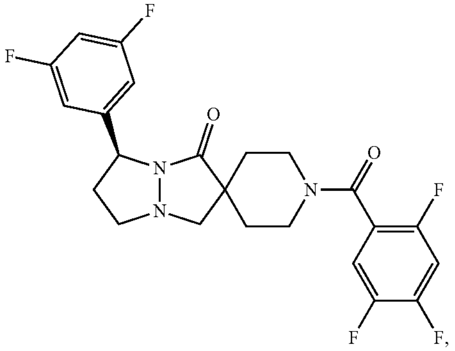

-continued
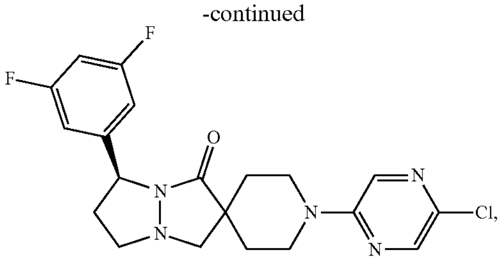
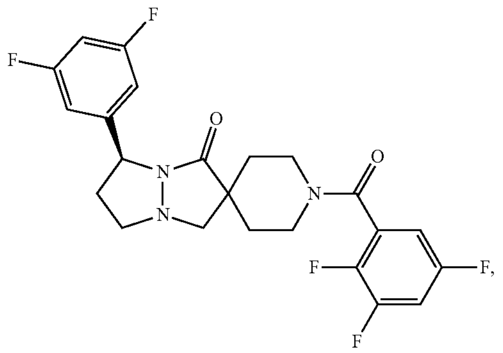
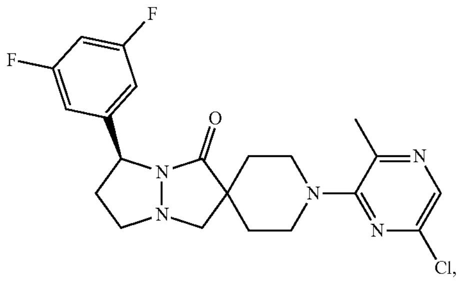
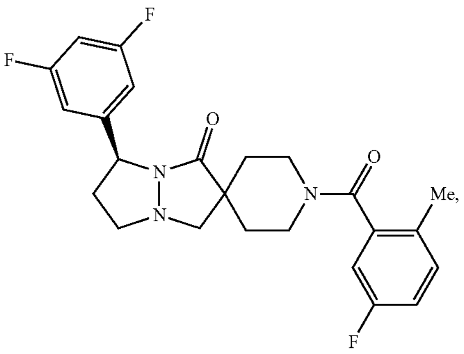
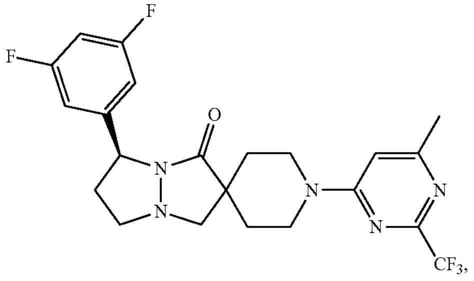
-continued
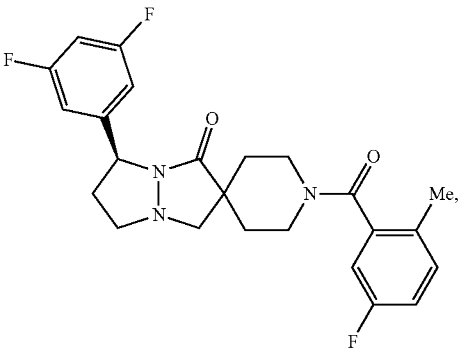
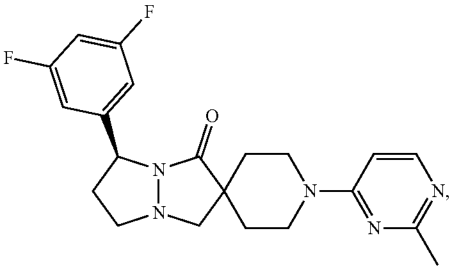
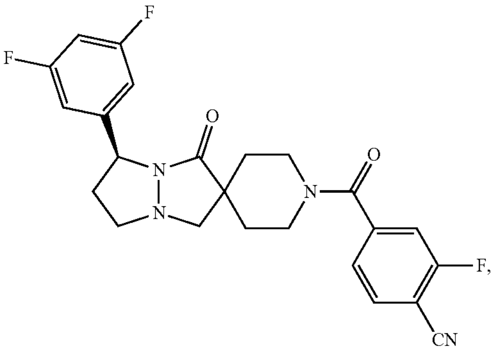
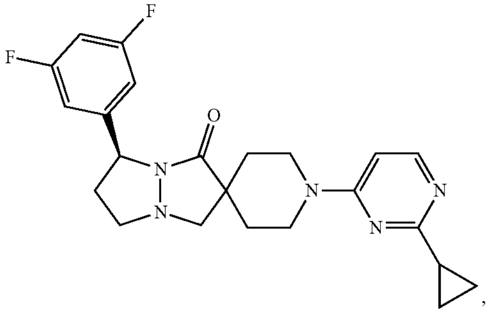
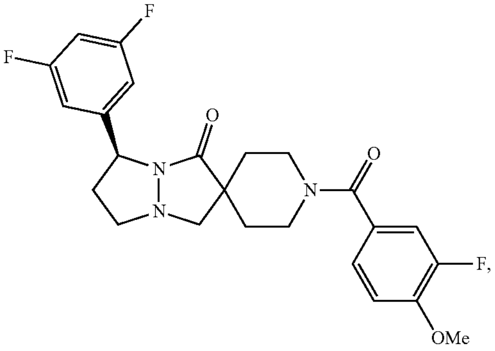

-continued
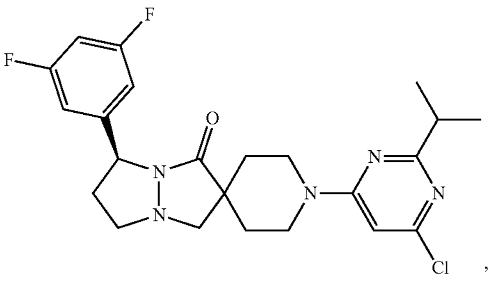
,
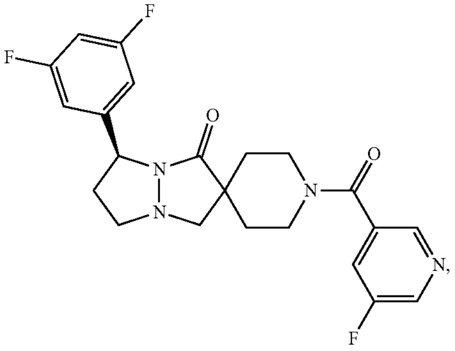
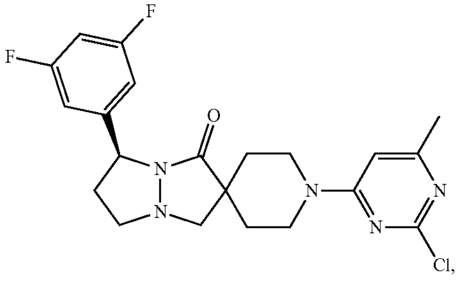
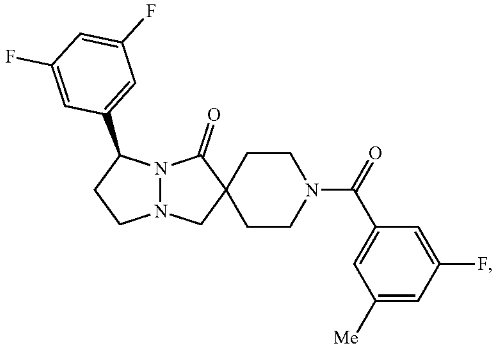
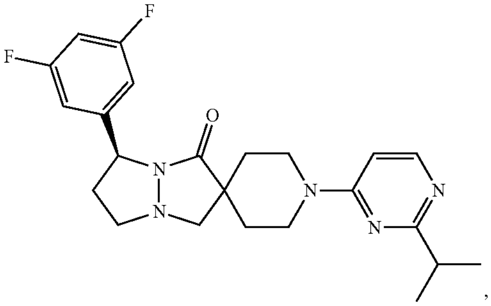
,
-continued
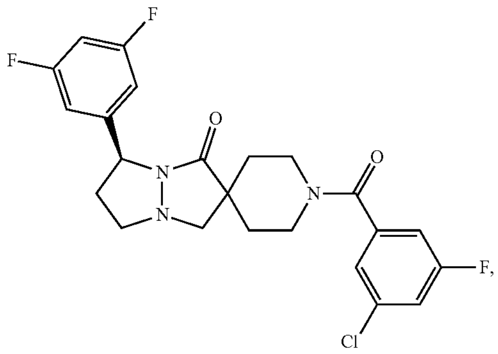
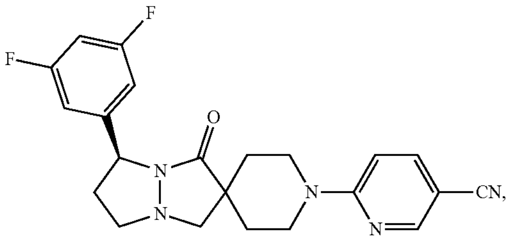
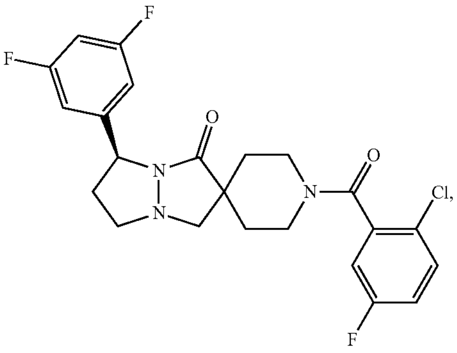
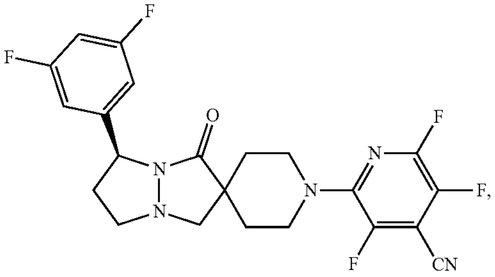
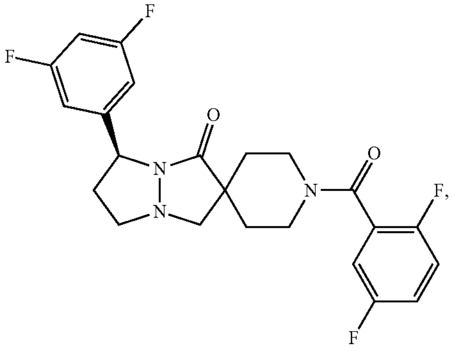

-continued
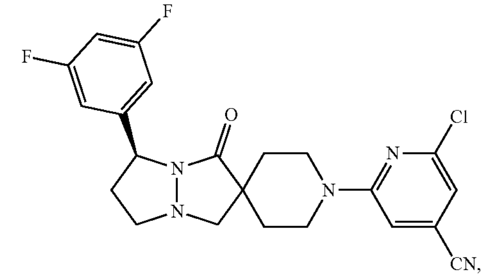
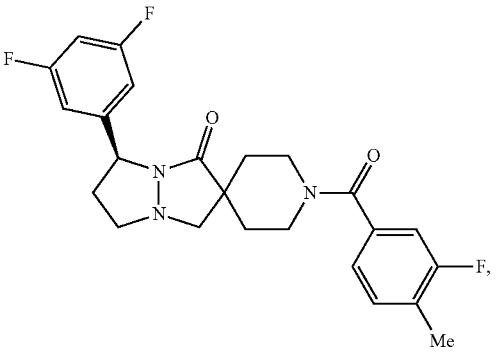
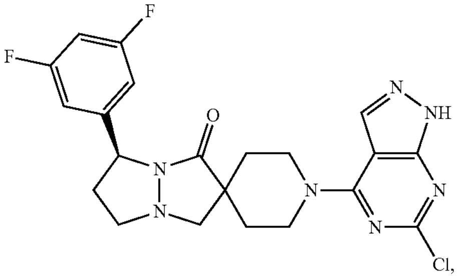
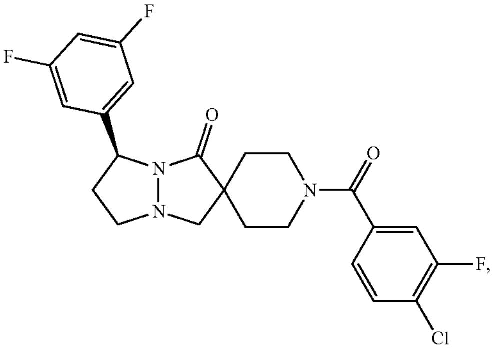
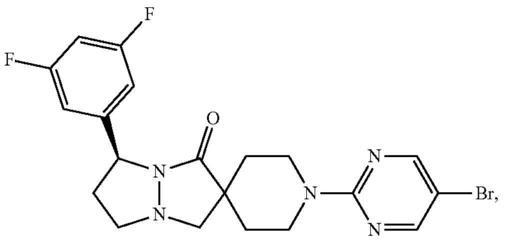
-continued
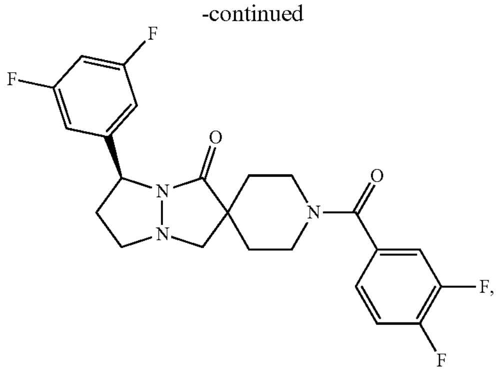
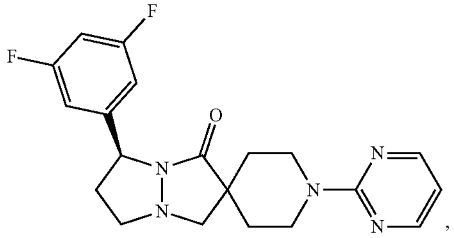
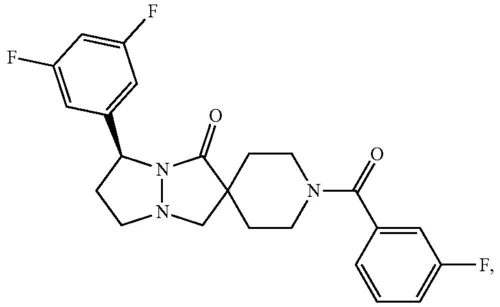
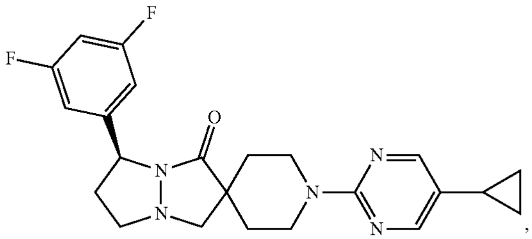
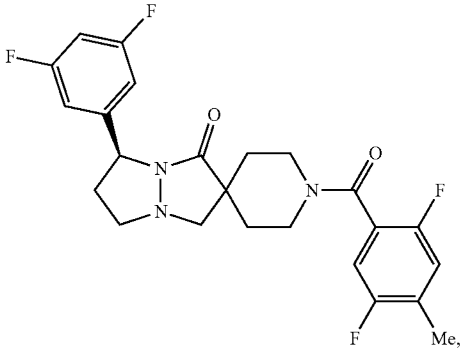
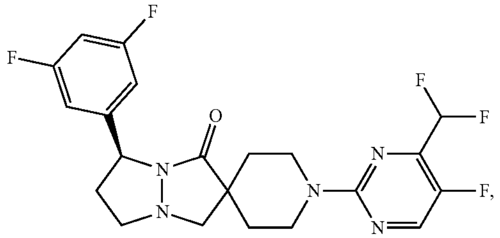

-continued
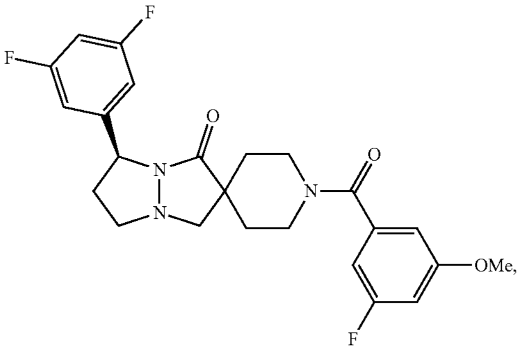
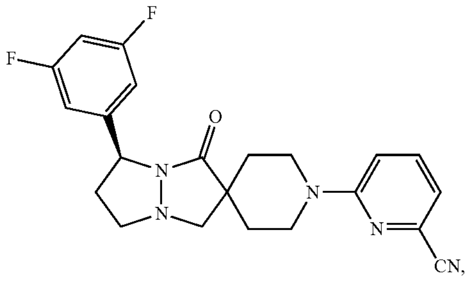
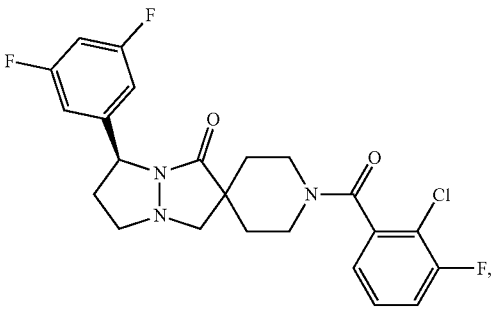
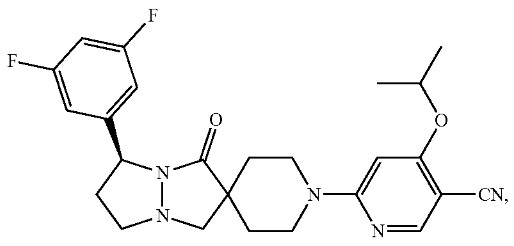
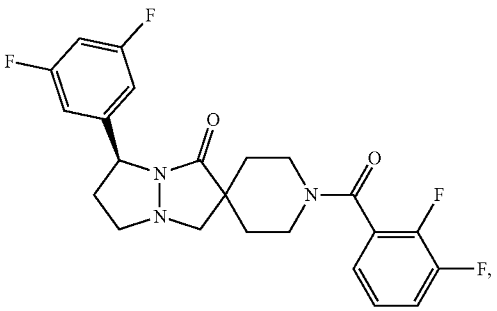
-continued
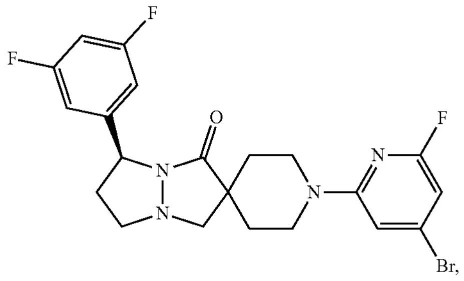
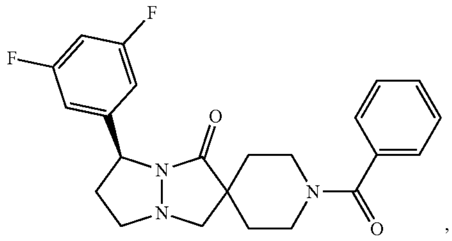
,
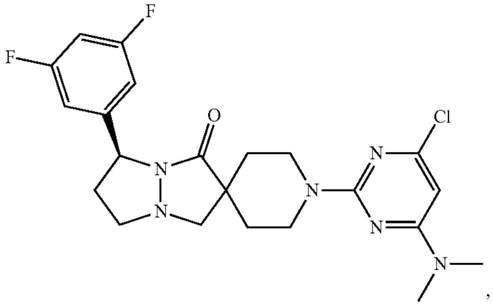
,
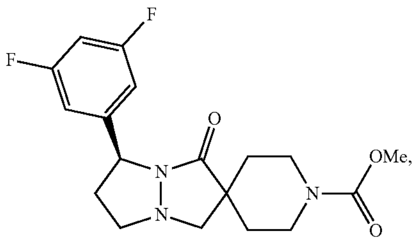
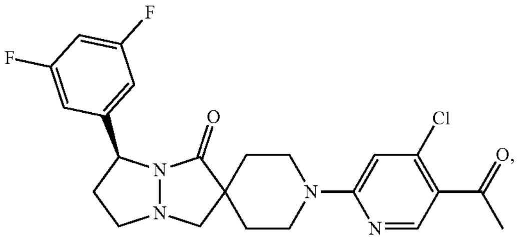
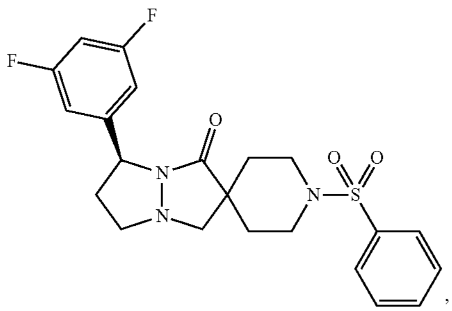
, -continued
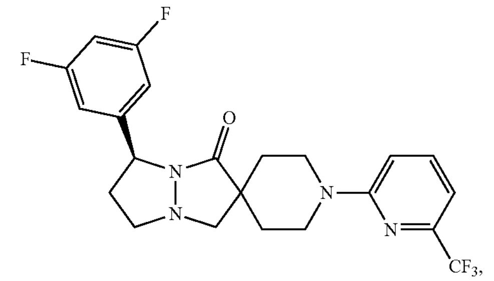
,
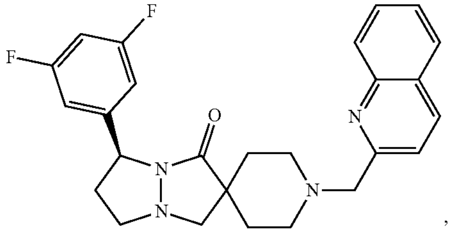
,
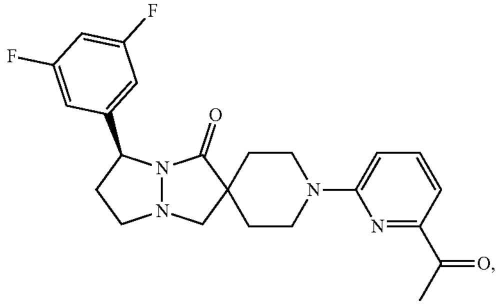
,
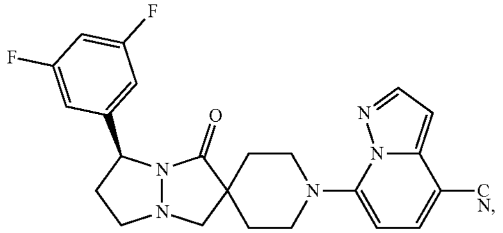
,
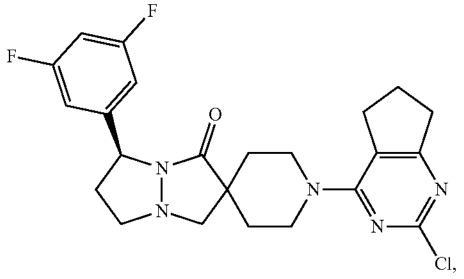
,
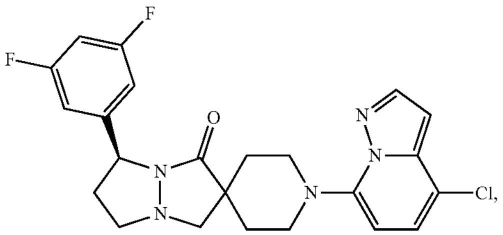
,
-continued
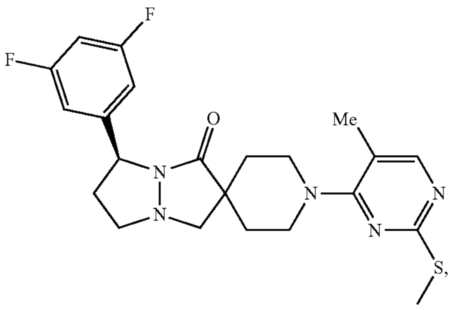
,
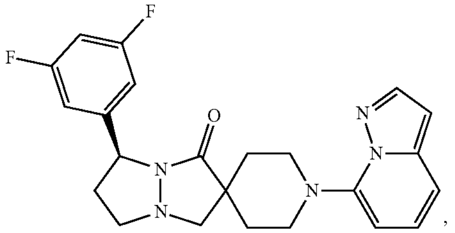
,
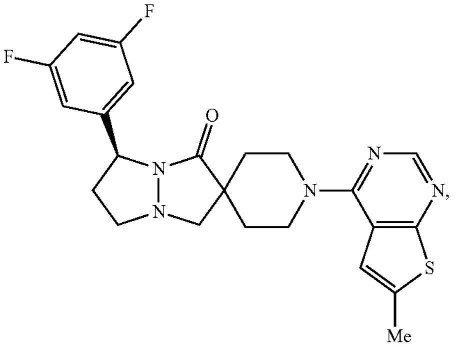
,
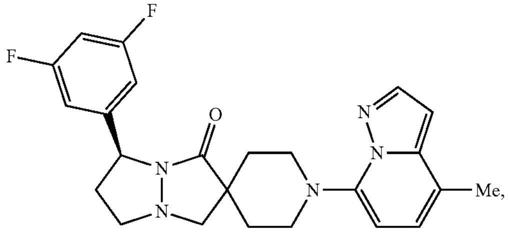
,
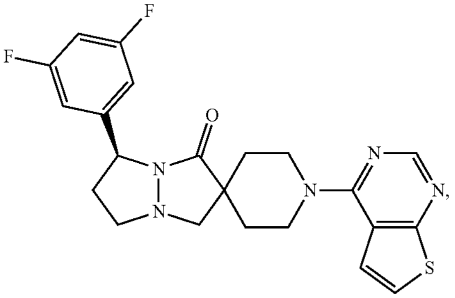
,
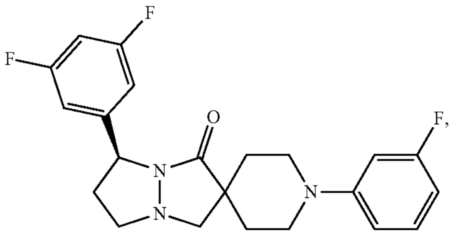
, -continued
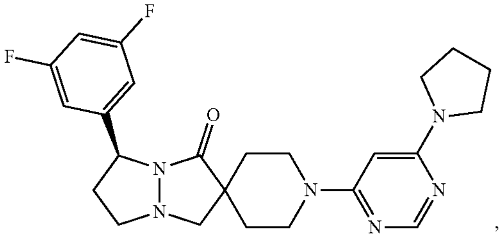
,
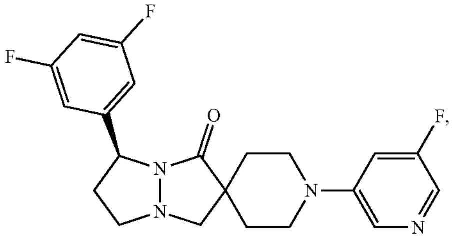
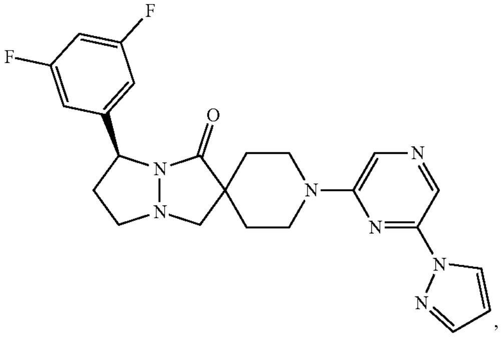
,
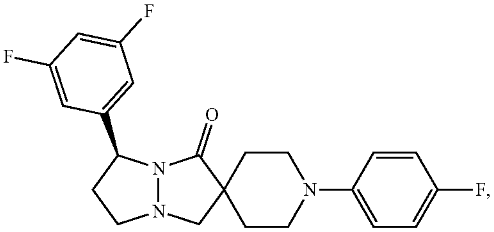
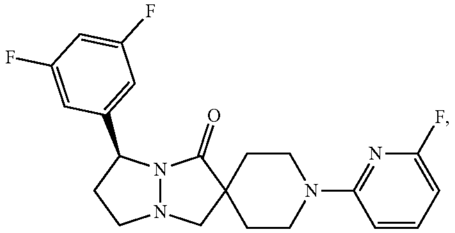
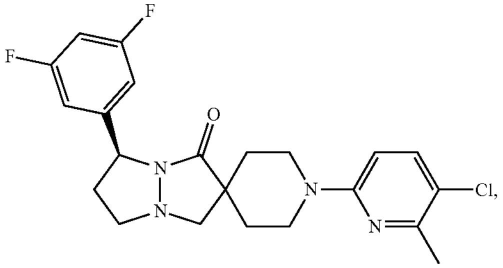
-continued
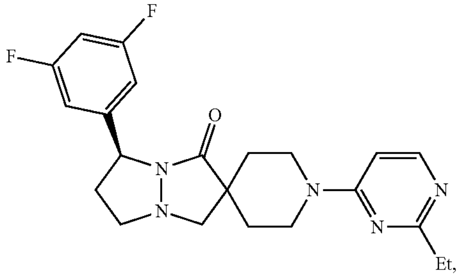
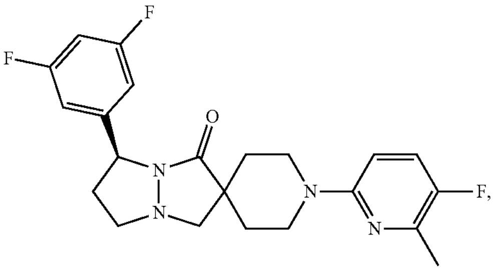
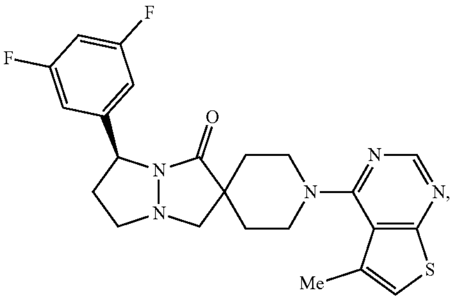
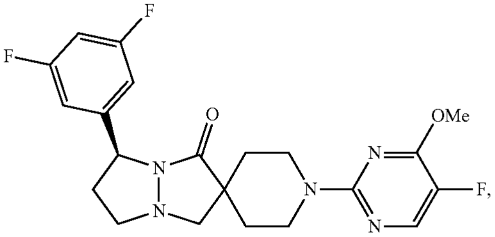
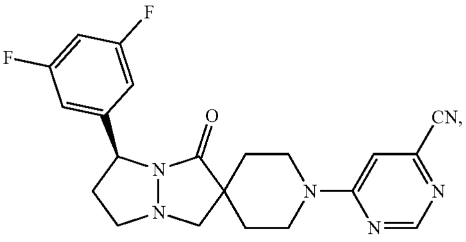
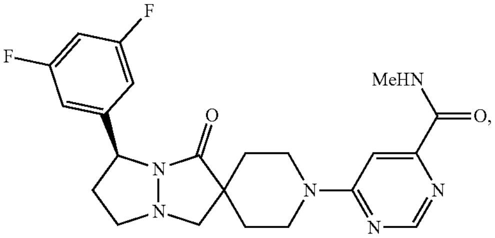

-continued
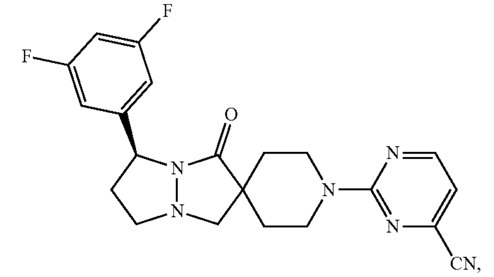
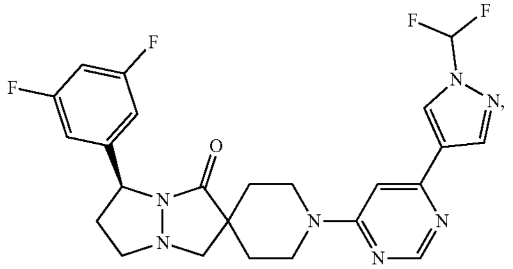
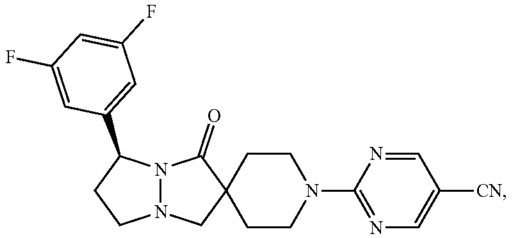
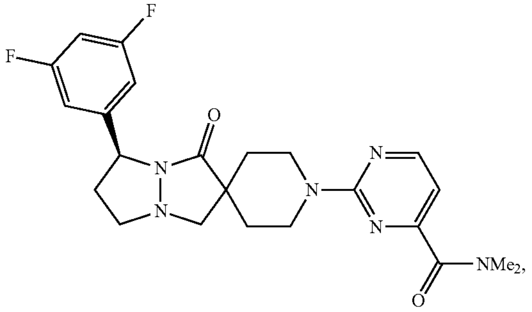
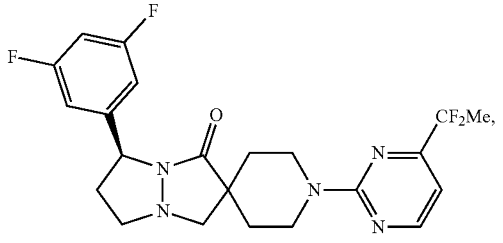
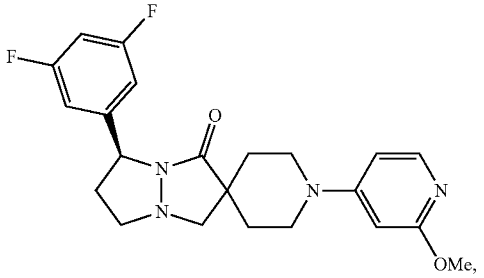
-continued
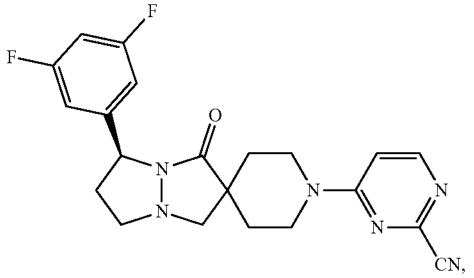
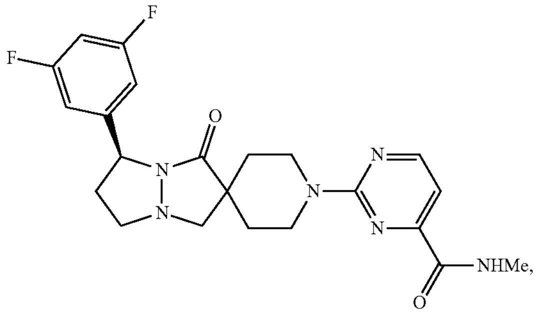
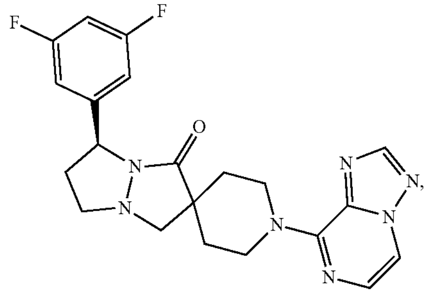
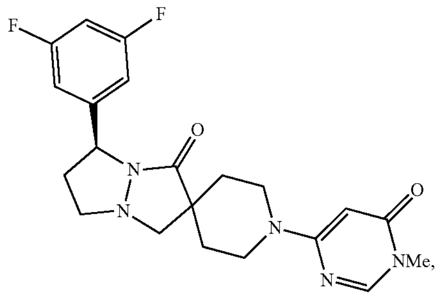
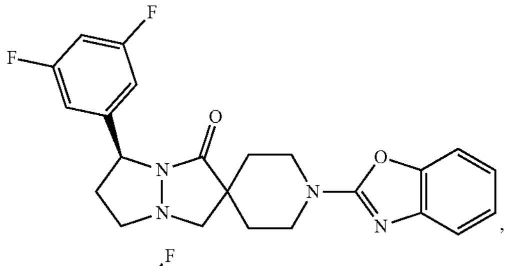
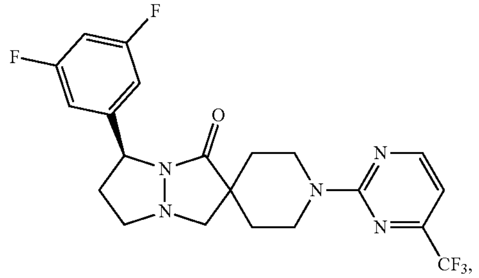

-continued

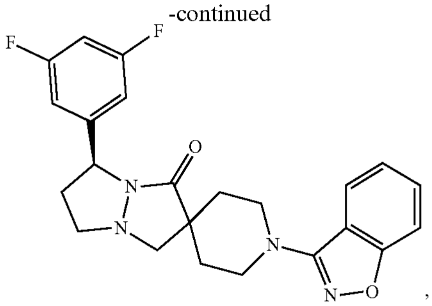

,

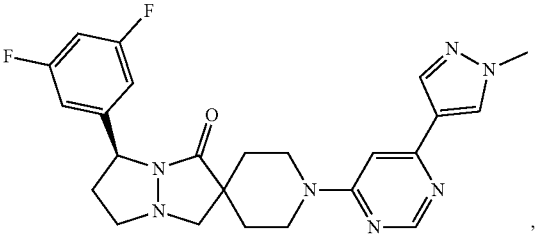

,

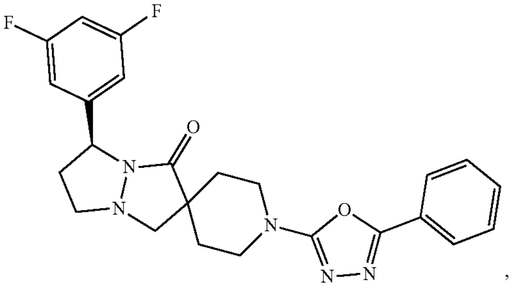

,

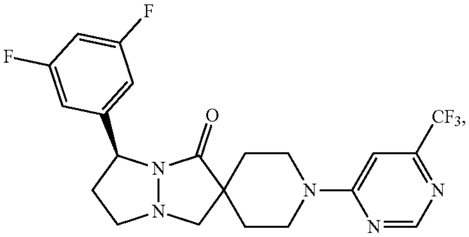

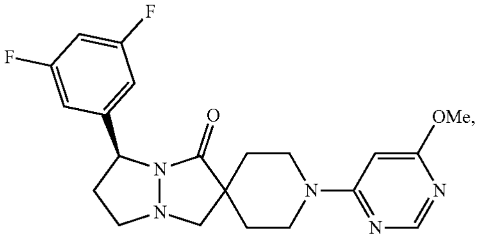

-continued

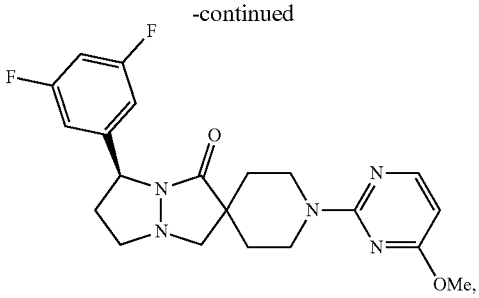

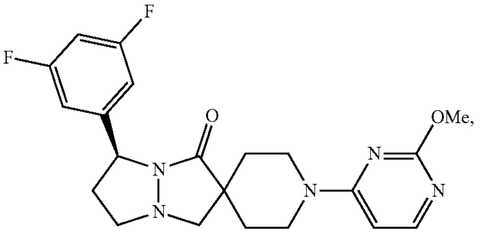

or

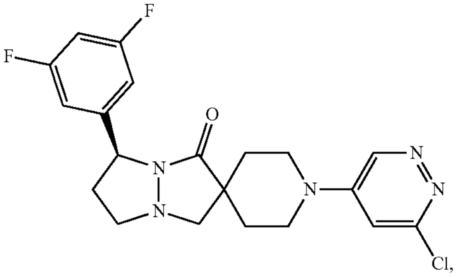

or a pharmaceutically acceptable salt thereof.

20. A method for treating RIPK1-dependent inflammation and cell death that occurs in inherited and sporadic diseases comprising administering to a patient in need thereof an effective amount of a compound, or pharmaceutically acceptable salt thereof, of claim 1.

21. A method of treating amyotrophic lateral sclerosis comprising administering to a patient in need thereof an effective amount of a compound, or pharmaceutically acceptable salt thereof, of claim 1.

22. A pharmaceutical composition comprising an effective amount of a compound of claim 1, or a pharmaceutically acceptable salt thereof and a pharmaceutically acceptable carrier.

23. A pharmaceutical composition comprising an effective amount of a compound of claim 1 and a pharmaceutically acceptable carrier.

* * * * *